United States Patent
Flannery et al.

(10) Patent No.: US 12,031,147 B2
(45) Date of Patent: Jul. 9, 2024

(54) ADENO-ASSOCIATED VIRUS VIRIONS WITH VARIANT CAPSIDS AND METHODS OF USE THEREOF

(71) Applicants: The Regents of the University of California, Oakland, CA (US); Novartis AG, Basel (CH)

(72) Inventors: John G. Flannery, Berkeley, CA (US); Scott F. Geller, El Cerrito, CA (US); Karen I. Guerin, Braintree, MA (US)

(73) Assignees: The Regents of the University of California, Oakland, CA (US); Novartis AG, Basel (CH)

( * ) Notice: Subject to any disclaimer, the term of this patent is extended or adjusted under 35 U.S.C. 154(b) by 274 days.

(21) Appl. No.: 17/332,855

(22) Filed: May 27, 2021

(65) Prior Publication Data

US 2021/0371879 A1    Dec. 2, 2021

Related U.S. Application Data

(60) Provisional application No. 63/187,154, filed on May 11, 2021, provisional application No. 63/032,206, filed on May 29, 2020.

(51) Int. Cl.
*C12N 15/86* (2006.01)
*C07K 14/005* (2006.01)

(52) U.S. Cl.
CPC ............ *C12N 15/86* (2013.01); *C07K 14/005* (2013.01); *C12N 2750/14121* (2013.01); *C12N 2750/14122* (2013.01); *C12N 2750/14143* (2013.01)

(58) Field of Classification Search
CPC .......... C12N 15/86; C12N 2750/14121; C12N 2750/14122; C12N 2750/14143; C12N 2750/14145; C07K 14/005; A61P 27/02
See application file for complete search history.

(56) References Cited

U.S. PATENT DOCUMENTS

| | | | |
|---|---|---|---|
| 2012/0164106 A1* | 6/2012 | Schaffer | C12N 15/86 435/235.1 |
| 2014/0294771 A1 | 10/2014 | Schaffer et al. | |
| 2018/0066285 A1 | 3/2018 | Ojala et al. | |
| 2019/0255192 A1* | 8/2019 | Kirn | C07K 14/005 |
| 2020/0095559 A1 | 3/2020 | Schaffer et al. | |
| 2020/0121746 A1 | 4/2020 | Schaffer et al. | |

FOREIGN PATENT DOCUMENTS

| | | |
|---|---|---|
| WO | WO 2012/145601 | 10/2012 |
| WO | WO 2016/154344 | 9/2016 |
| WO | WO 2018/022905 | 2/2018 |
| WO | WO 2019/046069 | 3/2018 |
| WO | WO 2019/006182 | 1/2019 |

* cited by examiner

*Primary Examiner* — Arthur S Leonard
*Assistant Examiner* — Josephine M Gonzales
(74) *Attorney, Agent, or Firm* — Bozicevic, Field & Francis LLP; Shweta Chandra

(57) ABSTRACT

The present disclosure provides recombinant adeno-associated virus (AAV) virions comprising: a) a variant capsid protein; and b) a heterologous nucleic acid comprising one or more nucleotide sequences encoding one or more heterologous gene products. The rAAV virions are useful for delivery of gene products to a retinal cell. The present disclosure provides methods of delivering a gene product to a retinal cell in an individual.

24 Claims, 52 Drawing Sheets
Specification includes a Sequence Listing.

FIG. 1A

AAV1

MAADGYDWDNSGRWWDKGAKKANKDDGRGVGYKYGNGDKGVNAADAAAAHDKAYDKAGDNYRYNHADARDTSGGNGRAVAKKRVGVGAKTAGKKRVSDS
SSGGKTGAKKRNGTGDSSVDGATAAVGTTMASGGGAMADNNGADGVGNASGNWHCDSTWGDRVTTSTRTWATYNNHYKSSASTGASNDNHYGYSTWGY
DNRHCHSRDWRNNNWGRKRNKNVKVTTNDGVTTANNTSTVVSDSYYVGSAHGCADVMYGYTNNGSAVGRSSYCYSMRTGNNTSYTVHSSYAHSSDRMN
DYYYNRTNSGSANKDSRGSAGMSVKNWGCYRRVSKTKTDNNNSNTWTGASKYNNGRSNGTAMASHKDDDKMSGVMGKSAGASNTADNVMTDKATNVAT
RGTVAVNSSSTDATGDVHAMGAGMVWDRDVYGWAKHTDGHHSMGGGKNKNTVANASATKASTYSTGVSVWKNSKRWNVYTSNYAKSANVDTVDNNGYT
RGTRYTR* (SEQ ID NO:58)

FIG. 1B

AAV2

MAADGYDWDTSGRWWKKGKARHKDDSRGVGYKYGNGDKGVNADAAAAHDKAYDRDSGDNYKYNHADARKDTSGGNGRAVAKKRVGVVKTAGKKRVHSVD
SSSGTGKAGARKRNGTGDADSVDGAASGGTNTMATGSGAMADNNGADGVGNSSGNWHCDSTWMGDRVTTSTRTWATYNNHYKSSSGASNDNHYGYSTW
GYDNRHCHSRDWRNNNWGRKRNKNVKVTNDGTTANNTSTVVTDSYYVGSAHGCADVMVYGYTNNGSAVGRSSYCYSMRTGNNTSYTDVHSSYAHSSD
RMNDYYYSRTNTSGTTTSRSAGASDRDSRNWGCYRRVSKTSADNNNSYSWTGATKYHNGRDSVNGAMASHKDDKSGVGKGSKTNVDKVMTDRTTNVAT
YGSVSTNRGNRAATADVNTGVGMVWDRDVYGMVWDRDVYGWAKHTDGHHSMGGGKHKNTVANSTTSAAKASTYSTGVSVWKNSKRWNYTSNYNKSVNVDTVDTNGVY
SRGTRYTRN* (SEQ ID NO:59)

FIG. 1C

AAV3A

MAADGYDWDNSGRWWAKGVKANHDNRRGVGYKYGGNGDKGVNADAAAHDKAYDKAGDNYKYNHADARDTSGGNGRAVAKKRGVAAKTAGKKGAVDSDS
SSGVGKSGKARKRNGTGDSSVDGAATSGSNTMASGGGAMADNNGADGVGNSSGNWHCDSWGDRVTTSTRTWATYNNHYKSSSGASNDNHYGYSTWGYD
NRHCHSRDWRNNNWGRKKSKNVRGVTNDGTTTANNTSTVVTDSYYVGSAHGCADVMVYGYTNNGSAVGRSSYCYSMRTGNNSYTDVHSSYAHSSDRMN
DYYYNRTGTTSGTTNSRSAGSMSARNWGCYRRSKTANDNNNSNWTAASKYHNGRDSVNGAMASHKDDKMHGNGKGTTASNADNVMTDRTTNVATYGTV
ANNSSNTATTGTVNHGAGMVWDRDVYGWAKHTDGHHSMGGGKHMKNTVANTTSAKASTYSTGVSVWKNSKRWNYTSNYNKSVNVDTVDTNGVYSRGTR
YTRN (SEQ ID NO: 60)

FIG. 1D

AAV3B

MAADGYDWDNSGRWWAKGVKANHDNRRGVGYKYGGNGDKGVNADAAAHDKAYDKAGDNYKYNHADARDTSGGNGRAVAKKRGVAAKTAGKKRVDSDSS
SGVGKSGKARKRNGTGDSSVDGAATSGSNTMASGGGAMADNNGADGVGNSSGNWHCDSWGDRVTTSTRTWATYNNHYKSSSGASNDNHYGYSTWGYDN
RHCHSRDWRNNNWGRKKKSKNVKVTNDGTTTANNTSTVVTDSYYVGSAHGCADVMVYGYTNNGSAVGRSSYCYSMRTGNNSYTDVHSSYAHSSDRMNDY
YYNRTGTTSGTTNSRSAGSMSARNWGCYRRSKTANDNNNSNWTAASKYHNGRDSVNGAMASHKDDKMHGNGKGTTASNADNVMTDRTTNVATYGTVAN
NSSNTATTRTVNDGAGMVWDRDVYGWAKHTDGHHSMGGGKHMKNTVANTTSAKASTYSTGVSVWKNSKRWNYTSNYNKSVNVDTVDTNGVYSRGTRYT
RN (SEQ ID NO: 61)

FIG. 1E

AAV4

MTDGYDWDNSGVRWWAGAKKANHDNARGVGYKYGGNGDKGVNAADAAAHDKAYDKAGDNYKYNHADARGDTSGGNGRAVAKKRVGVAGTAGKKRSDSS
TGGKKGKAKKKVDTGAGDGGSTSGAMSDDSMRAAAGGAAVGGGADGVGNASGDWHCDSTWSGHVTTTSTRTWVTYNNHYKRGSSNTYNGSTWGYDNRH
CHSRDWRNNNWGMRKAMRVKNVKVTTSNGTTVANNTSTVADSSYYVMDAGGSNDVMVYGYCGVTGNTSTDRNAYCYSMRTGNNTYSKVHSMYAHSSDR
MNDYWGSTTTGTTNAGTATTNTKRTNSNKKNWGSKGSKTANNYKATGSDSKYTHSTDGRWSATGMATAGADSKSNSAGKNGNTATVGTTSAATNATDT
DMWGNGGDSNSNTVDRTAGAVGMVWNRDYYGWAKHTDGHHSGGGKHKNTVANATTSSTVNSTYSTGVSVDWKRSKRWNVTSNYGNSWADAAGKYTRAG
TRYTHH* (SEQ ID NO:62)

FIG. 1F

AAV5

MSFVDHPPDWLEEVGEGLREFLGLEAGPPKPKPNQQHQDQARGLVLPGYNYLGPGNGLDRGEPVNRADEVAREHDISYNEQLEAGDNPYLKYNHADAE
FQEKLADDTSFGGNLGKAVFQAKKRVLEPFGLVEEGAKTAPTGKRIDDHFPKRKKARTEEDSKPSTSSDAEAGPSGSQQLIPAQPASSLGADTMSAG
GGGPLGDNNQGADGVGNASGDWHCDSTWMGDRVVTKSTRTWVLPSYNNHQYREIKSGSVDGSNANAYFGYSTPWGYFDFNRFHSHWSPRDWQRLINNY
WGFRPRSLRVKIFNIQVKEVTVQDSTTTIANNLITSTVQVFTDDDYQLPYVVGNGTEGCLPAFPPQVFTLPQYGYATLNRDNTENPTERSSFFCLEYFP
SKMLRTGNNFEFTYNFEEVPFHSSFAPSQNLFKLANPLVDQYLYRFVSTNNTGGVQFNKNLAGRYANTYKNWFPGPMGRTQGWNLGSGVNRASVSAFA
TTNRMELEGASYQVPPQPNGMTNNLQGSNTYALENTMIFNSQPANPGTTATYLEGNMLITSESETQPVNRVAYNVGGQMATNNQSSTTAPATGTYNLQ
EIVPGSVWMERDVYLQGPIWAKIPETGAHFHPSPAMGGFGLKHPPPMMLIKNTPVPGNITSFSDVPVSSFITQYSTGQVTVEMEWELKKENSKRWNPE
IQYTNNYNDPQFVDFAPDSTGEYRTTRPIGTRYLTRPL (SEQ ID NO:63)

FIG. 1G

AAV6

MAADGYDWDNSGRWWDKGAKKANKDDGRGVGYKYGNGDKGVNAADAAAHDKAYDKAGDNYRYNHADARDTSGGNGRAVAKKRVGVGAKTAGKKRVSDS
SSGGKTGAKKRNGTGDSSVDGATAAVGTTMASGGAMADNNGADGVGNASGNWHCDSTWGDRVTTSTRTWATYNNHYKSSASTGASNDNHYGYSTWGY
DNRHCHSRDWRNNNWGRKRNKNVKVTTNDGVTTANNTSTVVSDSYYVGSAHGCADVMYGYTNNGSAVGRSSYCYSMRTGNNTSYTDVHSSYAHSSDRM
NDYYNRTNSGSANKDSRGSAGMSVKNWGCYRRVSKTKTDNNNSNTWTGASKYNNGRSNGTAMASHKDKDKMSGVMGKSAGASNTADNVMTDKAINV
ATRGTVAVNSSSTDATGDVHVMGAGMVWDRDVYGWAKHTDGHHSMGGGKHKNTVANASATKASTYSTGVSVWKNSKRWNVYTSNYAKSANVDTVDNNG
YTRGTRYTR* (SEQ ID NO:64)

FIG. 1H

AAV7

MAADGYDWDNSGRWWDKGAKKANKDNGRGVGYKYGNGDKGVNAADAAAHDKAYDKAGDNYRYNHADARDTSGGNGRAVAKKRVGVGAKTAAKKRVSRS
DSSTGGKKGARKRNGTGDSSVDGAASSVGSGTVAAGGGAMADNNGADGVGNASGNWHCDSTWGDRVTTSTRTWATYNNHYKSSTAGSTNDNTYGYSTW
GYDNRHCHSRDWRNNNWGRKKRKNVGRSSYCYSMRTGNNSYSDVHSSYAHSSDRM
NDYYARTSNGTAGNRYGGSTMAAKNWGCRRVSKTDNNNSNAWTGATKYHNGRNSVNGVAMATHKDDRSSGVGKTGATNKTTNVMTNRTNVATYGV
SSNAANTAATVVNNGAGMVWNRDVYGWAKHTDGNHSMGGGKHKNTVANVTAKASTYSTGVSVWKNSKRWNYTSNKTGVDAVDSGVYSRGTRYTRN*
(SEQ ID NO:65)

FIG. 1I

AAV8

MAADGYDWDNSGRWWAKGAKKANKDDGRGVGYKYGNGDKGVNAADAAAHDKAYDAGDNYRYNHADARDTSGGNGRAVAKKRVGVGAKTAGKKRVSRSD
SSTGKKGARKRNGTGDSSVDGAASGVGNTMAAGGGAMADNNGADGVGSSSGNWHCDSTWGDRVTTSTRTWATYNNHYKSNGTSGATNDNTYGYSTW
GYDNRHCHSRDWRNNNWGRKRSKNVKVTNGTKTANNTSTVTDSYYVGSAHGCADVMYGYTNNGSAVGRSSYCYSMRTGNNTYTDVHSSYAHSSDRMND
YYYSRTTTGGTANTTGSGGNTMANAKNWGCYRRVSTTTGNNNSNAWTAGTKYHNGRNSANGAMATHKDDRSNGGKNAARDNADYSDVMTSKTTNVATY
GVADNNTAGTVNSGAGMVWNRDVYGWAKHTDGNHSMGGKHKNTVADTTNSKNSTYSTGVSVWKNSKRWNYTSNYYKSTSVDAVNTGVYSRGTRYTRN
* (SEQ ID NO:66)

FIG. 1J ancestral

MAADGYLPDWLEDNLSEGIREWWDLKPGAPKPKANQQKQDDGRGLVLPGYKYLGPFNGLDKGEPVNAADAAALEHDKAYDQQLKAGDNPYLRYNHADA
EFQERLQEDTSFGGNLGRAVFQAKKRVLEPLGLVEEGAKTAPGKKRPVEPSPQRSPDSSTGIGKKGQQPAKKRLNFGQTGDSESVPDPQPLGEPPAGP
SGLGSGTMAAGGGAPMADNNEGADGVGNASGNWHCDSTWLGDRVITTSTRTWALPTYNNHLYKQISSXSXGXTNDNHYFGYSTPWGYFDFNRFHCHFS
PRDWQRLINNNWGFRPKRLNFKLFNIQVKEVTTNDGVTTIANNLTSTVQVFSDSEYQLPYVLGSAHQGCLPPFPADVFMIPQYGYLTLNNGSQAVGRS
SFYCLEYFPSQMLRTGNNFTFSYTFEDVPFHSSYAHSQSLDRLMNPLIDQYLYYLXRTQSTGGTAGXXELLFSQXGPXXMSXQAKNWLPGPCYRQQRV
SKTLXQNNNSNFAWTGATKYHLNGRXSLVNPGVAMATHKDDEXRFFPSSGVLIFGKXXGAGXNNTXL XNVMXTEEEIKTTNPVATEXYGVVAXNLQSS
NTAPXTGXVNSQALPGMVWQNRDVYLQGPIWAKIPHTDGNFHPSPLMGGFGLKHPPPQILIKNTPVPANPPXXF XXAKFASFITQYSTGQVSVEIEW
ELQKENSKRWNPEIQYTSNYAKSXNVDFAVXXXGVYXEPRPIGTRYLTRNL (SEQ ID NO:67)

(X is any amino acid)

FIG. 2

```
AAV-2      570 PVATEQYGSVSTNLQRGNRQAATADVNTQGVLPGMVWQDRDV 611 (SEQ ID NO:68)
AAV-1      571 PVATERFGTVAVNFQSSSTDPATGDVHAMGALPGMVWQDRDV 612 (SEQ ID NO:69)
AAV-5      560 RVAYNVGGQMATNNQSSTTAPATGTYNLQEIVPGSVWMERDV 601 (SEQ ID NO:70)
AAV-6      571 PVATERFGTVAVNLQSSSTDPATGDVHVMGALPGMVWQDRDV 612 (SEQ ID NO:71)
AAV-7      572 PVATEEYGIVSSNLQAANTAAQTQVVNNQGALPGMVWQNRDV 613 (SEQ ID NO:72)
AAV-8      573 PVATEEYGIVADNLQQQNTAPQIGTVNSQGALPGMVWQNRDV 614 (SEQ ID NO:73)
AAV-9      571 PVATESYGQVATNHQSAQAQAQTGWVQNQGILPGMVWQDRDV 612 (SEQ ID NO:74)
AAV-10     573 PVATEQYGVVADNLQQANTGPIVGNVNSQGALPGMVWQNRDV 614 (SEQ ID NO:75)
AAV-4      569 ATDTDMWGNLPGGDQSNSNLPTVDRLTALGAVPGMVWQNRDI 610 (SEQ ID NO:76)
Ancestral  573 PVATEXYGVVAXNLQSSNTAPXTGXVNSQGALPGMVWQNRDV 613 (SEQ ID NO:77)
```

FIG. 3A

```
AAV1      ---TFSYTFEEVPFHSSYAHSQSLDRLMNPLIDQYLYYLNRTQ--NQSGSAQNKDLLFSRGS 467
AAV6      ---TFSYTFEDVPFHSSYAHSQSLDRLMNPLIDQYLYYLNRTQ--NQSGSAQNKDLLFSRGS 467
AAV3      ---FSYTFEDVPFHSSYAHSQSLDRLMNPLIDQYLYYLNRTQGTTSGTTNQSRLLFSQAG 467
AAV2      ---FSYTFEDVPFHSSYAHSQSLDRLMNPLIDQYLYYLSRTN--TPSGTTTQSRLQFSQAG 466
AAV8      NFQFTYTFEDVPFHSSYAHSQSLDRLMNPLIDQYLYYLSRTQTT--GGTANTQTLGFSQGG 469
AAV8.1    NFQFTYTFEDVPFHSSYAHSQSLDRLMNPLIDQYLYYLSRTQTT--GGTANTQTLGFSQGG 469
AAV8 rh8  FQFSYTFEDVPFHSSYAHSQSLDRLMNPLIDQYLYYLVRTQTTGTGGTQTLAFSQAGPS 469
AAV10     NFEFSYTFEDVPFHSSYAHSQSLDRLMNPLIDQYLYYLSRTQST--GGTQGTQQLLFSQAG 469
AAV7      -FEFSYSFEDVPFHSSYAHSQSLDRLMNPLIDQYLYYLARTQSNPGTAGNRELQFYQGG 469
AAV9      -FQFSYEFENVPFHSSYAHSQSLDRLMNPLIDQYLYYLSKTI---NGSGQNQQTLKFSVAG 467
AAV9.1    -FQFSYEFENVPFHSSYAHSQSLDRLMNPLIDQYLYYLSKTI---NGSGQNQQTLKFSVAG 467
AAV5      NFEFTYNFEEVPFHSSFAPSQNLFKLANPLVDQYLYRFVSTN-------NTGGVQFNKNL 453
                    **.***  *:**. .  :*** ** : .    *

AAV1      PAGMSVQPKNWLPGPCYRQQRVSKTKTDNNNSNFTWTGASKYNLNGRESIINPGTAMASH 527
AAV6      PAGMSVQPKNWLPGPCYRQQRVSKTKTDNNNSNFTWTGASKYNLNGRESIINPGTAMASH 527
AAV3      PQSMSLQARNWLPGPCYRQQRLSKTIANDNNNSNFPWTAASKYHLNGRDSLVNPGPAMASH 527
AAV2      ASDIRDQSRNWLPGPCYRQQRVSKTSADNNNSEYSWTGATKYHLNGRDSLVNPGPAMASH 526
AAV8      PNTMANQAKNWLPGPCYRQQRVSTTTGQNNNSNFAWTAGTKYHLNGRNSLANPGIAMATH 529
AAV8.1    PNTMANQAKNWLPGPCYRQQRVSTTTGQNNNSNFAWTAGTKYHLNGRNSLANPGIAMATH 529
AAV8 rh8  S---MANQARNWVPGPCYRQQRVSTTTNQNNNSNFAWTGAAKFKLNGRDSLMNPGVAMASH 527
AAV10     PANMSAQAKNWLPGPCYRQQRVSTTLSQNNNSNFAWTGATKYHLNGRDSLVNPGVAMATH 529
AAV7      PSTMAEQAKNWLPGPCFRQQRVSTTLDQNNNSNFAWPGASSWALNGRNSLMNPGPAMASH 527
AAV9      PSNMAVQGRNYIPGPSYRQQRVSTTVTQNNNSEFAWPGASSWALNGRNSLMNPGPAMASH 529
AAV9.1    PSNMAVQGRNYIPGPSYRQQRVSTTVTQNNNSEFAWPGASSWALNGRNSLMNPGPAMASH 527
AAV5      AGRYANTYKNWFPGPMGRTQGWNLGSGVNRASVSAFATTNRMELEGASYQVPPQPNGMTN 513
             . *:. ** * *  *  :* :        *                         ::
```

FIG. 3B

```
AAV1      KDDEDKFFPMSGVMIFGK--ESAGASNTALD-NVMITDEEEIKATNPVATERFGTVAVNF  584
AAV6      KDDKDKFFPMSGVMIFGK--ESAGASNTALD-NVMITDEEEIKATNPVATERFGTVAVNL  584
AAV3      KDEEKFFPMHGNLIFGK--EGTTASNAELD-NVMITDEEEIRTTNPVATEQYGTVANNL  584
AAV2      KDEEKFFPQSGVLIFGK--QGSEKTNVDIE-KVMITDEEEIRTTNPVATEQYGSVSTNL  583
AAV8      KDDEERFFPSNGILIFGK--QNAARDNADYS-DVMLTSEEEIKTTNPVATEEYGIVADNL  586
AAV8.1    KDDEERFFPSNGILIFGK--QNAARDNADYS-DVMLTSEEEIKTTNPVATEEYGIVADNL  586
AAV8 rh8  KDDDRFFPSSGVLIFGK--QGAGNDGVDYS-QVLITDEEEIKATNPVATEEYGAVAINN  584
AAV10     KDDEERFFPSSGVLIFGK--QGAGRDNVDYS-SVMLTSEEEIKTTNPVATEQYGVVADNL  586
AAV7      KDDEDRFFPSSGVLMFGK--TGAT-NKTTLE-NVLMTNEEEIRPTNPVATEEYGIVSSNL  585
AAV9      KEGEDRFFPLSGSLIFGK--QGTGRDNVDAD-KVMITNEEEIKTTNPVATESYGQVATNH  584
AAV9.1    KEGEDRFFPLSGSLIFGK--QGTGRDNVDAD-KVMITNEEEIKTTNPVATESYGQVATNH  584
AAV5      NLQGSNTYALENTMIFNSQPANPGTTATYLEGNMLITSESETQPVNRVAYNVGGQMATNN  573
          :.    . ::  :**    .          .  :: :.  .* ::  **        :
```

```
AAV1      QSSSTDPATGDVHAMGALPGMVWQDRDVYLQGPIWAKIPHTDGHFHPSPLMGGFGLKNPP  644
AAV6      QSSSTDPATGDVHVMGALPGMVWQDRDVYLQGPIWAKIPHTDGHFHPSPLMGGFGLKHPP  644
AAV3      QSSNTAPTTGTVNHQGALPGMVWQDRDVYLQGPIWAKIPHTDGHFHPSPLMGGFGLKHPP  644
AAV2      QRGNRQAATADVNTQGVLPGMVWQDRDVYLQGPIWAKIPHTDGNFHPSPLMGGFGLKHPP  643
AAV8      QQQNTAPQIGTVNSQGALPGMVWQNRDVYLQGPIWAKIPHTDGNFHPSPLMGGFGLKHPP  646
AAV8.1    QGQRQAAQIGTVNSQGALPGMVWQNRDVYLQGPIWAKIPHTDGNFHPSPLMGGFGLKHPP  646
AAV8 rh8  QAANTQAQTGLVHNQGVIPGMVWQNRDVYLQGPIWAKIPHTDGNFHPSPLMGGFGLKHPP  644
AAV10     QQANTGPIVGNVNSQGALPGMVWQNRDVYLQGPIWAKIPHTDGNFHPSPLMGGFGLKHPP  646
AAV7      QAANTAAQTQVVNNQGALPGMVWQNRDVYLQGPIWAKIPHTDGNFHPSPLMGGFGLKHPP  645
AAV9      QSAQAQAQTGWVQNQGILPGMVWQDRDVYLQGPIWAKIPHTDGNFHPSPLMGGFGMKHPP  644
AAV9.1    QSGQAQAATGMVQNQGILPGMVWQDRDVYLQGPIWAKIPHTDGNFHPSPLMGGFGMKHPP  644
AAV5      QSSTTAPAIGTYNLQEIVPGSVVMERDVYLQGPIWAKIPETGAHFHPSPAMGGFGLKHPP  633
          *    .     :  : :**  **  :***************  .****..****:*:**
```

FIG. 3C

```
AAV1     PQILIK-  650  (SEQ ID NO:78)
AAV6     PQILIK-  650  (SEQ ID NO:79)
AAV3     PQIMIK-  650  (SEQ ID NO:80)
AAV2     PQILIKN  650  (SEQ ID NO:81)
AAV8     PQILIKN  653  (SEQ ID NO:82)
AAV8.1   PQILIKN  653  (SEQ ID NO:83)
AAV8 rh8 PQILIKN  651  (SEQ ID NO:84)
AAV10    PQILIKN  653  (SEQ ID NO:85)
AAV7     PQILIKN  652  (SEQ ID NO:86)
AAV9     PQILIK-  650  (SEQ ID NO:87)
AAV9.1   PQILIK-  650  (SEQ ID NO:88)
AAV5     PMMLIKN  640  (SEQ ID NO:89)
         *  ::**
```

FIG. 4A
Retinoschisin-1
*Homo sapiens*

```
  1 msrkiegfll lllfgyeatl gisstedege dpwyqkackc dcqggpnalw sagatsldci
 61 pecpyhkplg fesgevtpdq itcsnpeqyv gwysswtank arlnsqgfgc awiskfqdss
121 qwlqidlkei kvisgiltqg rcdidewmtk ysvqyrtder lnwiyykdqt gnnrvfygns
181 drtstvqnll rppiisrfir liplgwhvri airmellecv skca (SEQ ID NO:90)
```

FIG. 4B
BDNF
*Homo sapiens*

```
  1 mtilfltmvi syfgcmkaap mkeanirgqg glaypgvrth gtlesvngpk agsrgltsla
 61 dtfehvieel ldedhkvrpn eennkdadly tsrvmlssqv plepplifli eeyknyldaa
121 nmsmmvlrhs dparrgelsv cdsisewvta adkktavdms ggtvtlekv pvskgqlkqy
181 fyetkcnpmg ytkegcrgid krhwnsqcrt tqsyvraltm dskkrigwrf iridtscvct
241 ltikrgr (SEQ ID NO:91)
```

FIG. 4C
RPE65
*Homo sapiens*

```
  1 msiqvehpag gykklfetve elsspltahv tgriplwltg sllrcgpglf evgsepfyhl
 61 fdgqailhkf dfkeghvtyh rrfirtdayv ramtekrivi tefgtcafpd pcknifsrff
121 syfrgvevtd nalvnvypvg edyyactetn fitkinpetl etikqvdlcn yvsvngatah
181 phiendgtvy nigncfgknf siaynivkip plqadkedpi skseivvqfp csdrfkpsyv
241 hsfgltpnyi vfvetpvkin lfkflsswsl wganymdcfe snetmgvwlh iadkkrkkyl
301 nnkyrtspfn lfhhintyed ngflivdlcc wkgfefvyny lylanlrenw eevkknarka
361 pqpevrryvl plnidkadtg knlvtlpntt atailcsdet iwlepevlfs gprqafefpq
421 inyqkycgkp ytyayglgln hfvpdrickl nvktketwvw qepdsypsep ifvshpdale
481 eddgvvlsvv vspgagqkpa yllilnakdl sevaraevei nipvtfhglf kks (SEQ ID NO:92)
```

FIG. 4D
Peripherin-2
*Homo sapiens*

```
  1 mallkvkfdq kkrvklaggl wlmnwfsvla giiifslglf lkielrkrsd vmnnseshfv
 61 pnsligmgvl scvfnslagk icydaldpak yarwkpwlkp ylaicvlfni ilflvalccf
121 llrgslentl ggqikngmky yrdtdtpgrc fmkktidmlq iefkccgnng frdwfeiqwi
181 snryldfssk evkdriksnv dgrylvdgvp fsccnpsspr pciqyqitnn sahysydhqt
241 eelnlwvrgc raallsyyss lmnsmgvvtl liwlfevtit igirylqtsi dgvsnpeese
301 sesqgwiler svpetwkafl esvkklgkgn qveaegadag qapeag (SEQ ID NO:93)
```

FIG. 4E
Peripherin
*Homo sapiens*

```
  1 mshhpsglra gfsstsyrrt fgpppslspg afsyssssrf sssrllgsas psssvrlgsf
 61 rspragagal lrlpserldf smaealngef latrsnekqe lqelndrfan fiekvrfleq
121 qnaalrgels qargqepara dqlcqqelre lrrelellgr erdrvqverd glaediaalk
181 qrleeetrkr edaehnlvlf rkdvddatls rlelerkies lmdeieflkk lheeelrdlq
241 vsvesqqvqq veveatvkpe ltaalrdira qyesiaaknl qeaeewyksk yadlsdaanr
301 nhealrqakq emnesrrqiq sltcevdglr gtneallrql releeqfale aggyqagaar
361 leeelrqlke emarhlreyq ellnvkmald ieiatyrkll egeesrisvp vhsfaslnik
421 ttvpeveppg dshsrktvli ktietrngev vtesqkeqrs eldkssahsy (SEQ ID NO:94)
```

FIG. 4F
RPGR-interacting protein-1
*Homo sapiens*

```
   1  mshlvdptsg dlpvrdidai plvlpaskgk nmktqpplsr mnreeledsf frlredhmlv
  61  kelswkqqde ikrirttllr itaagrdirv aeeaaplset arrgqkagwr qrlsmhqrpq
 121  mhrlqghfhc vgpasprraq prvqvghrql htaagpvpek pkrgprdrls ytappsfkeh
 181  atnenrgeva skpselvsgs nsiisfssvi smakpiglcm pnsahimasn tmqveeppks
 241  pekmwpkden feqrssleca qkaaelrasi kekvelirlk kliherniasi vmtkaqltev
 301  qeayetllqk ngqilsaahe alikqvnelr aelkeeskka vslksqledv silqmtlkef
 361  qervedleke rklindnydk llesmldssd sssqphwsne liaeqlqqqv sqlqdqldae
 421  ledkrkvlle isrekaqned iklevtnilq khkqevellq naatisqppd rqsepathpa
 481  vlqentqiep sepknqeekk lsqvlnelqv shaettlele ktrdmlilqr kinvcyqeel
 541  eammtkadnd nrdhkekler ltrlldiknn rikqlegiilr shdlptseqi kdvaygtrpl
 601  slcletlpah gdedkvdisl lhqgenlfel hihqafltsa alaqagdtqp ttfctysfyd
 661  fethctplsv gpqplydfts qyvmetdsif lhylqeasar ldihqamase hstlaagwic
 721  fdrvletvek vhglatliga ggeefgvley wmrlrfpikp slqacnkrkk aqvylstdvl
 781  ggrkaqeeef rseswepqne lwieitkccg lrsrwlgtqp spyavyrfft fsdhdtaiip
 841  asnnpyfrdq arfpvlvtsd ldhylrreal sihvfdddedl epgsylgrar vpllplakne
 901  sikgdfnltd paekpngsiq vqldwkfpyi ppesflkpea qtkgkdtkds skisseeeka
 961  sfpsqdqmas pevpieaggy rskrkpphgg erkekehqvv sysrrkhgkr igvqgknrme
1021  ylslnilngn tpeqvnytew kfsetnsfig dgfknqheee emtlshsalk qkeplhpvnd
1081  kesseqgsev seaqttdsdd vivppmsqky pkadsekmci eivslafype aevmsdenik
1141  qvvveykfyd lplsetetpv slrkpragee ihfhfskvid ldpqeqqgrr rflfdmlngq
1201  dpdqghlkft vvsdpldeek keceevgyay lqlwqilesg rdileqeldi vspedlatpi
1261  grlkvslqaa avlhaiykem tedlfs (SEQ ID NO:95)
```

FIG. 4G
Rab escort protein-1

```
  1 madtipsefd vivigtglpe siiaaacsrs grrvlhvdsr syygnwasf sfsgliswlk
 61 eyqensdivs dspvwqdqii eneeaialsr kdktiqhvev fcyasqdlhe dveeagalqk
121 nhalvtsans teaadsaflp tedeslstms cemiteqtps sdpenalevn gaevtgeken
181 hcddktcvps tsaedmsenv piaedtteqp kknritysqi ikegrrfnid lvskliysrg
241 llidiliksn vsryaefkni trilafregr veqvpcsrad vfnskqltmv ekrmlmkflt
301 fcmeyekypd eykgyeeitf yeyiktqklt pnlqvivmhs iamtsetass tidglkatkn
361 flhclgrygn tpflfplygq gelpqcfcrm cavfggiycl rhsvqclvvd kesrkckaii
421 dqfgqriise hflvedsyfp enmcsrvqyr qisravlitd rsvlktdsdq qisiltvpae
481 epgtfavrvi elcsstmtcm kgtylvhltc tssktaredl esvvqklfvp ytemeieneq
541 vekprilwal yfnmrdssdi srscyndlps nvyvcsgpdc glgndnavkq aetlfqeicp
601 nedfcppppn pediiildgds lqpeasessa ipeansetfk estnignlee sse (SEQ ID NO:96)
```

FIG. 4H
212-amino acid isoform of RdCVF

```
  1 maslfsgril irnnsdqdel dteaevsrrl enrlvliffg agacpqcqaf vpiikdffvr
 61 ltdefyvlra aqlalvyvsq dsteeqqdlf lkdmpkkwlf lpfeddirrd lgrqfsverl
121 pavvvlkpdg dvltrdgade iqrlgtacfa nwqeaaevld rnfqlpedle dqeprsitec
181 lrrhkyrvek aarggrdpgg gggeeggagg lf (SEQ ID NO:97)
```

FIG. 4I
156-amino acid isoform of RdCVF (isoform 1)

```
  1 mvdilgerhl vtckgatvea eaalqnkvva lyfaaarcap srdftplicd fytalvaear
 61 rpapfevvfv sadgssqeml dfmrelhgaw lalpfhdpyr heirkrynvt aipklvivkq
121 ngevitnkgr kqiregiac fqdwveaadi fqnfsv (SEQ ID NO:98)
```

FIG. 4J
135-amino acid isoform of RdCVF (isoform 2)

```
  1 mvdilgerhl vtckgatvea eaalqnkvva lyfaaarcap srdftplicd fytalvaear
 61 rpapfevvfv sadgssqeml dfmrelhgaw lalpfhdpyr qrsialiprl ecsgvilahc
121 nlcllgssds lalas (SEQ ID NO:99)
```

FIG. 4K

Rod cGMP-specific 3',5'-cyclic phosphodiesterase subunit alpha (PDE6α)
GenBank NP_00431

```
  1 mgevtaeeve kfldsnigfa kqyynlhyra klisdiigak eaavdfsnyh spssmeesei
 61 ifdllrdfqe nlqtekcifn vmkkicfliq adrmslfmyr trngiaelat rlfnvhkdav
121 ledclvmpdq eivfpldmgi vghvahskki anvpnteede hfcdfvdilt eyktknilas
181 pimngkdvva iimavnkvdg shftkrdeei likylnfani imkvyhisyl hncetrrgqi
241 liwsgskvfe eltdiergfh kalytvrafl ncdrysvgli dmtkqkeffd vwpvimgevp
301 pysgprtpdg reinfykvid yilhgkedik vipnpppdhw alvsqlpayv aqnglicnim
361 napaedffaf qkepidesgw miknvlsmpi vnkkeeivgv atfynrkdgk pfdemdetlm
421 esltqfigws vlnpdtyesm nklenrkdif qdivkyhvkc dneeiqkilk trevygkepw
481 eceeeeiaei lqaelpdadk yeinkfhfsd lplteielvk cgiqmyyelk vvdkfhipqe
541 alvrfmysls kgyrkityhn wrhgfnvgqt mfsllvtgki kryftdieal amvtaafchd
601 idhrgtnnly qmksqnpiak ihgssilerh hlefgktllr desinifqnl nrrqhehaih
661 mmdiailatd lalyfkkrtm fqkivdqskt yeseqewtqy mmieqtrkei vmammmtacd
721 lsaitkpwev qsqvallvaa efweggdler tviqqnpipm mdrnkadelp klqvgfidfv
781 ctfvykefsr fheeitpmld gitnnrkewk aladeydakm kvqeekkqkq qsaksaaagn
841 qpggnpspgg attsksccig (SEQ ID NO:100)
```

FIG. 4L

Rod cGMP-specific 3',5'-cyclic phosphodiesterase subunit beta isoform 1 (PDE6β isoform 1)
GenBank NP_000274

```
  1 mslseeqars fldqnpdfar qyfgkklspe nvaaacedgc ppdcdslrdl cqveestall
 61 elvqdmqesi nmervvfkvi rrictliqad rcslfmyrqr ngvaelatrl fsvqpdsvle
121 dclvppdsei vfpldigvvg hvaqtkkmvn vedvaecphf ssfadeltdy ktknmiatpi
181 mngkdvvavi mavnkingpf ftsededvfi kylnfatlyl kiyhlsyihn cetrrgqvil
241 wsankvfeel tdierqfhka fytvraylnc erysvgiidm tkekeffdvw svlmgesqpy
301 sgprtpdgre ivfykvidyi lhgkeeikvi ptpsadhwal asgipsyvae sgficnimna
361 sademfkfqe galddsgwli knvlsmpivn kkeeivgvat fynrkdgkpf deqdevlmes
421 itqflgwsvm ntdtydkmnk lenrkdiaqd mvlyhvkcdr deiqlilptr arlgkepadc
481 dedelgeiik eelpgpttfd iyefhfsdle cteldlvkcg iqmyyelgvv rkfqipqevl
541 vrflfsiskg yrrityhnwr hgfnvaqtmf tlimtgkiks yytdleafam vtagichdid
601 hrgtnnlyqm ksqnplakih gssilerhhl efgkfilsee tlniyqninr rqhehvihlm
661 diaiiatdla lyfkkramfq kivdeskknyq dkkswveyls lettrkeivm amumtacdis
721 aitkpwevgs kvalivaaef weqgdliertv ldqqpipmmd rnkaaelpkl qvgfidfvct
781 fvykefsrfh eeilpmfdrl qnnrkewkal adeyeakvka leekeeerv aakkvgteic
841 nggpapksst ccil (SEQ ID NO:101)
```

FIG. 4M

Rod cGMP-specific 3',5'-cyclic phosphodiesterase subunit beta isoform 2 (PDE6β isoform 2)
GenBank NP_001138763

```
  1 mslseeqars fldqnpdfar qyfgkklispe nvaaacedgc ppdcdslrdl cqveestall
 61 elvqdmqesi nmervvfkvi rrictilqad rcslfmyrqr ngvaelatrl fsvqpdsvle
121 dclvppdsei vfpldigvvg hvaqtkkmvn vedvaecphf ssfadeltdy ktknmiatpi
181 mngkdvvavi mavnklngpf ftsededvfi kylnfatlyl kiyhlsylhn cetrrgqvil
241 wsankvfeel tdierqfhka fytvraylnc erysvgildm tkekeffdvw svlmgesqpy
301 sgprtpdgre ivfykvidyi lhgkeeikvi ptpsadhwal asgipsyvae sgficnimna
361 sademfkfqe galddsgwli knvlsmpivn kkeeivgvat fynrkdgkpf deqdevlmes
421 itqflgwsvm ntdtydkmnk lenrkdiaqd mvlyhvkcdr deiqlilptr arlgkepadc
481 dedelgeilk eelpgpttfd iyefhfsdle cteldlvkcg iqmyyelgvv rkfqipqevl
541 vrflfsiskg yrrityhnwr hgfnvaqtmf tlimtgkiks yytdleafam vtagichdid
601 hrgtnnlyqm ksqnplakih gssilerhhl efgkfiisee tlniyqninr rqhehvihlm
661 diaiiatdla lyfkkramfq kivdesknyq dkkswveyls lettrkeivm amnmtacdls
721 aitkpwevgs kvallvaaef weqgdliertv ldqqpipmmd rnkaaelpkl qvgfidfvct
781 fvykefsrfh eeilpmfdri qnnrkewkal adeyeakvka leekeeerv aakkgteicn
841 ggpapksstc cil (SEQ ID NO:102)
```

FIG. 4N

Rod cGMP-specific 3',5'-cyclic phosphodiesterase subunit beta isoform 3 (PDE6β isoform 3)
GenBank NP_001138764

```
  1 mtkekeffdv wsvlmgesqp ysgprtpdgr eivfykvidy ilhgkeeikv iptpsadhwa
 61 lasgipsyva esgficnimn asademfkfq egalddsgwl iknvlsmpiv nkkeeivgva
121 tfynrkdgkp fdeqdevlme sitqflgwsv mntdtydkmn klenrkdiaq dmvlyhvkcd
181 rdeiqllipt rarlgkepad cdedelgeil keelpgpttf diyefhfsdl ecteldlvkc
241 giqmyyelgv vrkfqipqev lvrflfsisk qyrrityhnw rhgfnvaqtm ftllmtgklk
301 syytdleafa mvtagichdi dhrgtnnlyq mksqnpiakl hgssilerhh iefgkfllse
361 etlniyqnln rrqhehvihl mdiaiiatdi alyfkkramf qkivdeskny qdkkswveyl
421 slettrkeiv mammmtacdl saitkpwevq skvallvaae fweqgdlert vldqqpipmm
481 drnkaaeipk lqvgfidfvc tfvykefsrf heeilpmfdr lqnnrkewka iadeyeakvk
541 aleekeeeer vaakkvgtei cnggpapkss tccil (SEQ ID NO:103)
```

FIG. 4O

Cyclic nucleotide-gated cation channel alpha-3 isoform 1 (CNGA3 isoform 1)
GenBank NP_001289

```
  1 makintqysh psrthikvkt sdrdlnraen glsrahssse etssvlqpgi ametrglads
 61 gqgsftgqgi arlsrlifli rrwaarhvhh qdqgpdsfpd rfrgaelkev ssqesnaqan
121 vgsqepadrg rsawplakcn tntsnnteee kktkkkdaiv vdpssnlyyr wltaialpvf
181 ynwyllicra cfdelqseyl miwlvldysa dvlyvldvlv rartgflegg imvsdtnrlw
241 qhykttqfk ldvlslvptd laylkvgtny yfaiskfigf gtdswvypni sipehgrisr kyiyslywst
301 frignlviyi lliihwnaci yfaiskfigf vvvdflvgvi ifativgnvg smisnmnasr aefqakidsi
361 itlttigetp ppvkdeeylf fdylwankkt vdekeviksl pdkikaeiai nvhldtlkkv
421 kqymqfrkvt kdletrvirw fdylwankkt tvfspqdyic kkgdigkemy iinegklavv addgvtqfvv
481 rifqdceagl lvelviklrp tvfspqdyic gnrrtanirs igysdlfcls kddimealte ypeakkalee
541 lsdgsyfgei silnikgsks gnrrtanirs adpkdleekv eqlgssidtl qtrfarliae ynatqmkmkq
601 kgrqilmkdn lideelarag adpkdleekv evpgdatkte dkqq (SEQ ID NO:104)
661 rlsqlesqvk gggdkpladg evpgdatkte dkqq (SEQ ID NO:104)
```

FIG. 4P

Cyclic nucleotide-gated cation channel alpha-3 isoform 2 (CNGA3 isoform 2)
GenBank NP_001073347

```
  1 makintqysh psrthlkvkt sdrdlnraen qlsrahssse etssvlqpgi ametrglads
 61 gqgsftgqgi arlsrlifll rrwaarhvhh qdgqpdsfpd rfrgaelkev ssqesnaqan
121 vgsqepadrg rrkktkkkda ivvdpssnly yrwltaialp vfynwyllic racfdelqse
181 ylmlwivldy sadvlyvldv lvrartgfle qglmvsdtnr lwqhyktttq fkldvlslvp
241 tdlayikvgt nypevrfnrl lkfsrlfeff drtetrtnyp nmfrlgnlvi ylllihwna
301 clyfalskfi gfgtdswvyp nisipehgrl srkylyslyw stltlttige tpppvkdeey
361 lfvvvdflvg vlifatlvgn vgsmisnmna sraefqakid slkqymqfrk vtkdletrvi
421 rwfdylwank ktvdekevlk slpdklkaei alnvhldtlk kvrifqdcea qllvelvlkl
481 rptvfspgdy ickkgdlgke myllnegkla lskddlmeal teypeakkal eekgrqllmk
541 ksgnrrtani rslgysdifc lskddlmeal tlqtrfaril aeynatqmkm kqrlsqlesq
601 agadpkdlee kveqlgssld tlqtrfaril aeynatqmkm kqrlsqlesq vkgggdkpla
661 dgevpgdatk tedkqq (SEQ ID NO:105)
```

FIG. 4Q

Cyclic nucleotide-gated cation channel beta-3 (CNGB3)
GenBank NP_061971

```
  1 mfksltkvnk vkpigennen eqssrrneeg shpsnqsqqt taqeenkgee ksiktkstpv
 61 tseephtniq dkiskknssg dlttnpdpqn aaeptgtvpe qkemdpgkeg pnspqnkppa
121 apvineyada qlhnlvkrmr qrtalykkkl vegdisspea spqtakptav ppvkesddkp
181 tehyyrllwf kvkkmpltey lkriklpnsi dsytdrlyll willvtlayn wnccfiplrl
241 vfpyqtadni hywliadiic diilyldmlf iqprlqfvrg gdiivdsnel rkhyrtstkf
301 qldvasiipf dicylffgfn pmfranrmlk ytsffefnhh lesimdkayi yrvlrttgyl
361 lfilhinacv yywasnyegi gttrwvydge gneylrcyyw avrtlitigg lpepqtlfei
421 vfqllnffsg vfvfssllgq mrdvigaata nqnyfracmd dtiaymnnys ipklvqkrvr
481 twveytwdsq rmidesdilk tlpttvqial aidvnfsiis kvdlfkgcdt qmiydmilrl
541 ksvlylpgdf vckkgeigke myiikhgevq vlggpdgtkv lvtlkagsvf geisllaagg
601 gnrrtanvva hgfanlltld kktlqeilvh ypdserilmk karvllkqka ktaeatpprk
661 diallfppke etpklfktll ggtgkasiar llklkreqaa qkkensegge eegkenedkq
721 kenedkqken edkgkenedk dkgrepeekp ldrpectasp iaveeephsv rrtvlprgts
781 rqsliismap saeggeevlt ievkekakq   (SEQ ID NO:106)
```

FIG. 4R

Guanine nucleotide-binding protein G(t) subunit alpha-2 (GNAT2)
GenBank NP_005263

```
  1 mgsgasaedk elakrskele kklqedadke aktvklillg agesgkstiv kqmkiihqdg
 61 yspeeclefk aiiygnvlqs ilairamtt lgidyaepsc addgrqinni adsieegtmp
121 pelveviri wkdggvqacf eraaeyqind sasyinqie ritdpeylps eqdvlrsrvk
181 ttgiietkfs vkdlnfrmfd vggqrserkk wihcfegvtc iifcaalsay dmvleddev
241 nrmheslhlf nsicnhkffa atsivlfink kdlfeekikk vhlsicfpey dgnnsyddag
301 nyiksqfldi nmrkdvkeiy shmtcatdtq nvkfvfdavt diiikenlkd cglf   (SEQ ID NO:107)
```

FIG. 4S

RPGR – 815 amino acids
GenBank NP_000319

```
  1 mrepeelmpd sgavftfgks kfaennpgkf wfkndvpvhl scgdehsavv tgnnklymfg
 61 snnwgqlglg sksaiskptc vkalkpekvk laacgrnhtl vsteggnvya tggnneqqlg
121 lgdteerntf hvisfftseh kikqlsagsn tsaaltedgr lfmwgdnseg qiglknvsnv
181 cvpqqvtigk pvswiscgyy hsafvttdge lyvfgepeng kiglpnqllg nhrtpqivse
241 ipekviqvac ggehtvvite navytfgigq fgqlgigtfl fetsepkvie nirdqtisyi
301 scgenhtali tdiglmytfg dgrhgklglg lenftnhfip ticsnflrfi vklvacggch
361 mvvfaaphrg vakeiefdei ndtclsvatf lpyssitsgn viqrtlsarm rrererspd
421 sfsmrtlpp iegtlgisac flpnsvfprc serniqesvl seqdlmqpee pdylldemtk
481 eaeidnsstv esigettdil nmthimsins neksiklspv qkqkkqqtig eltqdtalte
541 nddsdeyeem semkegkack qhvsqgifmt qpattieafs deeveipeek egaedskgng
601 ieeqeveane envkvhggrk ekteilsddl tdkaedhefs kteelkledv deeinaenve
661 skkktvgdde svptgyhskt egaertndds saetiekkek anleeraice ynenpkgyml
721 ddadsslei lensettpsk dmkktkkifl fkrvpsingk ivknnneplp eiksigdqii
781 lksdnkdadq nhmsqnhqni pptnterrsk sctii (SEQ ID NO:108)
```

FIG. 4T

RPGR – 646 amino acids
GenBank CAB54002

```
  1 mrepeelmpd sgavftfgks kfaennpgkf wfkndvpvhl scgdehsavv tgnnklymfg
 61 snnwqlglg sksaiskptc vkalkpekvk laacgrnhtl vsteggnvya tggnneqqlg
121 igdteerntf hvisfftseh kikqlsagsn tsaaltedgr ifmwdnseg qiglknvsnv
181 cvpqqvtigk pvswiscgyy hsafvttdge lyvfgepeng kiglpnqlig nhrtpqivse
241 ipekviqvac ggehtvvlte navytfglgq fgqiglgtfl fetsepkvie nirdqtisyi
301 scgenhtali tdiglmytfg dgrhgkiglg lenftnhfip ticsnflrfi vklvacggch
361 mvvfaaphrg vakeiefdei ndtclsvatf lpyssltsgn vlqrtlsarm rrererspd
421 sfsmrtlpp iegtlglsac flpnsvfprc sernlqesvl seqdimqpee pdylldemtk
481 eaeidnsstv eslgettdii nmthimslns neksiklspv qkqkkqqtig eltqdtalte
541 nddsdeyeem semkegkack qhvsqgifmt qpattieafs deeveipeek egaedskgng
601 ieeqeveane envkvhggrk ekteilsddl tdkaeysash sqivsv (SEQ ID NO:109)
```

FIG. 4U

RPGR – 1152 amino acids

```
   1  mrepeelmpd sgavftfgks kfaennpgkf wfkndvpvhl scgdehsavv tgnnklymfg
  61  snnwqiglg sksaiskptc vkalkpekvk laacgrnhti vsteggnvya tggnneqqig
 121  lgdteerntf hvisfftseh kikqisagsn tsaaltedgr lfmwgdnseg qigiknvsnv
 181  cvpqqvtigk pvswiscgyy hsafvttdge lyvfgepeng kiglpnqlig nhrtpqlvse
 241  ipekviqvac ggehtvvite navytfgigq fgqlgigtfi fetsepkvie nirdqtisyi
 301  scgenhtali tdigimytfg dgrhgklgig lenftnhfip ticsnflrfi vklvacggch
 361  mvvfaaphrg vakeiefdei ndtclsvatf lpyssitsgn vlqrtlsarm rrererspd
 421  sfsmrrtlpp iegtlglsac flpnsvfprc sernlqesvi seqdlmqpee pdyildemtk
 481  eaeidnsstv eslgettdil nmthimslns neksikispv qkqkkqqtig eltqdtalte
 541  ndsdeyeem semkegkack qhvsqgifmt qpattieafs deeveipeek egaedskgng
 601  ieegeveane envkvhggrk ekteilsddi tdkaevsegk aksvgeaedg pegrgdgtce
 661  egssgaehwq deerekgekd kgrgemerpg egekelaeke ewkkrdgeeq eqkereqghq
 721  kernqemeeg geeehgegee eegdreeeee kegegkeege geevegerek eegerkkeer
 781  agkeekgeee gdqgegeeee tegrgeekee ggeveggeve egkgereeee eegegeeeeg
 841  egeeeegege eeegegkgee egeegegeee geeeegeege eegegeegee gegegeeeeg
 901  egegeeegeg egeeeegegk geeeegeeeg egeeegegeg gedgegegee eegewegeee
 961  egegeeeeg egegeeeege egeeerekeg eeegeeeeg eeegegeege gegeeeeege
1021  vegevegeeg egeeeeeege eegeerekeg egeenrrnre eeeeeegkyq etgeeenerq
1081  dgeeykkvsk ikgsvkygkh ktyqkksvtn tqgngkeqrs kmpvqskrll kngpsgskkf
1141  wnnvlphyle ik (SEQ ID NO:110)
```

FIG. 4V

RPGR – 1020 amino acids

```
   1  mrepeelmpd sgavftfgks kfaennpgkf wfkndvpvhl scgdehsavv tgnnklymfg
  61  snnwqiglg sksaiskptc vkalkpekvk iaacgrnhtl vsteggnvya tggnneqqlg
 121  lgdteerntf hvisfftseh kikqlsagsn tsaaitedgr lfmwgdnseg qigiknvsnv
 181  cvpqqvtigk pvswiscgyy hsafvttdge lyvfgepeng kiglpnqlig nhrtpqivse
 241  ipekviqvac ggehtvvlte navytfgigq fgqlglgtfl fetsepkvie nirdqtisyi
 301  scgenhtali tdiglmytfg dgrhgklglg lenftnhfip ticsnflrfi vklvacggch
 361  mvvfaaphrg vakeiefdei ndtclsvatf lpyssitsgn viqrtlsarm rrererspd
 421  sfsmrrtlpp iegtlglsac flpnsvfprc sernigesvl seqdlmqpee pdylldemtk
 481  eaeidnsstv eslgettdil nmthimsins neksiklspv qkqkkqqtig eltqdtalte
 541  nddsdeyeem semkegkack qhvsqqifmt qpattieafs deevgndtgq vgpqadtdge
 601  glqkevyrhe nnngvdqlda keiekesdgg h.sqkeseaee idseketkla eiagmkdlre
 661  rekstkkmsp ffgnlpdrgm nteseenkdf vkkresckqd vifdseresv ekpdsymega
 721  sesqgiadg fqqpeaiefs sgekeddeve tdqnirygrk liegqneket kpiisksmak
 781  ydfkcdrlse ipeekegaed skgngieeqe veaneenvkv hggrkektei lsddltdkae
 841  dhefskteel kledvdeein aenveskkkt vgddesvptg yhsktegaer tnddssaeti
 901  ekekanlee raiceynenp kgymiddads ssleilense ttpskdmkkt kkiflfkrvp
 961  sinqkivknn neplpeiksi gdqiilksdn kdadqnhmsq nhqnipptnt errsksctil
```

(SEQ ID NO:111)

FIG. 4W mGluR2

```
  1 MGSLLALLAL LLLWGAVAEG PAKKVLTLEG DLVLGGLFPV HQKGGPAEDC GPVNEHRGIQ
 61 RLEAMLFALD RINRDPHLLP GVRLGAHILD SCSKDTHALE QALDFVRASL SRGADGSRHI
121 CPDGSYATHG DAPTAITGVI GGSYSDVSIQ VANLLRLFQI PQISYASTSA KLSDKSRYDY
181 FARTVPPDFF QAKAMAEILR FFNWTYVSTV ASEGDYGETG IEAFELEARA RNICVATSEK
241 VGRAMSRAAF EGVVRALLQK PSARVAVLFT RSEDARELLA ASQRLNASFT WVASDGWGAL
301 ESVVAGSEGA AEGAITIELA SYPISDFASY FQSLDPWNNS RNPWFREFWE QRFRCSFRQR
361 DCAAHSLRAV PFEQESKIMF VVNAVYAMAH ALHNMHRALC PNTTRLCDAM RPVNGRRLYK
421 DFVLNVKFDA PFRPADTHNE VRFDRFGDGI GRYNIFTYLR AGSGRYRYQK VGYWAEGLTL
481 DTSLIPWASP SAGPLPASRC SEPCLQNEVK SVQPGEVCCW LCIPCQPYEY RLDEFTCADC
541 GLGYWPNASL TGCFELPQEY IRWGDAWAVG PVTIACLGAL ATLFVLGVFV RHNATPVVKA
601 SGRELCYILL GGVFLCYCMT FIFIAKPSTA VCTLRRLGLG TAFSVCYSAL LTKTNRIARI
661 FGGAREGAQR PRFISPASQV AICLALISGQ LLIVVAWLVV EAPGTGKETA PERREVVTLR
721 CNHRDASMLG SLAYNVLLIA LCTLYAFKTR KCPENFNEAK FIGFTMYTTC IIWLAFLPIF
781 YVTSSDYRVQ TTTMCVSVSL SGSVVLGCLF APKLHIILFQ PQKNVVSHRA PTSRFGSAAA
841 RASSSLGQGS GSQFVPTVCN GREVVDSTTS SL  (SEQ ID NO:122)
```

FIG. 5A

*Streptococcus pyogenes* Cas9

MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYLQNGRDMYVDQ
ELDINRLSDYDVDHIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD (SEQ ID NO:112)

FIG. 5B nSpCas9 (SpCas9 D10A)

MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYLQNGRDMYVDQE
LDINRLSDYDVDHIVPQSFLKDDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD (SEQ ID NO:113)

FIG. 5C
SpCas9 (H840A)
MDKKYSIGLDIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYLQNGRDMYVDQ
ELDINRLSDYDVDA̲IVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD (SEQ ID NO:114)

FIG. 5D

SpCas9 (D10A; H840A)
MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRKSEETITPWNFEEVVDKGASAQSFIERMTN
FDKNLPNEKVLPKHSLLYEYFTVYNELTKVKYVTEGMRKPAFLSGEQKKAIVDLLFKTNRKVTVKQLKEDYFKKIECFDSVEI
SGVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQ
ELDINRLSDYDVDAIVPQSFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFYKVREINNYHHAHDAYLN
AVVGTALIKKYPKLESEFVYGDYKVYDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKKYGGFDSPTVAYSVLVVAKVEKGKS
KKLKSVKELLGITIMERSSFEKNPIDFLEAKGYKEVKKDLIIKLPKYSLFELENGRKRMLASAGELQKGNELALPSKYVNFLYL
ASHYEKLKGSPEDNEQKQLFVEQHKHYLDEIIEQISEFSKRVILADANLDKVLSAYNKHRDKPIREQAENIIHLFTLTNLGAPA
AFKYFDTTIDRKRYTSTKEVLDATLIHQSITGLYETRIDLSQLGGD (SEQ ID NO:115)

FIG. 5E
enSpCas9 (nCas9 with K848A/K1003A/R1060A mutations)

MDKKYSIGLAIGTNSVGWAVITDEYKVPSKKFKVLGNTDRHSIKKNLIGALLFDSGETAEATRLKRTARRRYTRRKNRICYL
QEIFSNEMAKVDDSFFHRLEESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQLPGEKKNGLFGNLIALSLGLT
PNFKSNFDLAEDAKLQLSKDTYDDDLDNLLAQIGDQYADLFLAAKNLSDAILLSDILRVNTEITKAPLSASMIKRYDEHHQDL
TLLKALVRQQLPEKYKEIFFDQSKNGYAGYIDGGASQEEFYKFIKPILEKMDGTEELLVKLNREDLLRKQRTFDNGSIPHQIHL
GELHAILRRQEDFYPFLKDNREKIEKILTFRIPYYVGPLARGNSRFAWMTRKSEETITPWNFEEVVDKGASAQSFIERMTNFD
KNLPNEKVLPKHSLLYEYFTVYNELTKVKYVTEGMRKPAFLSGEQKKAIVDLLFKTNRKVTVKQLKEDYFKKIECFDSVEIS
GVEDRFNASLGTYHDLLKIIKDKDFLDNEENEDILEDIVLTLTLFEDREMIEERLKTYAHLFDDKVMKQLKRRRYTGWGRLS
RKLINGIRDKQSGKTILDFLKSDGFANRNFMQLIHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQILKEHPVENTQLQNEKLYLYYLQNGRDMYVDQE
LDINRLSDYDVDHIVPQSFLADDSIDNKVLTRSDKNRGKSDNVPSEEVVKKMKNYWRQLLNAKLITQRKFDNLTKAERGGL
SELDKAGFIKRQLVETRQITKHVAQILDSRMNTKYDENDKLIREVKVITLKSKLVSDFRKDFQFYKVREINNYHHAHDAYLN
AVVGTALIKKYPALESEFVYGDYKVYDVRKMIAKSEQEIGKATAKYFFYSNIMNFFKTEITLANGEIRKAPLIETNGETGEIV
WDKGRDFATVRKVLSMPQVNIVKKTEVQTGGFSKESILPKRNSDKLIARKKDWDPKKYGGFDSPTVAYSVLVAKVEKGK
SKKLKSVKELLGITIMERSSFEKNPIDFLEAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSAYNKHRDKPIREQAENIIHLFTLTNLGAP
AAFKYFDTTIDRKRYTSTKEVLDATLIHQSITGLYETRIDLSQLGGD (SEQ ID NO:116)

FIG. 5F nSpCas9-HF1

DKKYSIGLAIGTNSVGWAVITDEYKVPSKKFKVLGNTDRHSIKKNLIGALLFDSGETAEATRLKRTARRRYTRRKNRICYLQE
IFSNEMAKVDDSFFHRLEESFLVEEDKKHERHPIFGNIVDEVAYHEKYPTIYHLRKKLVDSTDKADLRLIYLALAHMIKFRGH
FLIEGDLNPDNSDVDKLFIQLVQTYNQLFEENPINASGVDAKAILSARLSKSRRLENLIAQLPGEKKNGLFGNLIALSLGLTPNF
KSNFDLAEDAKLQLSKDTYDDDLDNLLAQIGDQYADLFLAAKNLSDAILLSDILRVNTEITKAPLSASMIKRYDEHHQDLTLL
KALVRQQLPEKYKEIFFDQSKNGYAGYIDGGASQEEFYKFIKPILEKMDGTEELLVKLNREDLLRKQRTFDNGSIPHQIHLGE
LHAILRRQEDFYPFLKDNREKIEKILTFRIPYYVGPLARGNSRFAWMTRKSEETITPWNFEEVVDKGASAQSFIERMTAFDKN
LPNEKVLPKHSLLYEYFTVYNELTKVKYVTEGMRKPAFLSGEQKKAIVDLLFKTNRKVTVKQLKEDYFKKIECFDSVEISGV
EDRFNASLGTYHDLLKIIKDKDFLDNEENEDILEDIVLTLTLFEDREMIEERLKTYAHLFDDKVMKQLKRRRYTGWGALSRK
LINGIRDKQSGKTILDFLKSDGFANRNFMALIHDDSLTFKEDIQKAQVSGQGDSLHEHIANLAGSPAIKKGILQTVKVVDELV
KVMGRHKPENIVIEMARENQTTQKGQKNSRERMKRIEEGIKELGSQILKEHPVENTQLQNEKLYLYLQNGRDMYVDQELD
INRLSDYDVDHIVPQSFLKDDSIDNKVLTRSDKNRGKSDNVPSEEVVKKMKNYWRQLLNAKLITQRKFDNLTKAERGGLSE
LDKAGFIKRQLVETRAITKHVAQILDSRMNTKYDENDKLIREVKVITLKSKLVSDFRKDFQFYKVREINNYHHAHDAYLNAV
VGTALIKKYPKLESEFVYGDYKVYDVRKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPKKYGGFDSPTVAYSVLVVAKVEKGKSKK
LKSVKELLGITIMERSSFEKNPIDFLEAKGYKEVKKDLIIKLPKYSLFELENGRKRMLASAGELQKGNELALPSKYVNFLYLAS
HYEKLKGSPEDNEQKQLFVEQHKHYLDEIIEQISEFSKRVILADANLDKVLSAYNKHRDKPIREQAENIIHLFTLTNLGAPAAF
KYFDTTIDRKRYTSTKEVLDATLIHQSITGLYETRIDLSQLGGD (SEQ ID NO:117)

FIG. 6

*Staphylococcus aureus* Cas9

MKRNYILGLDIGITSVGYGIIDYETRDVDIDAGVRLFKEANVENNEGRRSKRGARRLKRRRRHRIQRVKKLLFDYNLLTDHSEL
SGINPYEARVKGLSQKLSEEEFSAALLHLAKRRGVHNVNEVEEDTGNELSTKEQISRNSKALEEKYVAELQLERLKKDGEV
RGSINRFKTSDYVKEAKQLLKVQKAYHQLDQSFIDTYIDLLETRRTYYEGPGEGSPFGWKDIKEWYEMLMGHCTYFPEELR
SVKYAYNADLYNALNDLNNLVITRDENEKLEYYEKFQIIENVFKQKKKPTLKQIAKEILVNEEDIKGYRVTSTGKPEFTNLKVY
HDIKDITARKEIIENAELLDQIAKILTIYQSSEDIQEELTNLNSELTQEEIEQISNLKGYTGTHNLSLKAINLILDELWHTNDNQIAI
FNRLKLVPKKVDLSQQKEIPTTLVDDFILSPVVKRSFIQSIKVINAIIKKYGLPNDIIIELAREKNSKDAQKMINEMQKRNRQTN
ERIEEIIRTTGKENAKYLIEKIKLHDMQEGKCLYSLEAIPLEDLLNNPFNYEVDHIIPRSVSFDNSFNNKVLVKQEENSKKGNR
TPFQYLSSSDSKISYETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFEEKQAESMPEIETEQEY
KEIFITPHQIKHIKDFKDYKYSHRVDKKPNRELINDTLYSTRKDDKGNTLIVNNLNGLYDKDNDKLKLINKSPEKLLMYHHDP
QTYQKLKLIMEQYGDEKNPLYKYEETGNYLTKYSKKDNGPVIKKIKYYGNKLNAHLDITDDYPNSRNKVVKLSLKPYRFDV
YLDNGVYKFVTVKNLDVIKKENYYEVNSKCYEEAKKLKKISNQAEFIASFYNNDLIKINGELYRVIGVNNDLLNRIEVNMIDITY
REYLENMNDKRPPRIIKTIASKTQSIKKYSTDILGNLYEVKSKKHPQIIKKG (SEQ ID NO:118)

FIG. 7A

*Francisella tularensis* Cpf1

```
   1 MSIYQEFVNK YSLSKTLRFE LIPQGKTLEN IKARGLILDD EKRAKDYKKA KQIIDKYHQF
  61 FIEEILSSVC ISEDLLQNYS DVYFKLKKSD DDNLQKDFKS AKDTIKKQIS EYIKDSEKFK
 121 NLFNQNLIDA KKGQESDLIL WLKQSKDNGI ELFKANSDIT DIDEALEIIK SFKGWTTYFK
 181 GFHENRKNVY SSNDIPTSII YRIVDDNLPK FLENKAKYES LKDKAPEAIN YEQIKKDLAE
 241 ELTFDIDYKT SEVNQRVFSL DEVFEIANFN NYLNQSGITK FNTIIGGKFV NGENTKRKGI
 301 NEYINLYSQQ INDKTLKKYK MSVLFKQILS DTESKSFVID KLEDDSDVVT TMQSFYEQIA
 361 AFKTVEEKSI KETLSLLFDD LKAQKLDLSK IYFKNDKSLT DLSQQVFDDY SVIGTAVLEY
 421 ITQQIAPKNL DNPSKKEQEL IAKKTEKAKY LSLETIKLAL EEFNKHRDID KQCRFEEILA
 481 NFAAIPMIFD EIAQNKDNLA QISIKYQNQG KKDLLQASAE DDVKAIKDLL DQTNNLLHKL
 541 KIFHISQSED KANILDKDEH FYLVFEECYF ELANIVPLYN KIRNYITQKP YSDEKFKLNF
 601 ENSTLANGWD KNKEPDNTAI LFIKDDKYYL GVMNKKNNKI FDDKAIKENK GEGYKKIVYK
 661 LLPGANKMLP KVFFSAKSIK FYNPSEDILR IRNHSTHTKN GSPQKGYEKF EFNIEDCRKF
 721 IDFYKQSISK HPEWKDFGFR FSDTQRYNSI DEFYREVENQ GYKLTFENIS ESYIDSVVNQ
 781 GKLYLFQIYN KDFSAYSKGR PNLHTLYWKA LFDERNLQDV VYKLNGEAEL FYRKQSIPKK
 841 ITHPAKEAIA NKNKDNPKKE SVFEYDLIKD KRFTEDKFFF HCPITINFKS SGANKFNDEI
 901 NLLLKEKAND VHILSIDRGE RHLAYYTLVD GKGNIIKQDT FNIIGNDRMK TNYHDKLAAI
 961 EKDRDSARKD WKKINNIKEM KEGYLSQVVH EIAKLVIEYN AIVVFEDLNF GFKRGRFKVE
1021 KQVYQKLEKM LIEKLNYLVF KDNEFDKTGG VLRAYQLTAP FETFKKMGKQ TGIIYYVPAG
1081 FTSKICPVTG FVNQLYPKYE SVSKSQEFFS KFDKICYNLD KGYFEFSFDY KNFGDKAAKG
1141 KWTIASFGSR LINFRNSDKN HNWDTREVYP TKELEKLLKD YSIEYGHGEC IKAAICGESD
1201 KKFFAKLTSV LNTILQMRNS KTGTELDYLI SPVADVNGNF FDSRQAPKNM PQDADANGAY
1261 HIGLKGLMLL GRIKNNQEGK KLNLVIKNEE YFEFVQNRNN (SEQ ID NO:119)
```

FIG. 7B

*Acidaminococcus sp.* BV3L6 type V CRISPR-associated protein Cpf1

TQFEGFTNLYQVSKTLRFELIPQGKTLKHIQEQGFIEEDKARNDHYKELKPIIDRIYKTYADQCLQLVQLDWENLSAAIDSYR
KEKTEETRNALIEEQATYRNAIHDYFIGRTDNLTDAINKRHAEIYKGLFKAELFNGKVLKQLGTVTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMIPKCSTQLKAVTAHFQTHTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMRNSNAATGEDYINSPVRDLNGVCFDSRFQN
PEWPMDADANGAYHIALKGQLLLNHLKESKDLKLQNGISNQDWLAYIQELRN (SEQ ID NO:120)

FIG. 7C

Cpf1 (AsCpf1 R1225A)
TQFEGFTNLYQVSKTLRFELIPQGKTLKHIQEQGFIEEDKARNDHYKELKPIIDRIYKTYADQCLQLVQLDWENLSAAIDSYR
KEKTEETRNALIEEQATYRNAIHDYFIGRTDNLTDAINKRHAEIYKGLFKAELFNGKVLKQLGTVTTTEHENALLRSFDKFTT
YFSGFYENRKNVFSAEDISTAIPHRIVQDNFPKFKENCHIFTRLITAVPSLREHFENVKKAIGIFVSTSIEEVFSFPFYNQLLTQTQ
IDLYNQLLGGISREAGTEKIKGLNEVLNLAIQKNDETAHIIASLPHRFIPLFKQILSDRNTLSFILEEFKSDEEVIQSFCKYKTLLR
NENVLETAEALFNELNSIDLTHIFISHKKLETISSALCDHWDTLRNALYERRISELTGKITKSAKEKVQRSLKHEDINLQEIISAA
GKELSEAFKQKTSEILSHAHAALDQPLPTTLKKQEEKEILKSQLDSLLGLYHLLDWFAVDESNEVDPEFSARLTGIKLEMEPSL
SFYNKARNYATKKPYSVEKFKLNFQMPTLASGWDVNKEKNNGAILFVKNGLYYLGIMPKQKGRYKALSFEPTEKTSEGFD
KMYYDYFPDAAKMIPKCSTQLKAVTAHFQTHTPILLSNNFIEPLEITKEIYDLNNPEKEPKKFQTAYAKKTGDQKGYREALC
KWIDFTRDFLSKYTKTTSIDLSSLRPSSQYKDLGEYYAELNPLLYHISFQRIAEKEIMDAVETGKLYLFQIYNKDFAKGHHGKP
NLHTLYWTGLFSPENLAKTSIKLNGQAELFYRPKSRMKRMAHRLGEKMLNKKLKDQKTPIPDTLYQELYDYVNHRLSHDLS
DEARALLPNVITKEVSHEIIKDRRFTSDKFFFHVPITLNYQAANSPSKFNQRVNAYLKEHPETPIIGIDRGERNLIYITVIDSTGKI
LEQRSLNTIQQFDYQKKLDNREKERVAARQAWSVVGTIKDLKQGYLSQVIHEIVDLMIHYQAVVLENLNFGFKSKRTGIAE
KAVYQQFEKMLIDKLNCLVLKDYPAEKVGGVLNPYQLTDQFTSFAKMGTQSGFLFYVPAPYTSKIDPLTGFVDPFVWKTIK
NHESRKHFLEGFDFLHYDVKTGDFILHFKMNRNLSFQRGLPGFMPAWDIVFEKNETQFDAKGTPFIAGKRIVPVIENHRFTGR
YRDLYPANELIALLEEKGIVFRDGSNILPKLLENDDSHAIDTMVALIRSVLQMANSNAATGEDYINSPVRDLNGVCFDSRFQN
PEWPMDADANGAYHIALKGQLLLNHLKESKDLKLQNGISNQDWLAYIQELRN (SEQ ID NO:121)

Variant 3 - cSLO

Variant 3 - Confocal

Variant 3, Group 2, OS

Variant 3, Group 4, OD

Variant 3, Group 9, OS

Variant 6, Group 4, OS

Variant 6, Group 6, OD

Variant 6, Group 9, OD

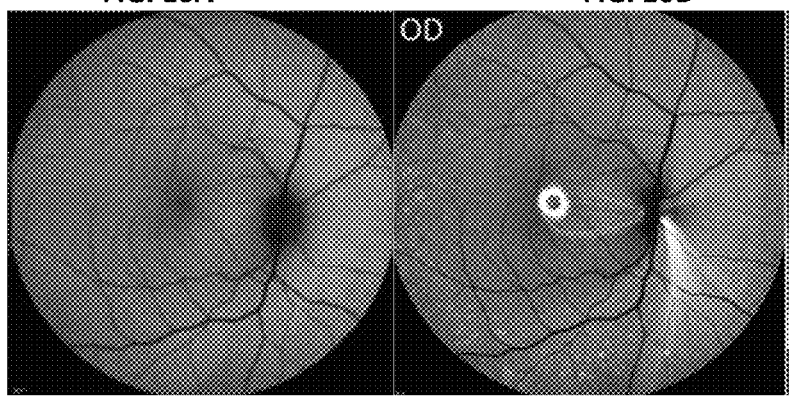
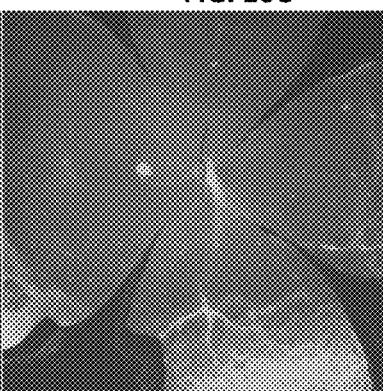
FIG. 10A  FIG. 10B  FIG. 10C

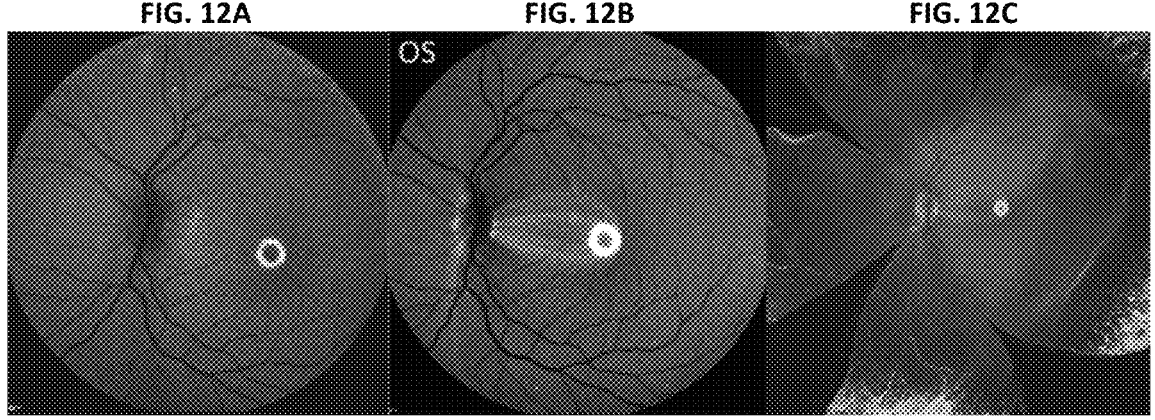

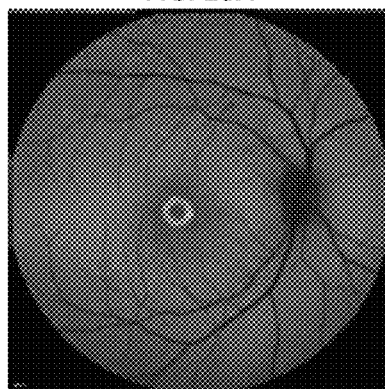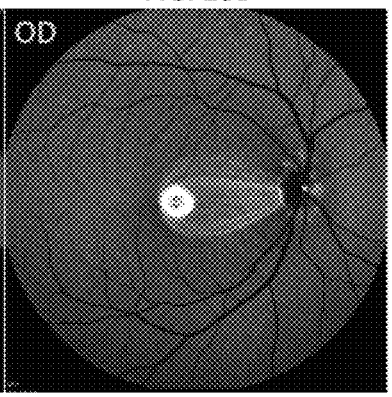

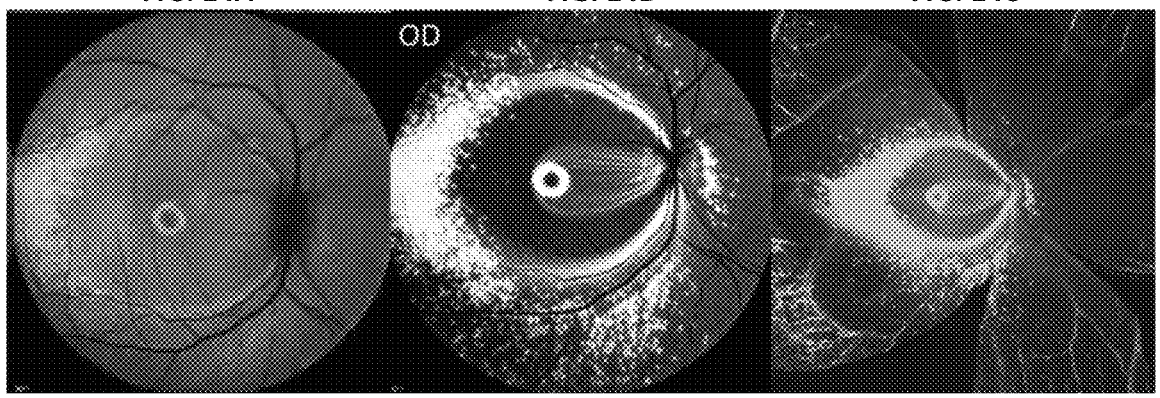
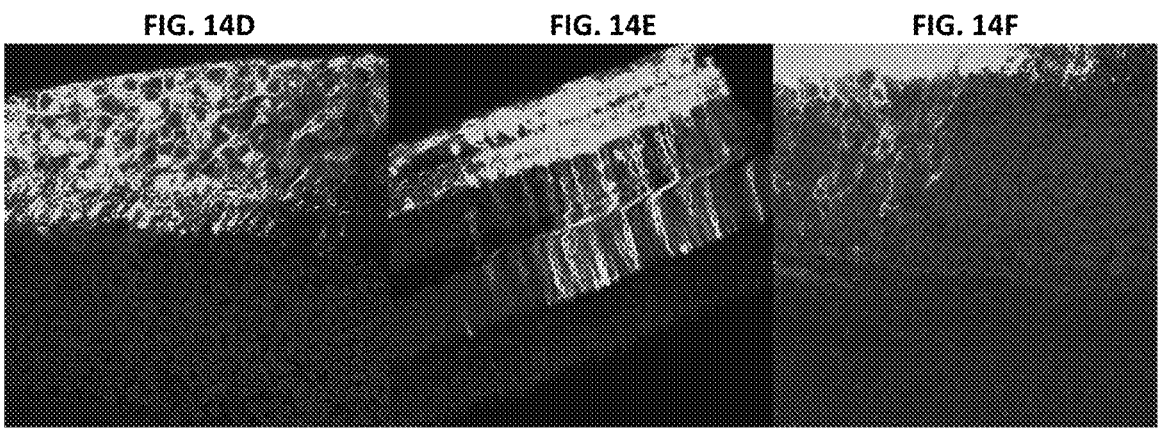
FIG. 14A  FIG. 14B  FIG. 14C
FIG. 14D  FIG. 14E  FIG. 14F

ADENO-ASSOCIATED VIRUS VIRIONS WITH VARIANT CAPSIDS AND METHODS OF USE THEREOF

CROSS-REFERENCE

This application claims the benefit of U.S. Provisional Patent Application No. 63/032,206, filed May 29, 2020, and U.S. Provisional Patent Application No. 63/187,154, filed May 11, 2021, which applications are incorporated herein by reference in their entirety.

STATEMENT REGARDING FEDERALLY SPONSORED RESEARCH

This invention was made with government support under EY022975 awarded by the National Institutes of Health. The government has certain rights in the invention.

INCORPORATION BY REFERENCE OF SEQUENCE LISTING PROVIDED AS A TEXT FILE

A sequence listing is provided herewith as a text file, "BERK-422_SEQ_LIST_ST25," created on May 27, 2021 and having a size of 350,289 bytes, the contents of which are herein incorporated by reference.

INTRODUCTION

Vision is mediated by cells located in the retina, a thin, layered structure lining the back of the eye. Photoreceptors, which lie at the back of the retina, respond to the absorption of photons, initiating a stream of signal processing that passes through second and third order neurons in the retina, including bipolar, horizontal and amacrine cells. Retinal pigment epithelium (RPE) cells, which lie underneath photoreceptors, promote the regeneration of the photon-detecting molecule, 11-cis retinal, via the visual cycle pathway and hence are essential for promoting this photoreceptor function. Retinal ganglion cells (RGCs) in the inner retina receive visual signals from third order neurons, and communicate the visual signals in the form of action potentials to the brain.

Mutations in genes expressed in retinal cells, including transcripts in photoreceptors, RPE, bipolar cells and other cells, result in a breakdown of visual signal processing and retinal degeneration. Many of the mutations underlying retinal degenerative disease result in the death of photoreceptor and RPE cells.

Adeno-associated virus (AAV) belongs to the Parvoviridae family and Dependovirus genus, whose members require co-infection with a helper virus such as adenovirus to promote replication, and AAV establishes a latent infection in the absence of a helper. Virions are composed of a 25 nm icosahedral capsid encompassing a 4.7 kb single-stranded DNA genome with two open reading frames: rep and cap. The non-structural rep gene encodes four regulatory proteins essential for viral replication, whereas cap encodes three structural proteins (VP1-3) that assemble into a 60-mer capsid shell. This viral capsid mediates the ability of AAV vectors to overcome many of the biological barriers of viral transduction—including cell surface receptor binding, endocytosis, intracellular trafficking, and unpackaging in the nucleus.

SUMMARY

The present disclosure provides recombinant adeno-associated virus (AAV) virions comprising: a) a variant capsid protein; and b) a heterologous nucleic acid comprising one or more nucleotide sequences encoding one or more heterologous gene products. The rAAV virions are useful for delivery of gene products to a retinal cell. The present disclosure provides methods of delivering a gene product to a retinal cell in an individual.

BRIEF DESCRIPTION OF THE DRAWINGS

FIG. 1A-1J provide amino acid sequences of AAV capsid proteins.

FIG. 2 provides amino acid sequences corresponding to amino acids 570-610 of AAV capsid protein VP1 of various AAV serotypes.

FIG. 3A-3C provide an alignment of amino acid sequences of AAV capsid protein loop IV (GH loop) regions. Insertion sites are shown in bold and underlining. The sequences shown in FIGS. 3A-3C have the following SEQ ID NOs:78-89.

FIG. 4A-4W provide amino acid sequences of exemplary heterologous gene products.

FIG. 5A-5F provides amino acid sequences of *Streptococcus pyogenes* Cas9 (FIG. 5A) and variants of *Streptococcus pyogenes* Cas9 (FIGS. 5B-5F).

FIG. 6 provides an amino acid sequence of *Staphylococcus aureus* Cas9.

FIG. 7A-7C provide amino acid sequences of *Francisella tularensis* Cpf1 (FIG. 7A), *Acidaminococcus* sp. BV3L6 Cpf1 (FIG. 7B), and a variant Cpf1 (FIG. 7C).

FIG. 10A-10C provide results observed in vivo in non-human primate retinas following intravitreal injection of recombinant AAV (rAAV) virions comprising a variant capsid corresponding to SEQ ID NO:16 (variant 1).

FIG. 12A-12F provide results observed in vivo in non-human primate retinas following intravitreal injection of recombinant AAV (rAAV) virions comprising a variant capsid corresponding to SEQ ID NO:5 (Variant 37).

FIG. 13A-13B provide results observed in vivo in non-human primate retinas following intravitreal injection of recombinant AAV (rAAV) virions comprising a variant capsid corresponding to SEQ ID NO:6 (Variant 38).

FIG. 14A-14F provide results observed in vivo in non-human primate retinas following intravitreal injection of recombinant AAV (rAAV) virions comprising a variant capsid corresponding to SEQ ID NO:26 (Variant 45).

DEFINITIONS

Figure 8:
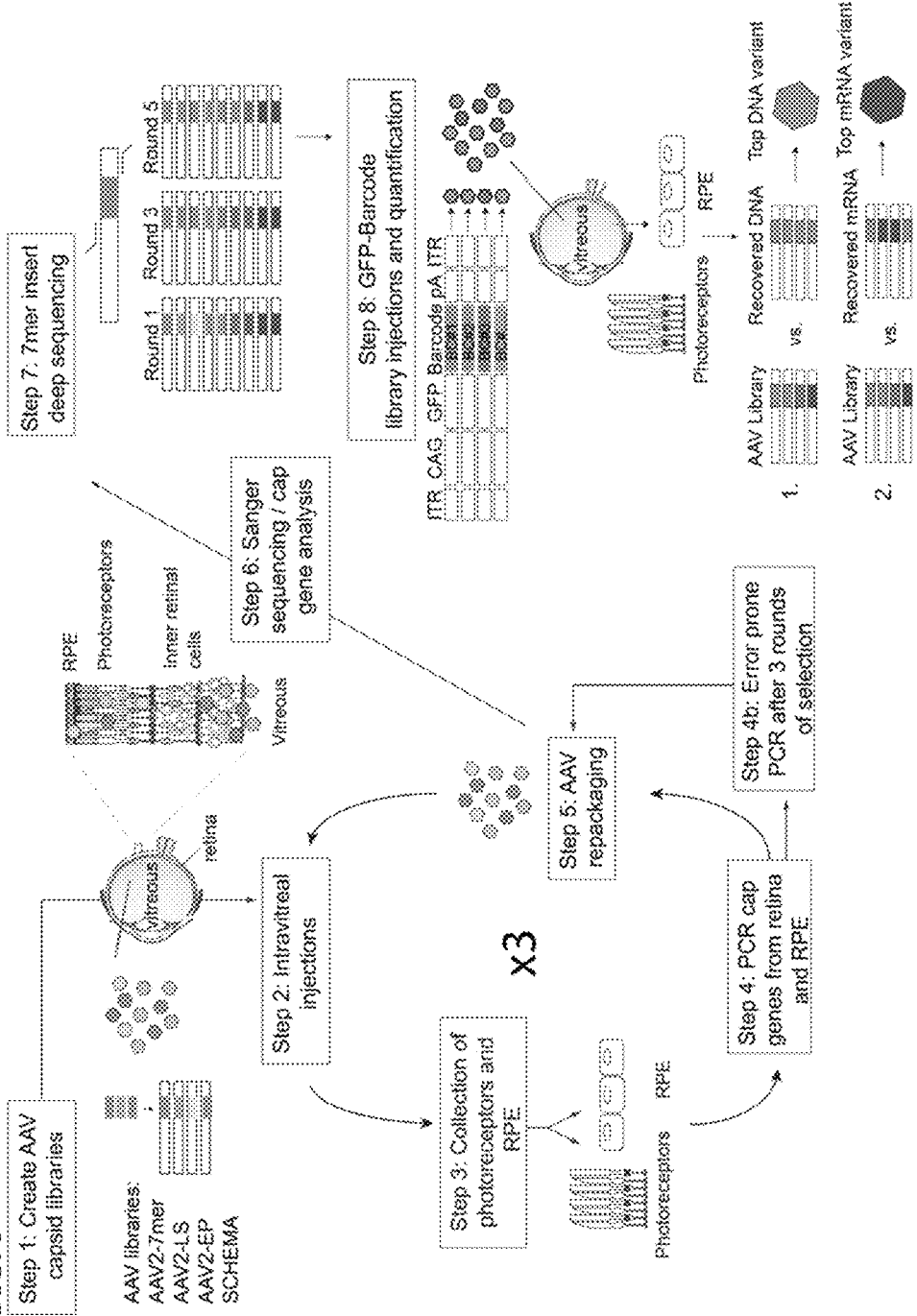
FIG. 8 is a series of schematic diagrams depicting an exemplary workflow of directed evolution of AAV in the primate retina.

The term "retinal cell" can refer herein to any of the cell types that comprise the retina, such as retinal ganglion cells; amacrine cells; horizontal cells; bipolar cells; photoreceptor cells including rods and cones; Müller glial cells; astrocytes (e.g., a retinal astrocyte); and retinal pigment epithelium.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), AAV type 10 (AAV-10), AAV type 11 (AAV-11), avian AAV, bovine AAV, canine AAV, equine AAV, primate AAV, non-primate AAV, and ovine AAV. See, e.g., Mori et al. (2004) Virology 330:375. The term "AAV" also includes chimeric AAV. "Primate AAV" refers to AAV isolated from a primate, "non-primate AAV" refers to AAV isolated from a non-primate mammal, "bovine AAV" refers to AAV isolated from a bovine mammal (e.g., a cow), etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component which it is capable of delivering into a cell for which the viral species is tropic. The term does not necessarily imply any replication capacity of the virus. As used herein, an "infectious" virus or viral particle is one that can access a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome (vg) copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA). Viral infectivity can be expressed as the ratio of infectious viral particles to total viral particles. Methods of determining the ratio of infectious viral particle to total viral particle are known in the art. See, e.g., Grainger et al. (2005) Mol. Ther. 11:S337 (describing a TCID50 infectious titer assay); and Zolotukhin et al. (1999) Gene Ther. 6:973.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In some cases, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wisconsin, USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty: 30.0.

A "gene" refers to a polynucleotide containing at least one open reading frame that is capable of encoding a particular protein after being transcribed and translated.

The term "guide RNA", as used herein, refers to an RNA that comprises: i) an "activator" nucleotide sequence that binds to a CRISPR/Cas effector polypeptide (e.g., a class 2 CRISPR/Cas effector polypeptide such as a type II, type V, or type VI CRISPR/Cas endonuclease) and activates the CRISPR/Cas effector polypeptide; and ii) a "targeter" nucleotide sequence that comprises a nucleotide sequence that hybridizes with a target nucleic acid. The "activator" nucleotide sequence and the "targeter" nucleotide sequence can be on separate RNA molecules (e.g., a "dual-guide RNA"); or can be on the same RNA molecule (a "single-guide RNA").

A "small interfering" or "short interfering RNA" or siRNA is an RNA duplex of nucleotides that is targeted to a gene interest (a "target gene"). An "RNA duplex" refers to the structure formed by the complementary pairing between two regions of an RNA molecule. siRNA is "targeted" to a gene in that the nucleotide sequence of the duplex portion of the siRNA is complementary to a nucleotide sequence of the targeted gene. In some cases, the length of the duplex of siRNAs is less than 30 nucleotides. In some cases, the duplex can be 29, 28, 27, 26, 25, 24, 23, 22, 21, 20, 19, 18, 17, 16, 15, 14, 13, 12, 11 or 10 nucleotides in length. In some cases, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some cases, the loop is 5, 6, 7, 8, 9, 10, 11, 12 or 13 nucleotides in length. The hairpin structure can also contain 3' or 5' overhang portions. In some cases, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA that is a fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV. As another example, a variant AAV capsid protein that comprises a heterologous peptide inserted into the GH loop of the capsid protein is a variant AAV capsid protein that includes an insertion of a peptide not normally included in a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of a substance generate a substance that is increasingly more isolated. An isolated plasmid, nucleic acid, vector, virus, host cell, or other substance is in some cases purified, e.g., from about 80% to about 90% pure, at least about 90% pure, at least about 95% pure, at least about 98% pure, or at least about 99%, or more, pure.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses, camels, etc); mammalian farm animals (e.g., sheep, goats, cows, etc.) mammalian pets (dogs, cats, etc.); and rodents (e.g., mice, rats, etc.). In some cases, the individual is a human.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an rAAV virion" includes a plurality of such virions and reference to "the capsid protein" includes reference to one or more capsid proteins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides recombinant adeno-associated virus (AAV) virions comprising: a) a variant capsid protein; and b) a heterologous nucleic acid comprising one or more nucleotide sequences encoding one or more heterologous gene products. The rAAV virions are useful for delivery of gene products to a retinal cell. The present disclosure provides methods of delivering a gene product to a retinal cell in an individual.

The present disclosure provides rAAV virions with altered capsid protein, where the rAAV virions exhibit greater ability to cross barriers between intravitreal fluid and retinal cells, and thus greater infectivity of a retinal cell compared to wild-type AAV, and where the rAAV virions comprise a a heterologous nucleic acid comprising one or more nucleotide sequences encoding one or more heterologous gene products. The present disclosure provides methods of delivering a gene product to a retinal cell in an individual. The present disclosure also provides methods of modifying a target nucleic acid present in a retinal cell.

The present disclosure provides rAAV virions with variant capsid protein, where the recombinant rAAV virions exhibit greater infectivity of a retinal cell compared to wild-type AAV; and where the rAAV virions comprise a heterologous nucleic acid comprising one or more nucleotide sequences encoding one or more heterologous gene products. The rAAV virions exhibit increased ability to cross a barrier between intravitreal fluid and retinal cells. The rAAV virions exhibit greater infectivity of a retinal cell, compared to the infectivity of a corresponding wild-type AAV for the retinal cell. The retinal cell can be a photoreceptor (e.g., rods; cones), a retinal ganglion cell (RGC), a Müller cell (a Müller glial cell), an astrocyte (e.g., a retinal astrocyte), a bipolar cell (e.g., an ON-bipolar cell; an OFF-bipolar cell), an amacrine cell, a horizontal cell, or a retinal pigment epithelium (RPE) cell. The present disclosure further provides methods of delivering a gene product to a retinal cell in an individual, and methods of treating an ocular disease. The present disclosure provides an rAAV virion with an altered capsid protein, where in some cases the rAAV virion exhibits at least 5-fold increased localization to one or more of the inner nuclear layer, the outer nuclear layer, the photoreceptor layer, the ganglion cell layer, and the retinal pigment epithelium, compared to the extent of localization to the inner nuclear layer, the outer nuclear layer, the photoreceptor layer, the ganglion cell layer, or the retinal pigment epithelium, by an AAV virion comprising the corresponding parental AAV capsid protein; and where the rAAV virions comprise a heterologous nucleic acid.

Variant AAV Capsid Polypeptides

The present disclosure provides a variant AAV capsid protein. As noted above, a variant AAV capsid protein of the present disclosure is altered, compared to a wild-type or other reference ("parental") AAV capsid protein. Alterations include insertions and swaps (e.g., replacements of a contiguous stretch of amino acids with a different contiguous stretch of amino acids).

In some cases, a variant AAV capsid protein of the present disclosure comprises an insertion of a heterologous peptide of from 7 amino acids to 10 amino acids in length, or from 10 amino acids to 20 amino acids in length, in an insertion site in a surface-accessible (e.g., solvent-accessible) portion of a parental AAV capsid protein, such that the variant capsid protein, when present in an AAV virion, confers increased infectivity of a retinal cell compared to the infectivity of the retinal cell by an AAV virion comprising the corresponding parental AAV capsid protein, particularly when the AAV virion is injected intravitreally. Thus, a variant AAV capsid protein of the present disclosure, when present in an AAV virion, confers increased ability of the AAV virion to cross a barrier between the intravitreal fluid ("vitreous") and a retinal cell, where such barriers include, e.g., the inner limiting membrane (ILM), the extracellular matrix of the retina, the cell membranes of the retinal cells themselves, inner nuclear layer, the outer nuclear layer, the photoreceptor layer, the ganglion cell layer, and the retinal pigment epithelium. In some cases, the retinal cell is a Müller cell. Other retinal cells include amacrine cells, bipolar cells, and horizontal cells. An "insertion of from about 10 amino acids to about 20 amino acids" is also referred to herein as a "peptide insertion" (e.g., a heterologous peptide insertion). An "insertion of from about 7 amino acids to about 10 amino acids" is also referred to herein as a "peptide insertion" (e.g., a heterologous peptide insertion). A "corresponding parental AAV capsid protein" refers to an AAV capsid protein of the same AAV serotype, without a heterologous peptide insertion. In some instances, the variant AAV capsid comprises a single heterologous peptide insert of from 10 amino acids to 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length). In some instances, the variant AAV capsid comprises a single heterologous peptide insert of from 7 amino acids to 10 amino acids in length (e.g., 7 amino acids, 8 amino acids, 9 amino acids, or 10 amino acids in length).

An alteration in an AAV capsid can also be a swap, e.g., a replacement of a contiguous stretch of amino acids with a heterologous peptide. Thus, a replacement is an insertion of a heterologous peptide in place of a contiguous stretch of amino acids. In some cases, a variant AAV capsid protein of the present disclosure comprises replacement of a contiguous stretch of amino acids with a heterologous peptide of from 7 amino acids to 10 amino acids in length or from 10 amino acids to 20 amino acids in length in a site in a surface-accessible (e.g., solvent-accessible) portion of a parental AAV capsid protein, such that the variant capsid protein, when present in an AAV virion, confers increased infectivity of a retinal cell compared to the infectivity of the retinal cell by an AAV virion comprising the corresponding parental AAV capsid protein, particularly when the AAV virion is injected intravitreally. Thus, a variant AAV capsid protein of the present disclosure, when present in an AAV virion, confers increased ability of the AAV virion to cross a barrier between the intravitreal fluid ("vitreous") and a retinal cell, where such barriers include, e.g., ILM, the extracellular matrix of the retina, the cell membranes of the retinal cells themselves, inner nuclear layer, the outer nuclear layer, the photoreceptor layer, the ganglion cell layer, and the retinal pigment epithelium. In some cases, the retinal cell is a Müller cell. Other retinal cells include amacrine cells, bipolar cells, and horizontal cells. A "replacement of from about 7 amino acids to about 10 amino acids" or "replacement of from about 10 amino acids to about 20 amino acids" is also referred to herein as a "peptide swap" (e.g., a replacement of a contiguous stretch of amino acids with a heterologous peptide). A "corresponding parental AAV capsid protein" refers to an AAV capsid protein of the same AAV serotype, without a heterologous peptide. In some instances, the variant AAV capsid comprises a single heterologous peptide replacement of from 7 amino acids to 10 amino acids (e.g., 7 amino acids, 8, amino acids, 9 amino acids, or 10 amino acids in length) or from 10 amino acids to 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length).

For purposes of the following discussion, "insertion" refers to both insertion of a heterologous peptide without replacement of a contiguous stretch of amino acids, and to insertion of a heterologous peptide that replaces a contiguous stretch of amino acids.

The insertion site is in the GH loop, or loop IV, of the AAV capsid protein, e.g., in a solvent-accessible portion of the GH loop, or loop IV, of the AAV capsid protein. For the GH loop/loop IV of AAV capsid, see, e.g., van Vliet et al. (2006) *Mol. Ther.* 14:809; Padron et al. (2005) *J. Virol.* 79:5047; and Shen et al. (2007) *Mol. Ther.* 15:1955. For example, the insertion site can be within amino acids 411-650 of an AAV capsid protein, as depicted in FIG. 3A-3C. For example, the insertion site can be within amino acids 570-611 of AAV2, within amino acids 571-612 of AAV1, within amino acids 560-601 of AAV5, within amino acids 571 to 612 of AAV6, within amino acids 572 to 613 of AAV7, within amino acids 573 to 614 of AAV5, within amino acids 571 to 612 of AAV5, or within amino acids 573 to 614 of AAV10, as depicted in FIG. 2. In some cases, the insertion site is between amino acids 588 and 589 of an AAV2 capsid protein, or a corresponding insertion site in an AAV of a different serotype. In some cases, the insertion site is between amino acids 587 and 588 of an AAV2 capsid protein, or a corresponding insertion site in an AAV of a different serotype. In some cases, the insertion site is between amino acids 575 and 576 of an AAV2 capsid protein, or a corresponding insertion site in an AAV of a different serotype. In some cases, the insertion site is between amino acids 584 and 585 of an AAV2 capsid protein, or a corresponding insertion site in an AAV of a different serotype. In some cases, the insertion site is between amino acids 590 and 591 of an AAV2 capsid protein, or a corresponding insertion site in an AAV of a different serotype. In some cases, the insertion site is between amino acids 584 and 585 of an AAV4 capsid protein, or a corresponding insertion site in an AAV of a different serotype. In some cases, the insertion site is between amino acids 575 and 576 of an AAV5 capsid protein, or a corresponding insertion site in an AAV of a different serotype. In some cases, the site for replacement is between amino acids 584 and 598 of an AAV2 capsid protein, or a corresponding site in an AAV of a different serotype.

In some cases, a heterologous peptide of from about 10 amino acids to about 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length) is inserted in an insertion site in the GH loop or loop IV of the capsid protein relative to a corresponding parental AAV capsid protein. In some cases, a heterologous peptide of from about 7 amino acids to about 10 amino acids in length (e.g., 7 amino acids, 8 amino acids, 9 amino acids, or 10 amino acids in length) is inserted in an insertion site in the GH loop or loop IV of the capsid protein relative to a corresponding parental AAV capsid protein. For example, the insertion site can be between amino acids 587 and 588 of AAV2, or between amino acids 588 and 589 of AAV2, or the corresponding positions of the capsid subunit of another AAV serotype. It should be noted that the insertion site 587/588 is based on an AAV2 capsid protein. A heterologous peptide of 10 amino acids to 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length) can be inserted in a corresponding site in an AAV serotype other than AAV2 (e.g., AAV8, AAV9, etc.). A heterologous peptide of 7 amino acids to 10 amino acids in length (e.g., 7 amino acids, 8 amino acids, 9 amino acids, or 10 amino acids in length) can be inserted in a corresponding site in an AAV serotype other than AAV2 (e.g., AAV8, AAV9, etc.). Those skilled in the art would know, based on a comparison of the amino acid sequences of capsid proteins of various AAV serotypes, where an insertion site "corresponding to amino acids 587-588 of AAV2" would be in a capsid protein of any given AAV serotype. Sequences corresponding to amino acids 570-611 of capsid protein VP1 of AAV2 (see FIG. 1B) in various AAV serotypes are shown in FIG. 2. See, e.g., GenBank Accession No. NP_049542 for AAV1; GenBank Accession No. NP_044927 for AAV4; GenBank Accession No. AAD13756 for AAV5; GenBank Accession No. AAB95459 for AAV6; GenBank Accession No. YP_077178 for AAV7; GenBank Accession No. YP_077180 for AAV8; GenBank Accession No. AAS99264 for AAV9; GenBank Accession No. AAT46337 for AAV10; and GenBank Accession No. AA088208 for AAVrh10. See, e.g., Santiago-Ortiz et al. (2015) Gene Ther. 22:934 for ancestral AAV capsid. Amino acid sequences of VP1 capsid protein of AAV of various serotypes are provided in FIG. 1A-1J.

For example, the insertion site can be between amino acids 587 and 588 of AAV2, between amino acids 590 and 591 of AAV1, between amino acids 575 and 576 of AAV5, between amino acids 590 and 591 of AAV6, between amino acids 589 and 590 of AAV7, between amino acids 590 and 591 of AAV8, between amino acids 588 and 589 of AAV9, between amino acids 588 and 589 of AAV10, or between amino acids 585 and 586 of AAV4. The insertion sites are underlined in FIG. 2; the amino acid numbering is based on the numbering depicted in FIG. 2.

In some cases, a subject capsid protein includes a GH loop comprising an amino acid sequence having at least about 85%, at least about 90%, at least about 95%, at least about 98%, at least about 99%, or 100%, amino acid sequence identity to an amino acid sequence set forth in FIG. 3A-3C; and having an insertion of a heterologous peptide of from 10 amino acids to about 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length). In some cases, a subject capsid protein includes a GH loop comprising an amino acid sequence having at least about 85%, at least about 90%, at least about 95%, at least about 98%, at least about 99%, or 100%, amino acid sequence identity to an amino acid sequence set forth in FIG. 3A-3C; and having an insertion of a heterologous peptide of from 7 amino acids to about 10 amino acids in length (e.g., 7 amino acids, 8 amino acids, 9 amino acids, or 10 amino acids in length).

In some cases, a variant AAV capsid protein of the present disclosure comprises a replacement, or substitution, of a segment, or sequence of consecutive amino acids, in a surface-accessible (e.g., solvent-accessible) portion of a parental AAV capsid, such that the variant capsid protein, when present in an AAV virion, confers increased infectivity of a retinal cell compared to the infectivity of the retinal cell by an AAV virion comprising the corresponding parental AAV capsid protein, particularly when the AAV virion is injected intravitreally. Thus, a subject variant AAV capsid protein comprising the sequence substitution, when present in an AAV virion, confers increased ability of the AAV virion to cross a barrier between the vitreous and a retinal cell, where such barriers include, e.g., the inner limiting membrane, the extracellular matrix of the retina, and the cell membranes of the retinal cells themselves. A "replacement of from about 7 consecutive amino acids to about 10 consecutive amino acids" or "replacement of from about 10 consecutive amino acids to about 20 consecutive amino acids" is also referred to herein as a "loop swap" (i.e., a heterologous peptide substitution). A "corresponding parental AAV capsid protein" in such instances refers to an AAV capsid protein of the same AAV serotype, without the subject loop swap. In some instances, the variant AAV capsid comprises a heterologous peptide substitution of 7 amino acids to about 10 amino acids in length (e.g., 7 amino acids, 8 amino acids, 9 amino acids, or 10 amino acids in length) or 10 amino acids to about 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length).

In some cases, a heterologous peptide of from about 7 amino acids to about 10 amino acids in length (e.g., 7 amino acids, 8 amino acids, 9 amino acids, or 10 amino acids in length) is substituted in for an equivalent number of consecutive amino acids in a corresponding parental AAV capsid protein. In some cases, a heterologous peptide of from about 10 amino acids to about 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length) is substituted in for an equivalent number of consecutive amino acids in a corresponding parental AAV capsid protein. In some cases, the substitution begins at around amino acid 588 of AAV2, or the corresponding position of the capsid subunit of another AAV serotype, and ends at around amino acid 598 of AAV2 or the corresponding position of the capsid subunit of another AAV serotype. It should be noted that the residues 588-598 are based on an AAV2 VP1 capsid protein. A heterologous peptide of 7 amino acids to about 10 amino acids in length (e.g., 7 amino acids, 8 amino acids, 9 amino acids, or 10 amino acids in length) can be substituted into a corresponding site in an AAV serotype other than AAV2 (e.g., AAV8, AAV9, etc.). A heterologous peptide of 10 amino acids to about 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length) can be substituted into a corresponding site in an AAV serotype other than AAV2 (e.g., AAV8, AAV9, etc.). Those skilled in the art would know, based on a comparison of the amino acid sequences of capsid proteins of various AAV serotypes, where a substitution site "corresponding to amino acids 588-598 of AAV2" would be in a capsid protein of any given AAV serotype. The amino acid residue corresponding to amino acids 588-598 of capsid protein VP1 of AAV2 (see FIG. 1B) in various AAV serotypes are shown in FIG. 2. See, e.g., GenBank Accession No. NP_049542 for AAV1; GenBank Accession No. NP_044927 for AAV4; GenBank Accession No. AAD13756 for AAV5; GenBank Accession No. AAB95459 for AAV6; GenBank Accession No. YP_077178 for AAV7; GenBank Accession No. YP_077180 for AAV8; GenBank Accession No. AAS99264 for AAV9, GenBank Accession No. AAT46337 for AAV10, and GenBank Accession No. AA088208 for AAVrh10. Amino acid sequences of VP1 capsid protein of AAV of various serotypes are provided in FIG. 1A-1J.

In some cases, a heterologous peptide of from about 7 amino acids to about 10 amino acids in length (e.g., 7 amino acids, 8 amino acids, 9 amino acids, or 10 amino acids in length) is substituted in for an equivalent number of consecutive amino acids in a corresponding parental AAV capsid protein. In some cases, a heterologous peptide of from about 10 amino acids to about 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length) is substituted in for an equivalent number of consecutive amino acids in a corresponding parental AAV capsid protein. In some cases, the substitution begins at around amino acid 585 of AAV2, or the corresponding position of the capsid subunit of another AAV serotype, and ends at around amino acid 598 of AAV2 or the corresponding position of the capsid subunit of another AAV serotype. It should be noted that the residues 585-598 are based on an AAV2 VP1 capsid protein. A heterologous peptide of 7 amino acids to about 10 amino acids in length (e.g., 7 amino acids, 8 amino acids, 9 amino acids, or 10 amino acids in length) can be substituted into a corresponding site in an AAV serotype other than AAV2 (e.g., AAV8, AAV9, etc.). A heterologous peptide of 10 amino acids to about 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length) can be substituted into a corresponding site in an AAV serotype other than AAV2 (e.g., AAV8, AAV9, etc.). Those skilled in the art would know, based on a comparison of the amino acid sequences of capsid proteins of various AAV serotypes, where a substitution site "corresponding to amino acids 585-598 of AAV2" would be in a capsid protein of any given AAV serotype. The amino acid residue corresponding to amino acids 585-598 of capsid protein VP1 of AAV2 (see FIG. 1B) in various AAV serotypes are shown in FIG. 2. See, e.g., GenBank Accession No. NP_049542 for AAV1; GenBank Accession No. NP_044927 for AAV4; GenBank Accession No. AAD13756 for AAV5; GenBank Accession No. AAB95459 for AAV6; GenBank Accession No. YP_077178 for AAV7; GenBank Accession No. YP_077180 for AAV8; GenBank Accession No. AAS99264 for AAV9, GenBank Accession No. AAT46337 for AAV10, and GenBank Accession No. AA088208 for AAVrh10.

Insertion/Replacement Peptides

As noted above, a heterologous peptide of from about 7 amino acids to about 20 amino acids in length is inserted into the GH loop of an AAV capsid, or replaces an equivalent number of consecutive amino acids in the GH loop of an AAV capsid. For simplicity, the term "insertion peptide" is used below to describe both a peptide that is inserted into a parental AAV capsid and a peptide that replaces a segment of contiguous amino acids in the GH loop of an AAV capsid. In some cases, the insertion peptide is from about 7 amino acids to about 10 amino acids in length (e.g., 7 amino acids, 8 amino acids, 9 amino acids, or 10 amino acids in length). In some cases, the insertion peptide is from about 10 amino acids to about 20 amino acids in length (e.g., 10 amino acids, 11 amino acids, 12 amino acids, 13 amino acids, 14 amino acids, 15 amino acids, 16 amino acids, 17 amino acids, 18 amino acids, 19 amino acids, or 20 amino acids in length).

In some cases, the insertion peptide has a length of 7 amino acids. In some cases, the insertion peptide has a length of 8 amino acids. In some cases, the insertion peptide has a length of 9 amino acids. In some cases, the insertion peptide has a length of 10 amino acids. In some cases, the insertion peptide has a length of 16 amino acids. In some cases, the insertion peptide has a length of 20 amino acids. In some cases, the insertion peptide has a length of 11 amino acids. In some cases, the insertion peptide has a length of 12 amino acids. In some cases, the insertion peptide has a length of 13 amino acids. In some cases, the insertion peptide has a length of 14 amino acids. In some cases, the insertion peptide has a length of 15 amino acids. In some cases, the insertion peptide has a length of 17 amino acids. In some cases, the insertion peptide has a length of 18 amino acids. In some cases, the insertion peptide has a length of 19 amino acids.

In some cases, the peptide insert is a peptide of Formula (I):

(SEQ ID NO: 46)

$X^1AX^2X^3X^4X^5TX^6X^7X^8$ where: $X^1$=L or I; $X^2$=H, L, R, or K; $X^3$=Q, G, S, or D; $X^4$=D, E, or A; $X^5$=T or A; $X^6$=K, N, or R; $X^7$=N, P, S, K, T, or A; and $X^8$=S, A, or C Peptides within Formula (I) include, e.g., LAHQDTTKNS (SEQ ID NO:1); LALGETTRAA (SEQ ID NO:2); LAHQDTTRPA (SEQ ID NO:3); LARQDTTKNA (SEQ ID NO:4); LAHQDSTKNA (SEQ ID NO:5); LAHQDATKNA (SEQ ID NO:6); LAHQDTTKPA (SEQ ID NO:7); IALSETTRPA (SEQ ID NO:8); LAHQDTTKKC (SEQ ID NO:9); LALGEATRPA (SEQ ID NO:10); LALGETTRTA (SEQ ID NO:11); LALSEATRPA (SEQ ID NO:12); LAKDETKNSA (SEQ ID NO:13); LALGETTKPA (SEQ ID NO:14); and LAHQATTKNA (SEQ ID NO:15).

In some cases, the peptide insert is a peptide of Formula (II):

(SEQ ID NO: 47)

$X^1AX^2X^3X^4TTX^5X^6X^7$ where: $X^1$=L or I; $X^2$=H, L, or R; $X^3$=Q, G, or S; $X^4$=D, E, or A; $X^5$=K or R; $X^6$=N, A, P, K, or T; and $X^7$=S, A, or C.

Peptides within Formula (II) include, e.g.: LAHQDTTKNS (SEQ ID NO:1); LALGETTRAA (SEQ ID NO:2); LAHQDTTRPA (SEQ ID NO:3); LARQDTTKNA (SEQ ID NO:4); LAHQDTTKPA (SEQ ID NO:7); IALSETTRPA (SEQ ID NO:8); LAHQDTTKKC (SEQ ID NO:9); LALGETTRTA (SEQ ID NO:11); LALGETTKPA (SEQ ID NO:14); and LAHQATTKNA (SEQ ID NO:15).

In some cases, the peptide insert is a peptide of Formula (III):

(SEQ ID NO: 48)

$LAHQX^1X^2TX^3X^4X^5$ where $X^1$ is D or A; $X^2$ is T, S, or A; $X^3$ is K or R; $X^4$ is N, P, or K; and $X^5$ is S, A, or C.

Peptides within Formula (III) include, e.g., LAHQDTTKNS (SEQ ID NO:1); LAHQDTTRPA (SEQ ID NO:3); LAHQDSTKNA (SEQ ID NO:5); LAHQDATKNA (SEQ ID NO:6); LAHQDTTKPA (SEQ ID NO:7); LAHQDTTKKC (SEQ ID NO:9); and LAHQATTKNA (SEQ ID NO:15).

In some cases, the peptide insert is a peptide of Formula (IV):

(SEQ ID NO: 49)

$LALX^1EX^2TX^3X^4A$ where $X^1$ is G or S; $X^2$ is T or A; $X^3$ is R or K; and $X^4$ is A, P, or T.

Peptides within Formula (IV) include, e.g., LAL-GETTRAA (SEQ ID NO:2); LALGEATRPA (SEQ ID NO:10); LALGETTRTA (SEQ ID NO:11); LALSEATRPA (SEQ ID NO:12); and LALGETTKPA (SEQ ID NO:14).

In some cases, the peptide insert is a peptide of Formula (V):

$$LX^1RGX^2RQX^3X^4X^5X^6X^7X^8VNX^9X^{10}$$ (SEQ ID NO: 50)

where $X^1$ is Q or H; $X^2$ is N, V, or K; $X^3$ is Q or V; $X^4$ is T, A, or P; $X^5$ is T, A, or S; $X^6$ is T or V; $X^7$ is A, E, or L; $X^8$ is D or E; $X^9$ is T, S, K, G, or I; and $X^{10}$ is Q or L.

In some cases, the peptide insert is a peptide of Formula (VI):

$$LX^1RGNRQX^2X^3TX^4DVNX^5X^6$$ (SEQ ID NO: 51)

where $X^1$ is Q or H; $X^2$ is A or T; $X^3$ is A or T; $X^4$ is A or E; $X^5$ is T, S, K, or I; and $X^6$ is Q or L.

In some cases, the peptide insert is a peptide of Formula (VII):

$$SX^1TX^2X^3PSX^4TTTQX^5X^6LQFSQ$$ (SEQ ID NO: 52)

where $X^1$ is R or K; $X^2$ is N or D; $X^3$ is T, S, or I; $X^4$ is G or E; $X^5$ is S or P; and $X^6$ is T, R, or S.

Examples of peptides are provided in Table 1, below.

TABLE 1

| SEQ ID NO: | PEPTIDE | LIBRARY |
|---|---|---|
| 1 | LAHQDTTKNS | 7-mer |
| 2 | LALGETTRAA | 7-mer |
| 3 | LAHQDTTRPA | 7-mer |
| 4 | LARQDTTKNA | 7-mer |
| 5 | LAHQDSTKNA | 7-mer |
| 6 | LAHQDATKNA | 7-mer |
| 7 | LAHQDTTKPA | 7-mer |
| 8 | IALSETTRPA | 7-mer |
| 9 | LAHQDTTKKC | 7-mer |
| 10 | LALGEATRPA | 7-mer |
| 11 | LALGETTRTA | 7-mer |
| 12 | LALSEATRPA | 7-mer |
| 13 | LAKDETKNSA | 7-mer |
| 14 | LALGETTKPA | 7-mer |
| 15 | LAHQATTKNA | 7-mer |
| 16 | LQRGNRQTTTADVNTQ | LS588 |
| 17 | LQRGNRQATTADVNTL | LS588 |
| 18 | LQRGNRQATTEDVNTQ | LS588 |
| 19 | LQRGNRQAATEDVNTQ | LS588 |

TABLE 1-continued

| SEQ ID NO: | PEPTIDE | LIBRARY |
|---|---|---|
| 20 | LQRGNRQAATADVNSL | LS588 |
| 21 | LQRGNRQAATADVNKL | LS588 |
| 22 | LQRGVRVPSVLEVNGQ | LS588 |
| 23 | LQRGNRQAATADVNIL | LS588 |
| 24 | LQRGKRQATTADVNTQ | LS588 |
| 25 | LHRGNRQAATADVNTL | LS588 |
| 26 | SRTNTPSGTTTQPTLQFSQ | LS454 |
| 27 | SKTDTPSGTTTQSRLQFSQ | LS454 |
| 28 | SRTDTPSETTTQSRLQFSQ | LS454 |
| 29 | SRTNSPSGTTTQSSLQFSQ | LS454 |
| 30 | SRTDIPSGTTTQSRLQFSQ | LS454 |

In some cases, a peptide insert of any one of Formulas I-VII, or a peptide as depicted in Table 1, further includes one or two linker amino acids at the N-terminus of the peptide and/or one or more amino acids at the C-terminus of the peptide. For example, in some cases, a peptide insert comprises: Thr-Gly-[peptide of any one of Formulas I-VII]-Gly-Leu-Ser. As another example, in some cases, a peptide insert comprises: Leu-Ala-[peptide of any one of Formulas I-VI]-Ala. As another example, in some cases, a peptide insert comprises: Leu-Gln-[peptide of any one of Formulas I-VII]-Gln. In some cases, a peptide insert does not include any linker amino acids.

In some cases, the peptide insert is a peptide of Formula (VIII):

$$X^1X^2X^3X^4TX^5X^6$$ (SEQ ID NO: 53)

where: $X^1$=H, L, R, or K; $X^2$=Q, G, S, or D; $X^3$=D, E, or A; $X^4$=T or A; $X^5$=K, N, or R; and $X^6$=N, P, S, K, T, or A.

Peptides within Formula (VIII) include, e.g., HQDTTKN (SEQ ID NO:31); LGETTRA (SEQ ID NO:32); HQDTTRP (SEQ ID NO:33); RQDTTKN (SEQ ID NO:34); HQDSTKN (SEQ ID NO:35); HQDATKNA (SEQ ID NO:36); HQDTTKP (SEQ ID NO:37); LSETTRP (SEQ ID NO:38); HQDTTKK (SEQ ID NO:39); LGEATRP (SEQ ID NO:40); LGETTRT (SEQ ID NO:41); LSEATRP (SEQ ID NO:42); KDETKNS (SEQ ID NO:43); LGETTKP (SEQ ID NO:44); and HQATTKN (SEQ ID NO:45). These peptides are set out in Table 2, below.

TABLE 2

| SEQ ID NO: | PEPTIDE | LENGTH |
|---|---|---|
| 31 | HQDTTKN | 7 |
| 32 | LGETTRA | 7 |
| 33 | HQDTTRP | 7 |
| 34 | RQDTTKN | 7 |

TABLE 2-continued

| SEQ ID NO: | PEPTIDE | LENGTH |
|---|---|---|
| 35 | HQDSTKN | 7 |
| 36 | HQDATKN | 7 |
| 37 | HQDTTKP | 7 |
| 38 | LSETTRP | 7 |
| 39 | HQDTTKK | 7 |
| 40 | LGEATRP | 7 |
| 41 | LGETTRT | 7 |
| 42 | LSEATRP | 7 |
| 43 | KDETKNS | 7 |
| 44 | LGETTKP | 7 |
| 45 | HQATTKN | 7 |

In some cases, a subject rAAV virion capsid does not include any other amino acid substitutions, insertions, or deletions, other than an insertion of from about 7 amino acids to about 20 amino acids (e.g., 7, 8, 9, 10, 11, 12, 13, 14, 15, 16, 17, 18, 19, or 20 amino acids) in the GH loop or loop IV relative to a corresponding parental AAV capsid protein. In other cases, a subject rAAV virion capsid includes from 1 to about 25 amino acid insertions, deletions, or substitutions, compared to the parental AAV capsid protein, in addition to an insertion of from about 7 amino acids to about 20 amino acids (e.g., 7, 8, 9, 10, 11, 12, 13, 14, 15, 16, 17, 18, 19, or 20 amino acids) in the GH loop or loop IV relative to a corresponding parental AAV capsid protein. For example, in some cases, a subject rAAV virion capsid includes from 1 to about 5, from about 5 to about 10, from about 10 to about 15, from about 15 to about 20, or from about 20 to about 25 amino acid insertions, deletions, or substitutions, compared to the parental AAV capsid protein, in addition to an insertion of from about 7 amino acids to about 20 amino acids (e.g., 7, 8, 9, 10, 11, 12, 13, 14, 15, 16, 17, 18, 19, or 20 amino acids) in the GH loop or loop IV relative to a corresponding parental AAV capsid protein. In certain instances, the deletion of one or more amino acids (e.g., 1, 2, 3, 4, 5, 6, 7, 8, 9, 10, 11, 12, 13, 14, 15, 16, 17, 18, 19, or 20 amino acids) compared to the parental AAV capsid protein occurs at the site of peptide insertion.

In some cases, a variant AAV capsid polypeptide of the present disclosure does not include one, two, three, or four, of the following amino acid substitutions: Y273F, Y444F, Y500F, and Y730F.

In some cases, a variant AAV capsid polypeptide of the present disclosure comprises, in addition to an insertion peptide as described above, one, two, three, or four, of the following amino acid substitutions: Y273F, Y444F, Y500F, and Y730F.

In some cases, a variant AAV capsid polypeptide of the present disclosure is a chimeric capsid, e.g., the capsid comprises a portion of an AAV capsid of a first AAV serotype and a portion of an AAV capsid of a second serotype; and comprises an insertion of from about 10 amino acids to about 20 amino acids (e.g., 10, 11, 12, 13, 14, 15, 16, 17, 18, 19, or 20 amino acids) in the GH loop or loop IV relative to a corresponding parental AAV capsid protein. In some cases, a variant AAV capsid polypeptide of the present disclosure is a chimeric capsid, e.g., the capsid comprises a portion of an AAV capsid of a first AAV serotype and a portion of an AAV capsid of a second serotype; and comprises an insertion of from about 7 amino acids to about 10 amino acids (e.g., 7, 8, 9, or 10 amino acids) in the GH loop or loop IV relative to a corresponding parental AAV capsid protein.

Recombinant AAV Virions

The present disclosure provides a recombinant AAV (rAAV) virion comprising: i) a variant AAV capsid polypeptide of the present disclosure; and ii) a heterologous nucleic acid comprising a nucleotide sequence encoding a heterologous polypeptide (i.e., a non-AAV polypeptide).

In some cases, an rAAV virion of the present disclosure comprises a capsid protein comprising an amino acid sequence having at least about 85%, at least about 90%, at least about 95%, at least about 98%, or at least about 99%, amino acid sequence identity to the amino acid sequence provided in any one of FIG. 1A-1J; and an insertion of from about 10 amino acids to about 20 amino acids (e.g., 10, 11, 12, 13, 14, 15, 16, 17, 18, 19, or 20 amino acids) in the GH loop or loop IV relative to a corresponding parental AAV capsid protein. In some cases, a subject rAAV virion comprises a capsid protein comprising an amino acid sequence having at least about 85%, at least about 90%, at least about 95%, at least about 98%, or at least about 99%, amino acid sequence identity to the amino acid sequence provided in FIG. 4; and an insertion of from about 10 amino acids to about 20 amino acids (e.g., 10, 11, 12, 13, 14, 15, 16, 17, 18, 19, or 20 amino acids) between amino acids 587 and 588 relative to the amino acid sequence depicted in FIG. 1B, or at a corresponding site relative to a corresponding parental AAV capsid protein.

In some cases, an rAAV virion of the present disclosure comprises a capsid protein comprising an amino acid sequence having at least about 85%, at least about 90%, at least about 95%, at least about 98%, or at least about 99%, amino acid sequence identity to the amino acid sequence provided in any one of FIG. 1A-1J; and an insertion of from about 7 amino acids to about 10 amino acids (e.g., 7, 8, 9, or 10 amino acids) in the GH loop or loop IV relative to a corresponding parental AAV capsid protein. In some cases, a subject rAAV virion comprises a capsid protein comprising an amino acid sequence having at least about 85%, at least about 90%, at least about 95%, at least about 98%, or at least about 99%, amino acid sequence identity to the amino acid sequence provided in FIG. 1B; and an insertion of from about 7 amino acids to about 10 amino acids (e.g., 7, 8, 9, or 10 amino acids) between amino acids 587 and 588 relative to the amino acid sequence depicted in FIG. 1B, or at a corresponding site relative to a corresponding parental AAV capsid protein.

In some cases, an rAAV virion of the present disclosure comprises a capsid protein comprising an amino acid sequence having at least about 85%, at least about 90%, at least about 95%, at least about 98%, or at least about 99%, amino acid sequence identity to the amino acid sequence provided in FIG. 1B; and an insertion of from about 10 amino acids to about 20 amino acids (e.g., 10, 11, 12, 13, 14, 15, 16, 17, 18, 19, or 20 amino acids) in the GH loop or loop IV relative to a corresponding parental AAV capsid protein. In some cases, a subject rAAV virion comprises a capsid protein comprising an amino acid sequence having at least about 85%, at least about 90%, at least about 95%, at least about 98%, or at least about 99%, amino acid sequence identity to the amino acid sequence provided in FIG. 1B; and an insertion of from about 10 amino acids to about 20 amino acids (e.g., 10, 11, 12, 13, 14, 15, 16, 17, 18, 19, or 20 amino acids) between amino acids 585 and 598 relative to the amino acid sequence depicted in FIG. 1B, or at a corresponding site relative to a corresponding parental AAV capsid protein. In some cases, an rAAV virion of the present disclosure comprises a capsid protein comprising an amino acid sequence having at least about 85%, at least about 90%, at least about 95%, at least about 98%, or at least about 99%, amino acid sequence identity to the amino acid sequence provided in FIG. 1B; and an insertion of from about 7 amino acids to about 10 amino acids (e.g., 7, 8, 9, or 10 amino acids) in the GH loop or loop IV relative to a corresponding parental AAV capsid protein. In some cases, a subject rAAV virion comprises a capsid protein comprising an amino acid sequence having at least about 85%, at least about 90%, at least about 95%, at least about 98%, or at least about 99%, amino acid sequence identity to the amino acid sequence provided in FIG. 1B; and an insertion of from about 7 amino acids to about 10 amino acids (e.g., 7, 8, 9, or 10 amino acids) between amino acids 585 and 598 relative to the amino acid sequence depicted in FIG. 1B, or at a corresponding site relative to a corresponding parental AAV capsid protein.

In some cases, a subject rAAV virion comprises a capsid protein that includes a GH loop comprising an amino acid sequence having at least about 85%, at least about 90%, at least about 95%, at least about 98%, at least about 99%, or 100%, amino acid sequence identity to an amino acid sequence set forth in any one of FIGS. 1A-1J, and comprising an insertion of from about 7 amino acids to about 10 amino acids (e.g., 7, 8, 9, or 10 amino acids), where the insertion site is between the bolded and underlined amino acids indicated in FIG. 2 and FIG. 3. In some cases, a subject rAAV virion comprises a capsid protein that includes a GH loop comprising an amino acid sequence having at least about 85%, at least about 90%, at least about 95%, at least about 98%, at least about 99%, or 100%, amino acid sequence identity to an amino acid sequence set forth in any one of FIGS. 1A-1J, and comprising an insertion of from about 7 amino acids to about 10 amino acids (e.g., 7, 8, 9, or 10 amino acids), where the insertion site is between the bolded and underlined amino acids indicated in FIG. 2 and FIG. 3.

In some cases, a subject rAAV virion comprises a capsid protein comprising an amino acid sequence having at least about 85%, at least about 90%, at least about 95%, at least about 98%, or at least about 99%, amino acid sequence identity to any one of the amino acid sequences provided in FIG. 1A-1J; and an insertion of from about 10 amino acids to about 20 amino acids (e.g., 10, 11, 12, 13, 14, 15, 16, 17, 18, 19, or 20 amino acids) between amino acids 587 and 588 of AAV2, or at a corresponding site relative to another AAV genotype. In some cases, the corresponding insertion site is a site as indicated by bold text and underlining in FIG. 2 or FIG. 3. In some cases, a subject rAAV virion comprises a capsid protein comprising an amino acid sequence having at least about 85%, at least about 90%, at least about 95%, at least about 98%, or at least about 99%, amino acid sequence identity to any one of the amino acid sequences provided in FIG. 1A-1J; and an insertion of from about 7 amino acids to about 10 amino acids (e.g., 7, 8, 9, or 10 amino acids) between amino acids 587 and 588 of AAV2, or at a corresponding site relative to another AAV genotype. In some cases, the corresponding insertion site is a site as indicated by bold text and underlining in FIG. 2 or FIG. 3.

An rAAV virion of the present disclosure exhibits at least 5-fold, at least 10-fold, at least 15-fold, at least 20-fold, at least 25-fold, at least 50-fold, or more than 50-fold, increased infectivity of a retinal cell, compared to the infectivity of the retinal cell by an AAV virion comprising the corresponding parental AAV capsid protein.

Whether a given rAAV virion exhibits increased infectivity of a retinal cell can be determined by detecting expression in a retinal cell of a heterologous gene product encoded by the rAAV virion, following intravitreal administration of the rAAV virion. For example, an rAAV virion of the present disclosure that comprises: a) a variant capsid of the present disclosure comprising a peptide insert or a peptide replacement, as described above; and b) a heterologous nucleotide sequence encoding a heterologous gene product, when administered intravitreally, results in a level of the heterologous gene product in a retinal cell, that is at least 2-fold, at least 5-fold, at least 10-fold, at least 15-fold, at least 20-fold, at least 25-fold, at least 50-fold, or more than 50-fold, greater than the level of the gene product in the retinal cell that results when a control rAAV virion that comprises: a) a control AAV capsid that does not comprises the peptide insert or the peptide replacement; and b) heterologous nucleotide sequence encoding the heterologous gene product is administered intravitreally.

Whether a given rAAV virion exhibits increased infectivity of a retinal cell can be determined by assessing a therapeutic effect of a therapeutic gene product encoded by the rAAV virion in a retinal cell. Therapeutic effects can include, e.g., a) a decrease in the rate of loss of visual function, e.g. visual field, visual acuity; b) an improvement in visual function, e.g. an improvement in visual field or visual acuity; c) a decrease in sensitivity to light, i.e. photophobia; a decrease in nystagmus; etc. For example, an rAAV virion of the present disclosure that comprises: a) a variant capsid of the present disclosure comprising a peptide insert or a peptide replacement, as described above; and b) a heterologous nucleotide sequence encoding a heterologous therapeutic gene product, when administered intravitreally, results in a therapeutic effect of the therapeutic gene product in a retinal cell, that is at least 2-fold, at least 5-fold, at least 10-fold, at least 15-fold, at least 20-fold, at least 25-fold, at least 50-fold, or more than 50-fold, greater than the therapeutic effect in the retinal cell that results when a control rAAV virion that comprises: a) a control AAV capsid that does not comprises the peptide insert or the peptide replacement; and b) heterologous nucleotide sequence encoding the heterologous therapeutic gene product is administered intravitreally. Tests for visual function are known in the art; and any such test can be used to determine whether an rAAV virion of the present disclosure exhibits increased infectivity of a retinal cell.

An rAAV virion of the present disclosure exhibits at least 5-fold, at least 10-fold, at least 15-fold, at least 20-fold, at least 25-fold, at least 50-fold, or more than 50-fold, increased ability to cross a barrier between the intravitreal fluid and a retinal cell, compared to the ability of a control rAAV virion comprising the corresponding parental AAV capsid protein (i.e., the AAV capsid protein without the insert peptide or replacement peptide).

In some cases, a subject rAAV virion exhibits at least 5-fold, at least 10-fold, at least 15-fold, at least 20-fold, at least 25-fold, at least 50-fold, or more than 50-fold, increased infectivity of a retinal cell, when administered via intravitreal injection, compared to the infectivity of the retinal cell by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased infectivity of a photoreceptor (rod or cone) cell, compared to the infectivity of the photoreceptor cell by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of a photoreceptor (rod or cone) cell, when administered via intravitreal injection, compared to the infectivity of the photoreceptor cell by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased infectivity of an RGC, compared to the infectivity of the RGC by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of an RGC, when administered via intravitreal injection, compared to the infectivity of the RGC by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased infectivity of an RPE cell, compared to the infectivity of the RPE cell by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of an RPE cell, when administered via intravitreal injection, compared to the infectivity of the RPE cell by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased infectivity of a Müller cell, compared to the infectivity of the Müller cell by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of a Müller cell, when administered via intravitreal injection, compared to the infectivity of the Müller cell by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased infectivity of a bipolar cell, compared to the infectivity of the bipolar cell by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of a bipolar cell, when administered via intravitreal injection, compared to the infectivity of the bipolar cell by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased infectivity of an amacrine cell, compared to the infectivity of the amacrine cell by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of an amacrine cell, when administered via intravitreal injection, compared to the infectivity of the amacrine cell by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased infectivity of a horizontal cell, compared to the infectivity of the horizontal cell by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of a horizontal cell, when administered via intravitreal injection, compared to the infectivity of the horizontal cell by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased infectivity of a retinal astrocyte, compared to the infectivity of the retinal astrocyte by an AAV virion comprising the corresponding parental AAV capsid protein.

In some cases, a subject rAAV virion exhibits at least 5-fold, at least 10-fold, at least 15-fold, at least 20-fold, at least 25-fold, at least 50-fold, or more than 50-fold, increased infectivity of a retinal astrocyte, when administered via intravitreal injection, compared to the infectivity of the retinal astrocyte by an AAV virion comprising the corresponding parental AAV capsid protein, when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased ability to cross extracellular matrix (ECM) of the retina, compared to the ability of an AAV virion comprising the corresponding parental AAV capsid protein to cross the ECM of the retina.

In some cases, a subject rAAV virion exhibits at least 5-fold, at least 10-fold, at least 15-fold, at least 20-fold, at least 25-fold, at least 50-fold, or more than 50-fold, increased ability, when administered via intravitreal injection, to cross extracellular matrix (ECM) of the retina, compared to the ability of an AAV virion comprising the corresponding parental AAV capsid protein to cross the ECM of the retina when administered via intravitreal injection.

In some cases, a subject rAAV virion exhibits at least 5-fold, at least 10-fold, at least 15-fold, at least 20-fold, at least 25-fold, at least 50-fold, or more than 50-fold, increased ability to cross the internal limiting membrane (ILM), compared to the ability of an AAV virion comprising the corresponding parental AAV capsid protein to cross the ILM.

In some cases, a subject rAAV virion exhibits at least 5-fold, at least 10-fold, at least 15-fold, at least 20-fold, at least 25-fold, at least 50-fold, or more than 50-fold, increased ability, when administered via intravitreal injection, to cross the ILM, compared to the ability of an AAV virion comprising the corresponding parental AAV capsid protein to cross the ILM when administered via intravitreal injection.

A subject rAAV virion can cross the ILM, and can also traverse cell layers, including Müller cells, amacrine cells, etc., to reach the photoreceptor cells and or RPE cells. For example, a subject rAAV virion, when administered via intravitreal injection, can cross the ILM, and can also traverse cell layers, including Müller cells, amacrine cells, etc., to reach the photoreceptor cells and or RPE cells.

In some cases, a subject rAAV virion exhibits at least 5-fold, at least 10-fold, at least 15-fold, at least 20-fold, at least 25-fold, at least 50-fold, or more than 50-fold, increased localization to one or more of the inner nuclear layer, the outer nuclear layer, the photoreceptor layer, the ganglion cell layer, and the retinal pigment epithelium, compared to the extent of localization to the inner nuclear layer, the outer nuclear layer, the photoreceptor layer, the ganglion cell layer, or the retinal pigment epithelium, by an AAV virion comprising the corresponding parental AAV capsid protein.

In some cases, a subject rAAV virion, when injected intravitreally, exhibits at least 5-fold, at least 10-fold, at least 15-fold, at least 20-fold, at least 25-fold, at least 50-fold, or more than 50-fold, increased localization past the ILM, compared to the extent of localization past the ILM by an intravitreally injected control AAV virion comprising the corresponding parental AAV capsid protein. For example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the retinal pigment epithelium (RPE), compared to the extent of localization to the RPE layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the photoreceptor (PR) layer, compared to the extent of localization to the PR layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the inner nuclear layer, compared to the extent of localization to the inner nuclear layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the outer nuclear layer, compared to the extent of localization to the outer nuclear layer by an intravitreally injected control AAV virion comprising the corresponding parental AAV capsid protein. As another example, in some cases, a subject rAAV virion, when injected intravitreally, exhibits at least 5-fold, at least 10-fold, at least 15-fold, at least 20-fold, at least 25-fold, at least 50-fold, or more than 50-fold, increased localization to the ganglion cell layer, compared to the extent of localization to the ganglion cell layer by an intravitreally injected control AAV virion comprising the corresponding parental AAV capsid protein.

In some cases, a subject rAAV virion selectively infects a retinal cell, e.g., a subject rAAV virion infects a retinal cell with 10-fold, 15-fold, 20-fold, 25-fold, 50-fold, or more than 50-fold, specificity than a non-retinal cell, e.g., a cell outside the eye. For example, in some cases, a subject rAAV virion selectively infects a retinal cell, e.g., a subject rAAV virion infects a photoreceptor cell with 10-fold, 15-fold, 20-fold, 25-fold, 50-fold, or more than 50-fold, specificity than a non-retinal cell, e.g., a cell outside the eye.

In some cases, a subject rAAV virion selectively infects a photoreceptor cell, e.g., a subject rAAV virion infects a photoreceptor cell with 10-fold, 15-fold, 20-fold, 25-fold, 50-fold, or more than 50-fold, specificity than a non-photoreceptor cell present in the eye, e.g., a retinal ganglion cell, a Müller cell, etc.

In some cases, a subject rAAV virion exhibits at least 10-fold, at least 15-fold, at least 20-fold, at least 25-fold, at least 50-fold, or more than 50-fold, increased infectivity of a photoreceptor cell, when administered via intravitreal injection, compared to the infectivity of the photoreceptor cell by an AAV virion comprising the corresponding parental AAV capsid protein, when administered via intravitreal injection.

Gene Products

An rAAV virion of the present disclosure comprises a heterologous nucleic acid comprising a nucleotide sequence encoding one or more gene products (one or more heterologous gene products). In some cases, the gene product is a polypeptide. In some cases, the gene product is an RNA. In some cases, an rAAV virion of the present disclosure comprises a heterologous nucleotide sequence encoding both a heterologous nucleic acid gene product and a heterologous polypeptide gene product. Where the gene product is an RNA, in some cases, the RNA gene product encodes a polypeptide. Where the gene product is an RNA, in some cases, the RNA gene product does not encode a polypeptide. In some cases, an rAAV virion of the present disclosure comprises a single heterologous nucleic acid comprising a nucleotide sequence encoding a single heterologous gene product. In some cases, an rAAV virion of the present disclosure comprises a single heterologous nucleic acid comprising a nucleotide sequence encoding two heterologous gene products. Where the single heterologous nucleic acid encodes two heterologous gene products, in some cases, nucleotide sequences encoding the two heterologous gene products are operably linked to the same promoter. Where the single heterologous nucleic acid encodes two heterologous gene products, in some cases, nucleotide sequences encoding the two heterologous gene products are operably linked to two different promoters. In some cases, an rAAV virion of the present disclosure comprises a single heterologous nucleic acid comprising a nucleotide sequence encoding three heterologous gene products. Where the single heterologous nucleic acid encodes three heterologous gene products, in some cases, nucleotide sequences encoding the three heterologous gene products are operably linked to the same promoter. Where the single heterologous nucleic acid encodes three heterologous gene products, in some cases, nucleotide sequences encoding the three heterologous gene products are operably linked to two or three different promoters. In some cases, an rAAV virion of the present disclosure comprises two heterologous nucleic acids, each comprising a nucleotide sequence encoding a heterologous gene product.

In some cases, the gene product is a polypeptide-encoding RNA. In some cases, the gene product is an interfering RNA. In some cases, the gene product is an aptamer. In some cases, the gene product is a polypeptide. In some cases, the gene product is a therapeutic polypeptide, e.g., a polypeptide that provides clinical benefit. In some cases, the gene product is a site-specific nuclease that provide for site-specific knock-down of gene function. In some cases, the gene product is an RNA-guided endonuclease that provides for modification of a target nucleic acid. In some cases, the gene products are: i) an RNA-guided endonuclease that provides for modification of a target nucleic acid; and ii) a guide RNA that comprises a first segment that binds to a target sequence in a target nucleic acid and a second segment that binds to the RNA-guided endonuclease. In some cases, the gene products are: i) an RNA-guided endonuclease that provides for modification of a target nucleic acid; ii) a first guide RNA that comprises a first segment that binds to a first target sequence in a target nucleic acid and a second segment that binds to the RNA-guided endonuclease; and iii) a first guide RNA that comprises a first segment that binds to a second target sequence in the target nucleic acid and a second segment that binds to the RNA-guided endonuclease.

Interfering RNA

Where the gene product is an interfering RNA (RNAi), suitable RNAi include RNAi that decrease the level of an apoptotic or angiogenic factor in a cell. For example, an RNAi can be an shRNA or siRNA that reduces the level of a gene product that induces or promotes apoptosis in a cell. Genes whose gene products induce or promote apoptosis are referred to herein as "pro-apoptotic genes" and the products of those genes (mRNA; protein) are referred to as "pro-apoptotic gene products." Pro-apoptotic gene products include, e.g., Bax, Bid, Bak, and Bad gene products. See, e.g., U.S. Pat. No. 7,846,730.

Interfering RNAs could also be against an angiogenic product, for example vascular endothelial growth factor (VEGF) (e.g., Cand5; see, e.g., U.S. Patent Publication No. 2011/0143400; U.S. Patent Publication No. 2008/0188437; and Reich et al. (2003) *Mol. Vis.* 9:210); VEGF receptor-1 (VEGFR1) (e.g., Sirna-027; see, e.g., Kaiser et al. (2010) *Am. J. Ophthalmol.* 150:33; and Shen et al. (2006) *Gene Ther.* 13:225); or VEGF receptor-2 (VEGFR2) (Kou et al. (2005) *Biochem.* 44:15064). See also, U.S. Pat. Nos. 6,649, 596, 6,399,586, 5,661,135, 5,639,872, and 5,639,736; and 7,947,659 and 7,919,473.

Aptamers

Where the gene product is an aptamer, exemplary aptamers of interest include an aptamer against VEGF. See, e.g., Ng et al. (2006) *Nat. Rev. Drug Discovery* 5:123; and Lee et al. (2005) *Proc. Natl. Acad. Sci. USA* 102:18902. For example, a VEGF aptamer can comprise the nucleotide sequence 5'-cgcaaucagugaaugcuuauacauccg-3' (SEQ ID NO:57). Also suitable for use is a platelet-derived growth factor (PDGF)-specific aptamer, e.g., E10030; see, e.g., Ni and Hui (2009) *Ophthalmologica* 223:401; and Akiyama et al. (2006) *J. Cell Physiol.* 207:407).

Polypeptides

Where the gene product is a polypeptide, in some cases, the polypeptide is a polypeptide that enhances function of a retinal cell, e.g., the function of a rod or cone photoreceptor cell, a retinal ganglion cell, a Müller cell, a bipolar cell, an amacrine cell, a horizontal cell, or a retinal pigment epithelial cell. Exemplary polypeptides include neuroprotective polypeptides (e.g., glial cell derived neurotrophic factor (GDNF), ciliary neurotrophic factor (CNTF), neurotrophin-4 (NT4), nerve growth factor (NGF), and neurturin (NTN)); anti-angiogenic polypeptides (e.g., a soluble VEGF receptor; a VEGF-binding antibody; a VEGF-binding antibody fragment (e.g., a single chain anti-VEGF antibody); endostatin; tumstatin; angiostatin; a soluble Flt polypeptide (Lai et al. (2005) *Mol. Ther.* 12:659); an Fc fusion protein comprising a soluble Flt polypeptide (see, e.g., Pechan et al. (2009) *Gene Ther.* 16:10); pigment epithelium-derived factor (PEDF); a soluble Tie-2 receptor; etc.); tissue inhibitor of metalloproteinases-3 (TIMP-3); a light-responsive opsin, e.g., a rhodopsin; anti-apoptotic polypeptides (e.g., Bcl-2, Bcl-Xl; XIAP); and the like. Suitable polypeptides include, but are not limited to, glial derived neurotrophic factor (GDNF); fibroblast growth factor; fibroblast growth factor 2; neurturin (NTN); ciliary neurotrophic factor (CNTF); nerve growth factor (NGF); neurotrophin-4 (NT4); brain derived neurotrophic factor (BDNF; e.g., a polypeptide comprising an amino acid sequence having at least about 90%, at least about 95%, at least about 98%, at least about 99%, or 100%, amino acid sequence identity to a contiguous stretch of from about 200 amino acids to 247 amino acids of the amino acid sequence depicted in FIG. 4B (SEQ ID NO:91)); epidermal growth factor; rhodopsin; X-linked inhibitor of apoptosis; and Sonic hedgehog.

Suitable polypeptides include, an opsin, a short-wavelength opsin (SW-opsin), a medium-wavelength opsin (MW-opsin), a long-wavelength opsin (LW-opsin), a rhodopsin, a cone opsin, a human opsin, a non-human opsin, a humanized opsin, and the like.

An MW-opsin polypeptide can comprise an amino acid sequence having at least 85%, at least 90%, at least 95%, at least 98%, at least 99%, or 100%, amino acid sequence identity to the following human MW-opsin amino acid sequence:

```
                                      (SEQ ID NO: 54)
MAQQWSLQRL AGRHPQDSYE DSTQSSIFTY TNSNSTRGPF

EGPNYHIAPR WVYHLTSVWM IFVVIASVFT NGLVLAATMK

FKKLRHPLNW ILVNLAVADL AETVIASTIS VVNQVYGYFV

LGHPMCVLEG YTVSLCGITG LWSLAIISWE RWMVVCKPFG

NVRFDAKLAI VGIAFSWIWA AVWTAPPIFG WSRYWPHGLK

TSCGPDVFSG SSYPGVQSYM IVLMVTCCIT PLSIIVLCYL

QVWLAIRAVA KQQKESESTQ KAEKEVTRMV VVMVLAFCFC

WGPYAFFACF AAANPGYPFH PLMAALPAFF AKSATIYNPV

IYVFMNRQFR NCILQLFGKK VDDGSELSSA SKTEVSSVSS

VSPA.
```

An LW-opsin can comprise an amino acid sequence having at least 85%, at least 90%, at least 95%, at least 98%, at least 99%, or 100%, amino acid sequence identity to the following human LW-opsin amino acid sequence:

```
                                        (SEQ ID NO: 55)
MAQQWSLQRL  AGRHPQDSYE  DSTQSSIFTY  TNSNSTRGPF

EGPNYHIAPR  WVYHLTSVWM  IFVVTASVFT  NGLVLAATMK

FKKLRHPLNW  ILVNLAVADL  AETVIASTIS  IVNQVSGYFV

LGHPMCVLEG  YTVSLCGITG  LWSLAIISWE  RWMVVCKPFG

NVRFDAKLAI  VGIAFSWIWA  AVWTAPPIFG  WSRYWPHGLK

TSCGPDVFSG  SSYPGVQSYM  IVLMVTCCII  PLAIIMLCYL

QVWLAIRAVA  KQQKESESTQ  KAEKEVTRMV  VVMIFAYCVC

WGPYTFFACF  AAANPGYAFH  PLMAALPAYF  AKSATIYNPV

IYVFMNRQFR  NCILQLFGKK  VDDGSELSSA  SKTEVSSVSS

VSPA.
```

An SW-opsin polypeptide can comprise an amino acid sequence having at least 85%, at least 87%, at least 90%, at least 95%, at least 98%, at least 99%, or 100%, amino acid sequence identity to the following human SW-opsin amino acid sequence:

```
                                        (SEQ ID NO: 56)
MRKMSEEEFY  LFKNISSVGP  WDGPQYHIAP  VWAFYLQAAF

MGTVFLIGFP  LNAMVLVATL  RYKKLRQPLN  YILVNVSFGG

FLLCIFSVFP  VFVASCNGYF  VFGRHVCALE  GFLGTVAGLV

TGWSLAFLAF  ERYIVICKPF  GNFRFSSKHA  LTVVLATWTI

GIGVSIPPFF  GWSRFIPEGL  QCSCGPDWYT  VGTKYRSESY

TWFLFIFCFI  VPLSLICFSY  TQLLRALKAV  AAQQQESATT

QKAEREVSRM  VVVMVGSFCV  CYVPYAAFAM  YMVNNRNHGL

DLRLVTIPSF  FSKSACIYNP  IIYCFMNKQF  QACIMKMVCG

KAMTDESDTC  SSQKTEVSTV  SSTQVGPN.
```

Suitable light-responsive opsins include, e.g., a light-responsive opsin as described in U.S. Patent Publication No. 2007/0261127 (e.g., channelrhodopsin-2; ChR2; Chop2); U.S. Patent Publication No. 2001/0086421; U.S. Patent Publication No. 2010/0015095; U.S. Patent Publication No. 2016/0002302; U.S. Patent Publication No. 2013/0347137; U.S. Patent Publication No. 2013/0019325; and Diester et al. (2011) Nat. Neurosci. 14:387. See, Thyagarajan et al. (2010) J Neurosci. 30(26):8745-8758; Lagali et al. (2008) Nat Neurosci. 11(6):667-675; Doroudchi et al. (2011) Mol Ther. 19(7):1220-1229; Henriksen et al. (2014) J. Ophthalmic Vis. Res. 9:374; Tomita et al. (2014) Mol. Ther. 22:1434.

Suitable polypeptides include light-gated ion channel polypeptides. See, e.g., Gaub et al. (2014) Proc. Natl. Acad. Sci. USA 111:E5574. For example, a suitable polypeptide is a light-gated ionotropic glutamate receptor (LiGluR). Expression of LiGluR in retinal ganglion cells and ON-bipolar cells, in the presence of a photoisomerizable compound, renders the cells responsive to light. LiGluR comprises a L439C substitution; see, Caporale et al. (2011) Mol Ther. 19:1212-1219; Volgraf et al. (2006) Nat Chem Biol. 2:47-52; and Gorostiza et al. (2007) Proc Natl Acad Sci USA. 104:10865-10870. Photoisomerizable compounds include, e.g., maleimide-azobenzene-glutamate 0 with peak efficiency at 460 nm ($MAG0_{460}$) $MAG0_{460}$ has the following structure:

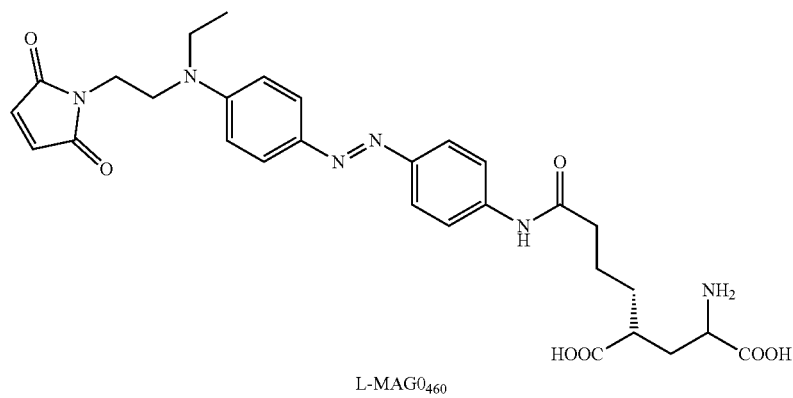

L-$MAG0_{460}$

Suitable polypeptides also include retinoschisin (e.g., a polypeptide comprising an amino acid sequence having at least about 90%, at least about 95%, at least about 98%, at least about 99%, or 100%, amino acid sequence identity to a contiguous stretch of from about 200 amino acids to 224 amino acids of the amino acid sequence depicted in FIG. 4A (SEQ ID NO:90). Suitable polypeptides include, e.g., retinitis pigmentosa GTPase regulator (RPGR)-interacting protein-1 (see, e.g., GenBank Accession Nos. Q96KN7, Q9EPQ2, and Q9GLM3) (e.g., a polypeptide comprising an amino acid sequence having at least about 90%, at least about 95%, at least about 98%, at least about 99%, or 100%, amino acid sequence identity to a contiguous stretch of from about 1150 amino acids to about 1200 amino acids, or from about 1200 amino acids to 1286 amino acids, of the amino acid sequence depicted in FIG. 4F (SEQ ID NO:95); peripherin-2 (Prph2) (see, e.g., GenBank Accession No. NP_000313 (e.g., a polypeptide comprising an amino acid sequence having at least about 90%, at least about 95%, at least about 98%, at least about 99%, or 100%, amino acid sequence identity to a contiguous stretch of from about 300 amino acids to 346 amino acids of the amino acid sequence depicted in FIG. 4D (SEQ ID NO:93); and Travis et al. (1991) Genomics 10:733); peripherin (e.g., a polypeptide comprising an amino acid sequence having at least about 90%, at least about 95%, at least about 98%, at least about 99%, or 100%, amino acid sequence identity to a contiguous stretch of from about 400 amino acids to about 470 amino acids of the amino acid sequence depicted in FIG. 4E (SEQ ID NO:94); a retinal pigment epithelium-specific protein (RPE65), (e.g., a polypeptide comprising an amino acid sequence having at least about 90%, at least about 95%, at least about 98%, at least about 99%, or 100%, amino acid sequence identity to a contiguous stretch of from about 200 amino acids to 247 amino acids of the amino acid sequence depicted in FIG. 4C (SEQ ID NO:92)) (see, e.g., GenBank AAC39660; and Morimura et al. (1998) *Proc. Natl. Acad. Sci. USA* 95:3088); rod-derived cone viability factor (RdCVF) (e.g., a polypeptide comprising an amino acid sequence having at least about 90%, at least about 95%, at least about 98%, at least about 99%, or 100%, amino acid sequence identity to the amino acid sequence depicted in any one of FIGS. 4H, 4I, and 4J; Rab escort protein 1 (REP1) (e.g., a polypeptide comprising an amino acid sequence having at least about 90%, at least about 95%, at least about 98%, at least about 99%, or 100%, amino acid sequence identity to the amino acid sequence depicted in FIG. 4G); retinitis pigmentosa GTPase regulator (RPGR) (e.g., a polypeptide comprising an amino acid sequence having at least about 90%, at least about 95%, at least about 98%, at least about 99%, or 100%, amino acid sequence identity to the amino acid sequence depicted in one of FIG. 4S-4V); and the like. For example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 4S. As another example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 4T. example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 4U. example, in some cases, a suitable RPGR polypeptide comprises an amino acid sequence having at least about 90%, at least about 95%, at least about 98%, at least about 99%, or 100%, amino acid sequence identity to the amino acid sequence depicted in FIG. 4V.

Suitable polypeptides also include: CHM (choroideremia (Rab escort protein 1 (REP1))), a polypeptide that, when defective or missing, causes choroideremia (see, e.g., Donnelly et al. (1994) *Hum. Mol. Genet.* 3:1017; and van Bokhoven et al. (1994) *Hum. Mol. Genet.* 3:1041); and Crumbs homolog 1 (CRB1), a polypeptide that, when defective or missing, causes Leber congenital amaurosis and retinitis pigmentosa (see, e.g., den Hollander et al. (1999) *Nat. Genet.* 23:217; and GenBank Accession No. CAM23328). For example, a suitable REP1 polypeptide can comprise an amino acid having at least about 90%, at least about 95%, at least about 98%, at least about 99%, or 100%, amino acid sequence identity to the amino acid sequence set depicted in FIG. 4G.

Suitable polypeptides include Rod cGMP-specific 3',5'-cyclic phosphodiesterase subunit alpha (PDE6α), Rod cGMP-specific 3',5'-cyclic phosphodiesterase subunit beta isoform 1 (PDE6β isoform 1), Rod cGMP-specific 3',5'-cyclic phosphodiesterase subunit beta isoform 2 (PDE6β isoform 2), Rod cGMP-specific 3',5'-cyclic phosphodiesterase subunit beta isoform 3 (PDE6β isoform 3). For example, a suitable PDE6a polypeptide can comprise an amino acid having at least about 90%, at least about 95%, at least about 98%, at least about 99%, or 100%, amino acid sequence identity to the amino acid sequence set depicted in FIG. 4K. As another example, a suitable PDE6β6 isoform 1 polypeptide can comprise an amino acid having at least about 90%, at least about 95%, at least about 98%, at least about 99%, or 100%, amino acid sequence identity to the amino acid sequence set depicted in FIG. 4L. As another example, a suitable PDE6β6 isoform 2 polypeptide can comprise an amino acid having at least about 90%, at least about 95%, at least about 98%, at least about 99%, or 100%, amino acid sequence identity to the amino acid sequence set depicted in FIG. 4M. As another example, a suitable PDE6β6 isoform 3 polypeptide can comprise an amino acid having at least about 90%, at least about 95%, at least about 98%, at least about 99%, or 100%, amino acid sequence identity to the amino acid sequence set depicted in FIG. 4N.

Suitable polypeptides also include polypeptides that, when defective or missing, lead to achromotopsia, where such polypeptides include, e.g., cone photoreceptor cGMP-gated channel subunit alpha (CNGA3) (see, e.g., GenBank Accession No. NP_001289; and Booij et al. (2011) *Ophthalmology* 118:160-167); cone photoreceptor cGMP-gated cation channel beta-subunit (CNGB3) (see, e.g., Kohl et al. (2005) *Eur J Hum Genet.* 13(3):302); guanine nucleotide binding protein (G protein), alpha transducing activity polypeptide 2 (GNAT2) (ACHM4); and ACHM5; and polypeptides that, when defective or lacking, lead to various forms of color blindness (e.g., L-opsin, M-opsin, and S-opsin). See Mancuso et al. (2009) *Nature* 461(7265):784-787.

For example, a suitable CNGA3 (also known as ACHM2) isoform 1 polypeptide can comprise an amino acid having at least about 90%, at least about 95%, at least about 98%, at least about 99%, or 100%, amino acid sequence identity to the amino acid sequence set depicted in FIG. 4O. As another example, a suitable CNGA3 (also known as ACHM2) isoform 2 polypeptide can comprise an amino acid having at least about 90%, at least about 95%, at least about 98%, at least about 99%, or 100%, amino acid sequence identity to the amino acid sequence set depicted in FIG. 4P.

As another example, a suitable CNGB3 (also known as ACHM3) polypeptide can comprise an amino acid having at least about 90%, at least about 95%, at least about 98%, at least about 99%, or 100%, amino acid sequence identity to the amino acid sequence set depicted in FIG. 4Q. As another example, GNAT2 (also known as ACHM4) can comprise an amino acid having at least about 90%, at least about 95%, at least about 98%, at least about 99%, or 100%, amino acid sequence identity to the amino acid sequence set depicted in FIG. 4R.

Other suitable polypeptides include, for example, G-protein coupled receptors (GPCRs), derived from human or other species, or functional fragments or variants thereof. n some cases, the GPCR is an inhibitory G-protein (G)-coupled GPCR. In some cases, the GPCR is a stimulatory G-protein (GO-coupled GPCR. In some cases, the GPCR is a stimulatory G-protein (GO-coupled GPCR. In some cases, the GPCR comprises a metabotropic glutamate receptor (mGluR). In more specific embodiments, the GPRC sequence comprises a functional fragment or variant of a GPRC sequence. In other more specific embodiments, the functional fragment or variant thereof retains one or more desired activities of a wild type GPRC, and has at least 70%, at least 80%, at least 90%, at least 95% or at least 99% or more identity the sequence of a wild type human GPRC.

Suitable polypeptides can also include metabotropic glutamate receptors (mGluRs) derived from human or other species, or functional fragments or variants thereof. For example, in some cases, the mGluR comprises one or more of mGluR1, mGluR2, mGluR3, mGluR4, mGluR5, mGluR6, mGluR7 and mGluR8, or a functional fragment or variant thereof. In other more specific embodiments, the functional fragment or variant thereof retains one or more desired activities of a wild type mGluR, and has at least 70%, at least 80%, at least 90%, at least 95% or at least 99% or more identity the sequence of a wild type human mGluR.

In more specific embodiments, the polypeptide is a human mGluR2 polypeptide sequence, such as an mGluR2 polypeptide sequence encoded by a polynucleotide sequence set forth in UniProtKB Q14416 or GenBank Accession No. NM_000839.5. In other specific embodiments, the polypeptide is a human mGluR2 polypeptide sequence, such as a polypeptide sequence set forth in UniProtKB Q14416 or GenBank Accession No. NP_000830.2. In addition, the mGluR2 polynucleotide and polypeptide sequences can also be functional fragments or variants thereof, such as those having at least 70%, at least 80%, at least 90%, at least 95% or at least 99% identity thereto. For example, in some cases, the polypeptide comprises an amino acid sequence having at least 70%, at least 80%, at least 90%, at least 95%, at least 99% identity, or 100% identity to amino acids 19-872 of the amino acid sequence depicted in FIG. 4W.

In additional embodiments of the disclosure, a suitable polypeptide comprises a fusion polypeptide which, in addition to containing a polypeptide sequence such as those discussed above, also further comprises one or more additional polypeptide sequences of interest.

For example, in some cases, a suitable polypeptide comprises a fusion polypeptide comprising an affinity tag, such as a SNAP sequence, a CLIP sequence and/or a HALO sequence.

In related embodiments, the SNAP sequence comprises the following amino acid sequence:

```
                                      (SEQ ID NO: 123)
MDKDCEMKRTTLDSPLGKLELSGCEQGLHRIIFLGKGTSAADAVEVPA

PAAVLGGPEPLMQATAWLNAYFHQPEAIEEFPVPALHHPVFQQESFTR

QVLWKLLKVVKFGEVISYSHLAALAGNPAATAAVKTALSGNPVPILIP

CHRVVQGDLDVGGYEGGLAVKEWLLAHEGHRLGKPGLG.
```

In other related embodiments, the SNAP sequence comprises the following amino acid sequence:

```
                                      (SEQ ID NO: 124)
DKDCEMKRTTLDSPLGKLELSGCEQGLHEIKLLGKGTSAADAVEVPAP

AAVLGGPEPLMQATAWLNAYFHQPEAIEEFPVPALHHPVFQQESFTRQ

VLWKLLKVVKFGEVISYQQLAALAGNPAATAAVKTALSGNPVPILIPC

HRVVSSSGAVGGYEGGLAVKEWLLAHEGHRLGKPGLG.
```

In more specific embodiments, the SNAP polypeptide is a sequence having at least 80%, at least 85%, at least 90%, at least 95%, at least 98%, or at least 99%, amino acid sequence identity to a SNAP sequence, such as those illustratively described herein, wherein the SNAP sequence is a sequence that binds to benzylguanine.

In another specific embodiment of the disclosure, a suitable polypeptide is a fusion polypeptide comprising a SNAP polypeptide sequence and an mGluR polypeptide sequence, such as an mGluR2 polypeptide sequence, or a functional fragment or variant thereof.

CRISPR/Cas Effector Polypeptides and Site-Specific Endonucleases

In some cases, a gene product of interest is a CRISPR/Cas effector polypeptide or a site-specific endonuclease that provide for site-specific knock-down of gene function, e.g., where the CRISPR/Cas effector polypeptide knocks out an allele associated with a retinal disease. For example, where a dominant allele encodes a defective copy of a gene that, when wild-type, is a retinal structural protein and/or provides for normal retinal function, a CRISPR/Cas effector polypeptide or site-specific endonuclease can be targeted to the defective allele and knock out the defective allele.

In addition to knocking out a defective allele, a CRISPR/Cas effector polypeptide or a site-specific endonuclease can also be used to stimulate homologous recombination with a donor DNA that encodes a functional copy of the protein encoded by the defective allele. Thus, e.g., a subject rAAV virion can be used to deliver both a CRISPR/Cas effector polypeptide that knocks out a defective allele, and can be used to deliver a functional copy of the defective allele, resulting in repair of the defective allele, thereby providing for production of a functional retinal protein (e.g., functional retinoschisin, functional RPE65, functional peripherin, etc.). See, e.g., Li et al. (2011) Nature 475:217. In some cases, a subject rAAV virion comprises a heterologous nucleotide sequence that encodes a CRISPR/Cas effector polypeptide; and a heterologous nucleotide sequence that encodes a functional copy of a defective allele, where the functional copy encodes a functional retinal protein. Functional retinal proteins include, e.g., retinoschisin, RPE65, retinitis pigmentosa GTPase regulator (RGPR)-interacting protein-1, peripherin, peripherin-2, RdCVF, and the like.

Site-specific endonucleases that are suitable for use include, e.g., zinc finger nucleases (ZFNs); meganucleases; and transcription activator-like effector nucleases (TALENs), where such site-specific endonucleases are non-naturally occurring and are modified to target a specific gene. Such site-specific nucleases can be engineered to cut specific locations within a genome, and non-homologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073. Suitable site-specific endonucleases include engineered meganucleases and re-engineered homing endonucleases. Suitable endonucleases include an I-TevI nuclease. Suitable meganucleases include I-SceI (see, e.g., Bellaiche et al. (1999) *Genetics* 152:1037); and I-CreI (see, e.g., Heath et al. (1997) *Nature Structural Biology* 4:468).

CRISPR/Cas Effector Polypeptides

In some cases, the gene product is a CRISPR/Cas effector polypeptide. In some cases, the gene product is an RNA comprising a nucleotide sequence encoding a CRISPR/Cas effector polypeptide. In some cases, the gene product is a guide RNA, e.g., a single-guide RNA. In some cases, the gene products are: 1) a guide RNA; and 2) a CRISPR/Cas effector polypeptide. The guide RNA can comprise: a) a protein-binding region that binds to the CRISPR/Cas effector polypeptide; and b) a region that binds to a target nucleic acid. A CRISPR/Cas effector polypeptide is sometimes referred to herein a "genome editing nuclease."

Examples of suitable CRISPR/Cas effector polypeptide are CRISPR/Cas endonucleases (e.g., class 2 CRISPR/Cas endonucleases such as a type II, type V, or type VI CRISPR/Cas endonucleases). A suitable CRISPR/Cas effector polypeptide is a CRISPR/Cas endonuclease (e.g., a class 2 CRISPR/Cas endonuclease such as a type II, type V, or type VI CRISPR/Cas endonuclease). In some cases, a genome targeting composition includes a class 2 CRISPR/Cas effector polypeptide. In some cases, a genome targeting composition includes a class 2 type II CRISPR/Cas effector polypeptide (e.g., a Cas9 protein). In some cases, a genome targeting composition includes a class 2 type V CRISPR/Cas effector polypeptide (e.g., a Cpf1 protein, a C2c1 protein, or a C2c3 protein). In some cases, a genome targeting composition includes a class 2 type VI CRISPR/Cas effector polypeptide (e.g., a C2c2 protein; also referred to as a "Cas13a" protein). Also suitable for use is a CasX protein. Also suitable for use is a CasY protein.

In some cases, a CRISPR/Cas effector polypeptide is a fusion protein that is fused to a heterologous polypeptide (also referred to as a "fusion partner"). In some cases, a CRISPR/Cas effector polypeptide is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.).

In some cases, the CRISPR/Cas effector polypeptide is a Type II CRISPR/Cas effector polypeptide. In some cases, the CRISPR/Cas effector polypeptide is a Cas9 polypeptide. The Cas9 protein is guided to a target site (e.g., stabilized at a target site) within a target nucleic acid sequence (e.g., a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA. In some cases, a Cas9 polypeptide comprises an amino acid sequence having at least 50%, at least 60%, at least 70%, at least 80%, at least 90%, at least 95%, at least 98%, at least 99%, or more than 99%, amino acid sequence identity to the *Streptococcus pyogenes* Cas9 depicted in FIG. 5A. In some cases, the Cas9 polypeptide used in a composition or method of the present disclosure is a *Staphylococcus aureus* Cas9 (saCas9) polypeptide. In some cases, the saCas9 polypeptide comprises an amino acid sequence having at least 85%, at least 90%, at least 95%, at least 98%, at least 99%, or 100%, amino acid sequence identity to the saCas9 amino acid sequence depicted in FIG. 5B.

In some cases, a suitable Cas9 polypeptide is a high-fidelity (HF) Cas9 polypeptide. Kleinstiver et al. (2016) *Nature* 529:490. For example, amino acids N497, R661, Q695, and Q926 of the amino acid sequence depicted in FIG. 5A are substituted, e.g., with alanine. For example, an HF Cas9 polypeptide can comprise an amino acid sequence having at least 90%, at least 95%, at least 98%, at least 99%, or 100%, amino acid sequence identity to the amino acid sequence depicted in FIG. 5A, where amino acids N497, R661, Q695, and Q926 are substituted, e.g., with alanine. In some cases, a suitable Cas9 polypeptide comprises an amino acid sequence as depicted in any one of FIG. 5A-5F. In some cases, a suitable Cas9 polypeptide comprises an amino acid sequence as depicted in FIG. 6.

In some cases, a suitable Cas9 polypeptide exhibits altered PAM specificity. See, e.g., Kleinstiver et al. (2015) *Nature* 523:481.

In some cases, the CRISPR/Cas effector polypeptide is a type V CRISPR/Cas endonuclease. In some cases, a type V CRISPR/Cas effector polypeptide is a Cpf1 protein. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence depicted in any one of FIG. 7A-7C.

In some cases, the CRISPR/Cas effector polypeptide is a CasX or a CasY polypeptide. CasX and CasY polypeptides are described in Burstein et al. (2017) *Nature* 542:237.

Enzymatically Inactive RNA-Guided Endonucleases

Also suitable for use is a CRISPR/Cas effector polypeptide with reduced enzymatic activity. Such a CRISPR/Cas effector polypeptide is referred to as a "dead" CRISPR/Cas effector polypeptide; for example, a Cas9 polypeptide that comprises certain amino acid substitutions such that it exhibits substantially no endonuclease activity, but such that it still binds to a target nucleic acid when complexed with a guide RNA, is referred to as a "dead" Cas9 or "dCas9." In some cases, a "dead" Cas9 protein has a reduced ability to cleave both the complementary and the non-complementary strands of a double stranded target nucleic acid. For example, a "nuclease defective" Cas9 lacks a functioning RuvC domain (i.e., does not cleave the non-complementary strand of a double stranded target DNA) and lacks a functioning HNH domain (i.e., does not cleave the complementary strand of a double stranded target DNA). As a non-limiting example, in some cases, the nuclease defective Cas9 protein harbors mutations at amino acid positions corresponding to residues D10 and H840 (e.g., D10A and H840A) of SEQ ID NO: 15 (or the corresponding residues of a homolog of Cas9) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid. A Cas9 protein that cannot cleave target nucleic acid (e.g., due to one or more mutations, e.g., in the catalytic domains of the RuvC and HNH domains) is referred to as a "nuclease defective Cas9", "dead Cas9" or simply "dCas9." Other residues can be mutated to achieve the above effects (i.e. inactivate one or the other nuclease portions). As non-limiting examples, residues D10, G12, G17, E762, H840, N854, N863, H982, H983, A984, D986, and/or A987 of *Streptococcus pyogenes* Cas9 (or the corresponding amino acids of a Cas9 homolog) can be altered (i.e., substituted). In some cases, two or more of D10, E762, H840, N854, N863, and D986 of *Streptococcus pyogenes* Cas9 (or the corresponding amino acids of a homolog) are substituted. In some cases, D10 and N863 of *Streptococcus pyogenes* Cas9 (or the corresponding amino acids of a Cas9 homolog) are substituted with Ala. Also, mutations other than alanine substitutions are suitable.

In some cases, the CRISPR/Cas effector polypeptide is an RNA-guided endonuclease (and it corresponding guide RNA) known as Cas9-synergistic activation mediator (Cas9-SAM). The RNA-guided endonuclease (e.g., Cas9) of the Cas9-SAM system is a "dead" Cas9 fused to a transcriptional activation domain (wherein suitable transcriptional activation domains include, e.g., VP64, p65, MyoD1, HSF1, RTA, and SET7/9) or a transcriptional repressor domain (where suitable transcriptional repressor domains include, e.g., a KRAB domain, a NuE domain, an NcoR domain, a SID domain, and a SID4X domain). The guide RNA of the Cas9-SAM system comprises a loop that binds an adapter protein fused to a transcriptional activator domain (e.g., VP64, p65, MyoD1, HSF1, RTA, or SET7/9) or a transcriptional repressor domain (e.g., a KRAB domain, a NuE domain, an NcoR domain, a SID domain, or a SID4X domain). For example, in some cases, the guide RNA is a single-guide RNA comprising an MS2 RNA aptamer inserted into one or two loops of the sgRNA; the dCas9 is a fusion polypeptide comprising dCas9 fused to VP64; and the adaptor/functional protein is a fusion polypeptide comprising: i) MS2; ii) p65; and iii) HSF1. See, e.g., U.S. Patent Publication No. 2016/0355797.

Also suitable for use is a chimeric polypeptide comprising: a) a dead CRISPR/Cas effector polypeptide; and b) a heterologous fusion polypeptide. Examples of suitable heterologous fusion polypeptides include a polypeptide having, e.g., methylase activity, demethylase activity, transcription activation activity, transcription repression activity, transcription release factor activity, histone modification activity, RNA cleavage activity, DNA cleavage activity, DNA integration activity, or nucleic acid binding activity.

Guide RNA

A nucleic acid that binds to a class 2 CRISPR/Cas effector polypeptide (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA." A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

In some cases, a guide RNA includes two separate nucleic acid molecules: an "activator" and a "targeter" and is referred to herein as a "dual guide RNA", a "double-molecule guide RNA", a "two-molecule guide RNA", or a "dgRNA." In some cases, the guide RNA is one molecule (e.g., for some class 2 CRISPR/Cas effector polypeptides, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Where the gene product is a CRISPR/Cas effector polypeptide, or is both a CRISPR/Cas effector polypeptide and a guide RNA, the gene product can modify a target nucleic acid. In some cases, e.g., where a target nucleic acid comprises a deleterious mutation in a defective allele (e.g., a deleterious mutation in a retinal cell target nucleic acid), the CRISPR/Cas effector polypeptide/guide RNA complex, together with a donor nucleic acid comprising a nucleotide sequence that corrects the deleterious mutation (e.g., a donor nucleic acid comprising a nucleotide sequence that encodes a functional copy of the protein encoded by the defective allele), can be used to correct the deleterious mutation, e.g., via homology-directed repair (HDR).

In some cases, the gene products are a CRISPR/Cas effector polypeptide and 2 separate sgRNAs, where the 2 separate sgRNAs provide for deletion of a target nucleic acid via non-homologous end joining (NHEJ).

In some cases, the gene products are: i) a CRISPR/Cas effector polypeptide; and ii) one guide RNA. In some cases, the guide RNA is a single-molecule (or "single guide") guide RNA (an "sgRNA"). In some cases, the guide RNA is a dual-molecule (or "dual-guide") guide RNA ("dgRNA").

In some cases, the gene products are: i) a CRISPR/Cas effector polypeptide; and ii) 2 separate sgRNAs, where the 2 separate sgRNAs provide for deletion of a target nucleic acid via non-homologous end joining (NHEJ). In some cases, the guide RNAs are sgRNAs. In some cases, the guide RNAs are dgRNAs.

In some cases, the gene products are: i) a Cpf1 polypeptide; and ii) a guide RNA precursor; in these cases, the precursor can be cleaved by the Cpf1 polypeptide to generate 2 or more guide RNAs.

The present disclosure provides a method of modifying a target nucleic acid in a retinal cell in an individual, where the target nucleic acid comprises a deleterious mutation, the method comprising administering to the individual (e.g., by intraocular; intravitreal; etc. administration) an rAAV virion of the present disclosure, where the rAAV virion comprises a heterologous nucleic acid comprising: i) a nucleotide sequence encoding a CRISPR/Cas effector polypeptide (e.g., a Cas9 polypeptide); ii) a nucleotide sequence encoding a sgRNA that comprises a nucleotide sequence that is complementary to the target nucleic acid; and iii) a nucleotide sequence encoding a donor DNA template that comprises a nucleotide sequence that corrects the deleterious mutation. Administration of the rAAV virion results in correction of the deleterious mutation in the target nucleic acid by HDR.

The present disclosure provides a method of modifying a target nucleic acid in a retinal cell in an individual, where the target nucleic acid comprises a deleterious mutation, the method comprising administering to the individual (e.g., by intraocular; intravitreal; etc. administration) an rAAV virion of the present disclosure, where the rAAV virion comprises a heterologous nucleic acid comprising: i) a nucleotide sequence encoding a CRISPR/Cas effector polypeptide (e.g., a Cas9 polypeptide); ii) a nucleotide sequence encoding a first sgRNA that comprises a nucleotide sequence that is complementary to a first sequence in the target nucleic acid; and iii) a nucleotide sequence encoding a second sgRNA that comprises a nucleotide sequence that is complementary to a second sequence in the target nucleic acid. Administration of the rAAV virion results in excision of the deleterious mutation in the target nucleic acid by NHEJ.

Regulatory Sequences

In some cases, a nucleotide sequence encoding a gene product of interest (a heterologous gene product(s)) is operably linked to a transcriptional control element. For example, in some cases, a nucleotide sequence encoding a gene product of interest is operably linked to a constitutive promoter. In other cases, a nucleotide sequence encoding a gene product of interest is operably linked to an inducible promoter. In some instances, a nucleotide sequence encoding a gene product of interest is operably linked to a tissue-specific or cell type-specific regulatory element. For example, in some instances, a nucleotide sequence encoding a gene product of interest is operably linked to a retinal cell-specific promoter. For example, in some instances, a nucleotide sequence encoding a gene product of interest is operably linked to a photoreceptor-specific regulatory element (e.g., a photoreceptor-specific promoter), e.g., a regulatory element that confers selective expression of the operably linked gene in a photoreceptor cell. Suitable photoreceptor-specific regulatory elements include, e.g., a rhodopsin promoter; a rhodopsin kinase promoter (Young et al. (2003) *Ophthalmol. Vis. Sci.* 44:4076); a beta phosphodiesterase gene promoter (Nicoud et al. (2007) *J. Gene Med.* 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) *Exp Eye Res.* 55:225).

Suitable promoters include, but are not limited to, a CAG promoter (Miyazaki et al. (1989) *Gene* 79:269); a cytomegalovirus (CMV) promoter; a glutamate metabotropic receptor-6 (grm6) promoter (Cronin et al. (2014) *EMBO Mol.*

Med. 6:1175); a Pleiades promoter (Portales-Casamar et al. (2010) Proc. Natl. Acad. Sci. USA 107:16589); a choline acetyltransferase (ChAT) promoter (Misawa et al. (1992) J. Biol. Chem. 267:20392); a vesicular glutamate transporter (V-glut) promoter (Zhang et al. (2011) Brain Res. 1377:1); a glutamic acid decarboxylase (GAD) promoter (Rasmussen et al. (2007) Brain Res. 1144:19; Ritter et al. (2016) J. Gene Med. 18:27); a cholecystokinin (CCK) promoter (Ritter et al. (2016) J. Gene Med. 18:27); a parvalbumin (PV) promoter; a somatostatin (SST) promoter; a neuropeptide Y (NPY) promoter; and a vasoactive intestinal peptide (VIP) promoter. Suitable promoters include, but are not limited to, a red cone opsin promoter, rhodopsin promoter, a rhodopsin kinase promoter, and a GluR promoter (e.g., a GluR6 promoter; also referred to as grm6). Suitable promoters include, but are not limited to, a vitelliform macular dystrophy 2 (VMD2) gene promoter, and an interphotoreceptor retinoid-binding protein (IRBP) gene promoter. Also suitable for use is an L7 promoter (Oberdick et al. (1990) Science 248:223), a thy-1 promoter, a recoverin promoter (Wiechmann and Howard (2003) Curr. Eye Res. 26:25); a calbindin promoter; and a beta-actin promoter. Suitable promoters include synthetic (non-naturally occurring) promoter/enhancer combinations.

Other suitable promoters useful in accordance with the present disclosure include, for example, a gamma-synuclein (SNCG) promoter (e.g., Chaffiol et al. (2017) Mol. Ther. 25(11) 2546), a CBh promoter (e.g., Grey et al. (2011) Hum. Gene Ther. 22(9):1143-53), a miniCAG promoter (e.g., Grey et al. (2011) Hum. Gene Ther. 22(9):1143-53), a neurofilament heavy (NEFH) promoter (Millington-Ward et al. (2020) Sci. Rep. 10:16515), a G protein-coupled receptor kinase 1 (GRK1) promoter (e.g., Khani et al. (2007) Invest. Ophthalmol. Vis. Sci. 48(9):3954-61), a retinaldehyde-binding protein 1 (RLBP1) promoter (e.g., Choi et al. (2015) Mol. Ther. Methods Clin. Dev. 2: 15022; Vogel et al. (2007) Invest. Ophthalmol. Vis. Sci. 48, 3872-3877), a vitelliform muscular dystrophy-2 (VMD2) promoter (e.g., Conlon et al. (2013) Hum. Gene Ther. Clin. Dev. 24, 23-28), a synapsin I (Syn1) promoter (e.g., Kugler et al. (2003)), an enhSyn1 promoter (e.g., Hioki et al. (2007) Gene Ther. 14(11):872-82), or a functional fragment or variant thereof.

Pharmaceutical Compositions

The present disclosure provides a pharmaceutical composition comprising: a) a subject rAAV virion, as described above; and b) a pharmaceutically acceptable carrier, diluent, excipient, or buffer. In some cases, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

Methods of Delivering a Gene Product to a Retinal Cell and Treatment Methods

The present disclosure provides a method of delivering a gene product to a retinal cell in an individual, the method comprising administering to the individual a subject rAAV virion as described above. The gene product can be a polypeptide or an interfering RNA (e.g., an shRNA, an siRNA, and the like), an aptamer, or a site-specific endonuclease (e.g., an RNA-guided endonuclease), as described above. Delivering a gene product to a retinal cell can provide for treatment of a retinal disease. The retinal cell can be a photoreceptor, a retinal ganglion cell, a Müller cell, a bipolar cell, an amacrine cell, a horizontal cell, or a retinal pigmented epithelial cell. In some cases, the retinal cell is a photoreceptor cell, e.g., a rod or cone cell.

The present disclosure provides a method modifying a target nucleic acid in a retinal cell, the method comprising contacting the retinal cell with: 1) an rAAV virion of the present disclosure, wherein the rAAV virion comprises a heterologous nucleic acid comprising a nucleotide sequence encoding a CRISPR/Cas effector polypeptide that binds a guide RNA; and 2) the guide RNA. The present disclosure provides a method modifying a target nucleic acid in a retinal cell, the method comprising contacting the retinal cell with an rAAV virion of the present disclosure, wherein the rAAV virion comprises a heterologous nucleic acid comprising a nucleotide sequence encoding: i) a CRISPR/Cas effector polypeptide that binds a guide RNA; and ii) the guide RNA. In some cases, the method comprises contacting the retinal cell with a donor DNA template. In some cases, the CRISPR/Cas effector polypeptide is a Cas9 polypeptide. In some cases, the guide RNA is a single-guide RNA.

The present disclosure provides a method of treating an ocular disease (e.g., a retinal disease), the method comprising administering to an individual in need thereof an effective amount of a subject rAAV virion as described above. A subject rAAV virion can be administered via intraocular injection, e.g. by intravitreal injection, by subretinal injection, by suprachoroidal injection, or by any other convenient mode or route of administration. Other convenient modes or routes of administration include, e.g., intravenous, intranasal, etc.

A "therapeutically effective amount" will fall in a relatively broad range that can be determined through experimentation and/or clinical trials. For example, for in vivo injection, i.e., injection directly into the eye, a therapeutically effective dose will be on the order of from about $10^6$ to about $10^{15}$ of the rAAV virions, e.g., from about $10^8$ to $10^{12}$ rAAV virions. For example, for in vivo injection, i.e., injection directly into the eye, a therapeutically effective dose will be on the order of from about $10^6$ viral genomes (vg) to about $10^{15}$ vg of the rAAV virions, e.g., from about $10^8$ vg to $10^{12}$ vg. For in vitro transduction, an effective amount of rAAV virions to be delivered to cells will be on the order of from about $10^8$ to about $10^{13}$ of the rAAV virions. For example, for in vitro transduction, an effective amount of rAAV virions to be delivered to cells will be on the order of from about $10^8$ to about $10^{13}$ vg of the rAAV virions. As another example, for in vitro transduction, an effective amount of rAAV virions to be delivered to cells will be on the order of from about 10 vg/cell to about $10^4$ vg/cell.

Other effective dosages can be readily established by one of ordinary skill in the art through routine trials establishing dose response curves.

In some cases, more than one administration (e.g., two, three, four or more administrations) may be employed to achieve the desired level of gene expression. In some cases, the more than one administration is administered at various intervals, e.g., daily, weekly, twice monthly, monthly, every 3 months, every 6 months, yearly, etc. In some cases, multiple administrations are administered over a period of time of from 1 month to 2 months, from 2 months to 4 months, from 4 months to 8 months, from 8 months to 12 months, from 1 year to 2 years, from 2 years to 5 years, or more than 5 years.

Ocular diseases that can be treated using a subject method include, but are not limited to, acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; non-retinopathy diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber hereditary optic neuropathy; retinopathy of prematurity; disorders of color vision, including achromatopsia, protanopia, deuteranopia, and tritanopia; and Bietti's crystalline dystrophy.

The present disclosure provides methods of treating retinal disease. The methods generally involve administering an rAAV virion of the present disclosure, or a composition comprising an rAAV virion of the present disclosure, to an eye of an individual in need thereof. Non-limiting methods for assessing treatment of retinal diseases include measuring functional changes, e.g. changes in visual acuity (e.g. BCVA), visual field (e.g. visual field perimetry), electrophysiological responsiveness to light and dark (e.g. ERG, VEP), color vision, and/or contrast sensitivity; measuring changes in anatomy or health using anatomical and/or photographic measures, e.g. OCT, fundus photography, and/or autofluorescence; and measuring ocular motility (e.g. nystagmus, fixation preference, and stability).

For example, one of ordinary skill in the art could readily determine an effective amount of rAAV virions by testing for an effect on one or more parameters, e.g. visual acuity, visual field, electrophysiological responsiveness to light and dark, color vision, contrast sensitivity, anatomy, retinal health and vasculature, ocular motility, fixation preference, and stability. In some cases, administering an effective amount of an rAAV virion of the present disclosure results in a decrease in the rate of loss of retinal function, anatomical integrity, or retinal health, e.g. a 2-fold, 3-fold, 4-fold, or 5-fold or more decrease in the rate of loss and hence progression of disease, e.g. a 10-fold decrease or more in the rate of loss and hence progression of disease. In some cases, administering an effective amount of an rAAV virion of the present disclosure results in a gain in retinal function, an improvement in retinal anatomy or health, and/or a stabilization in ocular motility, e.g. a 2-fold, 3-fold, 4-fold or 5-fold improvement or more in retinal function, retinal anatomy or health, and/or stability of the orbital, e.g. a 10-fold improvement or more in retinal function, retinal anatomy or health, and/or stability of the orbital.

Nucleic Acids and Host Cells

The present disclosure provides an isolated nucleic acid comprising a nucleotide sequence that encodes a subject variant adeno-associated virus (AAV) capsid protein as described above, where the variant AAV capsid protein comprises an insertion of from about 7 amino acids to about 20 amino acids in the GH loop or loop IV relative to a corresponding parental AAV capsid protein, or where the variant AAV capsid protein comprises a replacement of from about 7 amino acids to about 20 amino acids in the GH loop or loop IV relative to a corresponding parental AAV capsid protein with a heterologous peptide of from about 7 amino acids to about 20 amino acids; and where the variant capsid protein, when present in an AAV virion, provides for increased infectivity of a retinal cell compared to the infectivity of the retinal cell by an AAV virion comprising the corresponding parental AAV capsid protein. A subject isolated nucleic acid can be an AAV vector, e.g., a recombinant AAV vector.

Insertion Peptides

A variant AAV capsid protein encoded by a subject nucleic acid has an insertion peptide of from about 7 amino acids to about 10 amino acids in length, or from about 10 amino acids to about 20 amino acids in length, inserted into the GH loop of an AAV capsid. The insertion peptide has a length of 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, or 20 amino acids. Suitable insertion peptides are as described above. Suitable insertion peptides include a peptide of any one of Formulas I-VIII, as described above. Suitable insertion peptides include a peptide set forth in the table above. The insertion of the insertion peptide into a parental AAV capsid will in some cases replace an endogenous stretch of from about 7 amino acids to about 20 amino acids or from about 10 amino acids to about 20 amino acids in the GH loop or loop IV. Thus, in some cases, a variant AAV capsid protein encoded by a subject nucleic acid comprises a replacement of from about 7 amino acids to about 10 amino acids in the GH loop or loop IV relative to a corresponding parental AAV capsid protein with a heterologous peptide of from about 7 amino acids to about 10 amino acids, where suitable heterologous peptides include a peptide as described above. In other cases, a variant AAV capsid protein encoded by a subject nucleic acid comprises a replacement of from about 10 amino acids to about 20 amino acids in the GH loop or loop IV relative to a corresponding parental AAV capsid protein with a heterologous peptide of from about 10 amino acids to about 20 amino acids, where suitable heterologous peptides include a peptide of any one of Formulas I-VIII, or a peptide set forth in Table 1 or Table 2 above, as described above.

A subject recombinant AAV vector can be used to generate a subject recombinant AAV virion, as described above.

Thus, the present disclosure provides a recombinant AAV vector that, when introduced into a suitable cell, can provide for production of a subject recombinant AAV virion.

The present invention further provides host cells, e.g., isolated (genetically modified) host cells, comprising a subject nucleic acid. A subject host cell can be an isolated cell, e.g., a cell in in vitro culture. A subject host cell is useful for producing a subject rAAV virion, as described below. Where a subject host cell is used to produce a subject rAAV virion, it is referred to as a "packaging cell." In some cases, a subject host cell is stably genetically modified with a subject nucleic acid. In other instances, a subject host cell is transiently genetically modified with a subject nucleic acid.

A subject nucleic acid is introduced stably or transiently into a host cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, 293 cells, 293T cells, COS cells, HeLa cells, Vero cells, 3T3 mouse fibroblasts, C3H10T1/2 fibroblasts, CHO cells, and the like. Non-limiting examples of suitable host cells include, e.g., HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like. A subject host cell can also be made using a baculovirus to infect insect cells such as Sf9 cells, which produce AAV (see, e.g., U.S. Pat. No. 7,271,002; U.S. patent application Ser. No. 12/297,958)

In some cases, a subject genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other cases, a subject host cell further comprises an rAAV vector. An rAAV virion can be generated using a subject host cell. Methods of generating an rAAV virion are described in, e.g., U.S. Patent Publication No. 2005/0053922 and U.S. Patent Publication No. 2009/0202490.

Examples of Non-Limiting Aspects of the Disclosure

Aspects Set A

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A recombinant adeno-associated virus (rAAV) virion comprising:
 a) a variant AAV capsid protein, wherein the variant AAV capsid protein comprises an insertion of a heterologous peptide comprising the amino acid sequence set forth in any one of SEQ ID NOs:1-30, wherein the heterologous peptide has a length of from 10 amino acids to 20 amino acids, and wherein the variant capsid protein confers increased infectivity of a retinal cell compared to the infectivity of the retinal cell by a control AAV virion comprising a corresponding parental AAV capsid protein not comprising the heterologous peptide; and
 b) a heterologous nucleic acid comprising one or more nucleotide sequences encoding one or more heterologous gene products.

Aspect 2. The rAAV virion of aspect 1, wherein the heterologous peptide has a length of 10 amino acids.

Aspect 3. The rAAV virion of aspect 1, wherein the heterologous peptide has a length of 16 amino acids.

Aspect 4. The rAAV virion of aspect 1, wherein the heterologous peptide has a length of 20 amino acids.

Aspect 5. The rAAV virion of aspect 1, wherein the heterologous peptide comprises the amino acid sequence set forth in SEQ ID NO:16, and wherein the heterologous peptide has a length of 16 amino acids.

Aspect 6. The rAAV virion of aspect 1, wherein the heterologous peptide comprises the amino acid sequence set forth in SEQ ID NO:1, and wherein the heterologous peptide has a length of 10 amino acids.

Aspect 7. The rAAV virion of aspect 1, wherein the heterologous peptide comprises the amino acid sequence set forth in SEQ ID NO:2, and wherein the heterologous peptide has a length of 10 amino acids.

Aspect 8. The rAAV virion of aspect 1, wherein the heterologous peptide comprises the amino acid sequence set forth in SEQ ID NO:3, and wherein the heterologous peptide has a length of 10 amino acids.

Aspect 9. The rAAV virion of any one of aspects 1-8, wherein the rAAV virion exhibits at least 5-fold increased infectivity of a retinal cell compared to the infectivity of the retinal cell by a control AAV virion comprising the corresponding parental AAV capsid protein.

Aspect 10. The rAAV virion of any one of aspects 1-8, wherein the rAAV virion exhibits at least 10-fold increased infectivity of a retinal cell compared to the infectivity of the retinal cell by an AAV virion comprising the corresponding parental AAV capsid protein.

Aspect 11. The rAAV virion of any one of aspects 1-8, wherein the insertion of the heterologous peptide replaces a contiguous stretch of from 5 amino acids to 20 amino acids of a parental AAV capsid protein.

Aspect 12. The rAAV virion of any one of aspects 1-11, wherein the insertion site is within amino acids corresponding to amino acids 570 and 611 of VP1 of AAV2, or the corresponding position in the capsid protein of another AAV serotype.

Aspect 13. The rAAV virion of aspect 12, wherein the insertion site is between amino acids corresponding to amino acids 587 and 588 of VP1 of AAV2, or the corresponding position in the capsid protein of another AAV serotype.

Aspect 14. The rAAV virion of any one of aspects 1-11, wherein the insertion site is within amino acids corresponding to amino acids 585 and 598 of VP1 of AAV2, or the corresponding position in the capsid protein of another AAV serotype.

Aspect 15. The rAAV virion of any one of aspects 1-14, wherein the increased infectivity comprises increased specificity or selectivity for the retinal cell compared to the specificity or selectivity for the retinal cell by a control AAV virion comprising the corresponding to parental AAV capsid protein Aspect 16. The rAAV virion of any one of aspects 1-14, wherein the variant capsid protein induces a decreased level of immunogenicity in a retinal cell compared to the level of immunogenicity induced by a control AAV virion comprising the corresponding parental AAV capsid protein.

Aspect 17. The rAAV virion of any one of aspects 1-16, wherein the one or more heterologous gene products is an interfering RNA or an aptamer.

Aspect 18. The rAAV virion of any one of aspects 1-16, wherein the one or more heterologous gene products is a polypeptide.

Aspect 19. The rAAV virion of aspect 18, wherein the polypeptide is a neuroprotective polypeptide, an anti-angiogenic polypeptide, or a polypeptide that enhances function of a retinal cell.

Aspect 20. The rAAV virion of aspect 18, wherein the polypeptide is a light-responsive polypeptide, an opsin, a short-wavelength opsin (SW-opsin), a medium-wavelength opsin (MW-opsin), a long-wavelength opsin (LW-opsin), a rhodopsin, a cone opsin, a human opsin, a non-human opsin, a humanized opsin, or any combination thereof.

Aspect 21. The rAAV virion of aspect 18, wherein the polypeptide is a CRISPR/Cas effector polypeptide, a deaminase, a reverse transcriptase, or any combination or fusion thereof.

Aspect 22. The rAAV virion of any one of aspects 1-16, wherein the one or more heterologous gene products comprise a CRISPR/Cas effector polypeptide and a guide RNA.

Aspect 23. The rAAV virion of any one of aspects 1-22, wherein the retinal cell is a photoreceptor cell.

Aspect 24. The rAAV virion of aspect 23, wherein the photoreceptor cell is a cone cell.

Aspect 25. The rAAV virion of aspect 23, wherein the photoreceptor cell is a rod cell.

Aspect 26. The rAAV virion of any one of aspects 1-25, wherein the one or more nucleotide sequences is operably linked to a promoter.

Aspect 27. The rAAV virion of aspect 26, wherein the promoter is a retinal cell specific promoter.

Aspect 28. The rAAV virion of any one of aspects 1-22, wherein the retinal cell is a not a photoreceptor cell.

Aspect 29. The rAAV virion of any one of aspects 1-22, wherein the retinal cell is an ON-bipolar cell or an OFF-bipolar cell.

Aspect 30. The rAAV virion of aspect 29, wherein the one or more nucleotide sequences is operably linked to an ON-bipolar cell-specific promoter or an OFF-bipolar cell-specific promoter.

Aspect 31. The rAAV virion of any one of aspects 1-22, wherein the retinal cell is a retinal ganglion cell (RGC).

Aspect 32. The rAAV virion of aspect 33, wherein the one or more nucleotide sequences is operably linked to an RGC-specific promoter.

Aspect 33. The rAAV virion of any one of aspects 1-22, wherein the retinal cell is an amacrine cell.

Aspect 34. The rAAV virion of aspect 33, wherein the one or more nucleotide sequences is operably linked to an amacrine cell-specific promoter.

Aspect 35. The rAAV virion of any one of aspects 1-22, wherein the retinal cell is a horizontal cell.

Aspect 36. The rAAV virion of aspect 35, wherein the one or more nucleotide sequences is operably linked to a horizontal cell-specific promoter.

Aspect 37. A composition comprising a rAAV virion of any one of aspects 1-36.

Aspect 38. A pharmaceutical composition comprising:
a) a rAAV virion of any one of aspects 1-36; and
b) a pharmaceutically acceptable excipient.

Aspect 39. A method of delivering a gene product to a retinal cell, the method comprising contacting a rAAV virion according any one of aspects 1-36 with the retinal cell.

Aspect 40. A method of delivering a gene product to a retinal cell, the method comprising contacting a composition of aspect 37 or 38 with the retinal cell.

Aspect 41. The method of aspect 39 or 40, wherein the retinal cell is in vitro or ex vivo.

Aspect 42. The method of aspect 39 or 40, wherein the retinal cell is in vivo.

Aspect 43. A method of treating a retinal condition or disorder in a subject, the method comprising administering a therapeutically effective amount of an rAAV virion of any one of aspects 1-36 to the subject.

Aspect 44. A method of treating a retinal condition or disorder in a subject, comprising administering a therapeutically effective amount of a composition of aspect 37 or 38 to the subject.

Aspect 45. The method of aspect 43 or 44, wherein the administering comprises an intraocular injection or an intraocular infusion.

Aspect 46. The method of aspect 45, wherein the intraocular injection comprises intravitreal injection, subretinal injection, or suprachoroidal injection.

Aspect 47. The method of aspect 45, wherein the intraocular infusion is an intravitreal infusion, a subretinal infusion, or a suprachoroidal infusion.

Aspect 48. The method of any one of aspects 43-47, wherein the retinal condition or disorder is glaucoma, retinal degeneration, loss of photoreceptor function or activity, loss of photoreceptor cells, retinitis pigmentosa, macular degeneration, retinoschisis, Leber Congenital Amaurosis, diabetic retinopathy, achromotopsia, or color blindness.

Aspect 49. A variant adeno-associated virus (AAV) capsid polypeptide, wherein the variant AAV capsid protein comprises an insertion of a heterologous peptide comprising the amino acid sequence set forth in any one of SEQ ID NOs:1-30, wherein the heterologous peptide has a length of from 10 amino acids to 20 amino acids.

Aspect 50. A nucleic acid comprising a nucleotide sequence encoding the variant AAV capsid polypeptide of aspect 49.

Aspects Set B

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A recombinant adeno-associated virus (rAAV) virion comprising: a) a variant AAV capsid protein, wherein the variant AAV capsid protein comprises an insertion of a heterologous peptide comprising the amino acid sequence set forth in any one of SEQ ID NOs:1 and 4-30, wherein the heterologous peptide has a length of from 7 amino acids to 20 amino acids, and wherein the variant capsid protein confers increased infectivity of a retinal cell compared to the infectivity of the retinal cell by a control AAV virion comprising a corresponding parental AAV capsid protein not comprising the heterologous peptide; and b) a heterologous nucleic acid comprising one or more nucleotide sequences encoding one or more heterologous gene products.

Aspect 2. A recombinant adeno-associated virus (rAAV) virion comprising: a) a variant AAV capsid protein, wherein the variant AAV capsid protein comprises an insertion of a heterologous peptide comprising the amino acid sequence set forth in any one of SEQ ID NOs:2 and 3, wherein the heterologous peptide has a length of from 7 amino acids to 20 amino acids, and wherein the variant capsid protein confers increased infectivity of a retinal cell compared to the infectivity of the retinal cell by a control AAV virion comprising a corresponding parental AAV capsid protein not comprising the heterologous peptide; and b) a heterologous nucleic acid comprising one or more nucleotide sequences encoding one or more heterologous gene products.

Aspect 3. The rAAV virion of aspect 1 or 2, wherein the heterologous peptide has a length of 7 amino acids.

Aspect 4. The rAAV virion of aspect 1 or 2, wherein the heterologous peptide has a length of 10 amino acids, 16 amino acids, or 20 amino acids.

Aspect 5. The rAAV virion of aspect 1, wherein the heterologous peptide comprises the amino acid sequence set forth in SEQ ID NO:16, and wherein the heterologous peptide has a length of 16 amino acids.

Aspect 6. The rAAV virion of aspect 1, wherein the heterologous peptide comprises the amino acid sequence set forth in SEQ ID NO:1, and wherein the heterologous peptide has a length of 10 amino acids.

Aspect 7. The rAAV virion of aspect 2, wherein the heterologous peptide: a) comprises the amino acid sequence set forth in SEQ ID NO:2, and wherein the heterologous peptide has a length of 10 amino acids; or b) comprises the amino acid sequence set forth in SEQ ID NO:3, and wherein the heterologous peptide has a length of 10 amino acids.

Aspect 8. The rAAV virion of aspect 2, wherein the heterologous peptide comprises the amino acid sequence set forth in SEQ ID NO:32, and wherein the heterologous peptide has a length of 7 amino acids.

Aspect 9. The rAAV virion of aspect 2, wherein the heterologous peptide comprises the amino acid sequence set forth in SEQ ID NO:33, and wherein the heterologous peptide has a length of 7 amino acids.

Aspect 10. The rAAV virion of any one of aspects 1-9, wherein the rAAV virion exhibits at least 5-fold increased infectivity of a retinal cell compared to the infectivity of the retinal cell by a control AAV virion comprising the corresponding parental AAV capsid protein.

Aspect 11. The rAAV virion of any one of aspects 1-9, wherein the rAAV virion exhibits at least 10-fold increased infectivity of a retinal cell compared to the infectivity of the retinal cell by an AAV virion comprising the corresponding parental AAV capsid protein.

Aspect 12. The rAAV virion of any one of aspects 1-9, wherein the insertion of the heterologous peptide replaces a contiguous stretch of from 5 amino acids to 20 amino acids of a parental AAV capsid protein.

Aspect 13. The rAAV virion of any one of aspects 1-12, wherein the insertion site is within amino acids corresponding to amino acids 570 and 611 of VP1 of AAV2, or the corresponding position in the capsid protein of another AAV serotype.

Aspect 14. The rAAV virion of aspect 13, wherein the insertion site is between amino acids corresponding to amino acids 587 and 588 of VP1 of AAV2, or the corresponding position in the capsid protein of another AAV serotype.

Aspect 15. The rAAV virion of any one of aspects 1-12, wherein the insertion site is within amino acids corresponding to amino acids 585 and 598 of VP1 of AAV2, or the corresponding position in the capsid protein of another AAV serotype.

Aspect 16. The rAAV virion of any one of aspects 1-15, wherein the increased infectivity comprises increased specificity or selectivity for the retinal cell compared to the specificity or selectivity for the retinal cell by a control AAV virion comprising the corresponding to parental AAV capsid protein Aspect 17. The rAAV virion of any one of aspects 1-15, wherein the variant capsid protein induces a decreased level of immunogenicity in a retinal cell compared to the level of immunogenicity induced by a control AAV virion comprising the corresponding parental AAV capsid protein.

Aspect 18. The rAAV virion of any one of aspects 1-17, wherein the one or more heterologous gene products is an interfering RNA or an aptamer.

Aspect 19. The rAAV virion of any one of aspects 1-17, wherein the one or more heterologous gene products is a polypeptide.

Aspect 20. The rAAV virion of aspect 19, wherein the polypeptide is a neuroprotective polypeptide, an anti-angiogenic polypeptide, or a polypeptide that enhances function of a retinal cell.

Aspect 21. The rAAV virion of aspect 19, wherein the polypeptide is a light-responsive polypeptide, an opsin, a short-wavelength opsin (SW-opsin), a medium-wavelength opsin (MW-opsin), a long-wavelength opsin (LW-opsin), a rhodopsin, a cone opsin, a human opsin, a non-human opsin, a humanized opsin, or any combination thereof.

Aspect 22. The rAAV virion of aspect 19, wherein the polypeptide is a CRISPR/Cas effector polypeptide, a deaminase, a reverse transcriptase, or any combination or fusion thereof.

Aspect 23. The rAAV virion of any one of aspects 1-17, wherein the one or more heterologous gene products comprise a CRISPR/Cas effector polypeptide and a guide RNA.

Aspect 24. The rAAV virion of any one of aspects 1-23, wherein the retinal cell is a photoreceptor cell.

Aspect 25. The rAAV virion of aspect 24, wherein the photoreceptor cell is a cone cell.

Aspect 26. The rAAV virion of aspect 24, wherein the photoreceptor cell is a rod cell.

Aspect 27. The rAAV virion of any one of aspects 1-26, wherein the one or more nucleotide sequences is operably linked to a promoter.

Aspect 28. The rAAV virion of aspect 27, wherein the promoter is a retinal cell specific promoter.

Aspect 29. The rAAV virion of any one of aspects 1-23, wherein the retinal cell is a not a photoreceptor cell.

Aspect 30. The rAAV virion of any one of aspects 1-23, wherein the retinal cell is an ON-bipolar cell or an OFF-bipolar cell.

Aspect 31. The rAAV virion of aspect 30, wherein the one or more nucleotide sequences is operably linked to an ON-bipolar cell-specific promoter or an OFF-bipolar cell-specific promoter.

Aspect 32. The rAAV virion of any one of aspects 1-23, wherein the retinal cell is a retinal ganglion cell (RGC).

Aspect 33. The rAAV virion of aspect 32, wherein the one or more nucleotide sequences is operably linked to an RGC-specific promoter.

Aspect 34. The rAAV virion of any one of aspects 1-23, wherein the retinal cell is an amacrine cell.

Aspect 35. The rAAV virion of aspect 34, wherein the one or more nucleotide sequences is operably linked to an amacrine cell-specific promoter.

Aspect 36. The rAAV virion of any one of aspects 1-23, wherein the retinal cell is a horizontal cell.

Aspect 37. The rAAV virion of aspect 36, wherein the one or more nucleotide sequences is operably linked to a horizontal cell-specific promoter.

Aspect 38. A composition comprising a rAAV virion of any one of aspects 1-37.

Aspect 39. A pharmaceutical composition comprising:
a) a rAAV virion of any one of aspects 1-37; and
b) a pharmaceutically acceptable excipient.

Aspect 40. A method of delivering a gene product to a retinal cell, the method comprising contacting a rAAV virion according any one of aspects 1-37 with the retinal cell.

Aspect 41. A method of delivering a gene product to a retinal cell, the method comprising contacting a composition of aspect 38 or 39 with the retinal cell.

Aspect 42. The method of aspect 40 or 41, wherein the retinal cell is in vitro or ex vivo.

Aspect 43. The method of aspect 40 or 41, wherein the retinal cell is in vivo.

Aspect 44. A method of treating a retinal condition or disorder in a subject, the method comprising administering a therapeutically effective amount of an rAAV virion of any one of aspects 1-37 to the subject.

Aspect 45. A method of treating a retinal condition or disorder in a subject, comprising administering a therapeutically effective amount of a composition of aspect 38 or 39 to the subject.

Aspect 46. The method of aspect 44 or 45, wherein the administering comprises an intraocular injection or an intraocular infusion.

Aspect 47. The method of aspect 46, wherein the intraocular injection comprises intravitreal injection, subretinal injection, or suprachoroidal injection.

Aspect 48. The method of aspect 46, wherein the intraocular infusion is an intravitreal infusion, a subretinal infusion, or a suprachoroidal infusion.

Aspect 49. The method of any one of aspects 44-48, wherein the retinal condition or disorder is glaucoma, retinal degeneration, loss of photoreceptor function or activity, loss of photoreceptor cells, retinitis pigmentosa, macular degeneration, retinoschisis, Leber Congenital Amaurosis, diabetic retinopathy, achromotopsia, or color blindness.

Aspect 50. A variant adeno-associated virus (AAV) capsid polypeptide, wherein the variant AAV capsid protein comprises an insertion of a heterologous peptide comprising the amino acid sequence set forth in any one of SEQ ID NOs:1 and 4-30, wherein the heterologous peptide has a length of from 10 amino acids to 20 amino acids.

Aspect 51. A variant adeno-associated virus (AAV) capsid polypeptide, wherein the variant AAV capsid protein comprises an insertion of a heterologous peptide comprising the amino acid sequence set forth in any one of SEQ ID NOs:2 and 3, wherein the heterologous peptide has a length of from 10 amino acids to 20 amino acids.

Aspect 52. A nucleic acid comprising a nucleotide sequence encoding the variant AAV capsid polypeptide of aspect 50 or 51.

Aspect 53. A variant adeno-associated virus (AAV) capsid polypeptide, wherein the variant AAV capsid protein comprises an insertion of a heterologous peptide comprising the amino acid sequence set forth in any one of SEQ ID NOs:31 and 34-45, wherein the heterologous peptide has a length of from 7 amino acids to 10 amino acids.

Aspect 54. A variant adeno-associated virus (AAV) capsid polypeptide, wherein the variant AAV capsid protein comprises an insertion of a heterologous peptide comprising the amino acid sequence set forth in any one of SEQ ID NOs:32 and 33, wherein the heterologous peptide has a length of from 7 amino acids to 10 amino acids.

Aspect 55. A nucleic acid comprising a nucleotide sequence encoding the variant AAV capsid polypeptide of aspect 51 or 52.

Aspect 56. The rAAV virion of aspect 19, wherein the polypeptide is a metabotropic glutamate receptor (mGluR).

Aspect 57. The rAAV virion of aspect 19, wherein the polypeptide is a metabotropic glutamate receptor (mGluR) selected from the group consisting of mGluR1, mGluR2, mGluR3, mGluR4, mGluR5, mGluR6, mGluR7, and mGluR8, or a functional fragment or variant thereof.

Aspect 58. The rAAV virion of aspect 19, wherein the polypeptide is mGluR2, or a functional fragment or variant thereof.

Aspect 59. The rAAV virion of aspect 19, wherein the polypeptide comprises a fusion polypeptide.

Aspect 60. The rAAV virion of aspect 19, wherein the polypeptide comprises a fusion polypeptide comprising an affinity tag.

Aspect 61. The rAAV virion of aspect 19, wherein the polypeptide comprises a fusion polypeptide comprising an affinity tag, where the affinity tag comprises a SNAP sequence, a CLIP sequence or a HALO sequence.

Aspect 62. The rAAV virion of aspect 19, wherein the polypeptide comprises a fusion polypeptide comprising an affinity tag sequence and an mGluR sequence, where the affinity tag sequence comprises a SNAP sequence and the mGluR sequence comprises an mGluR2 sequence.

Aspect 63. The rAAV virion of aspect 27, wherein the promoter is selected from the group consisting of a SNCG promoter, a CAG promoter, a mini CAG promoter, a CBh promoter, a NEFH promoter, a GRK1 promoter, a RLBP1 promoter, a VMD2 promoter, a Syn1 promoter and a Syn1 (enhSyn1) promoter.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s);

nt, nucleotide(s); i.m., intramuscular(ly); i.p., intraperitoneal(ly); s.c., subcutaneous(ly); and the like.

Example 1: Characterization of rAAV Virions with Variant Capsids

Recombinant AAV virions containing capsids with LAL-GETTRAA (SEQ ID NO:2; "variant 3") or LAHQDTTRPA (SEQ ID NO:3; "variant 6") inserted between amino acid 587 and 588 of the AAV2 capsid protein in the AAV2 capsid were analyzed. The rAAV used to generate the virions included a nucleotide sequence encoding green fluorescent protein (GFP) fused to the C-terminus of ChrimsonR.

Cynomolgus macaques between 3-10 years of age were used. Bilateral intravitreal injections were performed once using a 30 g needle to deliver 5.0E+11 viral genomes per eye in a 50 µL volume. Onset and progression of GFP expression was monitored weekly by confocal scanning laser ophthalmoscopy (cSLO) imaging using the autofluorescence function of the Heidelberg Spectralis HRA/OCT system. Six to eight weeks after intravitreal injection the primates were euthanized and both eyes (whole globes) were carefully harvested. After enucleation, excess orbital tissue was carefully trimmed and removed. A small (5 mm) slit was made ~2 mm from the limbus and the whole eye was placed in a vial containing 4% paraformaldehyde (PFA) and incubated at 4° C. overnight. After overnight fixation, the PFA was decanted and replaced with phosphate buffered saline (PBS). The whole eye was dissected to remove the anterior structures (cornea, lens, and ciliary body) and then 4 cuts were made to the posterior eye to enable the tissue to lie nearly flat. A fluorescent dissection microscope was used to visualize GFP expression in the entire retina, by direct fluorescence upon filtered UV excitation. The retinal tissue was then dissected into central and peripheral pieces, separated from the underlying tissues, additionally rinsed in PBS, embedded in agarose, sectioned, mounted on microscope slides, and examined by laser-scanning confocal microscopy. After sectioning 4',6-diamidino-2-phenylindole (DAPI) was used to label cell nuclei. GFP expression is detected by direct fluorescence. Images are acquired at different magnifications to evaluate transduction in the different cell layers.

The data are depicted in FIG. 9A-9J.

Figure 9A:
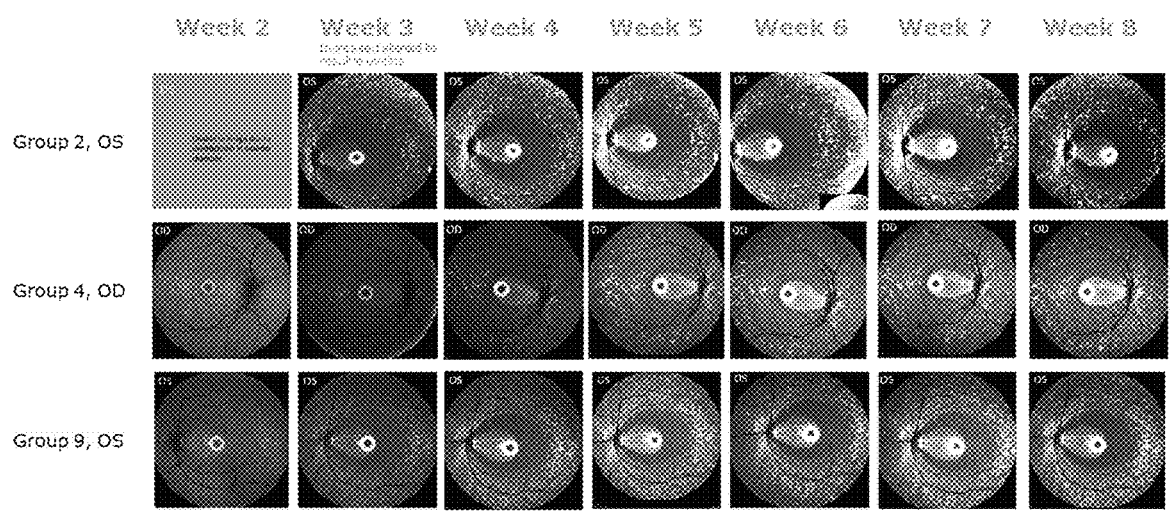
FIG. 9A-9J depict expression of green fluorescent protein (GFP) in non-human primate retina following intravitreal injection of recombinant AAV (rAAV) virions, comprising variant capsids as described herein.
Figure 9B:
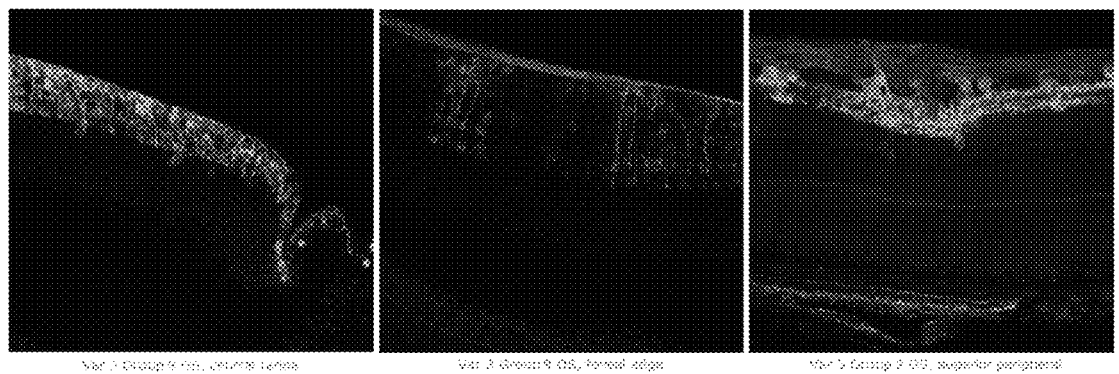
Figure 9C:
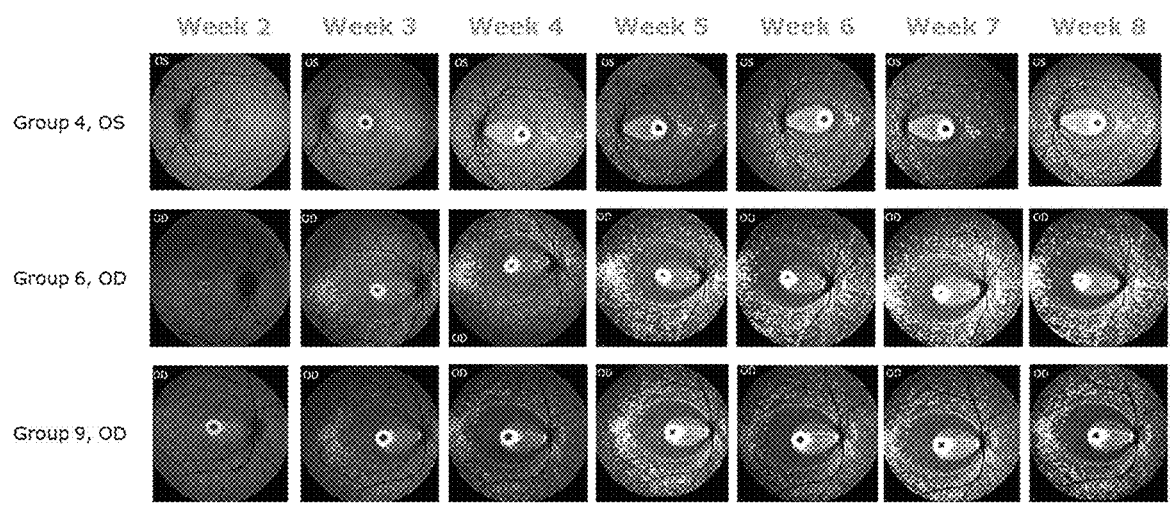

FIG. 9B (Variant 3) shows retinas expressing GFP in cells of the inner retina. Based on anatomical localization in the ganglion cell layer and the inner nuclear layer, rAAV particles appear to infect and express GFP in ganglion, amacrine, and Müller cells.

Figure 9D:
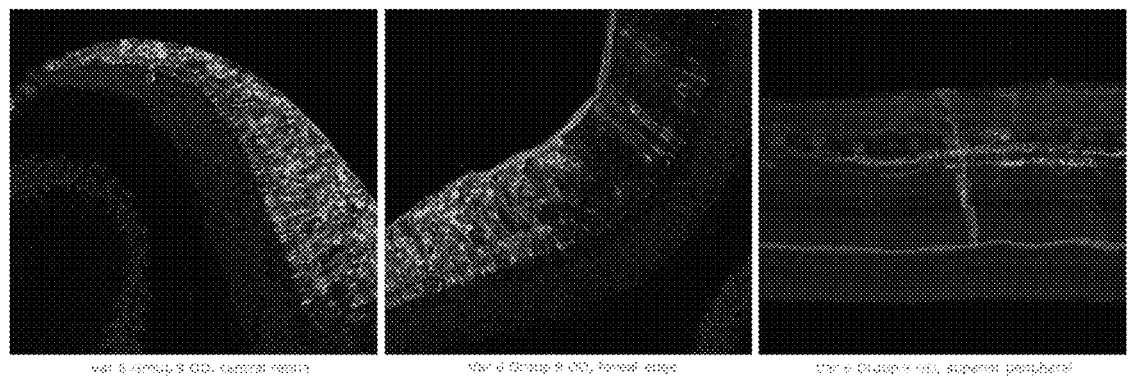
Figure 9E:
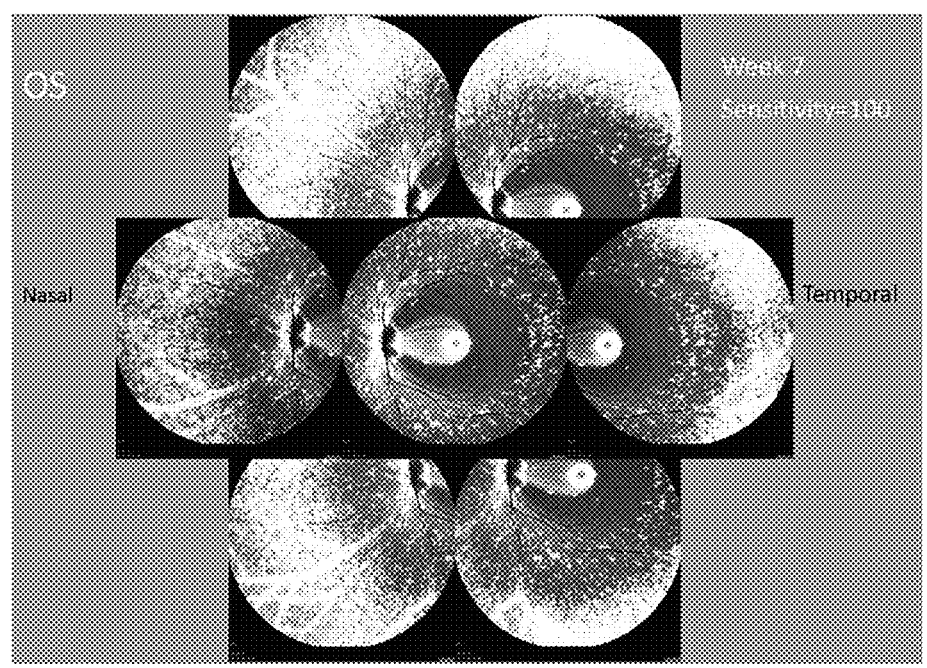
Figure 9F:
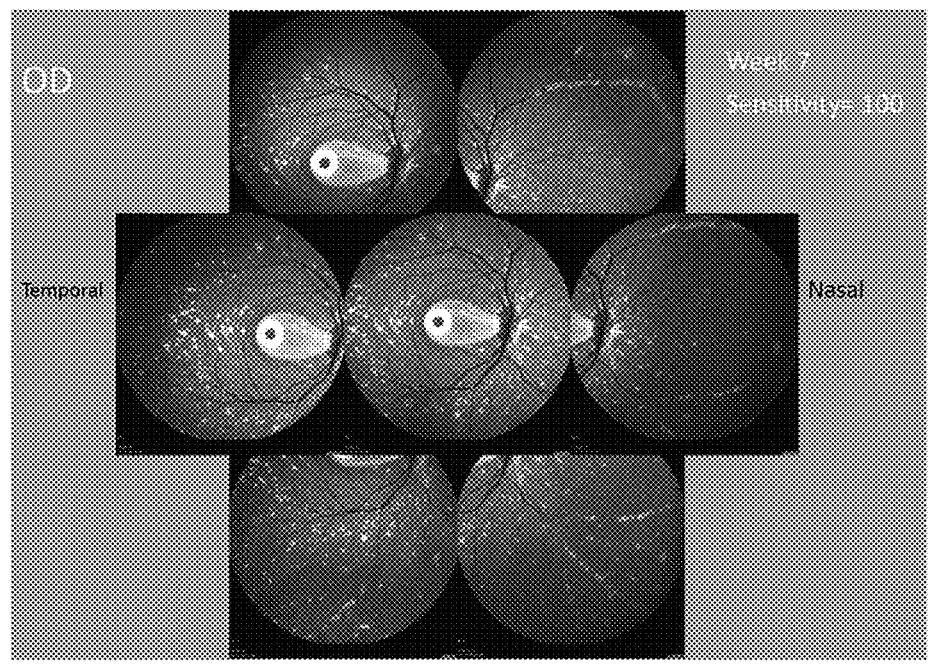
Figure 9G:
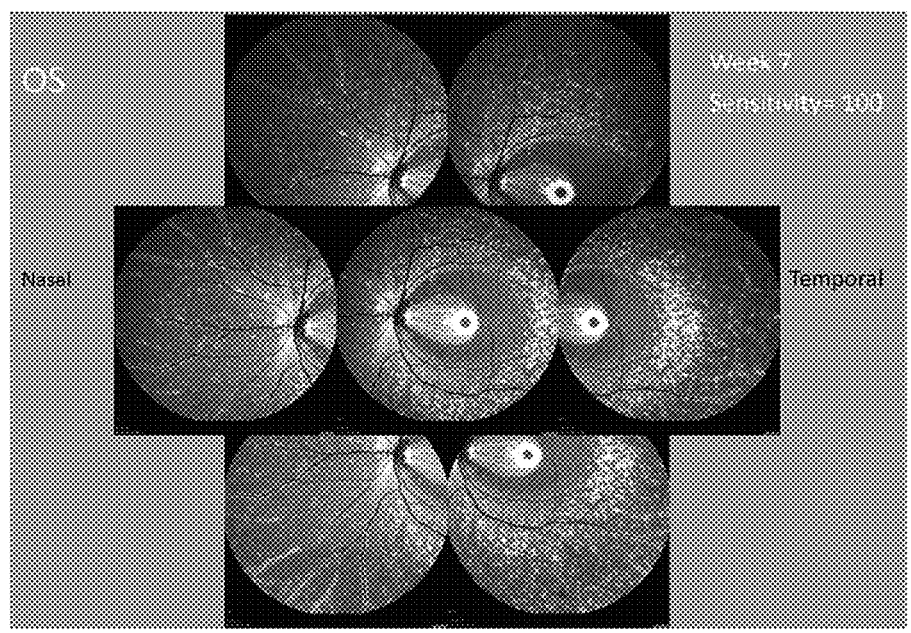
Figure 9H:
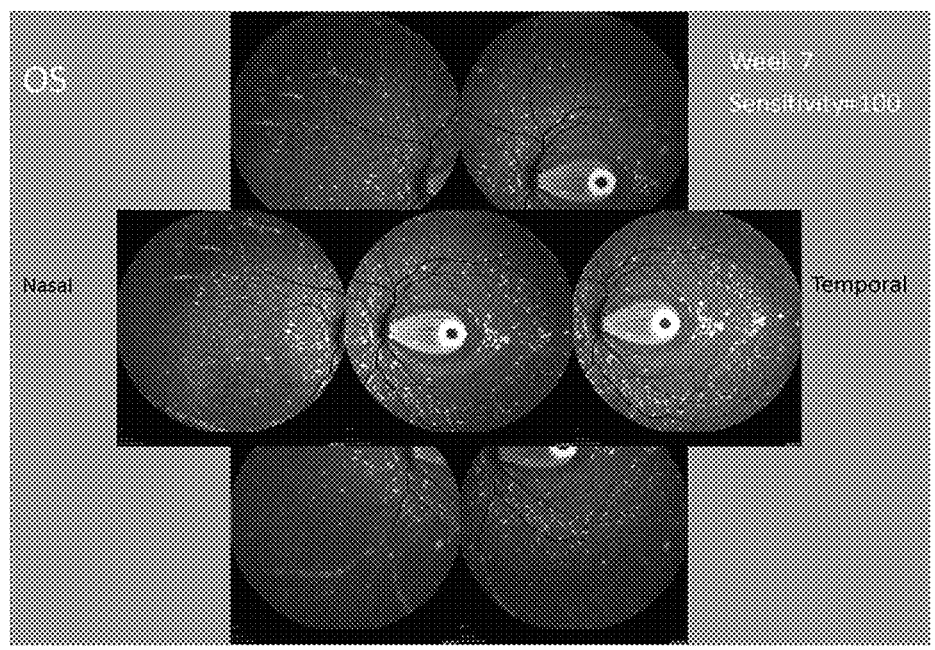
Figure 9I:
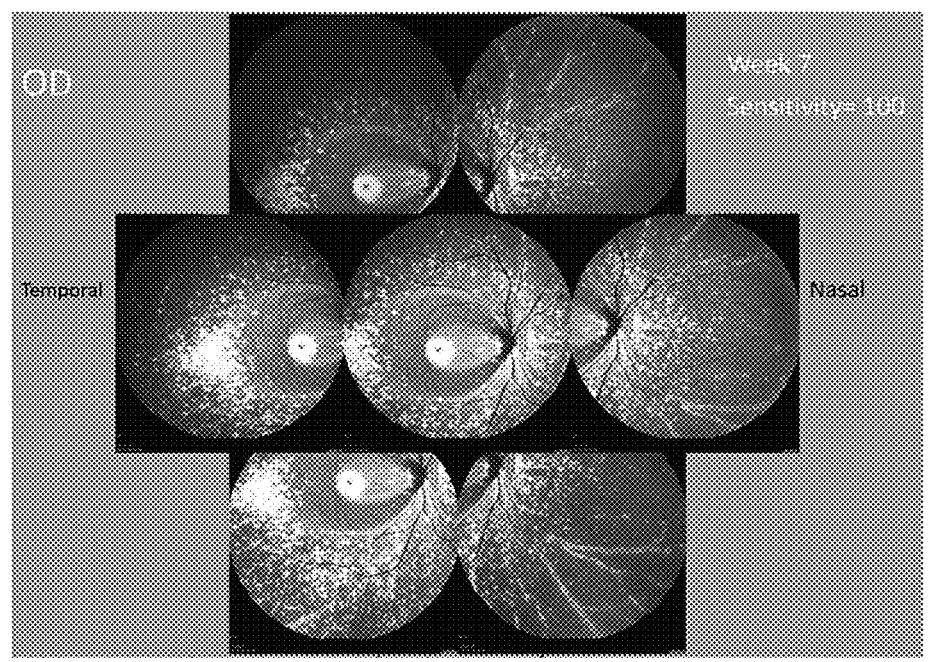
Figure 9J:
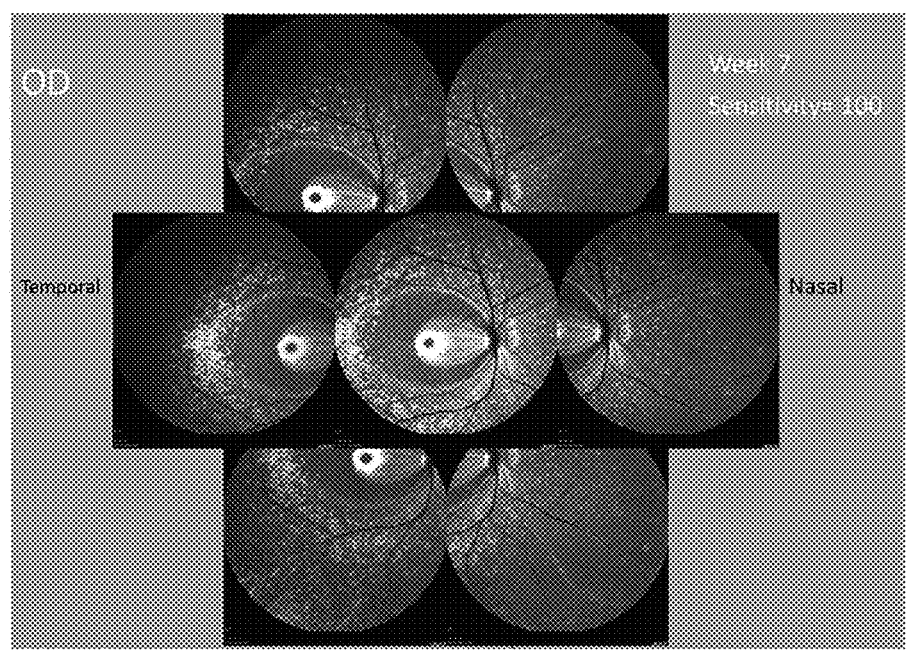

FIG. 9D (Variant 6) shows retinas expressing GFP in cells of the inner retina. Based on anatomical localization in the ganglion cell layer and the inner nuclear layer, rAAV particles appear to infect and express GFP in ganglion, amacrine, and Müller cells.

Example 2: Capsid Variants Associated with Enhanced Retinal Infectivity of AAV Virions Multiple rounds of in vivo selection were carried out in non-human primates, involving intravitreal administration of pooled AAV libraries, recovery of viral genome DNA from retinal cell layers and next generation sequencing of the recovered cap variant DNA after each round. Deep sequencing was performed on the initial plasmid library, the initial AAV packaged library and the cap variants DNA recovered after each round of selection. Capsid variants were analyzed on the amino acid level (i.e. variants with varying DNA sequences encoding the same amino acid sequence were pooled together for analysis). The number of reads for each amino acid sequences was then counted across the rounds of selection.

Exemplary variants for each library were identified using a multi-step analysis that included: (1) ranking of the capsid variants based on the enrichment in the final round of selection relative to the initial plasmid library; (2) determination of packaging efficiency by measuring the ratio of packaged AAV relative to the initial plasmid library (selection criteria: packaging factor>2); (3) determination of the distribution of reads between the central and peripheral retina in the final round of selection (selection criteria: at least 10% of total reads for this round are from the central retina). For variants with similar scores, variants with diversity in the amino acids sequence were selected.

The following capsids from the following libraries shown in Table 3, below, were selected for further evaluation.

TABLE 3

| SEQ ID NO: | Variant # | Peptide | Library |
|---|---|---|---|
| 1 | 2 | LAHQDTTKNS | 7-mer |
| 5 | 37 | LAHQDSTKNA | 7-mer |
| 6 | 38 | LAHQDATKNA | 7-mer |
| 12 | 48 | LALSEATRPA | 7-mer |
| 13 | 49 | LAKDETKNSA | 7-mer |
| 16 | 1 | LQRGNRQTTTADVNTQ | LS588 |
| 18 | 43 | LQRGNRQATTEDVNTQ | LS588 |
| 26 | 45 | SRTNTPSGTTTQPTLQFSQ | LS454 |
| 27 | 58 | SKTDTPSGTTTQSRLQFSQ | LS454 |

A. Packaging Efficiency of Capsid Variants Compared to AAV2 Parental Serotype

The viral genome used to generate recombinant AAV virions (rAAV) included a nucleotide sequence encoding green fluorescence protein (GFP) fused to the C-terminus of microbial algae opsin ChrimsonR. rAAV were generated by triple plasmid transfection in adherent HEK293T cells and purified by iodixanol gradient ultracentrifugation, followed by concentration and buffer exchange. The purified rAAV were formulated at 1-2E.0+13 viral genomes per milliliter (vg/mL) in DPBS supplemented with 200 mM NaCl and 0.001% Pluronic F-68. As shown in Table 4, all capsid variants can be packaged more efficiently than the AAV2 parental capsid.

TABLE 4

| SEQ ID NO: | Fold Increase in Yield (total vg) |
|---|---|
| AAV2 parental Capsid | 1.00 |
| 1 | 1.98 |
| 2 | 2.00 |
| 3 | 3.85 |
| 5 | 1.67 |
| 6 | 1.16 |
| 12 | 1.37 |
| 13 | 2.17 |
| 16 | 1.90 |
| 26 | 3.57 |
| 27 | 2.33 |

B. Capsid Variants Enhance Retinal Infectivity of AAV Virions In Vivo

Cynomolgus macaques and African Green monkeys between 3-10 years of age were used to evaluate the capsids in vivo. Bilateral intravitreal injections were performed using a 30 g needle to deliver 5.0E+11 viral genomes per eye in a 50 µL volume. Onset and progression of GFP expression was monitored weekly by confocal scanning laser ophthalmoscopy (cSLO) imaging using the autofluorescence function of the Heidelberg Spectralis HRA/OCT system.

Six to eight weeks after intravitreal injection, the primates were euthanized and both eyes (whole globes) were carefully harvested. After enucleation, excess orbital tissue was carefully trimmed and removed. A small (5 mm) slit was made ~2 mm from the limbus and the whole eye was placed in a vial containing 4% paraformaldehyde (PFA) and incubated at 4° C. overnight. After overnight fixation, the PFA was decanted and replaced with phosphate buffered saline (PBS). The whole eye was dissected to remove the anterior structures (cornea, lens, and ciliary body) and then 4 cuts were made to the posterior eye to enable the tissue to lie nearly flat. A fluorescent dissection microscope was used to visualize GFP expression in the entire retina, by direct fluorescence upon filtered UV excitation. The retinal tissue was then dissected into central and peripheral pieces, separated from the underlying tissues, additionally rinsed in PBS, embedded in agarose, sectioned, mounted on microscope slides, and examined by laser-scanning confocal microscopy. After sectioning 4',6-diamidino-2-phenylindole (DAPI) was used to label cell nuclei. GFP expression was detected by direct fluorescence. Images were acquired at different magnifications to evaluate transduction in the different cell layers.

The results of these experiments are shown in FIGS. 10-17.

FIGS. 10A-10C show results observed in vivo for SEQ ID NO: 16 (variant 1). FIG. 10A-10B provide cSLO images taken the Heidelberg Spectralis HRA/OCT 2 weeks (A) and 8 weeks (B) following intravitreal injection of 5.0E+11 vg of rAAV. FIG. 10C shows the extent of GFP expression in central and peripheral retina surface by direct fluorescence imaging. These images provide evidence of the transduction of retinal ganglion cells at the fovea and retinal periphery, as indicated by the presence of axons tracks in both cSLO (B) and whole-mount (C) images.

Figure 11A:
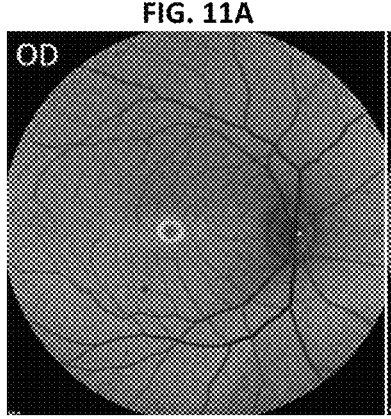
FIG. 11A-11E provide results observed in vivo in non-human primate retinas following intravitreal injection of recombinant AAV (rAAV) virions comprising a variant capsid corresponding to SEQ ID NO:1 (variant 2).
Figure 11B:
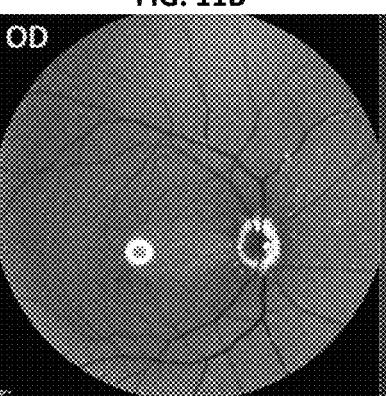
Figure 11C:
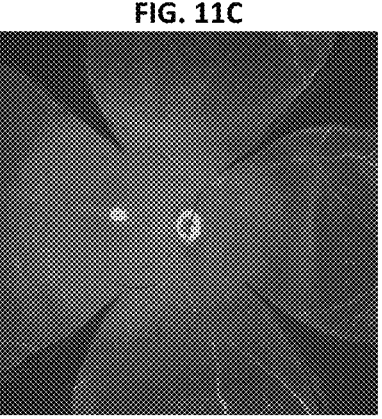
Figure 11D:
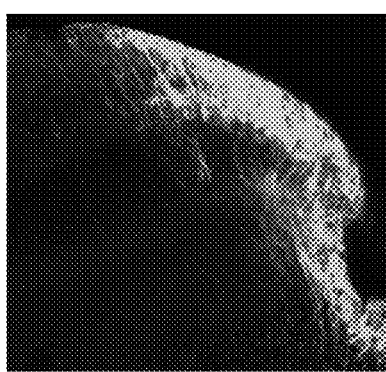
Figure 11E:
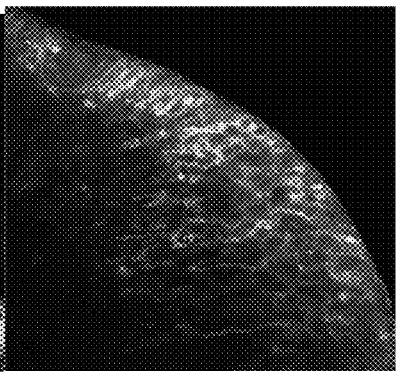

FIGS. 11A-11E show results observed in vivo for SEQ ID NO: 1 (variant 2). FIGS. 11A-11B provides cSLO images taken the Heidelberg Spectralis HRA/OCT 2 weeks (A) and 8 weeks (B) following intravitreal injection of 5.0E+11 vg of rAAV. FIG. 11C shows the extent of GFP expression in central and peripheral retina surface by direct fluorescence imaging. These images provide evidence of the transduction of retinal ganglion cells at the fovea, as indicated by the presence of axons tracks, in both cSLO (B) and whole-mount (C) images. FIGS. 11D-11E provides confocal images obtained from 100 um retinal section showing robust transduction of RGCs and Muller cells (D-E).

FIGS. 12A-12F show results observed in vivo for SEQ ID NO: 5 (Variant 37). FIGS. 12A-12B provides cSLO images taken the Heidelberg Spectralis HRA/OCT 2 weeks (A) and 8 weeks (B) following intravitreal injection of 5.0E+11 vg of rAAV. FIG. 12C shows the extent of GFP expression in central and peripheral retina surface by direct fluorescence imaging. These images provide evidence of the transduction of retinal ganglion cells at the fovea, as indicated by the presence of axons tracks, in both cSLO (B) and whole-mount (C) images, as well as transduction of the far periphery (C). FIGS. 12D-12F provides confocal images obtained from 100 um retinal section showing evidence of robust transduction of RGC (D), inner neurons and Muller cells (E-F).

FIGS. 13A-13B show results observed in vivo for SEQ ID NO: 6 (Variant 38). FIGS. 13A-13B provides cSLO images taken the Heidelberg Spectralis HRA/OCT 2 weeks (A) and 8 weeks (B) following intravitreal injection of 5.0E+11 vg of rAAV. These images provide evidence of the transduction of retinal ganglion cells at the fovea, as indicated by the presence of axons tracks in cSLO images (B).

FIGS. 14A-14F show results observed in vivo for SEQ ID NO: 26 (Variant 45). FIGS. 14A-14B provides cSLO images taken the Heidelberg Spectralis HRA/OCT 2 weeks (A) and 8 weeks (B) following intravitreal injection of 5.0E+11 vg of rAAV. FIG. 14C shows the extent of GFP expression in central and peripheral retina surface by direct fluorescence imaging. These images provide evidence of robust transduction of retinal ganglion cells in the central and temporal retina, as indicated by the presence of axons tracks, in both cSLO (B) and whole-mount (C) images, as well as transduction of the retinal periphery (C). FIGS. 14D-14F provides confocal images obtained from 100 um retinal section showing evidence of robust transduction of RGC (D) and inner neurons (F) in the central retina, and RGC and Muller cells in the temporal retina (E).

Figure 15A:
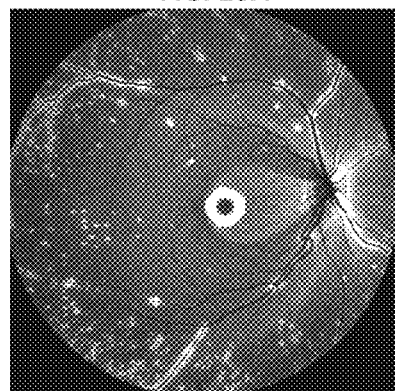
FIG. 15A-15B provide results observed in vivo in non-human primate retinas following intravitreal injection of recombinant AAV (rAAV) virions comprising a variant capsid corresponding to SEQ ID NO:12 (Variant 48).
Figure 15B:
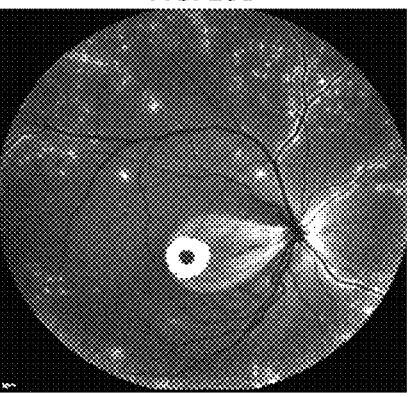

FIGS. 15A-15B show results observed in vivo for SEQ ID NO: 12 (Variant 48). FIGS. 15A-15B provides cSLO images taken the Heidelberg Spectralis HRA/OCT 2 weeks (A) and 6 weeks (B) following intravitreal injection of 5.0E+11 vg of rAAV. These images provide evidence of robust transduction of retinal ganglion cells in the central and peripheral retina, as indicated by the presence of axons tracks. High levels of transduction are visible near the retinal vasculature. This capsid variant is highly efficient at transducing retinal cells as indicated by the level and extent of signal seen in central and peripheral retina at 2 weeks following rAAV delivery (A).

Figures 16A, 16B, 16C:
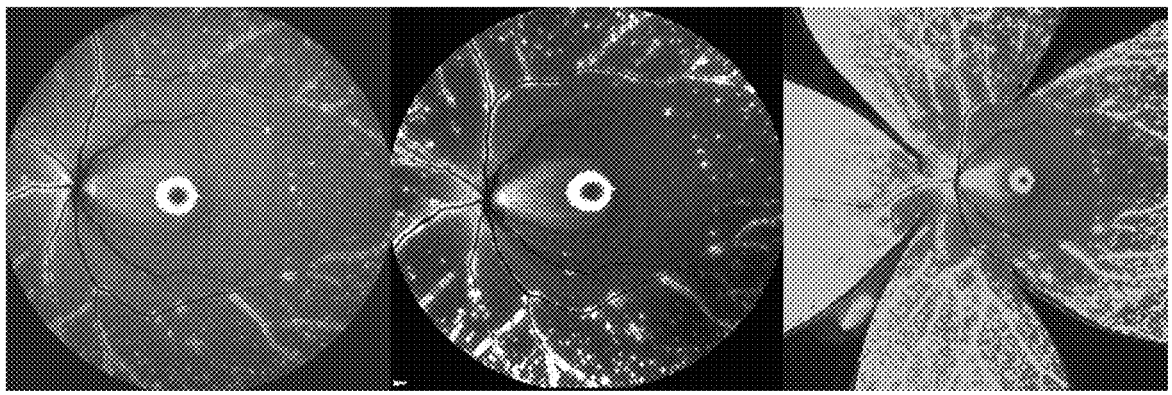
FIG. 16A-16E provide results observed in vivo in non-human primate retinas following intravitreal injection of recombinant AAV (rAAV) virions comprising a variant capsid corresponding to SEQ ID NO:13 (Variant 49).
Figures 16D, 16E:
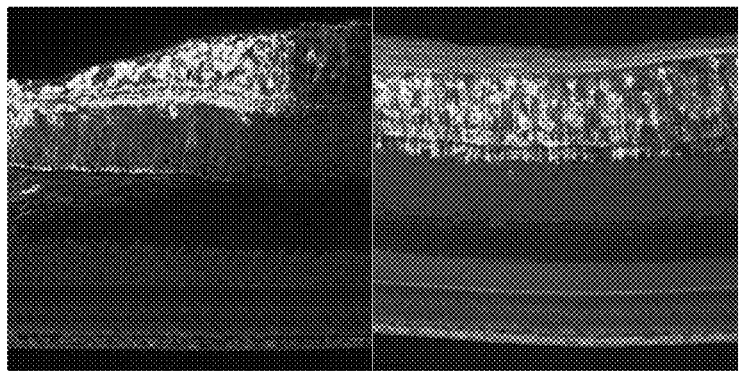

FIGS. 16A-16E show results observed in vivo for SEQ ID NO:13 (Variant 49). FIGS. 16A-16B provides cSLO images taken the Heidelberg Spectralis HRA/OCT 2 weeks (A) and 8 weeks (B) following intravitreal injection of 5.0E+11 vg of rAAV. These images provide evidence of robust transduction of retinal ganglion cells in the central and peripheral retina, as indicated by the presence of axons tracks, in both cSLO (B) and whole-mount (C) images, as well as transduction of the retinal periphery (C). Exceptionally high levels of transduction are visible in the retina periphery (C). This capsid variant is highly efficient at transducing retinal cells as indicated by the level and extent of signal seen in central and peripheral retina on at 2 weeks following rAAV delivery (A). FIG. 16C shows the extent of GFP expression in central and peripheral retina surface by direct fluorescence imaging. FIG. 16D provides confocal images obtained from 100 um retinal section showing robust transduction of RGC, inner neurons and Muller cells in the central retina. FIG. 16E provides confocal images obtained from 100 um retinal section showing very high transduction of RGCs in the peripheral retina.

Figures 17A, 17B:
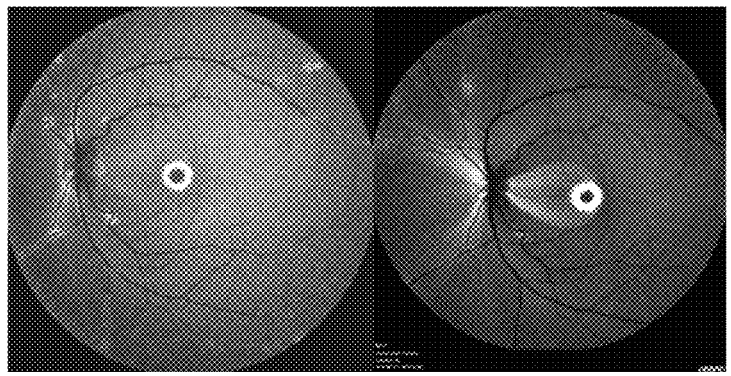
FIG. 17A-17B provide results observed in vivo in non-human primate retinas following intravitreal injection of recombinant AAV (rAAV) virions comprising a variant capsid corresponding to SEQ ID NO:27 (Variant 58).

FIGS. 17A-17B show results observed in vivo for SEQ ID NO:27 (Variant 58). FIGS. 17A-17B provides cSLO images taken the Heidelberg Spectralis HRA/OCT 2 weeks (A) and 6 weeks (B) following intravitreal injection of 5.0E+11 vg of rAAV. These images provide evidence of robust transduction of retinal ganglion cells in the central and peripheral retina, as indicated by the presence of axons tracks.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant adeno-associated virus (rAAV) virion comprising:
   a variant AAV2 capsid protein VP1, wherein the variant AAV2 capsid protein comprises an insertion of a heterologous peptide comprising the amino acid sequence set forth in any one of SEQ ID NOs:2 and 3 between amino acids 570 and 611 of the AAV2 capsid protein VP1, and wherein the variant AAV2 capsid protein confers increased infectivity of a retinal cell compared to the infectivity of the retinal cell by a control AAV virion comprising a corresponding parental AAV capsid protein not comprising the heterologous peptide; and
   a heterologous nucleic acid comprising one or more nucleotide sequences encoding one or more heterologous gene products.

2. The rAAV virion of claim 1, wherein the heterologous peptide has a length of 10 amino acids, 16 amino acids, or 20 amino acids.

3. The rAAV virion of claim 1, wherein:
   the heterologous peptide comprises the amino acid sequence set forth in SEQ ID NO:2, and wherein the heterologous peptide has a length of 10 amino acids; or
   the heterologous peptide comprises the amino acid sequence set forth in SEQ ID NO:3, and wherein the heterologous peptide has a length of 10 amino acids.

4. The rAAV virion of claim 1, wherein the rAAV virion exhibits at least 5-fold increased infectivity of a retinal cell compared to the infectivity of the retinal cell by a control AAV virion comprising the corresponding parental AAV2 capsid protein.

5. The rAAV virion of claim 1, wherein the insertion of the heterologous peptide replaces a contiguous stretch of from 5 amino acids to 20 amino acids between amino acids 570 and 611 of the AAV2 capsid protein VP1.

6. The rAAV virion of claim 1, wherein the insertion site is within amino acids 587 and 588 of the AAV2 capsid protein VP1.

7. The rAAV virion of claim 1, wherein the one or more heterologous gene products is an interfering RNA or an aptamer.

8. The rAAV virion of claim 1, wherein the one or more heterologous gene products is a polypeptide.

9. The rAAV virion of claim 8, wherein the polypeptide is:
   a) a neuroprotective polypeptide, an anti-angiogenic polypeptide, or a polypeptide that enhances function of a retinal cell; or
   b) a light-responsive polypeptide, an opsin, a short-wavelength opsin (SW-opsin), a medium-wavelength opsin (MW-opsin), a long-wavelength opsin (LW-opsin), a rhodopsin, a cone opsin, a human opsin, a non-human opsin, a humanized opsin, or any combination thereof; or
   c) a CRISPR/Cas effector polypeptide, a deaminase, a reverse transcriptase, or any combination or fusion thereof.

10. The rAAV virion of claim 8, wherein the polypeptide is a metabotropic glutamate receptor (mGluR) selected from the group consisting of mGluR1, mGluR2, mGluR3, mGluR4, mGluR5, mGluR6, mGluR7, and mGluR8, or a functional fragment or variant thereof.

11. The rAAV virion of claim 8, wherein the polypeptide comprises a fusion polypeptide.

12. The rAAV virion of claim 8, wherein the polypeptide comprises a fusion polypeptide comprising an affinity tag.

13. The rAAV virion of claim 8, wherein the polypeptide comprises a fusion polypeptide comprising an affinity tag sequence and an mGluR sequence, where the affinity tag sequence comprises a sequence having at least 80% amino acid sequence identity to SEQ ID NO:123 or SEQ ID NO:124 and the mGluR sequence comprises an mGluR2 sequence.

14. The rAAV virion of claim 1, wherein the one or more heterologous gene products comprise a CRISPR/Cas effector polypeptide and a guide RNA.

15. The rAAV virion of claim 1, wherein the retinal cell is a photoreceptor cell, an ON-bipolar cell, an OFF-bipolar cell, a retinal ganglion cell, an amacrine cell, or a horizontal cell.

16. The rAAV virion of claim 1, wherein the one or more nucleotide sequences is operably linked to a promoter.

17. The rAAV virion of claim 16, wherein the promoter is a retinal cell specific promoter.

18. The rAAV virion of claim 17, wherein:
   a) the retinal cell is an ON-bipolar cell or an OFF-bipolar cell, and the one or more nucleotide sequences is operably linked to an ON-bipolar cell-specific promoter or an OFF-bipolar cell-specific promoter; or
   b) the retinal cell is a retinal ganglion cell (RGC) and the one or more nucleotide sequences is operably linked to an RGC-specific promoter; or
   c) the retinal cell is an amacrine cell and the one or more nucleotide sequences is operably linked to an amacrine cell-specific promoter; or
   d) the retinal cell is a horizontal cell and the one or more nucleotide sequences is operably linked to a horizontal cell-specific promoter.

19. The rAAV virion of claim 1, wherein the retinal cell is a not a photoreceptor cell.

20. A composition comprising a rAAV virion of claim 1.

21. A pharmaceutical composition comprising:
   a) a rAAV virion of claim 1; and
   b) a pharmaceutically acceptable excipient.

22. The rAAV virion of claim 1, wherein the one or more heterologous gene products is therapeutic.

23. A method of treating a retinal condition or disorder in a subject, the method comprising administering a therapeutically effective amount of an rAAV virion of claim 22 to the subject.

24. A method of delivering one or more heterologous gene products to a retinal cell, the method comprising contacting a rAAV virion according to claim 1 with the retinal cell.

* * * * *

```
                              SEQUENCE LISTING

<160> NUMBER OF SEQ ID NOS: 124

<210> SEQ ID NO 1
<211> LENGTH: 10
<212> TYPE: PRT
<213> ORGANISM: Artificial sequence
<220> FEATURE:
<223> OTHER INFORMATION: synthetic sequence

<400> SEQUENCE: 1

Leu Ala His Gln Asp Thr Thr Lys Asn Ser
1               5                   10

<210> SEQ ID NO 2
<211> LENGTH: 10
<212> TYPE: PRT
<213> ORGANISM: Artificial sequence
<220> FEATURE:
<223> OTHER INFORMATION: synthetic sequence

<400> SEQUENCE: 2

Leu Ala Leu Gly Glu Thr Thr Arg Ala Ala
1               5                   10

<210> SEQ ID NO 3
<211> LENGTH: 10
<212> TYPE: PRT
<213> ORGANISM: Artificial sequence
<220> FEATURE:
<223> OTHER INFORMATION: synthetic sequence

<400> SEQUENCE: 3

Leu Ala His Gln Asp Thr Thr Arg Pro Ala
1               5                   10

<210> SEQ ID NO 4
<211> LENGTH: 10
<212> TYPE: PRT
<213> ORGANISM: Artificial sequence
<220> FEATURE:
<223> OTHER INFORMATION: synthetic sequence

<400> SEQUENCE: 4

Leu Ala Arg Gln Asp Thr Thr Lys Asn Ala
1               5                   10

<210> SEQ ID NO 5
<211> LENGTH: 10
<212> TYPE: PRT
<213> ORGANISM: Artificial sequence
<220> FEATURE:
<223> OTHER INFORMATION: synthetic sequence

<400> SEQUENCE: 5

Leu Ala His Gln Asp Ser Thr Lys Asn Ala
1               5                   10

<210> SEQ ID NO 6
<211> LENGTH: 10
<212> TYPE: PRT
<213> ORGANISM: Artificial sequence
```

```
<220> FEATURE:
<223> OTHER INFORMATION: synthetic sequence

<400> SEQUENCE: 6

Leu Ala His Gln Asp Ala Thr Lys Asn Ala
1               5                   10

<210> SEQ ID NO 7
<211> LENGTH: 10
<212> TYPE: PRT
<213> ORGANISM: Artificial sequence
<220> FEATURE:
<223> OTHER INFORMATION: synthetic sequence

<400> SEQUENCE: 7

Leu Ala His Gln Asp Thr Thr Lys Pro Ala
1               5                   10

<210> SEQ ID NO 8
<211> LENGTH: 10
<212> TYPE: PRT
<213> ORGANISM: Artificial sequence
<220> FEATURE:
<223> OTHER INFORMATION: synthetic sequence

<400> SEQUENCE: 8

Ile Ala Leu Ser Glu Thr Thr Arg Pro Ala
1               5                   10

<210> SEQ ID NO 9
<211> LENGTH: 10
<212> TYPE: PRT
<213> ORGANISM: Artificial sequence
<220> FEATURE:
<223> OTHER INFORMATION: synthetic sequence

<400> SEQUENCE: 9

Leu Ala His Gln Asp Thr Thr Lys Lys Cys
1               5                   10

<210> SEQ ID NO 10
<211> LENGTH: 10
<212> TYPE: PRT
<213> ORGANISM: Artificial sequence
<220> FEATURE:
<223> OTHER INFORMATION: synthetic sequence

<400> SEQUENCE: 10

Leu Ala Leu Gly Glu Ala Thr Arg Pro Ala
1               5                   10

<210> SEQ ID NO 11
<211> LENGTH: 10
<212> TYPE: PRT
<213> ORGANISM: Artificial sequence
<220> FEATURE:
<223> OTHER INFORMATION: synthetic sequence

<400> SEQUENCE: 11

Leu Ala Leu Gly Glu Thr Thr Arg Thr Ala
1               5                   10

<210> SEQ ID NO 12
<211> LENGTH: 10
<212> TYPE: PRT
<213> ORGANISM: Artificial sequence
<220> FEATURE:
```

```
<223> OTHER INFORMATION: synthetic sequence

<400> SEQUENCE: 12

Leu Ala Leu Ser Glu Ala Thr Arg Pro Ala
1               5                   10

<210> SEQ ID NO 13
<211> LENGTH: 10
<212> TYPE: PRT
<213> ORGANISM: Artificial sequence
<220> FEATURE:
<223> OTHER INFORMATION: synthetic sequence

<400> SEQUENCE: 13

Leu Ala Lys Asp Glu Thr Lys Asn Ser Ala
1               5                   10

<210> SEQ ID NO 14
<211> LENGTH: 10
<212> TYPE: PRT
<213> ORGANISM: Artificial sequence
<220> FEATURE:
<223> OTHER INFORMATION: synthetic sequence

<400> SEQUENCE: 14

Leu Ala Leu Gly Glu Thr Thr Lys Pro Ala
1               5                   10

<210> SEQ ID NO 15
<211> LENGTH: 10
<212> TYPE: PRT
<213> ORGANISM: Artificial sequence
<220> FEATURE:
<223> OTHER INFORMATION: synthetic sequence

<400> SEQUENCE: 15

Leu Ala His Gln Ala Thr Thr Lys Asn Ala
1               5                   10

<210> SEQ ID NO 16
<211> LENGTH: 16
<212> TYPE: PRT
<213> ORGANISM: Artificial sequence
<220> FEATURE:
<223> OTHER INFORMATION: synthetic sequence

<400> SEQUENCE: 16

Leu Gln Arg Gly Asn Arg Gln Thr Thr Thr Ala Asp Val Asn Thr Gln
1               5                   10                  15

<210> SEQ ID NO 17
<211> LENGTH: 16
<212> TYPE: PRT
<213> ORGANISM: Artificial sequence
<220> FEATURE:
<223> OTHER INFORMATION: synthetic sequence

<400> SEQUENCE: 17

Leu Gln Arg Gly Asn Arg Gln Ala Thr Thr Ala Asp Val Asn Thr Leu
1               5                   10                  15

<210> SEQ ID NO 18
<211> LENGTH: 16
<212> TYPE: PRT
<213> ORGANISM: Artificial sequence
<220> FEATURE:
<223> OTHER INFORMATION: synthetic sequence
```

<400> SEQUENCE: 18

Leu Gln Arg Gly Asn Arg Gln Ala Thr Thr Glu Asp Val Asn Thr Gln
1               5                   10                  15

<210> SEQ ID NO 19
<211> LENGTH: 16
<212> TYPE: PRT
<213> ORGANISM: Artificial sequence
<220> FEATURE:
<223> OTHER INFORMATION: synthetic sequence

<400> SEQUENCE: 19

Leu Gln Arg Gly Asn Arg Gln Ala Ala Thr Glu Asp Val Asn Thr Gln
1               5                   10                  15

<210> SEQ ID NO 20
<211> LENGTH: 16
<212> TYPE: PRT
<213> ORGANISM: Artificial sequence
<220> FEATURE:
<223> OTHER INFORMATION: synthetic sequence

<400> SEQUENCE: 20

Leu Gln Arg Gly Asn Arg Gln Ala Ala Thr Ala Asp Val Asn Ser Leu
1               5                   10                  15

<210> SEQ ID NO 21
<211> LENGTH: 16
<212> TYPE: PRT
<213> ORGANISM: Artificial sequence
<220> FEATURE:
<223> OTHER INFORMATION: synthetic sequence

<400> SEQUENCE: 21

Leu Gln Arg Gly Asn Arg Gln Ala Ala Thr Ala Asp Val Asn Lys Leu
1               5                   10                  15

<210> SEQ ID NO 22
<211> LENGTH: 16
<212> TYPE: PRT
<213> ORGANISM: Artificial sequence
<220> FEATURE:
<223> OTHER INFORMATION: synthetic sequence

<400> SEQUENCE: 22

Leu Gln Arg Gly Val Arg Val Pro Ser Val Leu Glu Val Asn Gly Gln
1               5                   10                  15

<210> SEQ ID NO 23
<211> LENGTH: 16
<212> TYPE: PRT
<213> ORGANISM: Artificial sequence
<220> FEATURE:
<223> OTHER INFORMATION: synthetic sequence

<400> SEQUENCE: 23

Leu Gln Arg Gly Asn Arg Gln Ala Ala Thr Ala Asp Val Asn Ile Leu
1               5                   10                  15

<210> SEQ ID NO 24
<211> LENGTH: 16
<212> TYPE: PRT
<213> ORGANISM: Artificial sequence
<220> FEATURE:
<223> OTHER INFORMATION: synthetic sequence

```
<400> SEQUENCE: 24

Leu Gln Arg Gly Lys Arg Gln Ala Thr Thr Ala Asp Val Asn Thr Gln
1               5                   10                  15

<210> SEQ ID NO 25
<211> LENGTH: 16
<212> TYPE: PRT
<213> ORGANISM: Artificial sequence
<220> FEATURE:
<223> OTHER INFORMATION: synthetic sequence

<400> SEQUENCE: 25

Leu His Arg Gly Asn Arg Gln Ala Ala Thr Ala Asp Val Asn Thr Leu
1               5                   10                  15

<210> SEQ ID NO 26
<211> LENGTH: 19
<212> TYPE: PRT
<213> ORGANISM: Artificial sequence
<220> FEATURE:
<223> OTHER INFORMATION: synthetic sequence

<400> SEQUENCE: 26

Ser Arg Thr Asn Thr Pro Ser Gly Thr Thr Thr Gln Pro Thr Leu Gln
1               5                   10                  15

Phe Ser Gln

<210> SEQ ID NO 27
<211> LENGTH: 19
<212> TYPE: PRT
<213> ORGANISM: Artificial sequence
<220> FEATURE:
<223> OTHER INFORMATION: synthetic sequence

<400> SEQUENCE: 27

Ser Lys Thr Asp Thr Pro Ser Gly Thr Thr Thr Gln Ser Arg Leu Gln
1               5                   10                  15

Phe Ser Gln

<210> SEQ ID NO 28
<211> LENGTH: 19
<212> TYPE: PRT
<213> ORGANISM: Artificial sequence
<220> FEATURE:
<223> OTHER INFORMATION: synthetic sequence

<400> SEQUENCE: 28

Ser Arg Thr Asp Thr Pro Ser Glu Thr Thr Thr Gln Ser Arg Leu Gln
1               5                   10                  15

Phe Ser Gln

<210> SEQ ID NO 29
<211> LENGTH: 19
<212> TYPE: PRT
<213> ORGANISM: Artificial sequence
<220> FEATURE:
<223> OTHER INFORMATION: synthetic sequence

<400> SEQUENCE: 29

Ser Arg Thr Asn Ser Pro Ser Gly Thr Thr Thr Gln Ser Ser Leu Gln
1               5                   10                  15

Phe Ser Gln
```

```
<210> SEQ ID NO 30
<211> LENGTH: 19
<212> TYPE: PRT
<213> ORGANISM: Artificial sequence
<220> FEATURE:
<223> OTHER INFORMATION: synthetic sequence

<400> SEQUENCE: 30

Ser Arg Thr Asp Ile Pro Ser Gly Thr Thr Thr Gln Ser Arg Leu Gln
1               5                   10                  15
Phe Ser Gln

<210> SEQ ID NO 31
<211> LENGTH: 7
<212> TYPE: PRT
<213> ORGANISM: Artificial sequence
<220> FEATURE:
<223> OTHER INFORMATION: synthetic sequence

<400> SEQUENCE: 31

His Gln Asp Thr Thr Lys Asn
1               5

<210> SEQ ID NO 32
<211> LENGTH: 7
<212> TYPE: PRT
<213> ORGANISM: Artificial sequence
<220> FEATURE:
<223> OTHER INFORMATION: synthetic sequence

<400> SEQUENCE: 32

Leu Gly Glu Thr Thr Arg Ala
1               5

<210> SEQ ID NO 33
<211> LENGTH: 7
<212> TYPE: PRT
<213> ORGANISM: Artificial sequence
<220> FEATURE:
<223> OTHER INFORMATION: synthetic sequence

<400> SEQUENCE: 33

His Gln Asp Thr Thr Arg Pro
1               5

<210> SEQ ID NO 34
<211> LENGTH: 7
<212> TYPE: PRT
<213> ORGANISM: Artificial sequence
<220> FEATURE:
<223> OTHER INFORMATION: synthetic sequence

<400> SEQUENCE: 34

Arg Gln Asp Thr Thr Lys Asn
1               5

<210> SEQ ID NO 35
<211> LENGTH: 7
<212> TYPE: PRT
<213> ORGANISM: Artificial sequence
<220> FEATURE:
<223> OTHER INFORMATION: synthetic sequence

<400> SEQUENCE: 35

His Gln Asp Ser Thr Lys Asn
1               5
```

```
<210> SEQ ID NO 36
<211> LENGTH: 7
<212> TYPE: PRT
<213> ORGANISM: Artificial sequence
<220> FEATURE:
<223> OTHER INFORMATION: synthetic sequence

<400> SEQUENCE: 36

His Gln Asp Ala Thr Lys Asn
1               5

<210> SEQ ID NO 37
<211> LENGTH: 7
<212> TYPE: PRT
<213> ORGANISM: Artificial sequence
<220> FEATURE:
<223> OTHER INFORMATION: synthetic sequence

<400> SEQUENCE: 37

His Gln Asp Thr Thr Lys Pro
1               5

<210> SEQ ID NO 38
<211> LENGTH: 7
<212> TYPE: PRT
<213> ORGANISM: Artificial sequence
<220> FEATURE:
<223> OTHER INFORMATION: synthetic sequence

<400> SEQUENCE: 38

Leu Ser Glu Thr Thr Arg Pro
1               5

<210> SEQ ID NO 39
<211> LENGTH: 7
<212> TYPE: PRT
<213> ORGANISM: Artificial sequence
<220> FEATURE:
<223> OTHER INFORMATION: synthetic sequence

<400> SEQUENCE: 39

His Gln Asp Thr Thr Lys Lys
1               5

<210> SEQ ID NO 40
<211> LENGTH: 7
<212> TYPE: PRT
<213> ORGANISM: Artificial sequence
<220> FEATURE:
<223> OTHER INFORMATION: synthetic sequence

<400> SEQUENCE: 40

Leu Gly Glu Ala Thr Arg Pro
1               5

<210> SEQ ID NO 41
<211> LENGTH: 7
<212> TYPE: PRT
<213> ORGANISM: Artificial sequence
<220> FEATURE:
<223> OTHER INFORMATION: synthetic sequence

<400> SEQUENCE: 41

Leu Gly Glu Thr Thr Arg Thr
1               5
```

```
<210> SEQ ID NO 42
<211> LENGTH: 7
<212> TYPE: PRT
<213> ORGANISM: Artificial sequence
<220> FEATURE:
<223> OTHER INFORMATION: synthetic sequence

<400> SEQUENCE: 42

Leu Ser Glu Ala Thr Arg Pro
1               5

<210> SEQ ID NO 43
<211> LENGTH: 7
<212> TYPE: PRT
<213> ORGANISM: Artificial sequence
<220> FEATURE:
<223> OTHER INFORMATION: synthetic sequence

<400> SEQUENCE: 43

Lys Asp Glu Thr Lys Asn Ser
1               5

<210> SEQ ID NO 44
<211> LENGTH: 7
<212> TYPE: PRT
<213> ORGANISM: Artificial sequence
<220> FEATURE:
<223> OTHER INFORMATION: synthetic sequence

<400> SEQUENCE: 44

Leu Gly Glu Thr Thr Lys Pro
1               5

<210> SEQ ID NO 45
<211> LENGTH: 7
<212> TYPE: PRT
<213> ORGANISM: Artificial sequence
<220> FEATURE:
<223> OTHER INFORMATION: synthetic sequence

<400> SEQUENCE: 45

His Gln Ala Thr Thr Lys Asn
1               5

<210> SEQ ID NO 46
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: The amino acid at position 1 is Leu or Ile
<220> FEATURE:
<221> NAME/KEY: SITE
<222> LOCATION: (3)..(3)
<223> OTHER INFORMATION: The amino acid at position 3 is His, Leu, Arg
      or Lys
<220> FEATURE:
<221> NAME/KEY: SITE
<222> LOCATION: (4)..(4)
<223> OTHER INFORMATION: The amino acid at position 4 is Gln, Gly, Ser
      or Asp
<220> FEATURE:
<221> NAME/KEY: SITE
<222> LOCATION: (5)..(5)
<223> OTHER INFORMATION: The amino acid at position 5 is Asp, Glu or Ala
<220> FEATURE:
<221> NAME/KEY: SITE
<222> LOCATION: (6)..(6)
```

```
<223> OTHER INFORMATION: The amino acid at position 6 is Thr or Ala
<220> FEATURE:
<221> NAME/KEY: SITE
<222> LOCATION: (8)..(8)
<223> OTHER INFORMATION: The amino acid at position 8 is Lys, Asn or Arg
<220> FEATURE:
<221> NAME/KEY: SITE
<222> LOCATION: (9)..(9)
<223> OTHER INFORMATION: The amino acid at position 9 is Asn, Pro, Ser,
      Lys, Thr or Ala
<220> FEATURE:
<221> NAME/KEY: SITE
<222> LOCATION: (10)..(10)
<223> OTHER INFORMATION: The amino acid at position 10 is Ser, Ala or
      Cys

<400> SEQUENCE: 46

Xaa Ala Xaa Xaa Xaa Xaa Thr Xaa Xaa Xaa
 1               5                   10

<210> SEQ ID NO 47
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: The amino acid at position 1 is Leu or Ile
<220> FEATURE:
<221> NAME/KEY: SITE
<222> LOCATION: (3)..(3)
<223> OTHER INFORMATION: The amino acid at position 3 is His, Leu or Arg
<220> FEATURE:
<221> NAME/KEY: SITE
<222> LOCATION: (4)..(4)
<223> OTHER INFORMATION: The amino acid at position 4 is Gln, Gly or Ser
<220> FEATURE:
<221> NAME/KEY: SITE
<222> LOCATION: (5)..(5)
<223> OTHER INFORMATION: The amino acid at position 5 is Asp, Glu or Ala
<220> FEATURE:
<221> NAME/KEY: SITE
<222> LOCATION: (8)..(8)
<223> OTHER INFORMATION: The amino acid at position 8 is Lys or Arg
<220> FEATURE:
<221> NAME/KEY: SITE
<222> LOCATION: (9)..(9)
<223> OTHER INFORMATION: The amino acid at position 9 is Asn, Ala, Pro,
      Lys or Thr
<220> FEATURE:
<221> NAME/KEY: SITE
<222> LOCATION: (10)..(10)
<223> OTHER INFORMATION: The amino acid at position 10 is Ser, Ala or
      Cys

<400> SEQUENCE: 47

Xaa Ala Xaa Xaa Xaa Thr Thr Xaa Xaa Xaa
 1               5                   10

<210> SEQ ID NO 48
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (5)..(5)
<223> OTHER INFORMATION: The amino acid at position 5 is Asp or Ala
<220> FEATURE:
<221> NAME/KEY: SITE
<222> LOCATION: (6)..(6)
<223> OTHER INFORMATION: The amino acid at position 6 is Thr, Ser or Ala
```

```
<220> FEATURE:
<221> NAME/KEY: SITE
<222> LOCATION: (8)..(8)
<223> OTHER INFORMATION: The amino acid at position 8 is Lys or Arg
<220> FEATURE:
<221> NAME/KEY: SITE
<222> LOCATION: (9)..(9)
<223> OTHER INFORMATION: The amino acid at position 9 is Asn, Pro or Lys
<220> FEATURE:
<221> NAME/KEY: SITE
<222> LOCATION: (10)..(10)
<223> OTHER INFORMATION: The amino acid at position 10 is Ser, Ala or
      Cys

<400> SEQUENCE: 48

Leu Ala His Gln Xaa Xaa Thr Xaa Xaa Xaa
1               5                   10

<210> SEQ ID NO 49
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (4)..(4)
<223> OTHER INFORMATION: The amino acid at position 4 is Gly or Ser
<220> FEATURE:
<221> NAME/KEY: SITE
<222> LOCATION: (6)..(6)
<223> OTHER INFORMATION: The amino acid at position 6 is Thr or Ala
<220> FEATURE:
<221> NAME/KEY: SITE
<222> LOCATION: (8)..(8)
<223> OTHER INFORMATION: The amino acid at position 8 is Arg or Lys
<220> FEATURE:
<221> NAME/KEY: SITE
<222> LOCATION: (9)..(9)
<223> OTHER INFORMATION: The amino acid at position 9 is Ala, Pro or Thr

<400> SEQUENCE: 49

Leu Ala Leu Xaa Glu Xaa Thr Xaa Xaa Ala
1               5                   10

<210> SEQ ID NO 50
<211> LENGTH: 17
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (2)..(2)
<223> OTHER INFORMATION: The amino acid at position 2 is Gln or His
<220> FEATURE:
<221> NAME/KEY: SITE
<222> LOCATION: (5)..(5)
<223> OTHER INFORMATION: The amino acid at position 5 is Asn, Val or Lys
<220> FEATURE:
<221> NAME/KEY: SITE
<222> LOCATION: (8)..(8)
<223> OTHER INFORMATION: The amino acid at position 8 is Gln or Val
<220> FEATURE:
<221> NAME/KEY: SITE
<222> LOCATION: (9)..(9)
<223> OTHER INFORMATION: The amino acid at position 9 is Thr, Ala or Pro
<220> FEATURE:
<221> NAME/KEY: SITE
<222> LOCATION: (10)..(10)
<223> OTHER INFORMATION: The amino acid at position 10 is Thr, Ala or
      Ser
<220> FEATURE:
<221> NAME/KEY: SITE
<222> LOCATION: (11)..(11)
```

```
<223> OTHER INFORMATION: The amino acid at position 11 is Thr or Val
<220> FEATURE:
<221> NAME/KEY: SITE
<222> LOCATION: (12)..(12)
<223> OTHER INFORMATION: The amino acid at position 12 is Ala, Glu or
      Lys
<220> FEATURE:
<221> NAME/KEY: SITE
<222> LOCATION: (13)..(13)
<223> OTHER INFORMATION: The amino acid at position 13 is Asp or Glu
<220> FEATURE:
<221> NAME/KEY: SITE
<222> LOCATION: (16)..(16)
<223> OTHER INFORMATION: The amino acid at position 16 is Thr, Ser, Lys,
      Gly or Ile
<220> FEATURE:
<221> NAME/KEY: SITE
<222> LOCATION: (17)..(17)
<223> OTHER INFORMATION: The amino acid at position 17 is Gln or Leu

<400> SEQUENCE: 50

Leu Xaa Arg Gly Xaa Arg Gln Xaa Xaa Xaa Xaa Xaa Xaa Val Asn Xaa
1               5                   10                  15

Xaa

<210> SEQ ID NO 51
<211> LENGTH: 16
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (2)..(2)
<223> OTHER INFORMATION: The amino acid at position 2 is Gln or His
<220> FEATURE:
<221> NAME/KEY: SITE
<222> LOCATION: (8)..(8)
<223> OTHER INFORMATION: The amino acid at position 8 is Ala or Thr
<220> FEATURE:
<221> NAME/KEY: SITE
<222> LOCATION: (9)..(9)
<223> OTHER INFORMATION: The amino acid at position 9 is Ala or Thr
<220> FEATURE:
<221> NAME/KEY: SITE
<222> LOCATION: (11)..(11)
<223> OTHER INFORMATION: The amino acid at position 11 is Ala or Glu
<220> FEATURE:
<221> NAME/KEY: SITE
<222> LOCATION: (15)..(15)
<223> OTHER INFORMATION: The amino acid at position 15 is Thr, Ser, Lys
      or Ile
<220> FEATURE:
<221> NAME/KEY: SITE
<222> LOCATION: (16)..(16)
<223> OTHER INFORMATION: The amino acid at position 16 is Gln or Leu

<400> SEQUENCE: 51

Leu Xaa Arg Gly Asn Arg Gln Xaa Xaa Thr Xaa Asp Val Asn Xaa Xaa
1               5                   10                  15

<210> SEQ ID NO 52
<211> LENGTH: 19
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (2)..(2)
<223> OTHER INFORMATION: The amino acid at position 2 is Arg or Lys
<220> FEATURE:
<221> NAME/KEY: SITE
<222> LOCATION: (4)..(4)
```

```
<223> OTHER INFORMATION: The amino acid at position 4 is Asn or Asp
<220> FEATURE:
<221> NAME/KEY: SITE
<222> LOCATION: (5)..(5)
<223> OTHER INFORMATION: The amino acid at position 5 is Thr, Ser or Ile
<220> FEATURE:
<221> NAME/KEY: SITE
<222> LOCATION: (8)..(8)
<223> OTHER INFORMATION: The amino acid at position 8 is Gly or Glu
<220> FEATURE:
<221> NAME/KEY: SITE
<222> LOCATION: (13)..(13)
<223> OTHER INFORMATION: The amino acid at position 13 is Ser or Pro
<220> FEATURE:
<221> NAME/KEY: SITE
<222> LOCATION: (14)..(14)
<223> OTHER INFORMATION: The amino acid at position 14 is Thr, Arg or
      Ser

<400> SEQUENCE: 52

Ser Xaa Thr Xaa Xaa Pro Ser Xaa Thr Thr Thr Gln Xaa Xaa Leu Gln
1               5                   10                  15

Phe Ser Gln

<210> SEQ ID NO 53
<211> LENGTH: 7
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (1)..(1)
<223> OTHER INFORMATION: The amino acid at position 1 is His, Leu, Arg
      or Lys
<220> FEATURE:
<221> NAME/KEY: SITE
<222> LOCATION: (2)..(2)
<223> OTHER INFORMATION: The amino acid at position 2 is Gln, Gly, Ser
      or Asp
<220> FEATURE:
<221> NAME/KEY: SITE
<222> LOCATION: (3)..(3)
<223> OTHER INFORMATION: The amino acid at position 3 is Asp, Glu or Ala
<220> FEATURE:
<221> NAME/KEY: SITE
<222> LOCATION: (4)..(4)
<223> OTHER INFORMATION: The amino acid at position 4 is Thr or Ala
<220> FEATURE:
<221> NAME/KEY: SITE
<222> LOCATION: (6)..(6)
<223> OTHER INFORMATION: The amino acid at position 6 is Lys, Asn or Arg
<220> FEATURE:
<221> NAME/KEY: SITE
<222> LOCATION: (7)..(7)
<223> OTHER INFORMATION: The amino acid at position 7 is Asn, Pro, Ser,
      Lys, Thr or Ala

<400> SEQUENCE: 53

Xaa Xaa Xaa Xaa Thr Xaa Xaa
1               5

<210> SEQ ID NO 54
<211> LENGTH: 364
<212> TYPE: PRT
<213> ORGANISM: Homo sapiens

<400> SEQUENCE: 54

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
                20                  25                  30
```

Ser Asn Ser Thr Arg Gly Pro Phe Glu Gly Pro Asn Tyr His Ile Ala
            35                  40                  45

Pro Arg Trp Val Tyr His Leu Thr Ser Val Trp Met Ile Phe Val Val
    50                  55                  60

Ile Ala Ser Val Phe Thr Asn Gly Leu Val Leu Ala Ala Thr Met Lys
65                  70                  75                  80

Phe Lys Lys Leu Arg His Pro Leu Asn Trp Ile Leu Val Asn Leu Ala
                85                  90                  95

Val Ala Asp Leu Ala Glu Thr Val Ile Ala Ser Thr Ile Ser Val Val
            100                 105                 110

Asn Gln Val Tyr Gly Tyr Phe Val Leu Gly His Pro Met Cys Val Leu
        115                 120                 125

Glu Gly Tyr Thr Val Ser Leu Cys Gly Ile Thr Gly Leu Trp Ser Leu
    130                 135                 140

Ala Ile Ile Ser Trp Glu Arg Trp Met Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ala Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
        195                 200                 205

Ser Gly Ser Ser Tyr Pro Gly Val Gln Ser Tyr Met Ile Val Leu Met
    210                 215                 220

Val Thr Cys Cys Ile Thr Pro Leu Ser Ile Ile Val Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270

Met Val Leu Ala Phe Cys Phe Cys Trp Gly Pro Tyr Ala Phe Phe Ala
        275                 280                 285

Cys Phe Ala Ala Ala Asn Pro Gly Tyr Pro Phe His Pro Leu Met Ala
    290                 295                 300

Ala Leu Pro Ala Phe Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
        355                 360

<210> SEQ ID NO 55
<211> LENGTH: 364
<212> TYPE: PRT
<213> ORGANISM: Homo sapiens

<400> SEQUENCE: 55

Met Ala Gln Gln Trp Ser Leu Gln Arg Leu Ala Gly Arg His Pro Gln
1               5                   10                  15

Asp Ser Tyr Glu Asp Ser Thr Gln Ser Ser Ile Phe Thr Tyr Thr Asn
            20                  25                  30

Ser Asn Ser Thr Arg Gly Pro Phe Glu Gly Pro Asn Tyr His Ile Ala 35                  40                  45
Pro Arg Trp Val Tyr His Leu Thr Ser Val Trp Met Ile Phe Val Val
 50                  55                  60

Thr Ala Ser Val Phe Thr Asn Gly Leu Val Leu Ala Ala Thr Met Lys
 65                  70                  75                  80

Phe Lys Lys Leu Arg His Pro Leu Asn Trp Ile Leu Val Asn Leu Ala
                 85                  90                  95

Val Ala Asp Leu Ala Glu Thr Val Ile Ala Ser Thr Ile Ser Ile Val
            100                 105                 110

Asn Gln Val Ser Gly Tyr Phe Val Leu Gly His Pro Met Cys Val Leu
            115                 120                 125

Glu Gly Tyr Thr Val Ser Leu Cys Gly Ile Thr Gly Leu Trp Ser Leu
            130                 135                 140

Ala Ile Ile Ser Trp Glu Arg Trp Met Val Val Cys Lys Pro Phe Gly
145                 150                 155                 160

Asn Val Arg Phe Asp Ala Lys Leu Ala Ile Val Gly Ile Ala Phe Ser
                165                 170                 175

Trp Ile Trp Ala Ala Val Trp Thr Ala Pro Pro Ile Phe Gly Trp Ser
            180                 185                 190

Arg Tyr Trp Pro His Gly Leu Lys Thr Ser Cys Gly Pro Asp Val Phe
            195                 200                 205

Ser Gly Ser Ser Tyr Pro Gly Val Gln Ser Tyr Met Ile Val Leu Met
210                 215                 220

Val Thr Cys Cys Ile Ile Pro Leu Ala Ile Ile Met Leu Cys Tyr Leu
225                 230                 235                 240

Gln Val Trp Leu Ala Ile Arg Ala Val Ala Lys Gln Gln Lys Glu Ser
                245                 250                 255

Glu Ser Thr Gln Lys Ala Glu Lys Glu Val Thr Arg Met Val Val Val
            260                 265                 270

Met Ile Phe Ala Tyr Cys Val Cys Trp Gly Pro Tyr Thr Phe Phe Ala
            275                 280                 285

Cys Phe Ala Ala Ala Asn Pro Gly Tyr Ala Phe His Pro Leu Met Ala
290                 295                 300

Ala Leu Pro Ala Tyr Phe Ala Lys Ser Ala Thr Ile Tyr Asn Pro Val
305                 310                 315                 320

Ile Tyr Val Phe Met Asn Arg Gln Phe Arg Asn Cys Ile Leu Gln Leu
                325                 330                 335

Phe Gly Lys Lys Val Asp Asp Gly Ser Glu Leu Ser Ser Ala Ser Lys
            340                 345                 350

Thr Glu Val Ser Ser Val Ser Ser Val Ser Pro Ala
            355                 360

<210> SEQ ID NO 56
<211> LENGTH: 348
<212> TYPE: PRT
<213> ORGANISM: Homo sapiens

<400> SEQUENCE: 56

Met Arg Lys Met Ser Glu Glu Phe Tyr Leu Phe Lys Asn Ile Ser
 1                   5                  10                  15

Ser Val Gly Pro Trp Asp Gly Pro Gln Tyr His Ile Ala Pro Val Trp
                 20                  25                  30

Ala Phe Tyr Leu Gln Ala Ala Phe Met Gly Thr Val Phe Leu Ile Gly
                 35                  40                  45

```
Phe Pro Leu Asn Ala Met Val Leu Val Ala Thr Leu Arg Tyr Lys Lys
 50                  55                  60

Leu Arg Gln Pro Leu Asn Tyr Ile Leu Val Asn Val Ser Phe Gly Gly
 65                  70                  75                  80

Phe Leu Leu Cys Ile Phe Ser Val Phe Pro Val Phe Val Ala Ser Cys
                 85                  90                  95

Asn Gly Tyr Phe Val Phe Gly Arg His Val Cys Ala Leu Glu Gly Phe
            100                 105                 110

Leu Gly Thr Val Ala Gly Leu Val Thr Gly Trp Ser Leu Ala Phe Leu
        115                 120                 125

Ala Phe Glu Arg Tyr Ile Val Ile Cys Lys Pro Phe Gly Asn Phe Arg
    130                 135                 140

Phe Ser Ser Lys His Ala Leu Thr Val Val Leu Ala Thr Trp Thr Ile
145                 150                 155                 160

Gly Ile Gly Val Ser Ile Pro Pro Phe Phe Gly Trp Ser Arg Phe Ile
                165                 170                 175

Pro Glu Gly Leu Gln Cys Ser Cys Gly Pro Asp Trp Tyr Thr Val Gly
            180                 185                 190

Thr Lys Tyr Arg Ser Glu Ser Tyr Thr Trp Phe Leu Phe Ile Phe Cys
        195                 200                 205

Phe Ile Val Pro Leu Ser Leu Ile Cys Phe Ser Tyr Thr Gln Leu Leu
    210                 215                 220

Arg Ala Leu Lys Ala Val Ala Ala Gln Gln Gln Glu Ser Ala Thr Thr
225                 230                 235                 240

Gln Lys Ala Glu Arg Glu Val Ser Arg Met Val Val Val Met Val Gly
                245                 250                 255

Ser Phe Cys Val Cys Tyr Val Pro Tyr Ala Ala Phe Ala Met Tyr Met
            260                 265                 270

Val Asn Asn Arg Asn His Gly Leu Asp Leu Arg Leu Val Thr Ile Pro
        275                 280                 285

Ser Phe Phe Ser Lys Ser Ala Cys Ile Tyr Asn Pro Ile Ile Tyr Cys
    290                 295                 300

Phe Met Asn Lys Gln Phe Gln Ala Cys Ile Met Lys Met Val Cys Gly
305                 310                 315                 320

Lys Ala Met Thr Asp Glu Ser Asp Thr Cys Ser Ser Gln Lys Thr Glu
                325                 330                 335

Val Ser Thr Val Ser Ser Thr Gln Val Gly Pro Asn
            340                 345
```

<210> SEQ ID NO 57
<211> LENGTH: 27
<212> TYPE: RNA
<213> ORGANISM: Artificial sequence
<220> FEATURE:
<223> OTHER INFORMATION: synthetic sequence

<400> SEQUENCE: 57
cgcaaucagu gaaugcuuau acauccg                                       27

<210> SEQ ID NO 58
<211> LENGTH: 497
<212> TYPE: PRT
<213> ORGANISM: Unknown
<220> FEATURE:
<223> OTHER INFORMATION: Virus of the Parvoviridae family and
      Dependovirus genus

<400> SEQUENCE: 58

```
Met Ala Ala Asp Gly Tyr Asp Trp Asp Asn Ser Gly Arg Trp Trp Asp
1               5                   10                  15

Lys Gly Ala Lys Lys Ala Asn Lys Asp Asp Gly Arg Gly Val Gly Tyr
            20                  25                  30

Lys Tyr Gly Asn Gly Asp Lys Gly Val Asn Ala Ala Asp Ala Ala Ala
            35                  40                  45

His Asp Lys Ala Tyr Asp Lys Ala Gly Asp Asn Tyr Arg Tyr Asn His
50                  55                  60

Ala Asp Ala Arg Asp Thr Ser Gly Gly Asn Gly Arg Ala Val Ala Lys
65                  70                  75                  80

Lys Arg Val Gly Val Gly Ala Lys Thr Ala Gly Lys Lys Arg Val Ser
                85                  90                  95

Asp Ser Ser Ser Gly Gly Lys Thr Gly Ala Lys Lys Arg Asn Gly Thr
                100                 105                 110

Gly Asp Ser Ser Val Asp Gly Ala Thr Ala Ala Val Gly Thr Thr Met
                115                 120                 125

Ala Ser Gly Gly Gly Ala Met Ala Asp Asn Asn Gly Ala Asp Gly Val
            130                 135                 140

Gly Asn Ala Ser Gly Asn Trp His Cys Asp Ser Thr Trp Gly Asp Arg
145                 150                 155                 160

Val Thr Thr Ser Thr Arg Thr Trp Ala Thr Tyr Asn Asn His Tyr Lys
                165                 170                 175

Ser Ser Ala Ser Thr Gly Ala Ser Asn Asp Asn His Tyr Gly Tyr Ser
                180                 185                 190

Thr Trp Gly Tyr Asp Asn Arg His Cys His Ser Arg Asp Trp Arg Asn
            195                 200                 205

Asn Asn Trp Gly Arg Lys Arg Asn Lys Asn Val Lys Val Thr Thr Asn
        210                 215                 220

Asp Gly Val Thr Thr Ala Asn Asn Thr Ser Thr Val Val Ser Asp Ser
225                 230                 235                 240

Tyr Tyr Val Gly Ser Ala His Gly Cys Ala Asp Val Met Tyr Gly Tyr
                245                 250                 255

Thr Asn Asn Gly Ser Ala Val Gly Arg Ser Ser Tyr Cys Tyr Ser Met
            260                 265                 270

Arg Thr Gly Asn Asn Thr Ser Tyr Thr Val His Ser Ser Tyr Ala His
        275                 280                 285

Ser Ser Asp Arg Met Asn Asp Tyr Tyr Tyr Asn Arg Thr Asn Ser Gly
        290                 295                 300

Ser Ala Asn Lys Asp Ser Arg Gly Ser Ala Gly Met Ser Val Lys Asn
305                 310                 315                 320

Trp Gly Cys Tyr Arg Arg Val Ser Lys Thr Lys Thr Asp Asn Asn Asn
                325                 330                 335

Ser Asn Thr Trp Thr Gly Ala Ser Lys Tyr Asn Asn Gly Arg Ser Asn
            340                 345                 350

Gly Thr Ala Met Ala Ser His Lys Asp Asp Lys Met Ser Gly Val
        355                 360                 365

Met Gly Lys Ser Ala Gly Ala Ser Asn Thr Ala Asp Asn Val Met Thr
    370                 375                 380

Asp Lys Ala Thr Asn Val Ala Thr Arg Gly Thr Val Ala Val Asn Ser
385                 390                 395                 400

Ser Ser Thr Asp Ala Thr Gly Asp Val His Ala Met Gly Ala Gly Met
            405                 410                 415
```

-continued

```
Val Trp Asp Arg Asp Val Tyr Gly Trp Ala Lys His Thr Asp Gly His
            420                 425                 430

His Ser Met Gly Gly Gly Lys Asn Lys Asn Thr Val Ala Asn Ala Ser
        435                 440                 445

Ala Thr Lys Ala Ser Thr Tyr Ser Thr Gly Val Ser Val Trp Lys Asn
    450                 455                 460

Ser Lys Arg Trp Asn Val Tyr Thr Ser Asn Tyr Ala Lys Ser Ala Asn
465                 470                 475                 480

Val Asp Thr Val Asp Asn Asn Gly Tyr Thr Arg Gly Thr Arg Tyr Thr
                485                 490                 495

Arg

<210> SEQ ID NO 59
<211> LENGTH: 499
<212> TYPE: PRT
<213> ORGANISM: Unknown
<220> FEATURE:
<223> OTHER INFORMATION: Virus of the Parvoviridae family and
      Dependovirus genus

<400> SEQUENCE: 59

Met Ala Ala Asp Gly Tyr Asp Trp Asp Thr Ser Gly Arg Trp Trp Lys
1               5                   10                  15

Lys Gly Lys Ala Arg His Lys Asp Asp Ser Arg Gly Val Gly Tyr Lys
            20                  25                  30

Tyr Gly Asn Gly Asp Lys Gly Val Asn Ala Asp Ala Ala His Asp
        35                  40                  45

Lys Ala Tyr Asp Arg Asp Ser Gly Asp Asn Tyr Lys Tyr Asn His Ala
    50                  55                  60

Asp Ala Arg Lys Asp Thr Ser Gly Gly Asn Gly Arg Ala Val Ala Lys
65                  70                  75                  80

Lys Arg Val Gly Val Val Lys Thr Ala Gly Lys Lys Arg Val His Ser
                85                  90                  95

Val Asp Ser Ser Ser Gly Thr Gly Lys Ala Gly Ala Arg Lys Arg Asn
            100                 105                 110

Gly Thr Gly Asp Ala Asp Ser Val Asp Gly Ala Ala Ser Gly Gly Thr
        115                 120                 125

Asn Thr Met Ala Thr Gly Ser Gly Ala Met Ala Asp Asn Asn Gly Ala
    130                 135                 140

Asp Gly Val Gly Asn Ser Ser Gly Asn Trp His Cys Asp Ser Thr Trp
145                 150                 155                 160

Met Gly Asp Arg Val Thr Thr Ser Thr Arg Thr Trp Ala Thr Tyr Asn
                165                 170                 175

Asn His Tyr Lys Ser Ser Gly Ala Ser Asn Asp Asn His Tyr Gly
            180                 185                 190

Tyr Ser Thr Trp Gly Tyr Asp Asn Arg His Cys His Ser Arg Asp Trp
        195                 200                 205

Arg Asn Asn Asn Trp Gly Arg Lys Arg Asn Lys Asn Val Lys Val Thr
    210                 215                 220

Asn Asp Gly Thr Thr Thr Ala Asn Asn Thr Ser Thr Val Val Thr Asp
225                 230                 235                 240

Ser Tyr Tyr Val Gly Ser Ala His Gly Cys Ala Asp Val Met Val Tyr
                245                 250                 255

Gly Tyr Thr Asn Asn Gly Ser Ala Val Gly Arg Ser Ser Tyr Cys Tyr
            260                 265                 270
```

```
Ser Met Arg Thr Gly Asn Asn Thr Ser Tyr Thr Asp Val His Ser Ser
            275                 280                 285

Tyr Ala His Ser Ser Asp Arg Met Asn Asp Tyr Tyr Tyr Ser Arg Thr
    290                 295                 300

Asn Thr Ser Gly Thr Thr Thr Ser Arg Ser Ala Gly Ala Ser Asp Arg
305                 310                 315                 320

Asp Ser Arg Asn Trp Gly Cys Tyr Arg Val Ser Lys Thr Ser Ala
                325                 330                 335

Asp Asn Asn Ser Tyr Ser Trp Thr Gly Ala Thr Lys Tyr His Asn
            340                 345                 350

Gly Arg Asp Ser Val Asn Gly Ala Met Ala Ser His Lys Asp Lys
            355                 360                 365

Ser Gly Val Gly Lys Gly Ser Lys Thr Asn Val Asp Lys Val Met Thr
    370                 375                 380

Asp Arg Thr Thr Asn Val Ala Thr Tyr Gly Ser Val Ser Thr Asn Arg
385                 390                 395                 400

Gly Asn Arg Ala Ala Thr Ala Asp Val Asn Thr Gly Val Gly Met Val
                405                 410                 415

Trp Asp Arg Asp Val Tyr Gly Trp Ala Lys His Thr Asp Gly His His
                420                 425                 430

Ser Met Gly Gly Gly Lys His Lys Asn Thr Val Ala Asn Ser Thr Thr
    435                 440                 445

Ser Ala Ala Lys Ala Ser Thr Tyr Ser Thr Gly Val Ser Val Trp Lys
    450                 455                 460

Asn Ser Lys Arg Trp Asn Tyr Thr Ser Asn Tyr Asn Lys Ser Val Asn
465                 470                 475                 480

Val Asp Thr Val Asp Thr Asn Gly Val Tyr Ser Arg Gly Thr Arg Tyr
                485                 490                 495

Thr Arg Asn

<210> SEQ ID NO 60
<211> LENGTH: 494
<212> TYPE: PRT
<213> ORGANISM: Unknown
<220> FEATURE:
<223> OTHER INFORMATION: Virus of the Parvoviridae family and
      Dependovirus genus

<400> SEQUENCE: 60

Met Ala Ala Asp Gly Tyr Asp Trp Asp Asn Ser Gly Arg Trp Trp Ala
1               5                   10                  15

Lys Gly Val Lys Ala Asn His Asp Arg Arg Gly Val Gly Tyr Lys
            20                  25                  30

Tyr Gly Gly Asn Gly Asp Lys Gly Val Asn Ala Asp Ala Ala His
            35                  40                  45

Asp Lys Ala Tyr Asp Lys Ala Gly Asp Asn Tyr Lys Tyr Asn His Ala
    50                  55                  60

Asp Ala Arg Asp Thr Ser Gly Gly Asn Gly Arg Ala Val Ala Lys Lys
65                  70                  75                  80

Arg Gly Val Ala Ala Lys Thr Ala Gly Lys Lys Gly Ala Val Asp Ser
                85                  90                  95

Asp Ser Ser Ser Gly Val Gly Lys Ser Gly Lys Ala Arg Lys Arg Asn
                100                 105                 110

Gly Thr Gly Asp Ser Ser Val Asp Gly Ala Ala Thr Ser Gly Ser Asn
            115                 120                 125
```

```
Thr Met Ala Ser Gly Gly Ala Met Ala Asp Asn Gly Ala Asp
    130                 135                 140
Gly Val Gly Asn Ser Ser Gly Asn Trp His Cys Asp Ser Trp Gly Asp
145                 150                 155                 160
Arg Val Thr Thr Ser Thr Arg Thr Trp Ala Thr Tyr Asn Asn His Tyr
            165                 170                 175
Lys Ser Ser Ser Gly Ala Ser Asn Asp Asn His Tyr Gly Tyr Ser Thr
        180                 185                 190
Trp Gly Tyr Asp Asn Arg His Cys His Ser Arg Asp Trp Arg Asn Asn
            195                 200                 205
Asn Trp Gly Arg Lys Lys Ser Lys Asn Val Arg Gly Val Thr Asn Asp
210                 215                 220
Gly Thr Thr Thr Ala Asn Asn Thr Ser Thr Val Val Thr Asp Ser Tyr
225                 230                 235                 240
Tyr Val Gly Ser Ala His Gly Cys Ala Asp Val Met Val Tyr Gly Tyr
                245                 250                 255
Thr Asn Asn Gly Ser Ala Val Gly Arg Ser Ser Tyr Cys Tyr Ser Met
            260                 265                 270
Arg Thr Gly Asn Asn Ser Tyr Thr Asp Val His Ser Ser Tyr Ala His
        275                 280                 285
Ser Ser Asp Arg Met Asn Asp Tyr Tyr Tyr Asn Arg Thr Gly Thr Thr
    290                 295                 300
Ser Gly Thr Thr Asn Ser Arg Ser Ala Gly Ser Met Ser Ala Arg Asn
305                 310                 315                 320
Trp Gly Cys Tyr Arg Arg Ser Lys Thr Ala Asn Asp Asn Asn Asn Ser
                325                 330                 335
Asn Trp Thr Ala Ala Ser Lys Tyr His Asn Gly Arg Asp Ser Val Asn
            340                 345                 350
Gly Ala Met Ala Ser His Lys Asp Asp Lys Met His Gly Asn Gly Lys
        355                 360                 365
Gly Thr Thr Ala Ser Asn Ala Asp Asn Val Met Thr Asp Arg Thr Thr
    370                 375                 380
Asn Val Ala Thr Tyr Gly Thr Val Ala Asn Asn Ser Ser Asn Thr Ala
385                 390                 395                 400
Thr Thr Gly Thr Val Asn His Gly Ala Gly Met Val Trp Asp Arg Asp
                405                 410                 415
Val Tyr Gly Trp Ala Lys His Thr Asp Gly His His Ser Met Gly Gly
            420                 425                 430
Gly Lys His Met Lys Asn Thr Val Ala Asn Thr Thr Ser Ala Lys Ala
        435                 440                 445
Ser Thr Tyr Ser Thr Gly Val Ser Val Trp Lys Asn Ser Lys Arg Trp
    450                 455                 460
Asn Tyr Thr Ser Asn Tyr Asn Lys Ser Val Asn Val Asp Thr Val Asp
465                 470                 475                 480
Thr Asn Gly Val Tyr Ser Arg Gly Thr Arg Tyr Thr Arg Asn
                485                 490
```

<210> SEQ ID NO 61
<211> LENGTH: 492
<212> TYPE: PRT
<213> ORGANISM: Unknown
<220> FEATURE:
<223> OTHER INFORMATION: Virus of the Parvoviridae family and
      Dependovirus genus

<400> SEQUENCE: 61

```
Met Ala Ala Asp Gly Tyr Asp Trp Asp Asn Ser Gly Arg Trp Trp Ala
1               5                   10                  15

Lys Gly Val Lys Ala Asn His Asp Asn Arg Arg Gly Val Gly Tyr Lys
            20                  25                  30

Tyr Gly Gly Asn Gly Asp Lys Gly Val Asn Ala Asp Ala Ala His
        35                  40                  45

Asp Lys Ala Tyr Asp Lys Ala Gly Asp Asn Tyr Lys Tyr Asn His Ala
    50                  55                  60

Asp Ala Arg Asp Thr Ser Gly Gly Asn Gly Arg Ala Val Ala Lys Lys
65                  70                  75                  80

Arg Gly Val Ala Ala Lys Thr Ala Gly Lys Arg Val Asp Ser Asp
                85                  90                  95

Ser Ser Ser Gly Val Gly Lys Ser Gly Lys Ala Arg Lys Arg Asn Gly
            100                 105                 110

Thr Gly Asp Ser Ser Val Asp Gly Ala Ala Thr Ser Gly Ser Asn Thr
        115                 120                 125

Met Ala Ser Gly Gly Ala Met Ala Asp Asn Gly Ala Asp Gly
        130                 135                 140

Val Gly Asn Ser Ser Gly Asn Trp His Cys Asp Ser Trp Gly Asp Arg
145                 150                 155                 160

Val Thr Thr Ser Thr Arg Thr Trp Ala Thr Tyr Asn Asn His Tyr Lys
                165                 170                 175

Ser Ser Ser Gly Ala Ser Asn Asp Asn His Tyr Gly Tyr Ser Thr Trp
            180                 185                 190

Gly Tyr Asp Asn Arg His Cys His Ser Arg Asp Trp Arg Asn Asn Asn
        195                 200                 205

Trp Gly Arg Lys Lys Ser Lys Asn Val Lys Val Thr Asn Asp Gly Thr
    210                 215                 220

Thr Thr Ala Asn Asn Thr Ser Thr Val Val Thr Asp Ser Tyr Tyr Val
225                 230                 235                 240

Gly Ser Ala His Gly Cys Ala Asp Val Met Val Tyr Gly Tyr Thr Asn
                245                 250                 255

Asn Gly Ser Ala Val Gly Arg Ser Ser Tyr Cys Tyr Ser Met Arg Thr
            260                 265                 270

Gly Asn Asn Ser Tyr Thr Asp Val His Ser Ser Tyr Ala His Ser Ser
        275                 280                 285

Asp Arg Met Asn Asp Tyr Tyr Tyr Asn Arg Thr Gly Thr Thr Ser Gly
    290                 295                 300

Thr Thr Asn Ser Arg Ser Ala Gly Ser Met Ser Ala Arg Asn Trp Gly
305                 310                 315                 320

Cys Tyr Arg Arg Ser Lys Thr Ala Asn Asp Asn Asn Ser Asn Trp
                325                 330                 335

Thr Ala Ala Ser Lys Tyr His Asn Gly Arg Asp Ser Val Asn Gly Ala
            340                 345                 350

Met Ala Ser His Lys Asp Asp Lys Met His Gly Asn Gly Lys Gly Thr
        355                 360                 365

Thr Ala Ser Asn Ala Asp Asn Val Met Thr Asp Arg Thr Thr Asn Val
    370                 375                 380

Ala Thr Tyr Gly Thr Val Ala Asn Asn Ser Ser Asn Thr Ala Thr Thr
385                 390                 395                 400

Arg Thr Val Asn Asp Gly Ala Gly Met Val Trp Asp Arg Asp Val Tyr
                405                 410                 415
```

```
Gly Trp Ala Lys His Thr Asp Gly His His Ser Met Gly Gly Lys
                420                 425                 430

His Met Lys Asn Thr Val Ala Asn Thr Thr Ser Ala Lys Ala Ser Thr
            435                 440                 445

Tyr Ser Thr Gly Val Ser Val Trp Lys Asn Ser Lys Arg Trp Asn Tyr
        450                 455                 460

Thr Ser Asn Tyr Asn Lys Ser Val Asn Val Asp Thr Val Asp Thr Asn
465                 470                 475                 480

Gly Val Tyr Ser Arg Gly Thr Arg Tyr Thr Arg Asn
                485                 490
```

<210> SEQ ID NO 62
<211> LENGTH: 496
<212> TYPE: PRT
<213> ORGANISM: Unknown
<220> FEATURE:
<223> OTHER INFORMATION: Virus of the Parvoviridae family and
      Dependovirus genus

<400> SEQUENCE: 62

```
Met Thr Asp Gly Tyr Asp Trp Asp Asn Ser Gly Val Arg Trp Trp Ala
1               5                   10                  15

Gly Ala Lys Lys Ala Asn His Asp Asn Ala Arg Gly Val Gly Tyr Lys
            20                  25                  30

Tyr Gly Gly Asn Gly Asp Lys Gly Val Asn Ala Ala Asp Ala Ala Ala
        35                  40                  45

His Asp Lys Ala Tyr Asp Lys Ala Gly Asp Asn Tyr Lys Tyr Asn His
    50                  55                  60

Ala Asp Ala Arg Gly Asp Thr Ser Gly Gly Asn Gly Arg Ala Val Ala
65                  70                  75                  80

Lys Lys Arg Val Gly Val Ala Gly Thr Ala Gly Lys Lys Arg Ser Asp
                85                  90                  95

Ser Ser Thr Gly Gly Lys Lys Gly Lys Ala Lys Lys Lys Val Asp Thr
            100                 105                 110

Gly Ala Gly Asp Gly Gly Ser Thr Ser Gly Ala Met Ser Asp Asp Ser
        115                 120                 125

Met Arg Ala Ala Ala Gly Gly Ala Ala Val Gly Gly Ala Asp Gly
    130                 135                 140

Val Gly Asn Ala Ser Gly Asp Trp His Cys Asp Ser Thr Trp Ser Gly
145                 150                 155                 160

His Val Thr Thr Thr Ser Thr Arg Thr Trp Val Thr Tyr Asn Asn His
                165                 170                 175

Tyr Lys Arg Gly Ser Ser Asn Thr Tyr Asn Gly Ser Thr Trp Gly Tyr
            180                 185                 190

Asp Asn Arg His Cys His Ser Arg Asp Trp Arg Asn Asn Trp Gly
        195                 200                 205

Met Arg Lys Ala Met Arg Val Lys Asn Val Lys Val Thr Thr Ser Asn
    210                 215                 220

Gly Thr Thr Val Ala Asn Asn Thr Ser Thr Val Ala Asp Ser Ser Tyr
225                 230                 235                 240

Tyr Val Met Asp Ala Gly Gly Ser Asn Asp Val Met Tyr Gly Tyr
                245                 250                 255

Cys Gly Val Thr Gly Asn Thr Ser Thr Asp Arg Asn Ala Tyr Cys Tyr
            260                 265                 270

Ser Met Arg Thr Gly Asn Asn Thr Tyr Ser Lys Val His Ser Met Tyr
        275                 280                 285
```

```
Ala His Ser Ser Asp Arg Met Asn Asp Tyr Trp Gly Ser Thr Thr Thr
        290                 295                 300

Gly Thr Thr Asn Ala Gly Thr Ala Thr Thr Asn Thr Lys Arg Thr Asn
305                 310                 315                 320

Ser Asn Lys Lys Asn Trp Gly Ser Lys Gly Ser Lys Thr Ala Asn Asn
                325                 330                 335

Tyr Lys Ala Thr Gly Ser Asp Ser Lys Tyr Thr His Ser Thr Asp Gly
            340                 345                 350

Arg Trp Ser Ala Thr Gly Met Ala Thr Ala Gly Ala Asp Ser Lys Ser
        355                 360                 365

Asn Ser Ala Gly Lys Asn Gly Asn Thr Ala Thr Val Gly Thr Thr Ser
    370                 375                 380

Ala Ala Thr Asn Ala Thr Asp Thr Asp Met Trp Gly Asn Gly Gly Asp
385                 390                 395                 400

Ser Asn Ser Asn Thr Val Asp Arg Thr Ala Gly Ala Val Gly Met Val
                405                 410                 415

Trp Asn Arg Asp Tyr Tyr Gly Trp Ala Lys His Thr Asp Gly His His
            420                 425                 430

Ser Gly Gly Gly Lys His Lys Asn Thr Val Ala Asn Ala Thr Thr Ser
        435                 440                 445

Ser Thr Val Asn Ser Thr Tyr Ser Thr Gly Val Ser Val Asp Trp Lys
    450                 455                 460

Arg Ser Lys Arg Trp Asn Val Thr Ser Asn Tyr Gly Asn Ser Trp Ala
465                 470                 475                 480

Asp Ala Ala Gly Lys Tyr Thr Arg Ala Gly Thr Arg Tyr Thr His His
                485                 490                 495

<210> SEQ ID NO 63
<211> LENGTH: 724
<212> TYPE: PRT
<213> ORGANISM: Unknown
<220> FEATURE:
<223> OTHER INFORMATION: Virus of the Parvoviridae family and
      Dependovirus genus

<400> SEQUENCE: 63

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
```

```
            145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
                180                 185                 190
Met Ser Ala Gly Gly Gly Pro Leu Gly Asp Asn Gln Gly Ala
                195                 200                 205
Asp Gly Val Gly Asn Ala Ser Gly Asp Trp His Cys Asp Ser Thr Trp
        210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
                260                 265                 270
Phe Asp Phe Asn Arg Phe His Ser His Trp Ser Pro Arg Asp Trp Gln
        275                 280                 285
Arg Leu Ile Asn Asn Tyr Trp Gly Phe Arg Pro Arg Ser Leu Arg Val
        290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
                340                 345                 350
Leu Pro Ala Phe Pro Pro Gln Val Phe Thr Leu Pro Gln Tyr Gly Tyr
                355                 360                 365
Ala Thr Leu Asn Arg Asp Asn Thr Glu Asn Pro Thr Glu Arg Ser Ser
        370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
                420                 425                 430
Gln Tyr Leu Tyr Arg Phe Val Ser Thr Asn Asn Thr Gly Gly Val Gln
        435                 440                 445
Phe Asn Lys Asn Leu Ala Gly Arg Tyr Ala Asn Thr Tyr Lys Asn Trp
        450                 455                 460
Phe Pro Gly Pro Met Gly Arg Thr Gln Gly Trp Asn Leu Gly Ser Gly
465                 470                 475                 480
Val Asn Arg Ala Ser Val Ser Ala Phe Ala Thr Thr Asn Arg Met Glu
                485                 490                 495
Leu Glu Gly Ala Ser Tyr Gln Val Pro Pro Gln Pro Asn Gly Met Thr
                500                 505                 510
Asn Asn Leu Gln Gly Ser Asn Thr Tyr Ala Leu Glu Asn Thr Met Ile
        515                 520                 525
Phe Asn Ser Gln Pro Ala Asn Pro Gly Thr Thr Ala Thr Tyr Leu Glu
        530                 535                 540
Gly Asn Met Leu Ile Thr Ser Glu Ser Glu Thr Gln Pro Val Asn Arg
545                 550                 555                 560
Val Ala Tyr Asn Val Gly Gly Gln Met Ala Thr Asn Asn Gln Ser Ser
                565                 570                 575
```

-continued

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
    595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 64
<211> LENGTH: 499
<212> TYPE: PRT
<213> ORGANISM: Unknown
<220> FEATURE:
<223> OTHER INFORMATION: Virus of the Parvoviridae family and
      Dependovirus genus

<400> SEQUENCE: 64

Met Ala Ala Asp Gly Tyr Leu Pro Asp Trp Leu Glu Asp Asn Leu Ser Glu Gly Ile Arg Glu Trp Trp Asp
1               5                   10                  15

Lys Gly Ala Lys Lys Ala Asn Lys Asp Asp Gly Arg Gly Val Gly Tyr
            20                  25                  30

Lys Tyr Gly Asn Gly Asp Lys Gly Val Asn Ala Ala Asp Ala Ala Ala
        35                  40                  45

His Asp Lys Ala Tyr Asp Lys Ala Gly Asp Asn Tyr Arg Tyr Asn His
    50                  55                  60

Ala Asp Ala Arg Asp Thr Ser Gly Gly Asn Gly Arg Ala Val Ala Lys
65                  70                  75                  80

Lys Arg Val Gly Val Gly Ala Lys Thr Ala Gly Lys Lys Arg Val Ser
                85                  90                  95

Asp Ser Ser Gly Gly Lys Thr Gly Ala Lys Lys Arg Asn Gly Thr
            100                 105                 110

Gly Asp Ser Ser Val Asp Gly Ala Thr Ala Ala Val Gly Thr Thr Met
        115                 120                 125

Ala Ser Gly Gly Gly Ala Met Ala Asp Asn Asn Gly Ala Asp Gly Val
    130                 135                 140

Gly Asn Ala Ser Gly Asn Trp His Cys Asp Ser Thr Trp Gly Asp Arg
145                 150                 155                 160

Val Thr Thr Ser Thr Arg Thr Trp Ala Thr Tyr Asn Asn His Tyr Lys
                165                 170                 175

Ser Ser Ala Ser Thr Gly Ala Ser Asn Asp Asn His Tyr Gly Tyr Ser
            180                 185                 190

Thr Trp Gly Tyr Asp Asn Arg His Cys His Ser Arg Asp Trp Arg Asn
        195                 200                 205

-continued

Asn Asn Trp Gly Arg Lys Arg Asn Lys Asn Val Lys Val Thr Thr Asn
            210                 215                 220

Asp Gly Val Thr Thr Ala Asn Asn Thr Ser Thr Val Val Ser Asp Ser
225                 230                 235                 240

Tyr Tyr Val Gly Ser Ala His Gly Cys Ala Asp Val Met Tyr Gly Tyr
                245                 250                 255

Thr Asn Asn Gly Ser Ala Val Gly Arg Ser Ser Tyr Cys Tyr Ser Met
            260                 265                 270

Arg Thr Gly Asn Asn Thr Ser Tyr Thr Asp Val His Ser Ser Tyr Ala
        275                 280                 285

His Ser Ser Asp Arg Met Asn Asp Tyr Tyr Asn Arg Thr Asn Ser
290                 295                 300

Gly Ser Ala Asn Lys Asp Ser Arg Gly Ser Ala Gly Met Ser Val Lys
305                 310                 315                 320

Asn Trp Gly Cys Tyr Arg Arg Val Ser Lys Thr Lys Thr Asp Asn Asn
                325                 330                 335

Asn Ser Asn Thr Trp Thr Gly Ala Ser Lys Tyr Asn Asn Gly Arg Ser
            340                 345                 350

Asn Gly Thr Ala Met Ala Ser His Lys Asp Asp Lys Asp Lys Met Ser
            355                 360                 365

Gly Val Met Gly Lys Ser Ala Gly Ala Ser Asn Thr Ala Asp Asn Val
370                 375                 380

Met Thr Asp Lys Ala Thr Asn Val Ala Thr Arg Gly Thr Val Ala Val
385                 390                 395                 400

Asn Ser Ser Ser Thr Asp Ala Thr Gly Asp Val His Val Met Gly Ala
                405                 410                 415

Gly Met Val Trp Asp Arg Asp Val Tyr Gly Trp Ala Lys His Thr Asp
            420                 425                 430

Gly His His Ser Met Gly Gly Gly Lys His Lys Asn Thr Val Ala Asn
        435                 440                 445

Ala Ser Ala Thr Lys Ala Ser Thr Tyr Ser Thr Gly Val Ser Val Trp
450                 455                 460

Lys Asn Ser Lys Arg Trp Asn Val Tyr Thr Ser Asn Tyr Ala Lys Ser
465                 470                 475                 480

Ala Asn Val Asp Thr Val Asp Asn Asn Gly Tyr Thr Arg Gly Thr Arg
                485                 490                 495

Tyr Thr Arg

<210> SEQ ID NO 65
<211> LENGTH: 487
<212> TYPE: PRT
<213> ORGANISM: Unknown
<220> FEATURE:
<223> OTHER INFORMATION: Virus of the Parvoviridae family and
      Dependovirus genus

<400> SEQUENCE: 65

Met Ala Ala Asp Gly Tyr Asp Trp Asp Asn Ser Gly Arg Trp Trp Asp
1               5                   10                  15

Lys Gly Ala Lys Lys Ala Asn Lys Asp Asn Gly Arg Gly Val Gly Tyr
                20                  25                  30

Lys Tyr Gly Asn Gly Asp Lys Gly Val Asn Ala Ala Asp Ala Ala Ala
            35                  40                  45

His Asp Lys Ala Tyr Asp Lys Ala Gly Asp Asn Tyr Arg Tyr Asn His
        50                  55                  60

```
Ala Asp Ala Arg Asp Thr Ser Gly Gly Asn Gly Arg Ala Val Ala Lys
 65                  70                  75                  80

Lys Arg Val Gly Val Gly Ala Lys Thr Ala Lys Lys Arg Val Ser
             85                  90                  95

Arg Ser Asp Ser Ser Thr Gly Gly Lys Lys Gly Ala Arg Lys Arg Asn
            100                 105                 110

Gly Thr Gly Asp Ser Ser Val Asp Gly Ala Ala Ser Ser Val Gly Ser
            115                 120                 125

Gly Thr Val Ala Ala Gly Gly Ala Met Ala Asp Asn Asn Gly Ala
130             135                 140

Asp Gly Val Gly Asn Ala Ser Gly Asn Trp His Cys Asp Ser Thr Trp
145                 150                 155                 160

Gly Asp Arg Val Thr Thr Ser Thr Arg Thr Trp Ala Thr Tyr Asn Asn
                165                 170                 175

His Tyr Lys Ser Ser Thr Ala Gly Ser Thr Asn Asp Asn Thr Tyr Gly
            180                 185                 190

Tyr Ser Thr Trp Gly Tyr Asp Asn Arg His Cys His Ser Arg Asp Trp
            195                 200                 205

Arg Asn Asn Asn Trp Gly Arg Lys Lys Arg Lys Asn Val Lys Val Thr
210                 215                 220

Thr Asn Asp Gly Val Thr Thr Ala Asn Asn Thr Ser Thr Val Ser Asp
225                 230                 235                 240

Ser Tyr Tyr Val Gly Ser Ala His Gly Cys Ala Asp Val Met Tyr Gly
                245                 250                 255

Tyr Thr Asn Asn Gly Ser Ser Val Gly Arg Ser Ser Tyr Cys Tyr Ser
                260                 265                 270

Met Arg Thr Gly Asn Asn Ser Tyr Ser Asp Val His Ser Ser Tyr Ala
            275                 280                 285

His Ser Ser Asp Arg Met Asn Asp Tyr Tyr Ala Arg Thr Ser Asn
            290                 295                 300

Gly Gly Thr Ala Gly Asn Arg Tyr Gly Gly Ser Thr Met Ala Ala Lys
305                 310                 315                 320

Asn Trp Gly Cys Arg Arg Val Ser Lys Thr Asp Asn Asn Ser Asn
                325                 330                 335

Ala Trp Thr Gly Ala Thr Lys Tyr His Asn Gly Arg Asn Ser Val Asn
            340                 345                 350

Gly Val Ala Met Ala Thr His Lys Asp Asp Asp Arg Ser Ser Gly Val
            355                 360                 365

Gly Lys Thr Gly Ala Thr Asn Lys Thr Thr Asn Val Met Thr Asn Arg
            370                 375                 380

Thr Asn Val Ala Thr Tyr Gly Val Ser Ser Asn Ala Ala Asn Thr Ala
385                 390                 395                 400

Ala Thr Val Val Asn Asn Gly Ala Gly Met Val Trp Asn Arg Asp Val
                405                 410                 415

Tyr Gly Trp Ala Lys His Thr Asp Gly Asn His Ser Met Gly Gly Gly
            420                 425                 430

Lys His Lys Asn Thr Val Ala Asn Val Thr Ala Lys Ala Ser Thr Tyr
            435                 440                 445

Ser Thr Gly Val Ser Val Trp Lys Asn Ser Lys Arg Trp Asn Tyr Thr
            450                 455                 460

Ser Asn Lys Thr Gly Val Asp Ala Val Asp Ser Gly Val Tyr Ser Arg
465                 470                 475                 480
```

Gly Thr Arg Tyr Thr Arg Asn
                485

<210> SEQ ID NO 66
<211> LENGTH: 490
<212> TYPE: PRT
<213> ORGANISM: Unknown
<220> FEATURE:
<223> OTHER INFORMATION: Virus of the Parvoviridae family and
      Dependovirus genus

<400> SEQUENCE: 66

Met Ala Ala Asp Gly Tyr Asp Trp Asp Asn Ser Gly Arg Trp Trp Ala
1               5                   10                  15

Lys Gly Ala Lys Lys Ala Asn Lys Asp Asp Gly Arg Gly Val Gly Tyr
            20                  25                  30

Lys Tyr Gly Asn Gly Asp Lys Gly Val Asn Ala Ala Asp Ala Ala Ala
            35                  40                  45

His Asp Lys Ala Tyr Asp Ala Gly Asp Asn Tyr Arg Tyr Asn His Ala
        50                  55                  60

Asp Ala Arg Asp Thr Ser Gly Gly Asn Gly Arg Ala Val Ala Lys Lys
65                  70                  75                  80

Arg Val Gly Val Gly Ala Lys Thr Ala Gly Lys Lys Arg Val Ser Arg
                85                  90                  95

Ser Asp Ser Ser Thr Gly Gly Lys Lys Gly Ala Arg Lys Arg Asn Gly
            100                 105                 110

Thr Gly Asp Ser Ser Val Asp Gly Ala Ala Ser Gly Val Gly Asn Thr
        115                 120                 125

Met Ala Ala Gly Gly Gly Ala Met Ala Asp Asn Asn Gly Ala Asp Gly
    130                 135                 140

Val Gly Ser Ser Ser Gly Asn Trp His Cys Asp Ser Thr Trp Gly Asp
145                 150                 155                 160

Arg Val Thr Thr Ser Thr Arg Thr Trp Ala Thr Tyr Asn Asn His Tyr
                165                 170                 175

Lys Ser Asn Gly Thr Ser Gly Gly Ala Thr Asn Asp Asn Thr Tyr Gly
            180                 185                 190

Tyr Ser Thr Trp Gly Tyr Asp Asn Arg His Cys His Ser Arg Asp Trp
        195                 200                 205

Arg Asn Asn Asn Trp Gly Arg Lys Arg Ser Lys Asn Val Lys Val Thr
    210                 215                 220

Asn Gly Thr Lys Thr Ala Asn Asn Thr Ser Thr Val Thr Asp Ser Tyr
225                 230                 235                 240

Tyr Val Gly Ser Ala His Gly Cys Ala Asp Val Met Tyr Gly Tyr Thr
                245                 250                 255

Asn Asn Gly Ser Ala Val Gly Arg Ser Ser Tyr Cys Tyr Ser Met Arg
            260                 265                 270

Thr Gly Asn Asn Thr Tyr Thr Asp Val His Ser Ser Tyr Ala His Ser
        275                 280                 285

Ser Asp Arg Met Asn Asp Tyr Tyr Tyr Ser Arg Thr Thr Thr Gly Gly
    290                 295                 300

Thr Ala Asn Thr Thr Gly Ser Gly Gly Asn Thr Met Ala Asn Ala Lys
305                 310                 315                 320

Asn Trp Gly Cys Tyr Arg Arg Val Ser Thr Thr Thr Gly Asn Asn
                325                 330                 335

Ser Asn Ala Trp Thr Ala Gly Thr Lys Tyr His Asn Gly Arg Asn Ser
            340                 345                 350

```
Ala Asn Gly Ala Met Ala Thr His Lys Asp Asp Arg Ser Asn Gly Gly
        355                 360                 365

Lys Asn Ala Ala Arg Asp Asn Ala Asp Tyr Ser Asp Val Met Thr Ser
370                 375                 380

Lys Thr Thr Asn Val Ala Thr Tyr Gly Val Ala Asp Asn Asn Thr Ala
385                 390                 395                 400

Gly Thr Val Asn Ser Gly Ala Gly Met Val Trp Asn Arg Asp Val Tyr
                405                 410                 415

Gly Trp Ala Lys His Thr Asp Gly Asn His Ser Met Gly Gly Gly Lys
            420                 425                 430

His Lys Asn Thr Val Ala Asp Thr Thr Asn Ser Lys Asn Ser Thr Tyr
        435                 440                 445

Ser Thr Gly Val Ser Val Trp Lys Asn Ser Lys Arg Trp Asn Tyr Thr
    450                 455                 460

Ser Asn Tyr Tyr Lys Ser Thr Ser Val Asp Ala Val Asn Thr Gly Val
465                 470                 475                 480

Tyr Ser Arg Gly Thr Arg Tyr Thr Arg Asn
                485                 490

<210> SEQ ID NO 67
<211> LENGTH: 737
<212> TYPE: PRT
<213> ORGANISM: Unknown
<220> FEATURE:
<223> OTHER INFORMATION: Virus of the Parvoviridae family and
      Dependovirus genus
<220> FEATURE:
<221> NAME/KEY: SITE
<222> LOCATION: (264)..(264)
<223> OTHER INFORMATION: Xaa can be any naturally occurring amino acid
<220> FEATURE:
<221> NAME/KEY: SITE
<222> LOCATION: (266)..(266)
<223> OTHER INFORMATION: Xaa can be any naturally occurring amino acid
<220> FEATURE:
<221> NAME/KEY: SITE
<222> LOCATION: (268)..(268)
<223> OTHER INFORMATION: Xaa can be any naturally occurring amino acid
<220> FEATURE:
<221> NAME/KEY: SITE
<222> LOCATION: (448)..(448)
<223> OTHER INFORMATION: Xaa can be any naturally occurring amino acid
<220> FEATURE:
<221> NAME/KEY: SITE
<222> LOCATION: (459)..(460)
<223> OTHER INFORMATION: Xaa can be any naturally occurring amino acid
<220> FEATURE:
<221> NAME/KEY: SITE
<222> LOCATION: (467)..(467)
<223> OTHER INFORMATION: Xaa can be any naturally occurring amino acid
<220> FEATURE:
<221> NAME/KEY: SITE
<222> LOCATION: (470)..(471)
<223> OTHER INFORMATION: Xaa can be any naturally occurring amino acid
<220> FEATURE:
<221> NAME/KEY: SITE
<222> LOCATION: (474)..(474)
<223> OTHER INFORMATION: Xaa can be any naturally occurring amino acid
<220> FEATURE:
<221> NAME/KEY: SITE
<222> LOCATION: (495)..(495)
<223> OTHER INFORMATION: Xaa can be any naturally occurring amino acid
<220> FEATURE:
<221> NAME/KEY: SITE
<222> LOCATION: (516)..(516)
<223> OTHER INFORMATION: Xaa can be any naturally occurring amino acid
<220> FEATURE:
<221> NAME/KEY: SITE
<222> LOCATION: (533)..(533)
```

```
<223> OTHER INFORMATION: Xaa can be any naturally occurring amino acid
<220> FEATURE:
<221> NAME/KEY: SITE
<222> LOCATION: (547)..(547)
<223> OTHER INFORMATION: Xaa can be any naturally occurring amino acid
<220> FEATURE:
<221> NAME/KEY: SITE
<222> LOCATION: (551)..(551)
<223> OTHER INFORMATION: Xaa can be any naturally occurring amino acid
<220> FEATURE:
<221> NAME/KEY: SITE
<222> LOCATION: (555)..(555)
<223> OTHER INFORMATION: Xaa can be any naturally occurring amino acid
<220> FEATURE:
<221> NAME/KEY: SITE
<222> LOCATION: (557)..(557)
<223> OTHER INFORMATION: Xaa can be any naturally occurring amino acid
<220> FEATURE:
<221> NAME/KEY: SITE
<222> LOCATION: (561)..(561)
<223> OTHER INFORMATION: Xaa can be any naturally occurring amino acid
<220> FEATURE:
<221> NAME/KEY: SITE
<222> LOCATION: (563)..(563)
<223> OTHER INFORMATION: Xaa can be any naturally occurring amino acid
<220> FEATURE:
<221> NAME/KEY: SITE
<222> LOCATION: (577)..(577)
<223> OTHER INFORMATION: Xaa can be any naturally occurring amino acid
<220> FEATURE:
<221> NAME/KEY: SITE
<222> LOCATION: (583)..(583)
<223> OTHER INFORMATION: Xaa can be any naturally occurring amino acid
<220> FEATURE:
<221> NAME/KEY: SITE
<222> LOCATION: (593)..(593)
<223> OTHER INFORMATION: Xaa can be any naturally occurring amino acid
<220> FEATURE:
<221> NAME/KEY: SITE
<222> LOCATION: (596)..(596)
<223> OTHER INFORMATION: Xaa can be any naturally occurring amino acid
<220> FEATURE:
<221> NAME/KEY: SITE
<222> LOCATION: (661)..(662)
<223> OTHER INFORMATION: Xaa can be any naturally occurring amino acid
<220> FEATURE:
<221> NAME/KEY: SITE
<222> LOCATION: (664)..(665)
<223> OTHER INFORMATION: Xaa can be any naturally occurring amino acid
<220> FEATURE:
<221> NAME/KEY: SITE
<222> LOCATION: (710)..(710)
<223> OTHER INFORMATION: Xaa can be any naturally occurring amino acid
<220> FEATURE:
<221> NAME/KEY: SITE
<222> LOCATION: (717)..(719)
<223> OTHER INFORMATION: Xaa can be any naturally occurring amino acid
<220> FEATURE:
<221> NAME/KEY: SITE
<222> LOCATION: (723)..(723)
<223> OTHER INFORMATION: Xaa can be any naturally occurring amino acid

<400> SEQUENCE: 67

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80
```

```
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Gly Pro Ser Gly Leu Gly Ser Gly Thr Met Ala Ala Gly Gly
        195                 200                 205
Gly Ala Pro Met Ala Asp Asn Asn Glu Gly Ala Asp Gly Val Gly Asn
210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Ser Xaa Ser Xaa Gly Xaa Thr Asn Asp Asn
            260                 265                 270
His Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Asp Gly Val Thr Thr Ile Ala Asn
                325                 330                 335
Asn Leu Thr Ser Thr Val Gln Val Phe Ser Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Met Ile Pro Gln Tyr Gly Tyr Leu Thr Leu Asn Asn
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Thr Phe Ser Tyr Thr
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Xaa
        435                 440                 445
Arg Thr Gln Ser Thr Gly Gly Thr Ala Gly Xaa Xaa Glu Leu Leu Phe
450                 455                 460
Ser Gln Xaa Gly Pro Xaa Xaa Met Ser Xaa Gln Ala Lys Asn Trp Leu
465                 470                 475                 480
Pro Gly Pro Cys Tyr Arg Gln Gln Arg Val Ser Lys Thr Leu Xaa Gln
                485                 490                 495
Asn Asn Asn Ser Asn Phe Ala Trp Thr Gly Ala Thr Lys Tyr His Leu
```

```
                500                 505                 510
Asn Gly Arg Xaa Ser Leu Val Asn Pro Gly Val Ala Met Ala Thr His
            515                 520                 525
Lys Asp Asp Glu Xaa Arg Phe Phe Pro Ser Ser Gly Val Leu Ile Phe
        530                 535                 540
Gly Lys Xaa Gly Ala Gly Xaa Asn Asn Thr Xaa Leu Xaa Asn Val Met
545                 550                 555                 560
Xaa Thr Xaa Glu Glu Glu Ile Lys Thr Thr Asn Pro Val Ala Thr Glu
                565                 570                 575
Xaa Tyr Gly Val Val Ala Xaa Asn Leu Gln Ser Ser Asn Thr Ala Pro
            580                 585                 590
Xaa Thr Gly Xaa Val Asn Ser Gln Gly Ala Leu Pro Gly Met Val Trp
        595                 600                 605
Gln Asn Arg Asp Val Tyr Leu Gln Gly Pro Ile Trp Ala Lys Ile Pro
    610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asn Pro Pro Xaa Xaa Phe Xaa Xaa Ala Lys Phe Ala Ser Phe Ile
            660                 665                 670
Thr Gln Tyr Ser Thr Gly Gln Val Ser Val Glu Ile Glu Trp Glu Leu
        675                 680                 685
Gln Lys Glu Asn Ser Lys Arg Trp Asn Pro Glu Ile Gln Tyr Thr Ser
    690                 695                 700
Asn Tyr Ala Lys Ser Xaa Asn Val Asp Phe Ala Val Xaa Xaa Xaa Gly
705                 710                 715                 720
Val Tyr Xaa Glu Pro Arg Pro Ile Gly Thr Arg Tyr Leu Thr Arg Asn
                725                 730                 735
Leu

<210> SEQ ID NO 68
<211> LENGTH: 42
<212> TYPE: PRT
<213> ORGANISM: Unknown
<220> FEATURE:
<223> OTHER INFORMATION: Virus of the Parvoviridae family and
      Dependovirus genus

<400> SEQUENCE: 68

Pro Val Ala Thr Glu Gln Tyr Gly Ser Val Ser Thr Asn Leu Gln Arg
1               5                  10                  15

Gly Asn Arg Gln Ala Ala Thr Ala Asp Val Asn Thr Gln Gly Val Leu
            20                  25                  30

Pro Gly Met Val Trp Gln Asp Arg Asp Val
        35                  40

<210> SEQ ID NO 69
<211> LENGTH: 42
<212> TYPE: PRT
<213> ORGANISM: Unknown
<220> FEATURE:
<223> OTHER INFORMATION: Virus of the Parvoviridae family and
      Dependovirus genus

<400> SEQUENCE: 69

Pro Val Ala Thr Glu Arg Phe Gly Thr Val Ala Val Asn Phe Gln Ser
1               5                  10                  15
```

```
Ser Ser Thr Asp Pro Ala Thr Gly Asp Val His Ala Met Gly Ala Leu
            20                  25                  30

Pro Gly Met Val Trp Gln Asp Arg Asp Val
        35                  40

<210> SEQ ID NO 70
<211> LENGTH: 42
<212> TYPE: PRT
<213> ORGANISM: Unknown
<220> FEATURE:
<223> OTHER INFORMATION: Virus of the Parvoviridae family and
      Dependovirus genus

<400> SEQUENCE: 70

Arg Val Ala Tyr Asn Val Gly Gly Gln Met Ala Thr Asn Asn Gln Ser
1               5                   10                  15

Ser Thr Thr Ala Pro Ala Thr Gly Thr Tyr Asn Leu Gln Glu Ile Val
            20                  25                  30

Pro Gly Ser Val Trp Met Glu Arg Asp Val
        35                  40

<210> SEQ ID NO 71
<211> LENGTH: 42
<212> TYPE: PRT
<213> ORGANISM: Unknown
<220> FEATURE:
<223> OTHER INFORMATION: Virus of the Parvoviridae family and
      Dependovirus genus

<400> SEQUENCE: 71

Pro Val Ala Thr Glu Arg Phe Gly Thr Val Ala Val Asn Leu Gln Ser
1               5                   10                  15

Ser Ser Thr Asp Pro Ala Thr Gly Asp Val His Val Met Gly Ala Leu
            20                  25                  30

Pro Gly Met Val Trp Gln Asp Arg Asp Val
        35                  40

<210> SEQ ID NO 72
<211> LENGTH: 42
<212> TYPE: PRT
<213> ORGANISM: Unknown
<220> FEATURE:
<223> OTHER INFORMATION: Virus of the Parvoviridae family and
      Dependovirus genus

<400> SEQUENCE: 72

Pro Val Ala Thr Glu Glu Tyr Gly Ile Val Ser Ser Asn Leu Gln Ala
1               5                   10                  15

Ala Asn Thr Ala Ala Gln Thr Gln Val Val Asn Asn Gln Gly Ala Leu
            20                  25                  30

Pro Gly Met Val Trp Gln Asn Arg Asp Val
        35                  40

<210> SEQ ID NO 73
<211> LENGTH: 42
<212> TYPE: PRT
<213> ORGANISM: Unknown
<220> FEATURE:
<223> OTHER INFORMATION: Virus of the Parvoviridae family and
      Dependovirus genus

<400> SEQUENCE: 73

Pro Val Ala Thr Glu Glu Tyr Gly Ile Val Ala Asp Asn Leu Gln Gln
```

```
                1               5                  10                  15
Gln Asn Thr Ala Pro Gln Ile Gly Thr Val Asn Ser Gln Gly Ala Leu
               20                  25                  30

Pro Gly Met Val Trp Gln Asn Arg Asp Val
               35                  40

<210> SEQ ID NO 74
<211> LENGTH: 42
<212> TYPE: PRT
<213> ORGANISM: Unknown
<220> FEATURE:
<223> OTHER INFORMATION: Virus of the Parvoviridae family and
      Dependovirus genus

<400> SEQUENCE: 74

Pro Val Ala Thr Glu Ser Tyr Gly Gln Val Ala Thr Asn His Gln Ser
1               5                  10                  15

Ala Gln Ala Gln Ala Gln Thr Gly Trp Val Gln Asn Gln Gly Ile Leu
               20                  25                  30

Pro Gly Met Val Trp Gln Asp Arg Asp Val
               35                  40

<210> SEQ ID NO 75
<211> LENGTH: 42
<212> TYPE: PRT
<213> ORGANISM: Unknown
<220> FEATURE:
<223> OTHER INFORMATION: Virus of the Parvoviridae family and
      Dependovirus genus

<400> SEQUENCE: 75

Pro Val Ala Thr Glu Gln Tyr Gly Val Val Ala Asp Asn Leu Gln Gln
1               5                  10                  15

Ala Asn Thr Gly Pro Ile Val Gly Asn Val Asn Ser Gln Gly Ala Leu
               20                  25                  30

Pro Gly Met Val Trp Gln Asn Arg Asp Val
               35                  40

<210> SEQ ID NO 76
<211> LENGTH: 42
<212> TYPE: PRT
<213> ORGANISM: Unknown
<220> FEATURE:
<223> OTHER INFORMATION: Virus of the Parvoviridae family and
      Dependovirus genus

<400> SEQUENCE: 76

Ala Thr Asp Thr Asp Met Trp Gly Asn Leu Pro Gly Gly Asp Gln Ser
1               5                  10                  15

Asn Ser Asn Leu Pro Thr Val Asp Arg Leu Thr Ala Leu Gly Ala Val
               20                  25                  30

Pro Gly Met Val Trp Gln Asn Arg Asp Ile
               35                  40

<210> SEQ ID NO 77
<211> LENGTH: 42
<212> TYPE: PRT
<213> ORGANISM: Unknown
<220> FEATURE:
<223> OTHER INFORMATION: Virus of the Parvoviridae family and
      Dependovirus genus
<220> FEATURE:
<221> NAME/KEY: SITE
<222> LOCATION: (6)..(6)
```

```
<223> OTHER INFORMATION: Xaa can be any naturally occurring amino acid
<220> FEATURE:
<221> NAME/KEY: SITE
<222> LOCATION: (12)..(12)
<223> OTHER INFORMATION: Xaa can be any naturally occurring amino acid
<220> FEATURE:
<221> NAME/KEY: SITE
<222> LOCATION: (22)..(22)
<223> OTHER INFORMATION: Xaa can be any naturally occurring amino acid
<220> FEATURE:
<221> NAME/KEY: SITE
<222> LOCATION: (25)..(25)
<223> OTHER INFORMATION: Xaa can be any naturally occurring amino acid

<400> SEQUENCE: 77

Pro Val Ala Thr Glu Xaa Tyr Gly Val Val Ala Xaa Asn Leu Gln Ser
1               5                   10                  15

Ser Asn Thr Ala Pro Xaa Thr Gly Xaa Val Asn Ser Gln Gly Ala Leu
            20                  25                  30

Pro Gly Met Val Trp Gln Asn Arg Asp Val
        35                  40

<210> SEQ ID NO 78
<211> LENGTH: 240
<212> TYPE: PRT
<213> ORGANISM: Unknown
<220> FEATURE:
<223> OTHER INFORMATION: Virus of the Parvoviridae family and
      Dependovirus genus

<400> SEQUENCE: 78

Thr Phe Ser Tyr Thr Phe Glu Glu Val Pro Phe His Ser Ser Tyr Ala
1               5                   10                  15

His Ser Gln Ser Leu Asp Arg Leu Met Asn Pro Leu Ile Asp Gln Tyr
            20                  25                  30

Leu Tyr Tyr Leu Asn Arg Thr Gln Asn Gln Ser Gly Ser Ala Gln Asn
        35                  40                  45

Lys Asp Leu Leu Phe Ser Arg Gly Ser Pro Ala Gly Met Ser Val Gln
    50                  55                  60

Pro Lys Asn Trp Leu Pro Gly Pro Cys Tyr Arg Gln Gln Arg Val Ser
65                  70                  75                  80

Lys Thr Lys Thr Asp Asn Asn Asn Ser Asn Phe Thr Trp Thr Gly Ala
                85                  90                  95

Ser Lys Tyr Asn Leu Asn Gly Arg Glu Ser Ile Ile Asn Pro Gly Thr
            100                 105                 110

Ala Met Ala Ser His Lys Asp Asp Glu Asp Lys Phe Phe Pro Met Ser
        115                 120                 125

Gly Val Met Ile Phe Gly Lys Glu Ser Ala Gly Ala Ser Asn Thr Ala
    130                 135                 140

Leu Asp Asn Val Met Ile Thr Asp Glu Glu Glu Ile Lys Ala Thr Asn
145                 150                 155                 160

Pro Val Ala Thr Glu Arg Phe Gly Thr Val Ala Val Asn Phe Gln Ser
                165                 170                 175

Ser Ser Thr Asp Pro Ala Thr Gly Asp Val His Ala Met Gly Ala Leu
            180                 185                 190

Pro Gly Met Val Trp Gln Asp Arg Asp Val Tyr Leu Gln Gly Pro Ile
        195                 200                 205

Trp Ala Lys Ile Pro His Thr Asp Gly His Phe His Pro Ser Pro Leu
    210                 215                 220

Met Gly Gly Phe Gly Leu Lys Asn Pro Pro Pro Gln Ile Leu Ile Lys
```

-continued

```
                225                 230                 235                 240

<210> SEQ ID NO 79
<211> LENGTH: 240
<212> TYPE: PRT
<213> ORGANISM: Unknown
<220> FEATURE:
<223> OTHER INFORMATION: Virus of the Parvoviridae family and
      Dependovirus genus

<400> SEQUENCE: 79

Thr Phe Ser Tyr Thr Phe Glu Asp Val Pro Phe His Ser Tyr Ala
1               5                   10                  15

His Ser Gln Ser Leu Asp Arg Leu Met Asn Pro Leu Ile Asp Gln Tyr
                20                  25                  30

Leu Tyr Tyr Leu Asn Arg Thr Gln Asn Gln Ser Gly Ser Ala Gln Asn
                35                  40                  45

Lys Asp Leu Leu Phe Ser Arg Gly Ser Pro Ala Gly Met Ser Val Gln
50                  55                  60

Pro Lys Asn Trp Leu Pro Gly Pro Cys Tyr Arg Gln Gln Arg Val Ser
65                  70                  75                  80

Lys Thr Lys Thr Asp Asn Asn Asn Ser Asn Phe Thr Trp Thr Gly Ala
                85                  90                  95

Ser Lys Tyr Asn Leu Asn Gly Arg Glu Ser Ile Ile Asn Pro Gly Thr
                100                 105                 110

Ala Met Ala Ser His Lys Asp Asp Lys Asp Lys Phe Phe Pro Met Ser
                115                 120                 125

Gly Val Met Ile Phe Gly Lys Glu Ser Ala Gly Ala Ser Asn Thr Ala
130                 135                 140

Leu Asp Asn Val Met Ile Thr Asp Glu Glu Glu Ile Lys Ala Thr Asn
145                 150                 155                 160

Pro Val Ala Thr Glu Arg Phe Gly Thr Val Ala Val Asn Leu Gln Ser
                165                 170                 175

Ser Ser Thr Asp Pro Ala Thr Gly Asp Val His Val Met Gly Ala Leu
                180                 185                 190

Pro Gly Met Val Trp Gln Asp Arg Asp Val Tyr Leu Gln Gly Pro Ile
                195                 200                 205

Trp Ala Lys Ile Pro His Thr Asp Gly His Phe His Pro Ser Pro Leu
210                 215                 220

Met Gly Gly Phe Gly Leu Lys His Pro Pro Pro Gln Ile Leu Ile Lys
225                 230                 235                 240

<210> SEQ ID NO 80
<211> LENGTH: 240
<212> TYPE: PRT
<213> ORGANISM: Unknown
<220> FEATURE:
<223> OTHER INFORMATION: Virus of the Parvoviridae family and
      Dependovirus genus

<400> SEQUENCE: 80

Phe Ser Tyr Thr Phe Glu Asp Val Pro Phe His Ser Ser Tyr Ala His
1               5                   10                  15

Ser Gln Ser Leu Asp Arg Leu Met Asn Pro Leu Ile Asp Gln Tyr Leu
                20                  25                  30

Tyr Tyr Leu Asn Arg Thr Gln Gly Thr Thr Ser Gly Thr Thr Asn Gln
                35                  40                  45

Ser Arg Leu Leu Phe Ser Gln Ala Gly Pro Gln Ser Met Ser Leu Gln
```

Ala Arg Asn Trp Leu Pro Gly Pro Cys Tyr Arg Gln Gln Arg Leu Ser
65                  70                  75                  80

Lys Thr Ala Asn Asp Asn Asn Ser Asn Phe Pro Trp Thr Ala Ala
            85                  90                  95

Ser Lys Tyr His Leu Asn Gly Arg Asp Ser Leu Val Asn Pro Gly Pro
                100                 105                 110

Ala Met Ala Ser His Lys Asp Asp Glu Glu Lys Phe Phe Pro Met His
            115                 120                 125

Gly Asn Leu Ile Phe Gly Lys Glu Gly Thr Thr Ala Ser Asn Ala Glu
                130                 135                 140

Leu Asp Asn Val Met Ile Thr Asp Glu Glu Glu Ile Arg Thr Thr Asn
145                 150                 155                 160

Pro Val Ala Thr Glu Gln Tyr Gly Thr Val Ala Asn Asn Leu Gln Ser
                165                 170                 175

Ser Asn Thr Ala Pro Thr Thr Gly Thr Val Asn His Gln Gly Ala Leu
                180                 185                 190

Pro Gly Met Val Trp Gln Asp Arg Asp Val Tyr Leu Gln Gly Pro Ile
                195                 200                 205

Trp Ala Lys Ile Pro His Thr Asp Gly His Phe His Pro Ser Pro Leu
                210                 215                 220

Met Gly Gly Phe Gly Leu Lys His Pro Pro Pro Gln Ile Met Ile Lys
225                 230                 235                 240

<210> SEQ ID NO 81
<211> LENGTH: 240
<212> TYPE: PRT
<213> ORGANISM: Unknown
<220> FEATURE:
<223> OTHER INFORMATION: Virus of the Parvoviridae family and
      Dependovirus genus

<400> SEQUENCE: 81

Phe Ser Tyr Thr Phe Glu Asp Val Pro Phe His Ser Ser Tyr Ala His
1               5                   10                  15

Ser Gln Ser Leu Asp Arg Leu Met Asn Pro Leu Ile Asp Gln Tyr Leu
                20                  25                  30

Tyr Tyr Leu Ser Arg Thr Asn Thr Pro Ser Gly Thr Thr Thr Gln Ser
            35                  40                  45

Arg Leu Gln Phe Ser Gln Ala Gly Ala Ser Asp Ile Arg Asp Gln Ser
    50                  55                  60

Arg Asn Trp Leu Pro Gly Pro Cys Tyr Arg Gln Gln Arg Val Ser Lys
65                  70                  75                  80

Thr Ser Ala Asp Asn Asn Ser Glu Tyr Ser Trp Thr Gly Ala Thr
            85                  90                  95

Lys Tyr His Leu Asn Gly Arg Asp Ser Leu Val Asn Pro Gly Pro Ala
                100                 105                 110

Met Ala Ser His Lys Asp Asp Glu Glu Lys Phe Phe Pro Gln Ser Gly
            115                 120                 125

Val Leu Ile Phe Gly Lys Gln Gly Ser Glu Lys Thr Asn Val Asp Ile
130                 135                 140

Glu Lys Val Met Ile Thr Asp Glu Glu Glu Ile Arg Thr Thr Asn Pro
145                 150                 155                 160

Val Ala Thr Glu Gln Tyr Gly Ser Val Ser Thr Asn Leu Gln Arg Gly
                165                 170                 175

```
Asn Arg Gln Ala Ala Thr Ala Asp Val Asn Thr Gln Gly Val Leu Pro
            180                 185                 190

Gly Met Val Trp Gln Asp Arg Asp Val Tyr Leu Gln Gly Pro Ile Trp
        195                 200                 205

Ala Lys Ile Pro His Thr Asp Gly His Phe His Pro Ser Pro Leu Met
210                 215                 220

Gly Gly Phe Gly Leu Lys His Pro Pro Gln Ile Leu Ile Lys Asn
225                 230                 235                 240
```

<210> SEQ ID NO 82
<211> LENGTH: 243
<212> TYPE: PRT
<213> ORGANISM: Unknown
<220> FEATURE:
<223> OTHER INFORMATION: Virus of the Parvoviridae family and
      Dependovirus genus

<400> SEQUENCE: 82

```
Asn Phe Gln Phe Thr Tyr Thr Phe Glu Asp Val Pro Phe His Ser Ser
1               5                   10                  15

Tyr Ala His Ser Gln Ser Leu Asp Arg Leu Met Asn Pro Leu Ile Asp
            20                  25                  30

Gln Tyr Leu Tyr Tyr Leu Ser Arg Thr Gln Thr Thr Gly Gly Thr Ala
        35                  40                  45

Asn Thr Gln Thr Leu Gly Phe Ser Gln Gly Gly Pro Asn Thr Met Ala
50                  55                  60

Asn Gln Ala Lys Asn Trp Leu Pro Gly Pro Cys Tyr Arg Gln Gln Arg
65                  70                  75                  80

Val Ser Thr Thr Thr Gly Gln Asn Asn Asn Ser Asn Phe Ala Trp Thr
                85                  90                  95

Ala Gly Thr Lys Tyr His Leu Asn Gly Arg Asn Ser Leu Ala Asn Pro
            100                 105                 110

Gly Ile Ala Met Ala Thr His Lys Asp Asp Glu Glu Arg Phe Phe Pro
        115                 120                 125

Ser Asn Gly Ile Leu Ile Phe Gly Lys Gln Asn Ala Ala Arg Asp Asn
130                 135                 140

Ala Asp Tyr Ser Asp Val Met Leu Thr Ser Glu Glu Glu Ile Lys Thr
145                 150                 155                 160

Thr Asn Pro Val Ala Thr Glu Glu Tyr Gly Ile Val Ala Asp Asn Leu
                165                 170                 175

Gln Gln Gln Asn Thr Ala Pro Gln Ile Gly Thr Val Asn Ser Gln Gly
            180                 185                 190

Ala Leu Pro Gly Met Val Trp Gln Asn Arg Asp Val Tyr Leu Gln Gly
        195                 200                 205

Pro Ile Trp Ala Lys Ile Pro His Thr Asp Gly Asn Phe His Pro Ser
210                 215                 220

Pro Leu Met Gly Gly Phe Gly Leu Lys His Pro Pro Pro Gln Ile Leu
225                 230                 235                 240

Ile Lys Asn
```

<210> SEQ ID NO 83
<211> LENGTH: 243
<212> TYPE: PRT
<213> ORGANISM: Unknown
<220> FEATURE:
<223> OTHER INFORMATION: Virus of the Parvoviridae family and
      Dependovirus genus

```
<400> SEQUENCE: 83

Asn Phe Gln Phe Thr Tyr Thr Phe Glu Asp Val Pro Phe His Ser Ser
1               5                   10                  15

Tyr Ala His Ser Gln Ser Leu Asp Arg Leu Met Asn Pro Leu Ile Asp
            20                  25                  30

Gln Tyr Leu Tyr Tyr Leu Ser Arg Thr Gln Thr Thr Gly Gly Thr Ala
        35                  40                  45

Asn Thr Gln Thr Leu Gly Phe Ser Gln Gly Gly Pro Asn Thr Met Ala
    50                  55                  60

Asn Gln Ala Lys Asn Trp Leu Pro Gly Pro Cys Tyr Arg Gln Gln Arg
65                  70                  75                  80

Val Ser Thr Thr Thr Gly Gln Asn Asn Asn Ser Asn Phe Ala Trp Thr
                85                  90                  95

Ala Gly Thr Lys Tyr His Leu Asn Gly Arg Asn Ser Leu Ala Asn Pro
            100                 105                 110

Gly Ile Ala Met Ala Thr His Lys Asp Asp Glu Glu Arg Phe Phe Pro
        115                 120                 125

Ser Asn Gly Ile Leu Ile Phe Gly Lys Gln Asn Ala Ala Arg Asp Asn
    130                 135                 140

Ala Asp Tyr Ser Asp Val Met Leu Thr Ser Glu Glu Ile Lys Thr
145                 150                 155                 160

Thr Asn Pro Val Ala Thr Glu Glu Tyr Gly Ile Val Ala Asp Asn Leu
                165                 170                 175

Gln Gly Gln Arg Gln Ala Ala Gln Ile Gly Thr Val Asn Ser Gln Gly
            180                 185                 190

Ala Leu Pro Gly Met Val Trp Gln Asn Arg Asp Val Tyr Leu Gln Gly
        195                 200                 205

Pro Ile Trp Ala Lys Ile Pro His Thr Asp Gly Asn Phe His Pro Ser
    210                 215                 220

Pro Leu Met Gly Gly Phe Gly Leu Lys His Pro Pro Pro Gln Ile Leu
225                 230                 235                 240

Ile Lys Asn

<210> SEQ ID NO 84
<211> LENGTH: 241
<212> TYPE: PRT
<213> ORGANISM: Unknown
<220> FEATURE:
<223> OTHER INFORMATION: Virus of the Parvoviridae family and
      Dependovirus genus

<400> SEQUENCE: 84

Phe Gln Phe Ser Tyr Thr Phe Glu Asp Val Pro Phe His Ser Ser Tyr
1               5                   10                  15

Ala His Ser Gln Ser Leu Asp Arg Leu Met Asn Pro Leu Ile Asp Gln
            20                  25                  30

Tyr Leu Tyr Tyr Leu Val Arg Thr Gln Thr Thr Gly Thr Gly Gly Thr
        35                  40                  45

Gln Thr Leu Ala Phe Ser Gln Ala Gly Pro Ser Ser Met Ala Asn Gln
    50                  55                  60

Ala Arg Asn Trp Val Pro Gly Pro Cys Tyr Arg Gln Gln Arg Val Ser
65                  70                  75                  80

Thr Thr Thr Asn Gln Asn Asn Asn Ser Asn Phe Ala Trp Thr Gly Ala
                85                  90                  95

Ala Lys Phe Lys Leu Asn Gly Arg Asp Ser Leu Met Asn Pro Gly Val
```

```
                100             105             110
Ala Met Ala Ser His Lys Asp Asp Asp Arg Phe Phe Pro Ser Ser
            115             120             125
Gly Val Leu Ile Phe Gly Lys Gln Gly Ala Gly Asn Asp Gly Val Asp
    130             135             140
Tyr Ser Gln Val Leu Ile Thr Asp Glu Glu Ile Lys Ala Thr Asn
145             150             155             160
Pro Val Ala Thr Glu Glu Tyr Gly Ala Val Ala Ile Asn Asn Gln Ala
                165             170             175
Ala Asn Thr Gln Ala Gln Thr Gly Leu Val His Asn Gln Gly Val Ile
            180             185             190
Pro Gly Met Val Trp Gln Asn Arg Asp Val Tyr Leu Gln Gly Pro Ile
        195             200             205
Trp Ala Lys Ile Pro His Thr Asp Gly Asn Phe His Pro Ser Pro Leu
    210             215             220
Met Gly Gly Phe Gly Leu Lys His Pro Pro Pro Gln Ile Leu Ile Lys
225             230             235             240
Asn
```

```
<210> SEQ ID NO 85
<211> LENGTH: 243
<212> TYPE: PRT
<213> ORGANISM: Unknown
<220> FEATURE:
<223> OTHER INFORMATION: Virus of the Parvoviridae family and
      Dependovirus genus

<400> SEQUENCE: 85

Asn Phe Glu Phe Ser Tyr Thr Phe Glu Asp Val Pro Phe His Ser Ser
1               5                   10                  15
Tyr Ala His Ser Gln Ser Leu Asp Arg Leu Met Asn Pro Leu Ile Asp
            20                  25                  30
Gln Tyr Leu Tyr Tyr Leu Ser Arg Thr Gln Ser Thr Gly Gly Thr Gln
        35                  40                  45
Gly Thr Gln Gln Leu Leu Phe Ser Gln Ala Gly Pro Ala Asn Met Ser
    50                  55                  60
Ala Gln Ala Lys Asn Trp Leu Pro Gly Pro Cys Tyr Arg Gln Gln Arg
65                  70                  75                  80
Val Ser Thr Thr Leu Ser Gln Asn Asn Asn Ser Asn Phe Ala Trp Thr
                85                  90                  95
Gly Ala Thr Lys Tyr His Leu Asn Gly Arg Asp Ser Leu Val Asn Pro
            100                 105                 110
Gly Val Ala Met Ala Thr His Lys Asp Asp Glu Glu Arg Phe Phe Pro
        115                 120                 125
Ser Ser Gly Val Leu Met Phe Gly Lys Gln Gly Ala Gly Arg Asp Asn
    130                 135                 140
Val Asp Tyr Ser Ser Val Met Leu Thr Ser Glu Glu Ile Lys Thr
145                 150                 155                 160
Thr Asn Pro Val Ala Thr Glu Gln Tyr Gly Val Val Ala Asp Asn Leu
                165                 170                 175
Gln Gln Ala Asn Thr Gly Pro Ile Val Gly Asn Val Asn Ser Gln Gly
            180                 185                 190
Ala Leu Pro Gly Met Val Trp Gln Asn Arg Asp Val Tyr Leu Gln Gly
        195                 200                 205
Pro Ile Trp Ala Lys Ile Pro His Thr Asp Gly Asn Phe His Pro Ser
```

```
            210                 215                 220
Pro Leu Met Gly Gly Phe Gly Leu Lys His Pro Pro Gln Ile Leu
225                 230                 235                 240

Ile Lys Asn

<210> SEQ ID NO 86
<211> LENGTH: 242
<212> TYPE: PRT
<213> ORGANISM: Unknown
<220> FEATURE:
<223> OTHER INFORMATION: Virus of the Parvoviridae family and
      Dependovirus genus

<400> SEQUENCE: 86

Phe Glu Phe Ser Tyr Ser Phe Glu Asp Val Pro Phe His Ser Tyr
1               5                   10                  15

Ala His Ser Gln Ser Leu Asp Arg Leu Met Asn Pro Leu Ile Asp Gln
                20                  25                  30

Tyr Leu Tyr Tyr Leu Ala Arg Thr Gln Ser Asn Pro Gly Gly Thr Ala
            35                  40                  45

Gly Asn Arg Glu Leu Gln Phe Tyr Gln Gly Gly Pro Ser Thr Met Ala
50                  55                  60

Glu Gln Ala Lys Asn Trp Leu Pro Gly Pro Cys Phe Arg Gln Gln Arg
65                  70                  75                  80

Val Ser Lys Thr Leu Asp Gln Asn Asn Asn Ser Asn Phe Ala Trp Thr
                85                  90                  95

Gly Ala Thr Lys Tyr His Leu Asn Gly Arg Asn Ser Leu Val Asn Pro
            100                 105                 110

Gly Val Ala Met Ala Thr His Lys Asp Asp Glu Asp Arg Phe Phe Pro
        115                 120                 125

Ser Ser Gly Val Leu Ile Phe Gly Lys Thr Gly Ala Thr Asn Lys Thr
130                 135                 140

Thr Leu Glu Asn Val Leu Met Thr Asn Glu Glu Glu Ile Arg Pro Thr
145                 150                 155                 160

Asn Pro Val Ala Thr Glu Glu Tyr Gly Ile Val Ser Ser Asn Leu Gln
                165                 170                 175

Ala Ala Asn Thr Ala Ala Gln Thr Gln Val Val Asn Asn Gln Gly Ala
            180                 185                 190

Leu Pro Gly Met Val Trp Gln Asn Arg Asp Val Tyr Leu Gln Gly Pro
        195                 200                 205

Ile Trp Ala Lys Ile Pro His Thr Asp Gly Asn Phe His Pro Ser Pro
    210                 215                 220

Leu Met Gly Gly Phe Gly Leu Lys His Pro Pro Gln Ile Leu Ile
225                 230                 235                 240

Lys Asn

<210> SEQ ID NO 87
<211> LENGTH: 240
<212> TYPE: PRT
<213> ORGANISM: Unknown
<220> FEATURE:
<223> OTHER INFORMATION: Virus of the Parvoviridae family and
      Dependovirus genus

<400> SEQUENCE: 87

Phe Gln Phe Ser Tyr Glu Phe Glu Asn Val Pro Phe His Ser Ser Tyr
1               5                   10                  15
```

```
Ala His Ser Gln Ser Leu Asp Arg Leu Met Asn Pro Leu Ile Asp Gln
             20                  25                  30

Tyr Leu Tyr Tyr Leu Ser Lys Thr Ile Asn Gly Ser Gly Gln Asn Gln
         35                  40                  45

Gln Thr Leu Lys Phe Ser Val Ala Gly Pro Ser Asn Met Ala Val Gln
 50                  55                  60

Gly Arg Asn Tyr Ile Pro Gly Pro Ser Tyr Arg Gln Gln Arg Val Ser
65                  70                  75                  80

Thr Thr Val Thr Gln Asn Asn Ser Glu Phe Ala Trp Pro Gly Ala
                 85                  90                  95

Ser Ser Trp Ala Leu Asn Gly Arg Asn Ser Leu Met Asn Pro Gly Pro
             100                 105                 110

Ala Met Ala Ser His Lys Glu Gly Glu Asp Arg Phe Phe Pro Leu Ser
             115                 120                 125

Gly Ser Leu Ile Phe Gly Lys Gln Gly Thr Gly Arg Asp Asn Val Asp
         130                 135                 140

Ala Asp Lys Val Met Ile Thr Asn Glu Glu Ile Lys Thr Thr Asn
145                 150                 155                 160

Pro Val Ala Thr Glu Ser Tyr Gly Gln Val Ala Thr Asn His Gln Ser
                 165                 170                 175

Ala Gln Ala Gln Ala Gln Thr Gly Trp Val Gln Asn Gln Gly Ile Leu
             180                 185                 190

Pro Gly Met Val Trp Gln Asp Arg Asp Val Tyr Leu Gln Gly Pro Ile
             195                 200                 205

Trp Ala Lys Ile Pro His Thr Asp Gly Asn Phe His Pro Ser Pro Leu
210                 215                 220

Met Gly Gly Phe Gly Met Lys His Pro Pro Gln Ile Leu Ile Lys
225                 230                 235                 240
```

<210> SEQ ID NO 88
<211> LENGTH: 240
<212> TYPE: PRT
<213> ORGANISM: Unknown
<220> FEATURE:
<223> OTHER INFORMATION: Virus of the Parvoviridae family and Dependovirus genus

<400> SEQUENCE: 88

```
Phe Gln Phe Ser Tyr Glu Phe Glu Asn Val Pro Phe His Ser Ser Tyr
1               5                   10                  15

Ala His Ser Gln Ser Leu Asp Arg Leu Met Asn Pro Leu Ile Asp Gln
             20                  25                  30

Tyr Leu Tyr Tyr Leu Ser Lys Thr Ile Asn Gly Ser Gly Gln Asn Gln
         35                  40                  45

Gln Thr Leu Lys Phe Ser Val Ala Gly Pro Ser Asn Met Ala Val Gln
 50                  55                  60

Gly Arg Asn Tyr Ile Pro Gly Pro Ser Tyr Arg Gln Gln Arg Val Ser
65                  70                  75                  80

Thr Thr Val Thr Gln Asn Asn Ser Glu Phe Ala Trp Pro Gly Ala
                 85                  90                  95

Ser Ser Trp Ala Leu Asn Gly Arg Asn Ser Leu Met Asn Pro Gly Pro
             100                 105                 110

Ala Met Ala Ser His Lys Glu Gly Glu Asp Arg Phe Phe Pro Leu Ser
             115                 120                 125

Gly Ser Leu Ile Phe Gly Lys Gln Gly Thr Gly Arg Asp Asn Val Asp
         130                 135                 140
```

```
Ala Asp Lys Val Met Ile Thr Asn Glu Glu Ile Lys Thr Thr Asn
145                 150                 155                 160

Pro Val Ala Thr Glu Ser Tyr Gly Gln Val Ala Thr Asn His Gln Ser
            165                 170                 175

Gly Gln Ala Gln Ala Ala Thr Gly Trp Val Gln Asn Gln Gly Ile Leu
            180                 185                 190

Pro Gly Met Val Trp Gln Asp Arg Asp Val Tyr Leu Gln Gly Pro Ile
            195                 200                 205

Trp Ala Lys Ile Pro His Thr Asp Gly Asn Phe His Pro Ser Pro Leu
            210                 215                 220

Met Gly Gly Phe Gly Met Lys His Pro Pro Gln Ile Leu Ile Lys
225                 230                 235                 240

<210> SEQ ID NO 89
<211> LENGTH: 240
<212> TYPE: PRT
<213> ORGANISM: Unknown
<220> FEATURE:
<223> OTHER INFORMATION: Virus of the Parvoviridae family and
      Dependovirus genus

<400> SEQUENCE: 89

Asn Phe Glu Phe Thr Tyr Asn Phe Glu Glu Val Pro Phe His Ser Ser
1               5                   10                  15

Phe Ala Pro Ser Gln Asn Leu Phe Lys Leu Ala Asn Pro Leu Val Asp
            20                  25                  30

Gln Tyr Leu Tyr Arg Phe Val Ser Thr Asn Asn Thr Gly Gly Val Gln
        35                  40                  45

Phe Asn Lys Asn Leu Ala Gly Arg Tyr Ala Asn Thr Tyr Lys Asn Trp
50                  55                  60

Phe Pro Gly Pro Met Gly Arg Thr Gln Gly Trp Asn Leu Gly Ser Gly
65                  70                  75                  80

Val Asn Arg Ala Ser Val Ser Ala Phe Ala Thr Thr Asn Arg Met Glu
                85                  90                  95

Leu Glu Gly Ala Ser Tyr Gln Val Pro Pro Gln Pro Asn Gly Met Thr
            100                 105                 110

Asn Asn Leu Gln Gly Ser Asn Thr Tyr Ala Leu Glu Asn Thr Met Ile
        115                 120                 125

Phe Asn Ser Gln Pro Ala Asn Pro Gly Thr Thr Ala Thr Tyr Leu Glu
130                 135                 140

Gly Asn Met Leu Ile Thr Ser Glu Ser Glu Thr Gln Pro Val Asn Arg
145                 150                 155                 160

Val Ala Tyr Asn Val Gly Gly Gln Met Ala Thr Asn Asn Gln Ser Ser
                165                 170                 175

Thr Thr Ala Pro Ala Thr Gly Thr Tyr Asn Leu Gln Glu Ile Val Pro
            180                 185                 190

Gly Ser Val Trp Met Glu Arg Asp Val Tyr Leu Gln Gly Pro Ile Trp
        195                 200                 205

Ala Lys Ile Pro Glu Thr Gly Ala His Phe His Pro Ser Pro Ala Met
210                 215                 220

Gly Gly Phe Gly Leu Lys His Pro Pro Pro Met Met Leu Ile Lys Asn
225                 230                 235                 240

<210> SEQ ID NO 90
<211> LENGTH: 224
<212> TYPE: PRT
```

<213> ORGANISM: Homo sapiens

<400> SEQUENCE: 90

```
Met Ser Arg Lys Ile Glu Gly Phe Leu Leu Leu Leu Phe Gly Tyr
1               5                   10                  15

Glu Ala Thr Leu Gly Leu Ser Ser Thr Glu Asp Glu Gly Glu Asp Pro
                20                  25                  30

Trp Tyr Gln Lys Ala Cys Lys Cys Asp Cys Gln Gly Pro Asn Ala
            35                  40                  45

Leu Trp Ser Ala Gly Ala Thr Ser Leu Asp Cys Ile Pro Glu Cys Pro
    50                  55                  60

Tyr His Lys Pro Leu Gly Phe Glu Ser Gly Glu Val Thr Pro Asp Gln
65                  70                  75                  80

Ile Thr Cys Ser Asn Pro Glu Gln Tyr Val Gly Trp Tyr Ser Ser Trp
                85                  90                  95

Thr Ala Asn Lys Ala Arg Leu Asn Ser Gln Gly Phe Gly Cys Ala Trp
                100                 105                 110

Leu Ser Lys Phe Gln Asp Ser Ser Gln Trp Leu Gln Ile Asp Leu Lys
            115                 120                 125

Glu Ile Lys Val Ile Ser Gly Ile Leu Thr Gln Gly Arg Cys Asp Ile
130                 135                 140

Asp Glu Trp Met Thr Lys Tyr Ser Val Gln Tyr Arg Thr Asp Glu Arg
145                 150                 155                 160

Leu Asn Trp Ile Tyr Tyr Lys Asp Gln Thr Gly Asn Asn Arg Val Phe
                165                 170                 175

Tyr Gly Asn Ser Asp Arg Thr Ser Thr Val Gln Asn Leu Leu Arg Pro
            180                 185                 190

Pro Ile Ile Ser Arg Phe Ile Arg Leu Ile Pro Leu Gly Trp His Val
        195                 200                 205

Arg Ile Ala Ile Arg Met Glu Leu Leu Glu Cys Val Ser Lys Cys Ala
210                 215                 220
```

<210> SEQ ID NO 91
<211> LENGTH: 247
<212> TYPE: PRT
<213> ORGANISM: Homo sapiens

<400> SEQUENCE: 91

```
Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
                20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
    50                  55                  60

His Val Ile Glu Glu Leu Leu Asp Glu Asp His Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Met Val Leu Arg
            115                 120                 125

His Ser Asp Pro Ala Arg Arg Gly Glu Leu Ser Val Cys Asp Ser Ile
```

```
              130                 135                 140
Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
                165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
        195                 200                 205

Arg Thr Thr Gln Ser Tyr Val Arg Ala Leu Thr Met Asp Ser Lys Lys
    210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

<210> SEQ ID NO 92
<211> LENGTH: 533
<212> TYPE: PRT
<213> ORGANISM: Homo sapiens

<400> SEQUENCE: 92

Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255
```

```
Val Lys Ile Asn Leu Phe Lys Phe Leu Ser Ser Trp Ser Leu Trp Gly
                260                 265                 270

Ala Asn Tyr Met Asp Cys Phe Glu Ser Asn Glu Thr Met Gly Val Trp
            275                 280                 285

Leu His Ile Ala Asp Lys Lys Arg Lys Lys Tyr Leu Asn Asn Lys Tyr
        290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Val
        370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
            420                 425                 430

Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
        515                 520                 525

Leu Phe Lys Lys Ser
        530

<210> SEQ ID NO 93
<211> LENGTH: 346
<212> TYPE: PRT
<213> ORGANISM: Homo sapiens

<400> SEQUENCE: 93

Met Ala Leu Leu Lys Val Lys Phe Asp Gln Lys Lys Arg Val Lys Leu
1               5                   10                  15

Ala Gln Gly Leu Trp Leu Met Asn Trp Phe Ser Val Leu Ala Gly Ile
            20                  25                  30

Ile Ile Phe Ser Leu Gly Leu Phe Leu Lys Ile Glu Leu Arg Lys Arg
        35                  40                  45

Ser Asp Val Met Asn Asn Ser Glu Ser His Phe Val Pro Asn Ser Leu
    50                  55                  60

Ile Gly Met Gly Val Leu Ser Cys Val Phe Asn Ser Leu Ala Gly Lys
65                  70                  75                  80

Ile Cys Tyr Asp Ala Leu Asp Pro Ala Lys Tyr Ala Arg Trp Lys Pro
                85                  90                  95
```

-continued

```
Trp Leu Lys Pro Tyr Leu Ala Ile Cys Val Leu Phe Asn Ile Ile Leu
                100                 105                 110

Phe Leu Val Ala Leu Cys Cys Phe Leu Leu Arg Gly Ser Leu Glu Asn
            115                 120                 125

Thr Leu Gly Gln Gly Leu Lys Asn Gly Met Lys Tyr Tyr Arg Asp Thr
        130                 135                 140

Asp Thr Pro Gly Arg Cys Phe Met Lys Lys Thr Ile Asp Met Leu Gln
145                 150                 155                 160

Ile Glu Phe Lys Cys Cys Gly Asn Asn Gly Phe Arg Asp Trp Phe Glu
                165                 170                 175

Ile Gln Trp Ile Ser Asn Arg Tyr Leu Asp Phe Ser Ser Lys Glu Val
            180                 185                 190

Lys Asp Arg Ile Lys Ser Asn Val Asp Gly Arg Tyr Leu Val Asp Gly
        195                 200                 205

Val Pro Phe Ser Cys Cys Asn Pro Ser Ser Pro Arg Pro Cys Ile Gln
210                 215                 220

Tyr Gln Ile Thr Asn Asn Ser Ala His Tyr Ser Tyr Asp His Gln Thr
                225                 230                 235                 240

Glu Glu Leu Asn Leu Trp Val Arg Gly Cys Arg Ala Ala Leu Leu Ser
                245                 250                 255

Tyr Tyr Ser Ser Leu Met Asn Ser Met Gly Val Val Thr Leu Leu Ile
            260                 265                 270

Trp Leu Phe Glu Val Thr Ile Thr Ile Gly Leu Arg Tyr Leu Gln Thr
        275                 280                 285

Ser Leu Asp Gly Val Ser Asn Pro Glu Glu Ser Glu Ser Glu Ser Gln
290                 295                 300

Gly Trp Leu Leu Glu Arg Ser Val Pro Glu Thr Trp Lys Ala Phe Leu
305                 310                 315                 320

Glu Ser Val Lys Lys Leu Gly Lys Gly Asn Gln Val Glu Ala Glu Gly
                325                 330                 335

Ala Asp Ala Gly Gln Ala Pro Glu Ala Gly
            340                 345

<210> SEQ ID NO 94
<211> LENGTH: 470
<212> TYPE: PRT
<213> ORGANISM: Homo sapiens

<400> SEQUENCE: 94

Met Ser His His Pro Ser Gly Leu Arg Ala Gly Phe Ser Ser Thr Ser
1               5                   10                  15

Tyr Arg Arg Thr Phe Gly Pro Pro Ser Leu Ser Pro Gly Ala Phe
            20                  25                  30

Ser Tyr Ser Ser Ser Ser Arg Phe Ser Ser Ser Arg Leu Leu Gly Ser
        35                  40                  45

Ala Ser Pro Ser Ser Ser Val Arg Leu Gly Ser Phe Arg Ser Pro Arg
    50                  55                  60

Ala Gly Ala Gly Ala Leu Leu Arg Leu Pro Ser Glu Arg Leu Asp Phe
65              70                  75                  80

Ser Met Ala Glu Ala Leu Asn Gln Glu Phe Leu Ala Thr Arg Ser Asn
                85                  90                  95

Glu Lys Gln Glu Leu Gln Glu Leu Asn Asp Arg Phe Ala Asn Phe Ile
            100                 105                 110

Glu Lys Val Arg Phe Leu Glu Gln Gln Asn Ala Ala Leu Arg Gly Glu
```

```
                115                 120                 125
Leu Ser Gln Ala Arg Gly Gln Glu Pro Ala Arg Ala Asp Gln Leu Cys
    130                 135                 140

Gln Gln Glu Leu Arg Glu Leu Arg Arg Glu Leu Glu Leu Leu Gly Arg
145                 150                 155                 160

Glu Arg Asp Arg Val Gln Val Glu Arg Asp Gly Leu Ala Glu Asp Leu
                165                 170                 175

Ala Ala Leu Lys Gln Arg Leu Glu Glu Glu Thr Arg Lys Arg Glu Asp
            180                 185                 190

Ala Glu His Asn Leu Val Leu Phe Arg Lys Asp Val Asp Asp Ala Thr
        195                 200                 205

Leu Ser Arg Leu Glu Leu Glu Arg Lys Ile Glu Ser Leu Met Asp Glu
    210                 215                 220

Ile Glu Phe Leu Lys Lys Leu His Glu Glu Glu Leu Arg Asp Leu Gln
225                 230                 235                 240

Val Ser Val Glu Ser Gln Gln Val Gln Val Glu Val Glu Ala Thr
                245                 250                 255

Val Lys Pro Glu Leu Thr Ala Ala Leu Arg Asp Ile Arg Ala Gln Tyr
            260                 265                 270

Glu Ser Ile Ala Ala Lys Asn Leu Gln Glu Ala Glu Glu Trp Tyr Lys
        275                 280                 285

Ser Lys Tyr Ala Asp Leu Ser Asp Ala Ala Asn Arg Asn His Glu Ala
    290                 295                 300

Leu Arg Gln Ala Lys Gln Glu Met Asn Glu Ser Arg Arg Gln Ile Gln
305                 310                 315                 320

Ser Leu Thr Cys Glu Val Asp Gly Leu Arg Gly Thr Asn Glu Ala Leu
                325                 330                 335

Leu Arg Gln Leu Arg Glu Leu Glu Glu Gln Phe Ala Leu Glu Ala Gly
            340                 345                 350

Gly Tyr Gln Ala Gly Ala Ala Arg Leu Glu Glu Glu Leu Arg Gln Leu
        355                 360                 365

Lys Glu Glu Met Ala Arg His Leu Arg Glu Tyr Gln Glu Leu Leu Asn
    370                 375                 380

Val Lys Met Ala Leu Asp Ile Glu Ile Ala Thr Tyr Arg Lys Leu Leu
385                 390                 395                 400

Glu Gly Glu Glu Ser Arg Ile Ser Val Pro Val His Ser Phe Ala Ser
                405                 410                 415

Leu Asn Ile Lys Thr Thr Val Pro Glu Val Glu Pro Pro Gln Asp Ser
            420                 425                 430

His Ser Arg Lys Thr Val Leu Ile Lys Thr Ile Glu Thr Arg Asn Gly
        435                 440                 445

Glu Val Val Thr Glu Ser Gln Lys Glu Gln Arg Ser Glu Leu Asp Lys
    450                 455                 460

Ser Ser Ala His Ser Tyr
465                 470

<210> SEQ ID NO 95
<211> LENGTH: 1286
<212> TYPE: PRT
<213> ORGANISM: Homo sapiens

<400> SEQUENCE: 95

Met Ser His Leu Val Asp Pro Thr Ser Gly Asp Leu Pro Val Arg Asp
1               5                   10                  15
```

```
Ile Asp Ala Ile Pro Leu Val Leu Pro Ala Ser Lys Gly Lys Asn Met
             20                  25                  30

Lys Thr Gln Pro Pro Leu Ser Arg Met Asn Arg Glu Glu Leu Glu Asp
         35                  40                  45

Ser Phe Phe Arg Leu Arg Glu Asp His Met Leu Val Lys Glu Leu Ser
     50                  55                  60

Trp Lys Gln Gln Asp Glu Ile Lys Arg Leu Arg Thr Thr Leu Leu Arg
 65                  70                  75                  80

Leu Thr Ala Ala Gly Arg Asp Leu Arg Val Ala Glu Glu Ala Ala Pro
                 85                  90                  95

Leu Ser Glu Thr Ala Arg Arg Gly Gln Lys Ala Gly Trp Arg Gln Arg
             100                 105                 110

Leu Ser Met His Gln Arg Pro Gln Met His Arg Leu Gln Gly His Phe
         115                 120                 125

His Cys Val Gly Pro Ala Ser Pro Arg Arg Ala Gln Pro Arg Val Gln
     130                 135                 140

Val Gly His Arg Gln Leu His Thr Ala Gly Ala Pro Val Pro Glu Lys
145                 150                 155                 160

Pro Lys Arg Gly Pro Arg Asp Arg Leu Ser Tyr Thr Ala Pro Pro Ser
             165                 170                 175

Phe Lys Glu His Ala Thr Asn Glu Asn Arg Gly Glu Val Ala Ser Lys
         180                 185                 190

Pro Ser Glu Leu Val Ser Gly Ser Asn Ser Ile Ile Ser Phe Ser Ser
     195                 200                 205

Val Ile Ser Met Ala Lys Pro Ile Gly Leu Cys Met Pro Asn Ser Ala
 210                 215                 220

His Ile Met Ala Ser Asn Thr Met Gln Val Glu Glu Pro Pro Lys Ser
225                 230                 235                 240

Pro Glu Lys Met Trp Pro Lys Asp Glu Asn Phe Glu Gln Arg Ser Ser
             245                 250                 255

Leu Glu Cys Ala Gln Lys Ala Ala Glu Leu Arg Ala Ser Ile Lys Glu
         260                 265                 270

Lys Val Glu Leu Ile Arg Leu Lys Lys Leu Leu His Glu Arg Asn Ala
     275                 280                 285

Ser Leu Val Met Thr Lys Ala Gln Leu Thr Glu Val Gln Glu Ala Tyr
 290                 295                 300

Glu Thr Leu Leu Gln Lys Asn Gln Gly Ile Leu Ser Ala Ala His Glu
305                 310                 315                 320

Ala Leu Leu Lys Gln Val Asn Glu Leu Arg Ala Glu Leu Lys Glu Glu
             325                 330                 335

Ser Lys Lys Ala Val Ser Leu Lys Ser Gln Leu Glu Asp Val Ser Ile
         340                 345                 350

Leu Gln Met Thr Leu Lys Glu Phe Gln Glu Arg Val Glu Asp Leu Glu
     355                 360                 365

Lys Glu Arg Lys Leu Leu Asn Asp Asn Tyr Asp Lys Leu Leu Glu Ser
 370                 375                 380

Met Leu Asp Ser Ser Asp Ser Ser Gln Pro His Trp Ser Asn Glu
385                 390                 395                 400

Leu Ile Ala Glu Gln Leu Gln Gln Val Ser Gln Leu Gln Asp Gln
             405                 410                 415

Leu Asp Ala Glu Leu Glu Asp Lys Arg Lys Val Leu Leu Glu Leu Ser
         420                 425                 430

Arg Glu Lys Ala Gln Asn Glu Asp Leu Lys Leu Glu Val Thr Asn Ile
```

```
                435                 440                 445
Leu Gln Lys His Lys Gln Glu Val Glu Leu Leu Gln Asn Ala Ala Thr
450                 455                 460
Ile Ser Gln Pro Pro Asp Arg Gln Ser Glu Pro Ala Thr His Pro Ala
465                 470                 475                 480
Val Leu Gln Glu Asn Thr Gln Ile Glu Pro Ser Glu Pro Lys Asn Gln
                485                 490                 495
Glu Glu Lys Lys Leu Ser Gln Val Leu Asn Glu Leu Gln Val Ser His
                500                 505                 510
Ala Glu Thr Thr Leu Glu Leu Glu Lys Thr Arg Asp Met Leu Ile Leu
            515                 520                 525
Gln Arg Lys Ile Asn Val Cys Tyr Gln Glu Glu Leu Glu Ala Met Met
        530                 535                 540
Thr Lys Ala Asp Asn Asp Asn Arg Asp His Lys Glu Lys Leu Glu Arg
545                 550                 555                 560
Leu Thr Arg Leu Leu Asp Leu Lys Asn Asn Arg Ile Lys Gln Leu Glu
                565                 570                 575
Gly Ile Leu Arg Ser His Asp Leu Pro Thr Ser Glu Gln Leu Lys Asp
                580                 585                 590
Val Ala Tyr Gly Thr Arg Pro Leu Ser Leu Cys Leu Glu Thr Leu Pro
            595                 600                 605
Ala His Gly Asp Glu Asp Lys Val Asp Ile Ser Leu Leu His Gln Gly
        610                 615                 620
Glu Asn Leu Phe Glu Leu His Ile His Gln Ala Phe Leu Thr Ser Ala
625                 630                 635                 640
Ala Leu Ala Gln Ala Gly Asp Thr Gln Pro Thr Thr Phe Cys Thr Tyr
                645                 650                 655
Ser Phe Tyr Asp Phe Glu Thr His Cys Thr Pro Leu Ser Val Gly Pro
                660                 665                 670
Gln Pro Leu Tyr Asp Phe Thr Ser Gln Tyr Val Met Glu Thr Asp Ser
            675                 680                 685
Leu Phe Leu His Tyr Leu Gln Glu Ala Ser Ala Arg Leu Asp Ile His
        690                 695                 700
Gln Ala Met Ala Ser Glu His Ser Thr Leu Ala Ala Gly Trp Ile Cys
705                 710                 715                 720
Phe Asp Arg Val Leu Glu Thr Val Glu Lys Val His Gly Leu Ala Thr
                725                 730                 735
Leu Ile Gly Ala Gly Glu Glu Phe Gly Val Leu Glu Tyr Trp Met
                740                 745                 750
Arg Leu Arg Phe Pro Ile Lys Pro Ser Leu Gln Ala Cys Asn Lys Arg
            755                 760                 765
Lys Lys Ala Gln Val Tyr Leu Ser Thr Asp Val Leu Gly Gly Arg Lys
        770                 775                 780
Ala Gln Glu Glu Glu Phe Arg Ser Glu Ser Trp Glu Pro Gln Asn Glu
785                 790                 795                 800
Leu Trp Ile Glu Ile Thr Lys Cys Cys Gly Leu Arg Ser Arg Trp Leu
                805                 810                 815
Gly Thr Gln Pro Ser Pro Tyr Ala Val Tyr Arg Phe Phe Thr Phe Ser
            820                 825                 830
Asp His Asp Thr Ala Ile Ile Pro Ala Ser Asn Asn Pro Tyr Phe Arg
            835                 840                 845
Asp Gln Ala Arg Phe Pro Val Leu Val Thr Ser Asp Leu Asp His Tyr
        850                 855                 860
```

```
Leu Arg Arg Glu Ala Leu Ser Ile His Val Phe Asp Asp Glu Asp Leu
865                 870                 875                 880

Glu Pro Gly Ser Tyr Leu Gly Arg Ala Arg Val Pro Leu Leu Pro Leu
                885                 890                 895

Ala Lys Asn Glu Ser Ile Lys Gly Asp Phe Asn Leu Thr Asp Pro Ala
            900                 905                 910

Glu Lys Pro Asn Gly Ser Ile Gln Val Gln Leu Asp Trp Lys Phe Pro
        915                 920                 925

Tyr Ile Pro Pro Glu Ser Phe Leu Lys Pro Glu Ala Gln Thr Lys Gly
    930                 935                 940

Lys Asp Thr Lys Asp Ser Ser Lys Ile Ser Ser Glu Glu Lys Ala
945                 950                 955                 960

Ser Phe Pro Ser Gln Asp Gln Met Ala Ser Pro Glu Val Pro Ile Glu
                965                 970                 975

Ala Gly Gln Tyr Arg Ser Lys Arg Lys Pro Pro His Gly Gly Glu Arg
            980                 985                 990

Lys Glu Lys Glu His Gln Val Val Ser Tyr Ser Arg Arg Lys His Gly
        995                 1000                1005

Lys Arg Ile Gly Val Gln Gly Lys Asn Arg Met Glu Tyr Leu Ser
    1010                1015                1020

Leu Asn Ile Leu Asn Gly Asn Thr Pro Glu Gln Val Asn Tyr Thr
    1025                1030                1035

Glu Trp Lys Phe Ser Glu Thr Asn Ser Phe Ile Gly Asp Gly Phe
    1040                1045                1050

Lys Asn Gln His Glu Glu Glu Met Thr Leu Ser His Ser Ala
    1055                1060                1065

Leu Lys Gln Lys Glu Pro Leu His Pro Val Asn Asp Lys Glu Ser
    1070                1075                1080

Ser Glu Gln Gly Ser Glu Val Ser Glu Ala Gln Thr Thr Asp Ser
    1085                1090                1095

Asp Asp Val Ile Val Pro Pro Met Ser Gln Lys Tyr Pro Lys Ala
    1100                1105                1110

Asp Ser Glu Lys Met Cys Ile Glu Ile Val Ser Leu Ala Phe Tyr
    1115                1120                1125

Pro Glu Ala Glu Val Met Ser Asp Glu Asn Ile Lys Gln Val Tyr
    1130                1135                1140

Val Glu Tyr Lys Phe Tyr Asp Leu Pro Leu Ser Glu Thr Glu Thr
    1145                1150                1155

Pro Val Ser Leu Arg Lys Pro Arg Ala Gly Glu Glu Ile His Phe
    1160                1165                1170

His Phe Ser Lys Val Ile Asp Leu Asp Pro Gln Glu Gln Gln Gly
    1175                1180                1185

Arg Arg Arg Phe Leu Phe Asp Met Leu Asn Gly Gln Asp Pro Asp
    1190                1195                1200

Gln Gly His Leu Lys Phe Thr Val Val Ser Asp Pro Leu Asp Glu
    1205                1210                1215

Glu Lys Lys Glu Cys Glu Glu Val Gly Tyr Ala Tyr Leu Gln Leu
    1220                1225                1230

Trp Gln Ile Leu Glu Ser Gly Arg Asp Ile Leu Glu Gln Glu Leu
    1235                1240                1245

Asp Ile Val Ser Pro Glu Asp Leu Ala Thr Pro Ile Gly Arg Leu
    1250                1255                1260
```

```
Lys Val Ser Leu Gln Ala Ala Ala Val Leu His Ala Ile Tyr Lys
1265                1270                1275

Glu Met Thr Glu Asp Leu Phe Ser
1280                1285

<210> SEQ ID NO 96
<211> LENGTH: 653
<212> TYPE: PRT
<213> ORGANISM: Unknown
<220> FEATURE:
<223> OTHER INFORMATION: Rab escort protein-1

<400> SEQUENCE: 96

Met Ala Asp Thr Leu Pro Ser Glu Phe Asp Val Ile Val Ile Gly Thr
1               5                   10                  15

Gly Leu Pro Glu Ser Ile Ile Ala Ala Ala Cys Ser Arg Ser Gly Arg
            20                  25                  30

Arg Val Leu His Val Asp Ser Arg Ser Tyr Tyr Gly Gly Asn Trp Ala
        35                  40                  45

Ser Phe Ser Phe Ser Gly Leu Leu Ser Trp Leu Lys Glu Tyr Gln Glu
    50                  55                  60

Asn Ser Asp Ile Val Ser Asp Ser Pro Val Trp Gln Asp Gln Ile Leu
65                  70                  75                  80

Glu Asn Glu Glu Ala Ile Ala Leu Ser Arg Lys Asp Lys Thr Ile Gln
                85                  90                  95

His Val Glu Val Phe Cys Tyr Ala Ser Gln Asp Leu His Glu Asp Val
            100                 105                 110

Glu Glu Ala Gly Ala Leu Gln Lys Asn His Ala Leu Val Thr Ser Ala
        115                 120                 125

Asn Ser Thr Glu Ala Ala Asp Ser Ala Phe Leu Pro Thr Glu Asp Glu
130                 135                 140

Ser Leu Ser Thr Met Ser Cys Glu Met Leu Thr Glu Gln Thr Pro Ser
145                 150                 155                 160

Ser Asp Pro Glu Asn Ala Leu Glu Val Asn Gly Ala Glu Val Thr Gly
                165                 170                 175

Glu Lys Glu Asn His Cys Asp Asp Lys Thr Cys Val Pro Ser Thr Ser
            180                 185                 190

Ala Glu Asp Met Ser Glu Asn Val Pro Ile Ala Glu Asp Thr Thr Glu
        195                 200                 205

Gln Pro Lys Lys Asn Arg Ile Thr Tyr Ser Gln Ile Ile Lys Glu Gly
210                 215                 220

Arg Arg Phe Asn Ile Asp Leu Val Ser Lys Leu Leu Tyr Ser Arg Gly
225                 230                 235                 240

Leu Leu Ile Asp Leu Leu Ile Lys Ser Asn Val Ser Arg Tyr Ala Glu
                245                 250                 255

Phe Lys Asn Ile Thr Arg Ile Leu Ala Phe Arg Glu Gly Arg Val Glu
            260                 265                 270

Gln Val Pro Cys Ser Arg Ala Asp Val Phe Asn Ser Lys Gln Leu Thr
        275                 280                 285

Met Val Glu Lys Arg Met Leu Met Lys Phe Leu Thr Phe Cys Met Glu
290                 295                 300

Tyr Glu Lys Tyr Pro Asp Glu Tyr Lys Gly Tyr Glu Glu Ile Thr Phe
305                 310                 315                 320

Tyr Glu Tyr Leu Lys Thr Gln Lys Leu Thr Pro Asn Leu Gln Tyr Ile
                325                 330                 335
```

```
Val Met His Ser Ile Ala Met Thr Ser Glu Thr Ala Ser Ser Thr Ile
            340                 345                 350

Asp Gly Leu Lys Ala Thr Lys Asn Phe Leu His Cys Leu Gly Arg Tyr
        355                 360                 365

Gly Asn Thr Pro Phe Leu Phe Pro Leu Tyr Gly Gln Gly Glu Leu Pro
    370                 375                 380

Gln Cys Phe Cys Arg Met Cys Ala Val Phe Gly Gly Ile Tyr Cys Leu
385                 390                 395                 400

Arg His Ser Val Gln Cys Leu Val Val Asp Lys Glu Ser Arg Lys Cys
                405                 410                 415

Lys Ala Ile Ile Asp Gln Phe Gly Gln Arg Ile Ile Ser Glu His Phe
            420                 425                 430

Leu Val Glu Asp Ser Tyr Phe Pro Glu Asn Met Cys Ser Arg Val Gln
        435                 440                 445

Tyr Arg Gln Ile Ser Arg Ala Val Leu Ile Thr Asp Arg Ser Val Leu
    450                 455                 460

Lys Thr Asp Ser Asp Gln Gln Ile Ser Ile Leu Thr Val Pro Ala Glu
465                 470                 475                 480

Glu Pro Gly Thr Phe Ala Val Arg Val Ile Glu Leu Cys Ser Ser Thr
                485                 490                 495

Met Thr Cys Met Lys Gly Thr Tyr Leu Val His Leu Thr Cys Thr Ser
            500                 505                 510

Ser Lys Thr Ala Arg Glu Asp Leu Glu Ser Val Val Gln Lys Leu Phe
        515                 520                 525

Val Pro Tyr Thr Glu Met Glu Ile Glu Asn Gln Val Glu Lys Pro
    530                 535                 540

Arg Ile Leu Trp Ala Leu Tyr Phe Asn Met Arg Asp Ser Ser Asp Ile
545                 550                 555                 560

Ser Arg Ser Cys Tyr Asn Asp Leu Pro Ser Asn Val Tyr Val Cys Ser
                565                 570                 575

Gly Pro Asp Cys Gly Leu Gly Asn Asp Asn Ala Val Lys Gln Ala Glu
            580                 585                 590

Thr Leu Phe Gln Glu Ile Cys Pro Asn Glu Asp Phe Cys Pro Pro Pro
        595                 600                 605

Pro Asn Pro Glu Asp Ile Ile Leu Asp Gly Asp Ser Leu Gln Pro Glu
    610                 615                 620

Ala Ser Glu Ser Ser Ala Ile Pro Glu Ala Asn Ser Glu Thr Phe Lys
625                 630                 635                 640

Glu Ser Thr Asn Leu Gly Asn Leu Glu Glu Ser Ser Glu
                645                 650

<210> SEQ ID NO 97
<211> LENGTH: 212
<212> TYPE: PRT
<213> ORGANISM: Unknown
<220> FEATURE:
<223> OTHER INFORMATION: amino acid isoform of RdCVF

<400> SEQUENCE: 97

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
        35                  40                  45
```

-continued

```
Ala Phe Val Pro Ile Leu Lys Asp Phe Phe Val Arg Leu Thr Asp Glu
 50                  55                  60

Phe Tyr Val Leu Arg Ala Ala Gln Leu Ala Leu Val Tyr Val Ser Gln
 65                  70                  75                  80

Asp Ser Thr Glu Glu Gln Gln Asp Leu Phe Leu Lys Asp Met Pro Lys
                 85                  90                  95

Lys Trp Leu Phe Leu Pro Phe Glu Asp Asp Leu Arg Arg Asp Leu Gly
                100                 105                 110

Arg Gln Phe Ser Val Glu Arg Leu Pro Ala Val Val Leu Lys Pro
                115                 120                 125

Asp Gly Asp Val Leu Thr Arg Asp Gly Ala Asp Glu Ile Gln Arg Leu
130                 135                 140

Gly Thr Ala Cys Phe Ala Asn Trp Gln Glu Ala Ala Glu Val Leu Asp
145                 150                 155                 160

Arg Asn Phe Gln Leu Pro Glu Asp Leu Glu Asp Gln Glu Pro Arg Ser
                165                 170                 175

Leu Thr Glu Cys Leu Arg Arg His Lys Tyr Arg Val Glu Lys Ala Ala
                180                 185                 190

Arg Gly Gly Arg Asp Pro Gly Gly Gly Gly Glu Glu Gly Gly Ala
                195                 200                 205

Gly Gly Leu Phe
    210

<210> SEQ ID NO 98
<211> LENGTH: 156
<212> TYPE: PRT
<213> ORGANISM: Unknown
<220> FEATURE:
<223> OTHER INFORMATION: amino acid isoform of RdCVF (isoform 1)

<400> SEQUENCE: 98

Met Val Asp Ile Leu Gly Glu Arg His Leu Val Thr Cys Lys Gly Ala
  1               5                  10                  15

Thr Val Glu Ala Glu Ala Ala Leu Gln Asn Lys Val Val Ala Leu Tyr
                 20                  25                  30

Phe Ala Ala Ala Arg Cys Ala Pro Ser Arg Asp Phe Thr Pro Leu Leu
             35                  40                  45

Cys Asp Phe Tyr Thr Ala Leu Val Ala Glu Ala Arg Arg Pro Ala Pro
 50                  55                  60

Phe Glu Val Val Phe Val Ser Ala Asp Gly Ser Ser Gln Glu Met Leu
 65                  70                  75                  80

Asp Phe Met Arg Glu Leu His Gly Ala Trp Leu Ala Leu Pro Phe His
                 85                  90                  95

Asp Pro Tyr Arg His Glu Leu Arg Lys Arg Tyr Asn Val Thr Ala Ile
                100                 105                 110

Pro Lys Leu Val Ile Val Lys Gln Asn Gly Glu Val Ile Thr Asn Lys
                115                 120                 125

Gly Arg Lys Gln Ile Arg Glu Arg Gly Leu Ala Cys Phe Gln Asp Trp
130                 135                 140

Val Glu Ala Ala Asp Ile Phe Gln Asn Phe Ser Val
145                 150                 155

<210> SEQ ID NO 99
<211> LENGTH: 135
<212> TYPE: PRT
<213> ORGANISM: Unknown
<220> FEATURE:
```

<223> OTHER INFORMATION: amino acid isoform of RdCVF (isoform 2)

<400> SEQUENCE: 99

```
Met Val Asp Ile Leu Gly Glu Arg His Leu Val Thr Cys Lys Gly Ala
1               5                   10                  15

Thr Val Glu Ala Glu Ala Ala Leu Gln Asn Lys Val Val Ala Leu Tyr
            20                  25                  30

Phe Ala Ala Ala Arg Cys Ala Pro Ser Arg Asp Phe Thr Pro Leu Leu
        35                  40                  45

Cys Asp Phe Tyr Thr Ala Leu Val Ala Glu Ala Arg Arg Pro Ala Pro
    50                  55                  60

Phe Glu Val Val Phe Val Ser Ala Asp Gly Ser Ser Gln Glu Met Leu
65                  70                  75                  80

Asp Phe Met Arg Glu Leu His Gly Ala Trp Leu Ala Leu Pro Phe His
                85                  90                  95

Asp Pro Tyr Arg Gln Arg Ser Leu Ala Leu Leu Pro Arg Leu Glu Cys
            100                 105                 110

Ser Gly Val Ile Leu Ala His Cys Asn Leu Cys Leu Leu Gly Ser Ser
        115                 120                 125

Asp Ser Leu Ala Leu Ala Ser
    130                 135
```

<210> SEQ ID NO 100
<211> LENGTH: 860
<212> TYPE: PRT
<213> ORGANISM: Homo sapiens

<400> SEQUENCE: 100

```
Met Gly Glu Val Thr Ala Glu Val Glu Lys Phe Leu Asp Ser Asn
1               5                   10                  15

Ile Gly Phe Ala Lys Gln Tyr Tyr Asn Leu His Tyr Arg Ala Lys Leu
            20                  25                  30

Ile Ser Asp Leu Leu Gly Ala Lys Glu Ala Ala Val Asp Phe Ser Asn
        35                  40                  45

Tyr His Ser Pro Ser Ser Met Glu Glu Ser Glu Ile Ile Phe Asp Leu
    50                  55                  60

Leu Arg Asp Phe Gln Glu Asn Leu Gln Thr Glu Lys Cys Ile Phe Asn
65                  70                  75                  80

Val Met Lys Lys Leu Cys Phe Leu Leu Gln Ala Asp Arg Met Ser Leu
                85                  90                  95

Phe Met Tyr Arg Thr Arg Asn Gly Ile Ala Glu Leu Ala Thr Arg Leu
            100                 105                 110

Phe Asn Val His Lys Asp Ala Val Leu Glu Asp Cys Leu Val Met Pro
        115                 120                 125

Asp Gln Glu Ile Val Phe Pro Leu Asp Met Gly Ile Val Gly His Val
    130                 135                 140

Ala His Ser Lys Lys Ile Ala Asn Val Pro Asn Thr Glu Glu Asp Glu
145                 150                 155                 160

His Phe Cys Asp Phe Val Asp Ile Leu Thr Glu Tyr Lys Thr Lys Asn
                165                 170                 175

Ile Leu Ala Ser Pro Ile Met Asn Gly Lys Asp Val Val Ala Ile Ile
            180                 185                 190

Met Ala Val Asn Lys Val Asp Gly Ser His Phe Thr Lys Arg Asp Glu
        195                 200                 205

Glu Ile Leu Leu Lys Tyr Leu Asn Phe Ala Asn Leu Ile Met Lys Val
```

-continued

```
            210                 215                 220
Tyr His Leu Ser Tyr Leu His Asn Cys Glu Thr Arg Gly Gln Ile
225                 230                 235                 240

Leu Leu Trp Ser Gly Ser Lys Val Phe Glu Leu Thr Asp Ile Glu
                    245                 250                 255

Arg Gln Phe His Lys Ala Leu Tyr Thr Val Arg Ala Phe Leu Asn Cys
                260                 265                 270

Asp Arg Tyr Ser Val Gly Leu Leu Asp Met Thr Lys Gln Lys Glu Phe
            275                 280                 285

Phe Asp Val Trp Pro Val Leu Met Gly Glu Val Pro Pro Tyr Ser Gly
290                 295                 300

Pro Arg Thr Pro Asp Gly Arg Glu Ile Asn Phe Tyr Lys Val Ile Asp
305                 310                 315                 320

Tyr Ile Leu His Gly Lys Glu Asp Ile Lys Val Ile Pro Asn Pro Pro
                325                 330                 335

Pro Asp His Trp Ala Leu Val Ser Gly Leu Pro Ala Tyr Val Ala Gln
                340                 345                 350

Asn Gly Leu Ile Cys Asn Ile Met Asn Ala Pro Ala Glu Asp Phe Phe
            355                 360                 365

Ala Phe Gln Lys Glu Pro Leu Asp Glu Ser Gly Trp Met Ile Lys Asn
370                 375                 380

Val Leu Ser Met Pro Ile Val Asn Lys Lys Glu Glu Ile Val Gly Val
385                 390                 395                 400

Ala Thr Phe Tyr Asn Arg Lys Asp Gly Lys Pro Phe Asp Glu Met Asp
                405                 410                 415

Glu Thr Leu Met Glu Ser Leu Thr Gln Phe Leu Gly Trp Ser Val Leu
            420                 425                 430

Asn Pro Asp Thr Tyr Glu Ser Met Asn Lys Leu Glu Asn Arg Lys Asp
                435                 440                 445

Ile Phe Gln Asp Ile Val Lys Tyr His Val Lys Cys Asp Asn Glu Glu
450                 455                 460

Ile Gln Lys Ile Leu Lys Thr Arg Glu Val Tyr Gly Lys Glu Pro Trp
465                 470                 475                 480

Glu Cys Glu Glu Glu Glu Leu Ala Glu Ile Leu Gln Ala Glu Leu Pro
                485                 490                 495

Asp Ala Asp Lys Tyr Glu Ile Asn Lys Phe His Phe Ser Asp Leu Pro
            500                 505                 510

Leu Thr Glu Leu Glu Leu Val Lys Cys Gly Ile Gln Met Tyr Tyr Glu
            515                 520                 525

Leu Lys Val Val Asp Lys Phe His Ile Pro Gln Glu Ala Leu Val Arg
            530                 535                 540

Phe Met Tyr Ser Leu Ser Lys Gly Tyr Arg Lys Ile Thr Tyr His Asn
545                 550                 555                 560

Trp Arg His Gly Phe Asn Val Gly Gln Thr Met Phe Ser Leu Leu Val
                565                 570                 575

Thr Gly Lys Leu Lys Arg Tyr Phe Thr Asp Leu Glu Ala Leu Ala Met
                580                 585                 590

Val Thr Ala Ala Phe Cys His Asp Ile Asp His Arg Gly Thr Asn Asn
            595                 600                 605

Leu Tyr Gln Met Lys Ser Gln Asn Pro Leu Ala Lys Leu His Gly Ser
            610                 615                 620

Ser Ile Leu Glu Arg His His Leu Glu Phe Gly Lys Thr Leu Leu Arg
625                 630                 635                 640
```

-continued

```
Asp Glu Ser Leu Asn Ile Phe Gln Asn Leu Asn Arg Arg Gln His Glu
                645                 650                 655

His Ala Ile His Met Met Asp Ile Ala Ile Ala Thr Asp Leu Ala
            660                 665                 670

Leu Tyr Phe Lys Lys Arg Thr Met Phe Gln Lys Ile Val Asp Gln Ser
            675                 680                 685

Lys Thr Tyr Glu Ser Glu Gln Glu Trp Thr Gln Tyr Met Met Leu Glu
        690                 695                 700

Gln Thr Arg Lys Glu Ile Val Met Ala Met Met Thr Ala Cys Asp
705                 710                 715                 720

Leu Ser Ala Ile Thr Lys Pro Trp Glu Val Gln Ser Gln Val Ala Leu
                725                 730                 735

Leu Val Ala Ala Glu Phe Trp Glu Gln Gly Asp Leu Glu Arg Thr Val
            740                 745                 750

Leu Gln Gln Asn Pro Ile Pro Met Met Asp Arg Asn Lys Ala Asp Glu
        755                 760                 765

Leu Pro Lys Leu Gln Val Gly Phe Ile Asp Phe Val Cys Thr Phe Val
    770                 775                 780

Tyr Lys Glu Phe Ser Arg Phe His Glu Glu Ile Thr Pro Met Leu Asp
785                 790                 795                 800

Gly Ile Thr Asn Asn Arg Lys Glu Trp Lys Ala Leu Ala Asp Glu Tyr
                805                 810                 815

Asp Ala Lys Met Lys Val Gln Glu Glu Lys Lys Gln Lys Gln Gln Ser
            820                 825                 830

Ala Lys Ser Ala Ala Ala Gly Asn Gln Pro Gly Gly Asn Pro Ser Pro
        835                 840                 845

Gly Gly Ala Thr Thr Ser Lys Ser Cys Cys Ile Gln
    850                 855                 860

<210> SEQ ID NO 101
<211> LENGTH: 854
<212> TYPE: PRT
<213> ORGANISM: Homo sapiens

<400> SEQUENCE: 101

Met Ser Leu Ser Glu Glu Gln Ala Arg Ser Phe Leu Asp Gln Asn Pro
1               5                   10                  15

Asp Phe Ala Arg Gln Tyr Phe Gly Lys Lys Leu Ser Pro Glu Asn Val
            20                  25                  30

Ala Ala Ala Cys Glu Asp Gly Cys Pro Pro Asp Cys Asp Ser Leu Arg
        35                  40                  45

Asp Leu Cys Gln Val Glu Glu Ser Thr Ala Leu Leu Glu Leu Val Gln
    50                  55                  60

Asp Met Gln Glu Ser Ile Asn Met Glu Arg Val Val Phe Lys Val Leu
65                  70                  75                  80

Arg Arg Leu Cys Thr Leu Leu Gln Ala Asp Arg Cys Ser Leu Phe Met
                85                  90                  95

Tyr Arg Gln Arg Asn Gly Val Ala Glu Leu Ala Thr Arg Leu Phe Ser
            100                 105                 110

Val Gln Pro Asp Ser Val Leu Glu Asp Cys Leu Val Pro Pro Asp Ser
        115                 120                 125

Glu Ile Val Phe Pro Leu Asp Ile Gly Val Val Gly His Val Ala Gln
    130                 135                 140

Thr Lys Lys Met Val Asn Val Glu Asp Val Ala Glu Cys Pro His Phe
```

```
            145                 150                 155                 160
        Ser Ser Phe Ala Asp Glu Leu Thr Asp Tyr Lys Thr Lys Asn Met Leu
                        165                 170                 175

Ala Thr Pro Ile Met Asn Gly Lys Asp Val Ala Val Ile Met Ala
                        180                 185                 190

Val Asn Lys Leu Asn Gly Pro Phe Thr Ser Glu Asp Glu Asp Val
                        195                 200                 205

Phe Leu Lys Tyr Leu Asn Phe Ala Thr Leu Tyr Leu Lys Ile Tyr His
            210                 215                 220

Leu Ser Tyr Leu His Asn Cys Glu Thr Arg Arg Gly Gln Val Leu Leu
        225                 230                 235                 240

Trp Ser Ala Asn Lys Val Phe Glu Glu Leu Thr Asp Ile Glu Arg Gln
                        245                 250                 255

Phe His Lys Ala Phe Tyr Thr Val Arg Ala Tyr Leu Asn Cys Glu Arg
                        260                 265                 270

Tyr Ser Val Gly Leu Leu Asp Met Thr Lys Glu Lys Glu Phe Phe Asp
                        275                 280                 285

Val Trp Ser Val Leu Met Gly Glu Ser Gln Pro Tyr Ser Gly Pro Arg
            290                 295                 300

Thr Pro Asp Gly Arg Glu Ile Val Phe Tyr Lys Val Ile Asp Tyr Ile
        305                 310                 315                 320

Leu His Gly Lys Glu Glu Ile Lys Val Ile Pro Thr Pro Ser Ala Asp
                        325                 330                 335

His Trp Ala Leu Ala Ser Gly Leu Pro Ser Tyr Val Ala Glu Ser Gly
                        340                 345                 350

Phe Ile Cys Asn Ile Met Asn Ala Ser Ala Asp Glu Met Phe Lys Phe
                        355                 360                 365

Gln Glu Gly Ala Leu Asp Asp Ser Gly Trp Leu Ile Lys Asn Val Leu
                        370                 375                 380

Ser Met Pro Ile Val Asn Lys Lys Glu Glu Ile Val Gly Val Ala Thr
        385                 390                 395                 400

Phe Tyr Asn Arg Lys Asp Gly Lys Pro Phe Asp Glu Gln Asp Glu Val
                        405                 410                 415

Leu Met Glu Ser Leu Thr Gln Phe Leu Gly Trp Ser Val Met Asn Thr
                        420                 425                 430

Asp Thr Tyr Asp Lys Met Asn Lys Leu Glu Asn Arg Lys Asp Ile Ala
                        435                 440                 445

Gln Asp Met Val Leu Tyr His Val Lys Cys Asp Arg Asp Glu Ile Gln
        450                 455                 460

Leu Ile Leu Pro Thr Arg Ala Arg Leu Gly Lys Glu Pro Ala Asp Cys
        465                 470                 475                 480

Asp Glu Asp Glu Leu Gly Glu Ile Leu Lys Glu Leu Pro Gly Pro
                        485                 490                 495

Thr Thr Phe Asp Ile Tyr Glu Phe His Phe Ser Asp Leu Glu Cys Thr
                        500                 505                 510

Glu Leu Asp Leu Val Lys Cys Gly Ile Gln Met Tyr Tyr Glu Leu Gly
                        515                 520                 525

Val Val Arg Lys Phe Gln Ile Pro Gln Glu Val Leu Val Arg Phe Leu
                        530                 535                 540

Phe Ser Ile Ser Lys Gly Tyr Arg Arg Ile Thr Tyr His Asn Trp Arg
        545                 550                 555                 560

His Gly Phe Asn Val Ala Gln Thr Met Phe Thr Leu Leu Met Thr Gly
                        565                 570                 575
```

```
Lys Leu Lys Ser Tyr Tyr Thr Asp Leu Glu Ala Phe Ala Met Val Thr
                580                 585                 590

Ala Gly Leu Cys His Asp Ile Asp His Arg Gly Thr Asn Asn Leu Tyr
            595                 600                 605

Gln Met Lys Ser Gln Asn Pro Leu Ala Lys Leu His Gly Ser Ser Ile
610                 615                 620

Leu Glu Arg His His Leu Glu Phe Gly Lys Phe Leu Leu Ser Glu Glu
625                 630                 635                 640

Thr Leu Asn Ile Tyr Gln Asn Leu Asn Arg Arg Gln His Glu His Val
                645                 650                 655

Ile His Leu Met Asp Ile Ala Ile Ile Ala Thr Asp Leu Ala Leu Tyr
                660                 665                 670

Phe Lys Lys Arg Ala Met Phe Gln Lys Ile Val Asp Glu Ser Lys Asn
            675                 680                 685

Tyr Gln Asp Lys Lys Ser Trp Val Glu Tyr Leu Ser Leu Glu Thr Thr
690                 695                 700

Arg Lys Glu Ile Val Met Ala Met Met Met Thr Ala Cys Asp Leu Ser
705                 710                 715                 720

Ala Ile Thr Lys Pro Trp Glu Val Gln Ser Lys Val Ala Leu Leu Val
                725                 730                 735

Ala Ala Glu Phe Trp Glu Gln Gly Asp Leu Glu Arg Thr Val Leu Asp
            740                 745                 750

Gln Gln Pro Ile Pro Met Met Asp Arg Asn Lys Ala Ala Glu Leu Pro
        755                 760                 765

Lys Leu Gln Val Gly Phe Ile Asp Phe Val Cys Thr Phe Val Tyr Lys
    770                 775                 780

Glu Phe Ser Arg Phe His Glu Glu Ile Leu Pro Met Phe Asp Arg Leu
785                 790                 795                 800

Gln Asn Asn Arg Lys Glu Trp Lys Ala Leu Ala Asp Glu Tyr Glu Ala
                805                 810                 815

Lys Val Lys Ala Leu Glu Glu Lys Glu Glu Glu Arg Val Ala Ala
                820                 825                 830

Lys Lys Val Gly Thr Glu Ile Cys Asn Gly Gly Pro Ala Pro Lys Ser
            835                 840                 845

Ser Thr Cys Cys Ile Leu
        850

<210> SEQ ID NO 102
<211> LENGTH: 853
<212> TYPE: PRT
<213> ORGANISM: Homo sapiens

<400> SEQUENCE: 102

Met Ser Leu Ser Glu Glu Gln Ala Arg Ser Phe Leu Asp Gln Asn Pro
1               5                   10                  15

Asp Phe Ala Arg Gln Tyr Phe Gly Lys Lys Leu Ser Pro Glu Asn Val
                20                  25                  30

Ala Ala Ala Cys Glu Asp Gly Cys Pro Pro Asp Cys Asp Ser Leu Arg
            35                  40                  45

Asp Leu Cys Gln Val Glu Glu Ser Thr Ala Leu Glu Leu Val Gln
        50                  55                  60

Asp Met Gln Glu Ser Ile Asn Met Glu Arg Val Val Phe Lys Val Leu
65                  70                  75                  80

Arg Arg Leu Cys Thr Leu Leu Gln Ala Asp Arg Cys Ser Leu Phe Met
```

-continued

```
                85                  90                  95
Tyr Arg Gln Arg Asn Gly Val Ala Glu Leu Ala Thr Arg Leu Phe Ser
            100                 105                 110

Val Gln Pro Asp Ser Val Leu Glu Asp Cys Leu Val Pro Pro Asp Ser
            115                 120                 125

Glu Ile Val Phe Pro Leu Asp Ile Gly Val Val His Val Ala Gln
            130                 135                 140

Thr Lys Lys Met Val Asn Val Glu Asp Val Ala Glu Cys Pro His Phe
145                 150                 155                 160

Ser Ser Phe Ala Asp Glu Leu Thr Asp Tyr Lys Thr Lys Asn Met Leu
                165                 170                 175

Ala Thr Pro Ile Met Asn Gly Lys Asp Val Ala Val Ile Met Ala
                180                 185                 190

Val Asn Lys Leu Asn Gly Pro Phe Phe Thr Ser Glu Asp Glu Asp Val
                195                 200                 205

Phe Leu Lys Tyr Leu Asn Phe Ala Thr Leu Tyr Leu Lys Ile Tyr His
            210                 215                 220

Leu Ser Tyr Leu His Asn Cys Glu Thr Arg Arg Gly Gln Val Leu Leu
225                 230                 235                 240

Trp Ser Ala Asn Lys Val Phe Glu Glu Leu Thr Asp Ile Glu Arg Gln
                245                 250                 255

Phe His Lys Ala Phe Tyr Thr Val Arg Ala Tyr Leu Asn Cys Glu Arg
                260                 265                 270

Tyr Ser Val Gly Leu Leu Asp Met Thr Lys Glu Lys Glu Phe Phe Asp
                275                 280                 285

Val Trp Ser Val Leu Met Gly Glu Ser Gln Pro Tyr Ser Gly Pro Arg
                290                 295                 300

Thr Pro Asp Gly Arg Glu Ile Val Phe Tyr Lys Val Ile Asp Tyr Ile
305                 310                 315                 320

Leu His Gly Lys Glu Glu Ile Lys Val Ile Pro Thr Pro Ser Ala Asp
                325                 330                 335

His Trp Ala Leu Ala Ser Gly Leu Pro Ser Tyr Val Ala Glu Ser Gly
                340                 345                 350

Phe Ile Cys Asn Ile Met Asn Ala Ser Ala Asp Glu Met Phe Lys Phe
                355                 360                 365

Gln Glu Gly Ala Leu Asp Asp Ser Gly Trp Leu Ile Lys Asn Val Leu
            370                 375                 380

Ser Met Pro Ile Val Asn Lys Lys Glu Glu Ile Val Gly Val Ala Thr
385                 390                 395                 400

Phe Tyr Asn Arg Lys Asp Gly Lys Pro Phe Asp Glu Gln Asp Glu Val
                405                 410                 415

Leu Met Glu Ser Leu Thr Gln Phe Leu Gly Trp Ser Val Met Asn Thr
                420                 425                 430

Asp Thr Tyr Asp Lys Met Asn Lys Leu Glu Asn Arg Lys Asp Ile Ala
                435                 440                 445

Gln Asp Met Val Leu Tyr His Val Lys Cys Asp Arg Asp Glu Ile Gln
            450                 455                 460

Leu Ile Leu Pro Thr Arg Ala Arg Leu Gly Lys Glu Pro Ala Asp Cys
465                 470                 475                 480

Asp Glu Asp Glu Leu Gly Glu Ile Leu Lys Glu Leu Pro Gly Pro
                485                 490                 495

Thr Thr Phe Asp Ile Tyr Glu Phe His Phe Ser Asp Leu Glu Cys Thr
                500                 505                 510
```

```
Glu Leu Asp Leu Val Lys Cys Gly Ile Gln Met Tyr Tyr Glu Leu Gly
            515                 520                 525

Val Val Arg Lys Phe Gln Ile Pro Gln Glu Val Leu Val Arg Phe Leu
        530                 535                 540

Phe Ser Ile Ser Lys Gly Tyr Arg Arg Ile Thr Tyr His Asn Trp Arg
545                 550                 555                 560

His Gly Phe Asn Val Ala Gln Thr Met Phe Thr Leu Leu Met Thr Gly
                565                 570                 575

Lys Leu Lys Ser Tyr Tyr Thr Asp Leu Glu Ala Phe Ala Met Val Thr
            580                 585                 590

Ala Gly Leu Cys His Asp Ile Asp His Arg Gly Thr Asn Asn Leu Tyr
        595                 600                 605

Gln Met Lys Ser Gln Asn Pro Leu Ala Lys Leu His Gly Ser Ser Ile
    610                 615                 620

Leu Glu Arg His His Leu Glu Phe Gly Lys Phe Leu Leu Ser Glu Glu
625                 630                 635                 640

Thr Leu Asn Ile Tyr Gln Asn Leu Asn Arg Arg Gln His Glu His Val
                645                 650                 655

Ile His Leu Met Asp Ile Ala Ile Ile Ala Thr Asp Leu Ala Leu Tyr
            660                 665                 670

Phe Lys Lys Arg Ala Met Phe Gln Lys Ile Val Asp Glu Ser Lys Asn
        675                 680                 685

Tyr Gln Asp Lys Lys Ser Trp Val Glu Tyr Leu Ser Leu Glu Thr Thr
    690                 695                 700

Arg Lys Glu Ile Val Met Ala Met Met Met Thr Ala Cys Asp Leu Ser
705                 710                 715                 720

Ala Ile Thr Lys Pro Trp Glu Val Gln Ser Lys Val Ala Leu Leu Val
                725                 730                 735

Ala Ala Glu Phe Trp Glu Gln Gly Asp Leu Glu Arg Thr Val Leu Asp
            740                 745                 750

Gln Gln Pro Ile Pro Met Met Asp Arg Asn Lys Ala Ala Glu Leu Pro
        755                 760                 765

Lys Leu Gln Val Gly Phe Ile Asp Phe Val Cys Thr Phe Val Tyr Lys
    770                 775                 780

Glu Phe Ser Arg Phe His Glu Glu Ile Leu Pro Met Phe Asp Arg Leu
785                 790                 795                 800

Gln Asn Asn Arg Lys Glu Trp Lys Ala Leu Ala Asp Glu Tyr Glu Ala
                805                 810                 815

Lys Val Lys Ala Leu Glu Glu Lys Glu Glu Glu Arg Val Ala Ala
            820                 825                 830

Lys Lys Gly Thr Glu Ile Cys Asn Gly Gly Pro Ala Pro Lys Ser Ser
        835                 840                 845

Thr Cys Cys Ile Leu
    850

<210> SEQ ID NO 103
<211> LENGTH: 575
<212> TYPE: PRT
<213> ORGANISM: Homo sapiens

<400> SEQUENCE: 103

Met Thr Lys Glu Lys Glu Phe Phe Asp Val Trp Ser Val Leu Met Gly
1               5                   10                  15

Glu Ser Gln Pro Tyr Ser Gly Pro Arg Thr Pro Asp Gly Arg Glu Ile
```

-continued

```
                20                  25                  30
Val Phe Tyr Lys Val Ile Asp Tyr Ile Leu His Gly Lys Glu Ile
            35                  40                  45
Lys Val Ile Pro Thr Pro Ser Ala Asp His Trp Ala Leu Ala Ser Gly
        50                  55                  60
Leu Pro Ser Tyr Val Ala Glu Ser Gly Phe Ile Cys Asn Ile Met Asn
65                      70                  75                  80
Ala Ser Ala Asp Glu Met Phe Lys Phe Gln Glu Gly Ala Leu Asp Asp
                    85                  90                  95
Ser Gly Trp Leu Ile Lys Asn Val Leu Ser Met Pro Ile Val Asn Lys
            100                 105                 110
Lys Glu Glu Ile Val Gly Val Ala Thr Phe Tyr Asn Arg Lys Asp Gly
        115                 120                 125
Lys Pro Phe Asp Glu Gln Asp Glu Val Leu Met Glu Ser Leu Thr Gln
    130                 135                 140
Phe Leu Gly Trp Ser Val Met Asn Thr Asp Thr Tyr Asp Lys Met Asn
145                 150                 155                 160
Lys Leu Glu Asn Arg Lys Asp Ile Ala Gln Asp Met Val Leu Tyr His
                165                 170                 175
Val Lys Cys Asp Arg Asp Glu Ile Gln Leu Ile Leu Pro Thr Arg Ala
            180                 185                 190
Arg Leu Gly Lys Glu Pro Ala Asp Cys Asp Glu Asp Glu Leu Gly Glu
        195                 200                 205
Ile Leu Lys Glu Glu Leu Pro Gly Pro Thr Thr Phe Asp Ile Tyr Glu
    210                 215                 220
Phe His Phe Ser Asp Leu Glu Cys Thr Glu Leu Asp Leu Val Lys Cys
225                 230                 235                 240
Gly Ile Gln Met Tyr Tyr Glu Leu Gly Val Val Arg Lys Phe Gln Ile
                245                 250                 255
Pro Gln Glu Val Leu Val Arg Phe Leu Phe Ser Ile Ser Lys Gly Tyr
            260                 265                 270
Arg Arg Ile Thr Tyr His Asn Trp Arg His Gly Phe Asn Val Ala Gln
        275                 280                 285
Thr Met Phe Thr Leu Leu Met Thr Gly Lys Leu Lys Ser Tyr Tyr Thr
    290                 295                 300
Asp Leu Glu Ala Phe Ala Met Val Thr Ala Gly Leu Cys His Asp Ile
305                 310                 315                 320
Asp His Arg Gly Thr Asn Asn Leu Tyr Gln Met Lys Ser Gln Asn Pro
                325                 330                 335
Leu Ala Lys Leu His Gly Ser Ser Ile Leu Glu Arg His His Leu Glu
            340                 345                 350
Phe Gly Lys Phe Leu Leu Ser Glu Glu Thr Leu Asn Ile Tyr Gln Asn
        355                 360                 365
Leu Asn Arg Arg Gln His Glu His Val Ile His Leu Met Asp Ile Ala
    370                 375                 380
Ile Ile Ala Thr Asp Leu Ala Leu Tyr Phe Lys Lys Arg Ala Met Phe
385                 390                 395                 400
Gln Lys Ile Val Asp Glu Ser Lys Asn Tyr Gln Asp Lys Lys Ser Trp
                405                 410                 415
Val Glu Tyr Leu Ser Leu Glu Thr Thr Arg Lys Glu Ile Val Met Ala
            420                 425                 430
Met Met Met Thr Ala Cys Asp Leu Ser Ala Ile Thr Lys Pro Trp Glu
        435                 440                 445
```

Val Gln Ser Lys Val Ala Leu Leu Val Ala Ala Glu Phe Trp Glu Gln
            450                 455                 460

Gly Asp Leu Glu Arg Thr Val Leu Asp Gln Gln Pro Ile Pro Met Met
465                 470                 475                 480

Asp Arg Asn Lys Ala Ala Glu Leu Pro Lys Leu Gln Val Gly Phe Ile
                485                 490                 495

Asp Phe Val Cys Thr Phe Val Tyr Lys Glu Phe Ser Arg Phe His Glu
                500                 505                 510

Glu Ile Leu Pro Met Phe Asp Arg Leu Gln Asn Asn Arg Lys Glu Trp
                515                 520                 525

Lys Ala Leu Ala Asp Glu Tyr Glu Ala Lys Val Lys Ala Leu Glu Glu
                530                 535                 540

Lys Glu Glu Glu Arg Val Ala Ala Lys Lys Val Gly Thr Glu Ile
545                 550                 555                 560

Cys Asn Gly Gly Pro Ala Pro Lys Ser Ser Thr Cys Cys Ile Leu
                565                 570                 575

<210> SEQ ID NO 104
<211> LENGTH: 694
<212> TYPE: PRT
<213> ORGANISM: Homo sapiens

<400> SEQUENCE: 104

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
                20                  25                  30

Ser Arg Ala His Ser Ser Ser Glu Glu Thr Ser Ser Val Leu Gln Pro
                35                  40                  45

Gly Ile Ala Met Glu Thr Arg Gly Leu Ala Asp Ser Gly Gln Gly Ser
            50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
                100                 105                 110

Gln Glu Ser Asn Ala Gln Ala Asn Val Gly Ser Gln Glu Pro Ala Asp
                115                 120                 125

Arg Gly Arg Ser Ala Trp Pro Leu Ala Lys Cys Asn Thr Asn Thr Ser
                130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
                180                 185                 190

Asp Glu Leu Gln Ser Glu Tyr Leu Met Leu Trp Leu Val Leu Asp Tyr
                195                 200                 205

Ser Ala Asp Val Leu Tyr Val Leu Asp Val Leu Val Arg Ala Arg Thr
                210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu

-continued

```
                245                 250                 255
Val Pro Thr Asp Leu Ala Tyr Leu Lys Val Gly Thr Asn Tyr Pro Glu
            260                 265                 270
Val Arg Phe Asn Arg Leu Leu Lys Phe Ser Arg Leu Phe Glu Phe Phe
            275                 280                 285
Asp Arg Thr Glu Thr Arg Thr Asn Tyr Pro Asn Met Phe Arg Ile Gly
            290                 295                 300
Asn Leu Val Leu Tyr Ile Leu Ile Ile His Trp Asn Ala Cys Ile
305                 310                 315                 320
Tyr Phe Ala Ile Ser Lys Phe Ile Gly Phe Gly Thr Asp Ser Trp Val
                325                 330                 335
Tyr Pro Asn Ile Ser Ile Pro Glu His Gly Arg Leu Ser Arg Lys Tyr
            340                 345                 350
Ile Tyr Ser Leu Tyr Trp Ser Thr Leu Thr Leu Thr Thr Ile Gly Glu
                355                 360                 365
Thr Pro Pro Pro Val Lys Asp Glu Glu Tyr Leu Phe Val Val Val Asp
            370                 375                 380
Phe Leu Val Gly Val Leu Ile Phe Ala Thr Ile Val Gly Asn Val Gly
385                 390                 395                 400
Ser Met Ile Ser Asn Met Asn Ala Ser Arg Ala Glu Phe Gln Ala Lys
                405                 410                 415
Ile Asp Ser Ile Lys Gln Tyr Met Gln Phe Arg Lys Val Thr Lys Asp
                420                 425                 430
Leu Glu Thr Arg Val Ile Arg Trp Phe Asp Tyr Leu Trp Ala Asn Lys
            435                 440                 445
Lys Thr Val Asp Glu Lys Glu Val Leu Lys Ser Leu Pro Asp Lys Leu
            450                 455                 460
Lys Ala Glu Ile Ala Ile Asn Val His Leu Asp Thr Leu Lys Lys Val
465                 470                 475                 480
Arg Ile Phe Gln Asp Cys Glu Ala Gly Leu Leu Val Glu Leu Val Leu
                485                 490                 495
Lys Leu Arg Pro Thr Val Phe Ser Pro Gly Asp Tyr Ile Cys Lys Lys
            500                 505                 510
Gly Asp Ile Gly Lys Glu Met Tyr Ile Ile Asn Glu Gly Lys Leu Ala
            515                 520                 525
Val Val Ala Asp Asp Gly Val Thr Gln Phe Val Val Leu Ser Asp Gly
            530                 535                 540
Ser Tyr Phe Gly Glu Ile Ser Ile Leu Asn Ile Lys Gly Ser Lys Ser
545                 550                 555                 560
Gly Asn Arg Arg Thr Ala Asn Ile Arg Ser Ile Gly Tyr Ser Asp Leu
                565                 570                 575
Phe Cys Leu Ser Lys Asp Asp Leu Met Glu Ala Leu Thr Glu Tyr Pro
            580                 585                 590
Glu Ala Lys Lys Ala Leu Glu Glu Lys Gly Arg Gln Ile Leu Met Lys
            595                 600                 605
Asp Asn Leu Ile Asp Glu Glu Leu Ala Arg Ala Gly Ala Asp Pro Lys
            610                 615                 620
Asp Leu Glu Glu Lys Val Glu Gln Leu Gly Ser Ser Leu Asp Thr Leu
625                 630                 635                 640
Gln Thr Arg Phe Ala Arg Leu Leu Ala Glu Tyr Asn Ala Thr Gln Met
            645                 650                 655
Lys Met Lys Gln Arg Leu Ser Gln Leu Glu Ser Gln Val Lys Gly Gly
            660                 665                 670
```

```
Gly Asp Lys Pro Leu Ala Asp Gly Glu Val Pro Gly Asp Ala Thr Lys
            675                 680                 685
Thr Glu Asp Lys Gln Gln
    690

<210> SEQ ID NO 105
<211> LENGTH: 676
<212> TYPE: PRT
<213> ORGANISM: Homo sapiens

<400> SEQUENCE: 105

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Arg Lys Lys Thr Lys Lys Lys Asp Ala Ile Val Val Asp
    130                 135                 140

Pro Ser Ser Asn Leu Tyr Tyr Arg Trp Leu Thr Ala Ile Ala Leu Pro
145                 150                 155                 160

Val Phe Tyr Asn Trp Tyr Leu Leu Ile Cys Arg Ala Cys Phe Asp Glu
                165                 170                 175

Leu Gln Ser Glu Tyr Leu Met Leu Trp Leu Val Leu Asp Tyr Ser Ala
            180                 185                 190

Asp Val Leu Tyr Val Leu Asp Val Leu Val Arg Ala Arg Thr Gly Phe
        195                 200                 205

Leu Glu Gln Gly Leu Met Val Ser Asp Thr Asn Arg Leu Trp Gln His
    210                 215                 220

Tyr Lys Thr Thr Thr Gln Phe Lys Leu Asp Val Leu Ser Leu Val Pro
225                 230                 235                 240

Thr Asp Leu Ala Tyr Leu Lys Val Gly Thr Asn Tyr Pro Glu Val Arg
                245                 250                 255

Phe Asn Arg Leu Leu Lys Phe Ser Arg Leu Phe Glu Phe Phe Asp Arg
            260                 265                 270

Thr Glu Thr Arg Thr Asn Tyr Pro Asn Met Phe Arg Ile Gly Asn Leu
        275                 280                 285

Val Leu Tyr Ile Leu Ile Ile Ile His Trp Asn Ala Cys Ile Tyr Phe
    290                 295                 300

Ala Ile Ser Lys Phe Ile Gly Phe Gly Thr Asp Ser Trp Val Tyr Pro
305                 310                 315                 320

Asn Ile Ser Ile Pro Glu His Gly Arg Leu Ser Arg Lys Tyr Ile Tyr
                325                 330                 335

Ser Leu Tyr Trp Ser Thr Leu Thr Leu Thr Thr Ile Gly Glu Thr Pro
```

```
            340                 345                 350
Pro Pro Val Lys Asp Glu Glu Tyr Leu Phe Val Val Asp Phe Leu
        355                 360                 365
Val Gly Val Leu Ile Phe Ala Thr Ile Val Gly Asn Val Gly Ser Met
    370                 375                 380
Ile Ser Asn Met Asn Ala Ser Arg Ala Glu Phe Gln Ala Lys Ile Asp
385                 390                 395                 400
Ser Ile Lys Gln Tyr Met Gln Phe Arg Lys Val Thr Lys Asp Leu Glu
                405                 410                 415
Thr Arg Val Ile Arg Trp Phe Asp Tyr Leu Trp Ala Asn Lys Lys Thr
            420                 425                 430
Val Asp Glu Lys Glu Val Leu Lys Ser Leu Pro Asp Lys Leu Lys Ala
        435                 440                 445
Glu Ile Ala Ile Asn Val His Leu Asp Thr Leu Lys Lys Val Arg Ile
    450                 455                 460
Phe Gln Asp Cys Glu Ala Gly Leu Leu Val Glu Leu Val Leu Lys Leu
465                 470                 475                 480
Arg Pro Thr Val Phe Ser Pro Gly Asp Tyr Ile Cys Lys Lys Gly Asp
                485                 490                 495
Ile Gly Lys Glu Met Tyr Ile Ile Asn Glu Gly Lys Leu Ala Val Val
            500                 505                 510
Ala Asp Asp Gly Val Thr Gln Phe Val Val Leu Ser Asp Gly Ser Tyr
        515                 520                 525
Phe Gly Glu Ile Ser Ile Leu Asn Ile Lys Gly Ser Lys Ser Gly Asn
    530                 535                 540
Arg Arg Thr Ala Asn Ile Arg Ser Ile Gly Tyr Ser Asp Leu Phe Cys
545                 550                 555                 560
Leu Ser Lys Asp Asp Leu Met Glu Ala Leu Thr Glu Tyr Pro Glu Ala
                565                 570                 575
Lys Lys Ala Leu Glu Glu Lys Gly Arg Gln Ile Leu Met Lys Asp Asn
            580                 585                 590
Leu Ile Asp Glu Glu Leu Ala Arg Ala Gly Ala Asp Pro Lys Asp Leu
        595                 600                 605
Glu Glu Lys Val Glu Gln Leu Gly Ser Ser Leu Asp Thr Leu Gln Thr
    610                 615                 620
Arg Phe Ala Arg Leu Leu Ala Glu Tyr Asn Ala Thr Gln Met Lys Met
625                 630                 635                 640
Lys Gln Arg Leu Ser Gln Leu Glu Ser Gln Val Lys Gly Gly Gly Asp
                645                 650                 655
Lys Pro Leu Ala Asp Gly Glu Val Pro Gly Asp Ala Thr Lys Thr Glu
            660                 665                 670
Asp Lys Gln Gln
        675

<210> SEQ ID NO 106
<211> LENGTH: 809
<212> TYPE: PRT
<213> ORGANISM: Homo sapiens

<400> SEQUENCE: 106

Met Phe Lys Ser Leu Thr Lys Val Asn Lys Val Lys Pro Ile Gly Glu
1               5                   10                  15
Asn Asn Glu Asn Glu Gln Ser Ser Arg Arg Asn Glu Glu Gly Ser His
            20                  25                  30
```

```
Pro Ser Asn Gln Ser Gln Thr Ala Gln Glu Glu Asn Lys Gly
         35                  40                  45

Glu Glu Lys Ser Leu Lys Thr Lys Ser Thr Pro Val Thr Ser Glu Glu
 50                  55                  60

Pro His Thr Asn Ile Gln Asp Lys Leu Ser Lys Lys Asn Ser Ser Gly
 65              70                  75                  80

Asp Leu Thr Thr Asn Pro Asp Pro Gln Asn Ala Ala Glu Pro Thr Gly
                 85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
            115                 120                 125

Asp Ala Gln Leu His Asn Leu Val Lys Arg Met Arg Gln Arg Thr Ala
130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190

Lys Lys Met Pro Leu Thr Glu Tyr Leu Lys Arg Ile Lys Leu Pro Asn
            195                 200                 205

Ser Ile Asp Ser Tyr Thr Asp Arg Leu Tyr Leu Trp Leu Leu Leu
            210                 215                 220

Val Thr Leu Ala Tyr Asn Trp Asn Cys Cys Phe Ile Pro Leu Arg Leu
225                 230                 235                 240

Val Phe Pro Tyr Gln Thr Ala Asp Asn Ile His Tyr Trp Leu Ile Ala
                245                 250                 255

Asp Ile Ile Cys Asp Ile Ile Tyr Leu Tyr Asp Met Leu Phe Ile Gln
                260                 265                 270

Pro Arg Leu Gln Phe Val Arg Gly Gly Asp Ile Ile Val Asp Ser Asn
            275                 280                 285

Glu Leu Arg Lys His Tyr Arg Thr Ser Thr Lys Phe Gln Leu Asp Val
            290                 295                 300

Ala Ser Ile Ile Pro Phe Asp Ile Cys Tyr Leu Phe Gly Phe Asn
305                 310                 315                 320

Pro Met Phe Arg Ala Asn Arg Met Leu Lys Tyr Thr Ser Phe Phe Glu
                325                 330                 335

Phe Asn His His Leu Glu Ser Ile Met Asp Lys Ala Tyr Ile Tyr Arg
            340                 345                 350

Val Ile Arg Thr Thr Gly Tyr Leu Leu Phe Ile Leu His Ile Asn Ala
            355                 360                 365

Cys Val Tyr Tyr Trp Ala Ser Asn Tyr Glu Gly Ile Gly Thr Thr Arg
370                 375                 380

Trp Val Tyr Asp Gly Glu Gly Asn Glu Tyr Leu Arg Cys Tyr Tyr Trp
385                 390                 395                 400

Ala Val Arg Thr Leu Ile Thr Ile Gly Gly Leu Pro Glu Pro Gln Thr
                405                 410                 415

Leu Phe Glu Ile Val Phe Gln Leu Leu Asn Phe Ser Gly Val Phe
                420                 425                 430

Val Phe Ser Ser Leu Ile Gly Gln Met Arg Asp Val Ile Gly Ala Ala
            435                 440                 445

Thr Ala Asn Gln Asn Tyr Phe Arg Ala Cys Met Asp Asp Thr Ile Ala
```

450                 455                 460
Tyr Met Asn Asn Tyr Ser Ile Pro Lys Leu Val Gln Lys Arg Val Arg
465                 470                 475                 480

Thr Trp Tyr Glu Tyr Thr Trp Asp Ser Gln Arg Met Leu Asp Glu Ser
                485                 490                 495

Asp Leu Leu Lys Thr Leu Pro Thr Thr Val Gln Leu Ala Leu Ala Ile
                500                 505                 510

Asp Val Asn Phe Ser Ile Ile Ser Lys Val Asp Leu Phe Lys Gly Cys
                515                 520                 525

Asp Thr Gln Met Ile Tyr Asp Met Leu Leu Arg Leu Lys Ser Val Leu
                530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
                580                 585                 590

Ile Ser Leu Leu Ala Ala Gly Gly Asn Arg Arg Thr Ala Asn Val
595                 600                 605

Val Ala His Gly Phe Ala Asn Leu Leu Thr Leu Asp Lys Lys Thr Leu
                610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
                660                 665                 670

Pro Lys Leu Phe Lys Thr Leu Leu Gly Gly Thr Gly Lys Ala Ser Leu
                675                 680                 685

Ala Arg Leu Leu Lys Leu Lys Arg Glu Gln Ala Ala Gln Lys Lys Glu
                690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Lys Pro Leu Asp
                740                 745                 750

Arg Pro Glu Cys Thr Ala Ser Pro Ile Ala Val Glu Glu Pro His
                755                 760                 765

Ser Val Arg Arg Thr Val Leu Pro Arg Gly Thr Ser Arg Gln Ser Leu
                770                 775                 780

Ile Ile Ser Met Ala Pro Ser Ala Glu Gly Gly Glu Glu Val Leu Thr
785                 790                 795                 800

Ile Glu Val Lys Glu Lys Ala Lys Gln
                805

<210> SEQ ID NO 107
<211> LENGTH: 354
<212> TYPE: PRT
<213> ORGANISM: Homo sapiens

<400> SEQUENCE: 107

Met Gly Ser Gly Ala Ser Ala Glu Asp Lys Glu Leu Ala Lys Arg Ser
1               5                   10                  15

```
Lys Glu Leu Glu Lys Lys Leu Gln Glu Asp Ala Asp Lys Glu Ala Lys
                20                  25                  30

Thr Val Lys Leu Leu Leu Gly Ala Gly Glu Ser Gly Lys Ser Thr
        35                  40                  45

Ile Val Lys Gln Met Lys Ile Ile His Gln Asp Gly Tyr Ser Pro Glu
    50                  55                  60

Glu Cys Leu Glu Phe Lys Ala Ile Ile Tyr Gly Asn Val Leu Gln Ser
65                  70                  75                  80

Ile Leu Ala Ile Ile Arg Ala Met Thr Thr Leu Gly Ile Asp Tyr Ala
                85                  90                  95

Glu Pro Ser Cys Ala Asp Asp Gly Arg Gln Leu Asn Asn Leu Ala Asp
                100                 105                 110

Ser Ile Glu Glu Gly Thr Met Pro Pro Glu Leu Val Glu Val Ile Arg
            115                 120                 125

Arg Leu Trp Lys Asp Gly Gly Val Gln Ala Cys Phe Glu Arg Ala Ala
        130                 135                 140

Glu Tyr Gln Leu Asn Asp Ser Ala Ser Tyr Tyr Leu Asn Gln Leu Glu
145                 150                 155                 160

Arg Ile Thr Asp Pro Glu Tyr Leu Pro Ser Glu Gln Asp Val Leu Arg
                165                 170                 175

Ser Arg Val Lys Thr Thr Gly Ile Ile Glu Thr Lys Phe Ser Val Lys
            180                 185                 190

Asp Leu Asn Phe Arg Met Phe Asp Val Gly Gly Gln Arg Ser Glu Arg
        195                 200                 205

Lys Lys Trp Ile His Cys Phe Glu Gly Val Thr Cys Ile Ile Phe Cys
210                 215                 220

Ala Ala Leu Ser Ala Tyr Asp Met Val Leu Val Glu Asp Asp Glu Val
225                 230                 235                 240

Asn Arg Met His Glu Ser Leu His Leu Phe Asn Ser Ile Cys Asn His
                245                 250                 255

Lys Phe Phe Ala Ala Thr Ser Ile Val Leu Phe Leu Asn Lys Lys Asp
            260                 265                 270

Leu Phe Glu Glu Lys Ile Lys Lys Val His Leu Ser Ile Cys Phe Pro
        275                 280                 285

Glu Tyr Asp Gly Asn Asn Ser Tyr Asp Asp Ala Gly Asn Tyr Ile Lys
    290                 295                 300

Ser Gln Phe Leu Asp Leu Asn Met Arg Lys Asp Val Lys Glu Ile Tyr
305                 310                 315                 320

Ser His Met Thr Cys Ala Thr Asp Thr Gln Asn Val Lys Phe Val Phe
                325                 330                 335

Asp Ala Val Thr Asp Ile Ile Leu Lys Glu Asn Leu Lys Asp Cys Gly
            340                 345                 350

Leu Phe

<210> SEQ ID NO 108
<211> LENGTH: 815
<212> TYPE: PRT
<213> ORGANISM: Homo sapiens

<400> SEQUENCE: 108

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
            20                  25                  30
```

```
Lys Asn Asp Val Pro Val His Leu Ser Cys Gly Asp Glu His Ser Ala
             35                  40                  45

Val Val Thr Gly Asn Asn Lys Leu Tyr Met Phe Gly Ser Asn Asn Trp
 50                  55                  60

Gly Gln Leu Gly Leu Gly Ser Lys Ser Ala Ile Ser Lys Pro Thr Cys
 65                  70                  75                  80

Val Lys Ala Leu Lys Pro Glu Lys Val Lys Leu Ala Ala Cys Gly Arg
                 85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
            115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
            195                 200                 205

Gly Glu Leu Tyr Val Phe Gly Glu Pro Glu Asn Gly Lys Leu Gly Leu
            210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
        275                 280                 285

Ile Glu Asn Ile Arg Asp Gln Thr Ile Ser Tyr Ile Ser Cys Gly Glu
    290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
            355                 360                 365

Arg Gly Val Ala Lys Glu Ile Glu Phe Asp Glu Ile Asn Asp Thr Cys
    370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Arg Glu Arg Glu
                405                 410                 415

Arg Ser Pro Asp Ser Phe Ser Met Arg Arg Thr Leu Pro Pro Ile Glu
            420                 425                 430

Gly Thr Leu Gly Leu Ser Ala Cys Phe Leu Pro Asn Ser Val Phe Pro
            435                 440                 445

Arg Cys Ser Glu Arg Asn Leu Gln Glu Ser Val Leu Ser Glu Gln Asp
```

```
            450                 455                 460
Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Gln Gln Thr
            515                 520                 525

Ile Gly Glu Leu Thr Gln Asp Thr Ala Leu Thr Glu Asn Asp Asp Ser
        530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Glu Ile Pro Glu Glu Lys Glu Gly
                580                 585                 590

Ala Glu Asp Ser Lys Gly Asn Gly Ile Glu Glu Gln Glu Val Glu Ala
            595                 600                 605

Asn Glu Glu Asn Val Lys Val His Gly Gly Arg Lys Glu Lys Thr Glu
610                 615                 620

Ile Leu Ser Asp Asp Leu Thr Asp Lys Ala Glu Asp His Glu Phe Ser
625                 630                 635                 640

Lys Thr Glu Glu Leu Lys Leu Glu Asp Val Asp Glu Glu Ile Asn Ala
                645                 650                 655

Glu Asn Val Glu Ser Lys Lys Lys Thr Val Gly Asp Asp Glu Ser Val
            660                 665                 670

Pro Thr Gly Tyr His Ser Lys Thr Glu Gly Ala Glu Arg Thr Asn Asp
            675                 680                 685

Asp Ser Ser Ala Glu Thr Ile Glu Lys Lys Glu Lys Ala Asn Leu Glu
        690                 695                 700

Glu Arg Ala Ile Cys Glu Tyr Asn Glu Asn Pro Lys Gly Tyr Met Leu
705                 710                 715                 720

Asp Asp Ala Asp Ser Ser Ser Leu Glu Ile Leu Glu Asn Ser Glu Thr
                725                 730                 735

Thr Pro Ser Lys Asp Met Lys Lys Thr Lys Lys Ile Phe Leu Phe Lys
            740                 745                 750

Arg Val Pro Ser Ile Asn Gln Lys Ile Val Lys Asn Asn Glu Pro
            755                 760                 765

Leu Pro Glu Ile Lys Ser Ile Gly Asp Gln Ile Ile Leu Lys Ser Asp
        770                 775                 780

Asn Lys Asp Ala Asp Gln Asn His Met Ser Gln Asn His Gln Asn Ile
785                 790                 795                 800

Pro Pro Thr Asn Thr Glu Arg Arg Ser Lys Ser Cys Thr Ile Leu
            805                 810                 815

<210> SEQ ID NO 109
<211> LENGTH: 646
<212> TYPE: PRT
<213> ORGANISM: Homo sapiens

<400> SEQUENCE: 109

Met Arg Glu Pro Glu Glu Leu Met Pro Asp Ser Gly Ala Val Phe Thr
1               5                   10                  15
```

```
Phe Gly Lys Ser Lys Phe Ala Glu Asn Asn Pro Gly Lys Phe Trp Phe
            20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
        50                  55                  60

Gly Gln Leu Gly Leu Gly Ser Lys Ser Ala Ile Ser Lys Pro Thr Cys
 65                 70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
            115                 120                 125

Thr Phe His Val Ile Ser Phe Phe Thr Ser Glu His Lys Ile Lys Gln
            130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
            195                 200                 205

Gly Glu Leu Tyr Val Phe Gly Glu Pro Glu Asn Gly Lys Leu Gly Leu
            210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
            260                 265                 270

Gln Leu Gly Leu Gly Thr Phe Leu Phe Glu Thr Ser Glu Pro Lys Val
            275                 280                 285

Ile Glu Asn Ile Arg Asp Gln Thr Ile Ser Tyr Ile Ser Cys Gly Glu
290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
            355                 360                 365

Arg Gly Val Ala Lys Glu Ile Glu Phe Asp Ile Asn Asp Thr Cys
            370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
                405                 410                 415

Arg Ser Pro Asp Ser Phe Ser Met Arg Arg Thr Leu Pro Pro Ile Glu
            420                 425                 430

Gly Thr Leu Gly Leu Ser Ala Cys Phe Leu Pro Asn Ser Val Phe Pro
```

```
                         435                 440                 445
Arg Cys Ser Glu Arg Asn Leu Gln Glu Ser Val Leu Ser Glu Gln Asp
450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                    485                 490                 495

Thr Asp Ile Leu Asn Met Thr His Ile Met Ser Leu Asn Ser Asn Glu
                500                 505                 510

Lys Ser Leu Lys Leu Ser Pro Val Gln Lys Gln Lys Gln Gln Thr
            515                 520                 525

Ile Gly Glu Leu Thr Gln Asp Thr Ala Leu Thr Glu Asn Asp Asp Ser
530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                    565                 570                 575

Glu Ala Phe Ser Asp Glu Glu Val Glu Ile Pro Glu Glu Lys Glu Gly
                580                 585                 590

Ala Glu Asp Ser Lys Gly Asn Gly Ile Glu Glu Gln Glu Val Glu Ala
                595                 600                 605

Asn Glu Glu Asn Val Lys Val His Gly Gly Arg Lys Gly Lys Thr Glu
610                 615                 620

Ile Leu Ser Asp Asp Leu Thr Asp Lys Ala Glu Tyr Ser Ala Ser His
625                 630                 635                 640

Ser Gln Ile Val Ser Val
                    645

<210> SEQ ID NO 110
<211> LENGTH: 1152
<212> TYPE: PRT
<213> ORGANISM: Homo sapiens

<400> SEQUENCE: 110

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
        50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
                100                 105                 110

Gly Asn Asn Glu Gly Gln Leu Gly Leu Gly Asp Thr Glu Glu Arg Asn
            115                 120                 125

Thr Phe His Val Ile Ser Phe Phe Thr Ser Glu His Lys Ile Lys Gln
        130                 135                 140

Leu Ser Ala Gly Ser Asn Thr Ser Ala Ala Leu Thr Glu Asp Gly Arg
145                 150                 155                 160
```

```
Leu Phe Met Trp Gly Asp Asn Ser Glu Gly Gln Ile Gly Leu Lys Asn
                165                 170                 175
Val Ser Asn Val Cys Val Pro Gln Gln Val Thr Ile Gly Lys Pro Val
            180                 185                 190
Ser Trp Ile Ser Cys Gly Tyr Tyr His Ser Ala Phe Val Thr Thr Asp
        195                 200                 205
Gly Glu Leu Tyr Val Phe Gly Glu Pro Glu Asn Gly Lys Leu Gly Leu
    210                 215                 220
Pro Asn Gln Leu Leu Gly Asn His Arg Thr Pro Gln Leu Val Ser Glu
225                 230                 235                 240
Ile Pro Glu Lys Val Ile Gln Val Ala Cys Gly Gly Glu His Thr Val
                245                 250                 255
Val Leu Thr Glu Asn Ala Val Tyr Thr Phe Gly Leu Gly Gln Phe Gly
            260                 265                 270
Gln Leu Gly Leu Gly Thr Phe Leu Phe Glu Thr Ser Glu Pro Lys Val
        275                 280                 285
Ile Glu Asn Ile Arg Asp Gln Thr Ile Ser Tyr Ile Ser Cys Gly Glu
    290                 295                 300
Asn His Thr Ala Leu Ile Thr Asp Ile Gly Leu Met Tyr Thr Phe Gly
305                 310                 315                 320
Asp Gly Arg His Gly Lys Leu Gly Leu Gly Leu Glu Asn Phe Thr Asn
                325                 330                 335
His Phe Ile Pro Thr Leu Cys Ser Asn Phe Leu Arg Phe Ile Val Lys
            340                 345                 350
Leu Val Ala Cys Gly Gly Cys His Met Val Val Phe Ala Ala Pro His
        355                 360                 365
Arg Gly Val Ala Lys Glu Ile Glu Phe Asp Glu Ile Asn Asp Thr Cys
    370                 375                 380
Leu Ser Val Ala Thr Phe Leu Pro Tyr Ser Ser Leu Thr Ser Gly Asn
385                 390                 395                 400
Val Leu Gln Arg Thr Leu Ser Ala Arg Met Arg Arg Arg Glu Arg Glu
                405                 410                 415
Arg Ser Pro Asp Ser Phe Ser Met Arg Arg Thr Leu Pro Pro Ile Glu
            420                 425                 430
Gly Thr Leu Gly Leu Ser Ala Cys Phe Leu Pro Asn Ser Val Phe Pro
        435                 440                 445
Arg Cys Ser Glu Arg Asn Leu Gln Glu Ser Val Leu Ser Glu Gln Asp
    450                 455                 460
Leu Met Gln Pro Glu Glu Pro Asp Tyr Leu Leu Asp Glu Met Thr Lys
465                 470                 475                 480
Glu Ala Glu Ile Asp Asn Ser Ser Thr Val Glu Ser Leu Gly Glu Thr
                485                 490                 495
Thr Asp Ile Leu Asn Met Thr His Ile Met Ser Leu Asn Ser Asn Glu
            500                 505                 510
Lys Ser Leu Lys Leu Ser Pro Val Gln Lys Gln Lys Gln Gln Thr
        515                 520                 525
Ile Gly Glu Leu Thr Gln Asp Thr Ala Leu Thr Glu Asn Asp Asp Ser
    530                 535                 540
Asp Glu Tyr Glu Glu Met Ser Glu Met Lys Glu Gly Lys Ala Cys Lys
545                 550                 555                 560
Gln His Val Ser Gln Gly Ile Phe Met Thr Gln Pro Ala Thr Thr Ile
                565                 570                 575
Glu Ala Phe Ser Asp Glu Glu Val Glu Ile Pro Glu Glu Lys Glu Gly
```

```
                580                   585                    590
Ala Glu Asp Ser Lys Gly Asn Gly Ile Glu Glu Gln Glu Val Glu Ala
            595                   600                    605
Asn Glu Glu Asn Val Lys Val His Gly Gly Arg Lys Glu Lys Thr Glu
            610                   615                    620
Ile Leu Ser Asp Asp Leu Thr Asp Lys Ala Glu Val Ser Glu Gly Lys
625                       630                   635                    640
Ala Lys Ser Val Gly Glu Ala Glu Asp Gly Pro Glu Gly Arg Gly Asp
                    645                   650                    655
Gly Thr Cys Glu Glu Gly Ser Ser Gly Ala Glu His Trp Gln Asp Glu
                660                   665                    670
Glu Arg Glu Lys Gly Glu Lys Asp Lys Gly Arg Gly Glu Met Glu Arg
            675                   680                    685
Pro Gly Glu Gly Glu Lys Glu Leu Ala Glu Lys Glu Glu Trp Lys Lys
            690                   695                    700
Arg Asp Gly Glu Glu Gln Glu Gln Lys Glu Arg Glu Gln Gly His Gln
705                       710                   715                    720
Lys Glu Arg Asn Gln Glu Met Glu Glu Gly Glu Glu Glu His Gly
                    725                   730                    735
Glu Gly Glu Glu Glu Gly Asp Arg Glu Glu Glu Glu Glu Lys Glu
                740                   745                    750
Gly Glu Gly Lys Glu Gly Glu Gly Glu Glu Val Glu Gly Glu Arg
                755                   760                    765
Glu Lys Glu Glu Gly Glu Arg Lys Lys Glu Glu Arg Ala Gly Lys Glu
            770                   775                    780
Glu Lys Gly Glu Glu Gly Asp Gln Gly Glu Gly Glu Glu Glu
785                       790                   795                    800
Thr Glu Gly Arg Gly Glu Glu Lys Glu Glu Gly Glu Val Glu Gly
                    805                   810                    815
Gly Glu Val Glu Glu Gly Lys Gly Glu Arg Glu Glu Glu Glu Glu
                    820                   825                    830
Gly Glu Gly Glu Glu Glu Glu Gly Glu Gly Glu Glu Glu Gly Glu
                835                   840                    845
Gly Glu Glu Glu Glu Gly Glu Gly Lys Gly Glu Glu Glu Gly Glu Glu
            850                   855                    860
Gly Glu Gly Glu Glu Glu Gly Glu Glu Gly Glu Gly Glu Gly Glu Glu
865                       870                   875                    880
Glu Glu Gly Glu Gly Glu Gly Glu Glu Gly Glu Gly Glu Gly Glu
                    885                   890                    895
Glu Glu Glu Gly Glu Gly Glu Gly Glu Gly Glu Gly Glu Gly
                900                   905                    910
Glu Glu Glu Gly Glu Gly Lys Gly Glu Glu Glu Gly Glu Glu Gly
                    915                   920                    925
Glu Gly Glu Gly Glu Glu Glu Gly Glu Gly Glu Gly Glu Asp Gly
                930                   935                    940
Glu Gly Glu Gly Glu Glu Glu Gly Glu Trp Glu Gly Glu Glu
945                       950                   955                    960
Glu Gly Glu Gly Glu Gly Glu Glu Gly Gly Glu Gly Glu Glu
                    965                   970                    975
Gly Glu Gly Glu Gly Glu Glu Glu Gly Gly Glu Gly Glu Glu
                    980                   985                    990
Glu Glu Gly Glu Glu Gly Glu  Glu Glu Gly Glu Gly  Glu Glu Glu
            995                   1000                    1005
```

-continued

```
Gly Glu Gly Glu Gly Glu Glu Glu Glu Gly Glu Val Glu Gly
        1010            1015                1020

Glu Val Glu Gly Glu Gly Glu Gly Glu Gly Glu     Glu Glu Glu
        1025            1030                1035

Gly Glu Glu Gly Glu Glu Arg Glu Lys Glu Gly     Glu Gly Glu
        1040            1045                1050

Glu Asn Arg Arg Asn Arg Glu Glu Glu Glu Glu     Glu Gly Lys
        1055            1060                1065

Tyr Gln Glu Thr Gly Glu Glu Asn Glu Arg Gln     Asp Gly Glu
        1070            1075                1080

Glu Tyr Lys Lys Val Ser Lys Ile Lys Gly Ser Val Lys Tyr Gly
        1085            1090                1095

Lys His Lys Thr Tyr Gln Lys Lys Ser Val Thr     Asn Thr Gln Gly
        1100            1105                1110

Asn Gly Lys Glu Gln Arg Ser Lys Met Pro Val     Gln Ser Lys Arg
        1115            1120                1125

Leu Leu Lys Asn Gly Pro Ser Gly Ser Lys Lys Phe Trp Asn Asn
        1130            1135                1140

Val Leu Pro His Tyr Leu Glu Leu Lys
        1145            1150

<210> SEQ ID NO 111
<211> LENGTH: 1020
<212> TYPE: PRT
<213> ORGANISM: Homo sapiens

<400> SEQUENCE: 111

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
        50                  55                  60

Gly Gln Leu Gly Leu Gly Ser Lys Ser Ala Ile Ser Lys Pro Thr Cys
65              70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
        115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
        195                 200                 205

Gly Glu Leu Tyr Val Phe Gly Glu Pro Glu Asn Gly Lys Leu Gly Leu
```

-continued

```
              210                 215                 220
Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
                260                 265                 270

Gln Leu Gly Leu Gly Thr Phe Leu Phe Glu Thr Ser Glu Pro Lys Val
                275                 280                 285

Ile Glu Asn Ile Arg Asp Gln Thr Ile Ser Tyr Ile Ser Cys Gly Glu
                290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
                340                 345                 350

Leu Val Ala Cys Gly Gly Cys His Met Val Val Phe Ala Ala Pro His
                355                 360                 365

Arg Gly Val Ala Lys Glu Ile Glu Phe Asp Glu Ile Asn Asp Thr Cys
                370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Glu Arg Glu
                405                 410                 415

Arg Ser Pro Asp Ser Phe Ser Met Arg Arg Thr Leu Pro Pro Ile Glu
                420                 425                 430

Gly Thr Leu Gly Leu Ser Ala Cys Phe Leu Pro Asn Ser Val Phe Pro
                435                 440                 445

Arg Cys Ser Glu Arg Asn Leu Gln Glu Ser Val Leu Ser Glu Gln Asp
                450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
                500                 505                 510

Lys Ser Leu Lys Leu Ser Pro Val Gln Lys Gln Lys Gln Gln Thr
                515                 520                 525

Ile Gly Glu Leu Thr Gln Asp Thr Ala Leu Thr Glu Asn Asp Asp Ser
                530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Gly Asn Asp Thr Gly Gln Val Gly
                580                 585                 590

Pro Gln Ala Asp Thr Asp Gly Glu Gly Leu Gln Lys Glu Val Tyr Arg
                595                 600                 605

His Glu Asn Asn Asn Gly Val Asp Gln Leu Asp Ala Lys Glu Ile Glu
                610                 615                 620

Lys Glu Ser Asp Gly Gly His Ser Gln Lys Glu Ser Glu Ala Glu Glu
625                 630                 635                 640
```

```
Ile Asp Ser Glu Lys Glu Thr Lys Leu Ala Glu Ile Ala Gly Met Lys
            645                 650                 655

Asp Leu Arg Glu Arg Glu Lys Ser Thr Lys Lys Met Ser Pro Phe Phe
            660                 665                 670

Gly Asn Leu Pro Asp Arg Gly Met Asn Thr Glu Ser Glu Glu Asn Lys
            675                 680                 685

Asp Phe Val Lys Lys Arg Glu Ser Cys Lys Gln Asp Val Ile Phe Asp
        690                 695                 700

Ser Glu Arg Glu Ser Val Glu Lys Pro Asp Ser Tyr Met Glu Gly Ala
705                 710                 715                 720

Ser Glu Ser Gln Gln Gly Ile Ala Asp Gly Phe Gln Gln Pro Glu Ala
            725                 730                 735

Ile Glu Phe Ser Ser Gly Glu Lys Glu Asp Asp Glu Val Glu Thr Asp
            740                 745                 750

Gln Asn Ile Arg Tyr Gly Arg Lys Leu Ile Glu Gln Gly Asn Glu Lys
            755                 760                 765

Glu Thr Lys Pro Ile Ile Ser Lys Ser Met Ala Lys Tyr Asp Phe Lys
        770                 775                 780

Cys Asp Arg Leu Ser Glu Ile Pro Glu Glu Lys Glu Gly Ala Glu Asp
785                 790                 795                 800

Ser Lys Gly Asn Gly Ile Glu Glu Gln Glu Val Glu Ala Asn Glu Glu
            805                 810                 815

Asn Val Lys Val His Gly Gly Arg Lys Glu Lys Thr Glu Ile Leu Ser
            820                 825                 830

Asp Asp Leu Thr Asp Lys Ala Glu Asp His Glu Phe Ser Lys Thr Glu
            835                 840                 845

Glu Leu Lys Leu Glu Asp Val Asp Glu Glu Ile Asn Ala Glu Asn Val
        850                 855                 860

Glu Ser Lys Lys Lys Thr Val Gly Asp Asp Glu Ser Val Pro Thr Gly
865                 870                 875                 880

Tyr His Ser Lys Thr Glu Gly Ala Glu Arg Thr Asn Asp Asp Ser Ser
            885                 890                 895

Ala Glu Thr Ile Glu Lys Lys Glu Lys Ala Asn Leu Glu Glu Arg Ala
            900                 905                 910

Ile Cys Glu Tyr Asn Glu Asn Pro Lys Gly Tyr Met Leu Asp Asp Ala
        915                 920                 925

Asp Ser Ser Ser Leu Glu Ile Leu Glu Asn Ser Glu Thr Thr Pro Ser
        930                 935                 940

Lys Asp Met Lys Lys Thr Lys Lys Ile Phe Leu Phe Lys Arg Val Pro
945                 950                 955                 960

Ser Ile Asn Gln Lys Ile Val Lys Asn Asn Glu Pro Leu Pro Glu
            965                 970                 975

Ile Lys Ser Ile Gly Asp Gln Ile Ile Leu Lys Ser Asp Asn Lys Asp
            980                 985                 990

Ala Asp Gln Asn His Met Ser Gln Asn His Gln Asn Ile Pro Pro Thr
            995                 1000                1005

Asn Thr Glu Arg Arg Ser Lys Ser Cys Thr Ile Leu
        1010                1015                1020

<210> SEQ ID NO 112
<211> LENGTH: 1368
<212> TYPE: PRT
<213> ORGANISM: Streptococcus pyogenes
```

```
<400> SEQUENCE: 112

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415
```

```
Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830
```

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser

-continued

```
            1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 113
<211> LENGTH: 1368
<212> TYPE: PRT
<213> ORGANISM: Streptococcus pyogenes

<400> SEQUENCE: 113

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240
```

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
        260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp

-continued

```
                660             665             670
Lys Gln Ser Gly Lys Thr Ile Leu Asp Phe Leu Lys Ser Asp Gly Phe
            675             680             685
Ala Asn Arg Asn Phe Met Gln Leu Ile His Asp Asp Ser Leu Thr Phe
690             695             700
Lys Glu Asp Ile Gln Lys Ala Gln Val Ser Gly Gln Gly Asp Ser Leu
705             710             715             720
His Glu His Ile Ala Asn Leu Ala Gly Ser Pro Ala Ile Lys Lys Gly
                725             730             735
Ile Leu Gln Thr Val Lys Val Val Asp Glu Leu Val Lys Val Met Gly
            740             745             750
Arg His Lys Pro Glu Asn Ile Val Ile Glu Met Ala Arg Glu Asn Gln
        755             760             765
Thr Thr Gln Lys Gly Gln Lys Asn Ser Arg Glu Arg Met Lys Arg Ile
770             775             780
Glu Glu Gly Ile Lys Glu Leu Gly Ser Gln Ile Leu Lys Glu His Pro
785             790             795             800
Val Glu Asn Thr Gln Leu Gln Asn Glu Lys Leu Tyr Leu Tyr Tyr Leu
            805             810             815
Gln Asn Gly Arg Asp Met Tyr Val Asp Gln Glu Leu Asp Ile Asn Arg
        820             825             830
Leu Ser Asp Tyr Asp Val Asp His Ile Val Pro Gln Ser Phe Leu Lys
    835             840             845
Asp Asp Ser Ile Asp Asn Lys Val Leu Thr Arg Ser Asp Lys Asn Arg
850             855             860
Gly Lys Ser Asp Asn Val Pro Ser Glu Glu Val Val Lys Lys Met Lys
865             870             875             880
Asn Tyr Trp Arg Gln Leu Leu Asn Ala Lys Leu Ile Thr Gln Arg Lys
            885             890             895
Phe Asp Asn Leu Thr Lys Ala Glu Arg Gly Gly Leu Ser Glu Leu Asp
        900             905             910
Lys Ala Gly Phe Ile Lys Arg Gln Leu Val Glu Thr Arg Gln Ile Thr
    915             920             925
Lys His Val Ala Gln Ile Leu Asp Ser Arg Met Asn Thr Lys Tyr Asp
930             935             940
Glu Asn Asp Lys Leu Ile Arg Glu Val Lys Val Ile Thr Leu Lys Ser
945             950             955             960
Lys Leu Val Ser Asp Phe Arg Lys Asp Phe Gln Phe Tyr Lys Val Arg
            965             970             975
Glu Ile Asn Asn Tyr His His Ala His Asp Ala Tyr Leu Asn Ala Val
        980             985             990
Val Gly Thr Ala Leu Ile Lys Lys  Tyr Pro Lys Leu Glu  Ser Glu Phe
            995             1000             1005
Val Tyr  Gly Asp Tyr Lys Val  Tyr Asp Val Arg Lys  Met Ile Ala
1010             1015             1020
Lys Ser  Glu Gln Glu Ile Gly  Lys Ala Thr Ala Lys  Tyr Phe Phe
    1025             1030             1035
Tyr Ser  Asn Ile Met Asn Phe  Phe Lys Thr Glu Ile  Thr Leu Ala
    1040             1045             1050
Asn Gly  Glu Ile Arg Lys Arg  Pro Leu Ile Glu Thr  Asn Gly Glu
    1055             1060             1065
Thr Gly  Glu Ile Val Trp Asp  Lys Gly Arg Asp Phe  Ala Thr Val
    1070             1075             1080
```

Arg Lys Val Leu Ser Met Pro Gln Val Asn Ile Val Lys Lys Thr
    1085            1090                1095

Glu Val Gln Thr Gly Gly Phe Ser Lys Glu Ser Ile Leu Pro Lys
    1100            1105                1110

Arg Asn Ser Asp Lys Leu Ile Ala Arg Lys Lys Asp Trp Asp Pro
    1115            1120                1125

Lys Lys Tyr Gly Gly Phe Asp Ser Pro Thr Val Ala Tyr Ser Val
    1130            1135                1140

Leu Val Val Ala Lys Val Glu Lys Gly Lys Ser Lys Lys Leu Lys
    1145            1150                1155

Ser Val Lys Glu Leu Leu Gly Ile Thr Ile Met Glu Arg Ser Ser
    1160            1165                1170

Phe Glu Lys Asn Pro Ile Asp Phe Leu Glu Ala Lys Gly Tyr Lys
    1175            1180                1185

Glu Val Lys Lys Asp Leu Ile Ile Lys Leu Pro Lys Tyr Ser Leu
    1190            1195                1200

Phe Glu Leu Glu Asn Gly Arg Lys Arg Met Leu Ala Ser Ala Gly
    1205            1210                1215

Glu Leu Gln Lys Gly Asn Glu Leu Ala Leu Pro Ser Lys Tyr Val
    1220            1225                1230

Asn Phe Leu Tyr Leu Ala Ser His Tyr Glu Lys Leu Lys Gly Ser
    1235            1240                1245

Pro Glu Asp Asn Glu Gln Lys Gln Leu Phe Val Glu Gln His Lys
    1250            1255                1260

His Tyr Leu Asp Glu Ile Ile Glu Gln Ile Ser Glu Phe Ser Lys
    1265            1270                1275

Arg Val Ile Leu Ala Asp Ala Asn Leu Asp Lys Val Leu Ser Ala
    1280            1285                1290

Tyr Asn Lys His Arg Asp Lys Pro Ile Arg Glu Gln Ala Glu Asn
    1295            1300                1305

Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

<210> SEQ ID NO 114
<211> LENGTH: 1368
<212> TYPE: PRT
<213> ORGANISM: Streptococcus pyogenes

<400> SEQUENCE: 114

Met Asp Lys Lys Tyr Ser Ile Gly Leu Asp Ile Gly Thr Asn Ser
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys

```
            65                  70                  75                  80
Tyr Leu Gln Glu Ile Phe Ser Asn Glu Met Ala Lys Val Asp Asp Ser
                    85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
                130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
                210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

```
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
```

| | | 1310 | | | 1315 | | | 1320 | | |

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 115
<211> LENGTH: 1368
<212> TYPE: PRT
<213> ORGANISM: Streptococcus pyogenes

<400> SEQUENCE: 115

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

```
Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
```

```
                740             745             750
Arg His Lys Pro Glu Asn Ile Val Ile Glu Met Ala Arg Glu Asn Gln
                    755             760             765

Thr Thr Gln Lys Gly Gln Lys Asn Ser Arg Glu Arg Met Lys Arg Ile
770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
                805             810             815

Gln Asn Gly Arg Asp Met Tyr Val Asp Gln Glu Leu Asp Ile Asn Arg
                820             825             830

Leu Ser Asp Tyr Asp Val Asp Ala Ile Val Pro Gln Ser Phe Leu Lys
                835             840             845

Asp Asp Ser Ile Asp Asn Lys Val Leu Thr Arg Ser Asp Lys Asn Arg
                850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
                885             890             895

Phe Asp Asn Leu Thr Lys Ala Glu Arg Gly Gly Leu Ser Glu Leu Asp
                900             905             910

Lys Ala Gly Phe Ile Lys Arg Gln Leu Val Glu Thr Arg Gln Ile Thr
                915             920             925

Lys His Val Ala Gln Ile Leu Asp Ser Arg Met Asn Thr Lys Tyr Asp
                930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
                965             970             975

Glu Ile Asn Asn Tyr His His Ala His Asp Ala Tyr Leu Asn Ala Val
                980             985             990

Val Gly Thr Ala Leu Ile Lys Lys Tyr Pro Lys Leu Glu Ser Glu Phe
                995            1000            1005

Val Tyr Gly Asp Tyr Lys Val Tyr Asp Val Arg Lys Met Ile Ala
           1010            1015            1020

Lys Ser Glu Gln Glu Ile Gly Lys Ala Thr Ala Lys Tyr Phe Phe
           1025            1030            1035

Tyr Ser Asn Ile Met Asn Phe Phe Lys Thr Glu Ile Thr Leu Ala
           1040            1045            1050

Asn Gly Glu Ile Arg Lys Arg Pro Leu Ile Glu Thr Asn Gly Glu
           1055            1060            1065

Thr Gly Glu Ile Val Trp Asp Lys Gly Arg Asp Phe Ala Thr Val
           1070            1075            1080

Arg Lys Val Leu Ser Met Pro Gln Val Asn Ile Val Lys Lys Thr
           1085            1090            1095

Glu Val Gln Thr Gly Gly Phe Ser Lys Glu Ser Ile Leu Pro Lys
           1100            1105            1110

Arg Asn Ser Asp Lys Leu Ile Ala Arg Lys Lys Asp Trp Asp Pro
           1115            1120            1125

Lys Lys Tyr Gly Gly Phe Asp Ser Pro Thr Val Ala Tyr Ser Val
           1130            1135            1140

Leu Val Val Ala Lys Val Glu Lys Gly Lys Ser Lys Lys Leu Lys
           1145            1150            1155
```

-continued

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 116
<211> LENGTH: 1368
<212> TYPE: PRT
<213> ORGANISM: Streptococcus pyogenes

<400> SEQUENCE: 116

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His

```
            145                 150                 155                 160
Met Ile Lys Phe Arg Gly His Phe Leu Ile Glu Gly Asp Leu Asn Pro
                    165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
            195                 200                 205
Lys Ala Ile Leu Ser Ala Arg Leu Ser Lys Ser Arg Arg Leu Glu Asn
225             210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
```

```
Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Ala
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990
```

Val Gly Thr Ala Leu Ile Lys Lys Tyr Pro Ala Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Ala Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 117
<211> LENGTH: 1367
<212> TYPE: PRT

<213> ORGANISM: Streptococcus pyogenes

<400> SEQUENCE: 117

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

```
Gln Arg Thr Phe Asp Asn Gly Ser Ile Pro His Gln Ile His Leu Gly
                405                 410                 415
Glu Leu His Ala Ile Leu Arg Arg Gln Glu Asp Phe Tyr Pro Phe Leu
            420                 425                 430
Lys Asp Asn Arg Glu Lys Ile Glu Lys Ile Leu Thr Phe Arg Ile Pro
        435                 440                 445
Tyr Tyr Val Gly Pro Leu Ala Arg Gly Asn Ser Arg Phe Ala Trp Met
    450                 455                 460
Thr Arg Lys Ser Glu Glu Thr Ile Thr Pro Trp Asn Phe Glu Glu Val
465                 470                 475                 480
Val Asp Lys Gly Ala Ser Ala Gln Ser Phe Ile Glu Arg Met Thr Ala
                485                 490                 495
Phe Asp Lys Asn Leu Pro Asn Glu Lys Val Leu Pro Lys His Ser Leu
            500                 505                 510
Leu Tyr Glu Tyr Phe Thr Val Tyr Asn Glu Leu Thr Lys Val Lys Tyr
        515                 520                 525
Val Thr Glu Gly Met Arg Lys Pro Ala Phe Leu Ser Gly Glu Gln Lys
    530                 535                 540
Lys Ala Ile Val Asp Leu Leu Phe Lys Thr Asn Arg Lys Val Thr Val
545                 550                 555                 560
Lys Gln Leu Lys Glu Asp Tyr Phe Lys Lys Ile Glu Cys Phe Asp Ser
                565                 570                 575
Val Glu Ile Ser Gly Val Glu Asp Arg Phe Asn Ala Ser Leu Gly Thr
            580                 585                 590
Tyr His Asp Leu Leu Lys Ile Ile Lys Asp Lys Asp Phe Leu Asp Asn
        595                 600                 605
Glu Glu Asn Glu Asp Ile Leu Glu Asp Ile Val Leu Thr Leu Thr Leu
    610                 615                 620
Phe Glu Asp Arg Glu Met Ile Glu Glu Arg Leu Lys Thr Tyr Ala His
625                 630                 635                 640
Leu Phe Asp Asp Lys Val Met Lys Gln Leu Lys Arg Arg Arg Tyr Thr
                645                 650                 655
Gly Trp Gly Ala Leu Ser Arg Lys Leu Ile Asn Gly Ile Arg Asp Lys
            660                 665                 670
Gln Ser Gly Lys Thr Ile Leu Asp Phe Leu Lys Ser Asp Gly Phe Ala
        675                 680                 685
Asn Arg Asn Phe Met Ala Leu Ile His Asp Asp Ser Leu Thr Phe Lys
    690                 695                 700
Glu Asp Ile Gln Lys Ala Gln Val Ser Gly Gln Gly Asp Ser Leu His
705                 710                 715                 720
Glu His Ile Ala Asn Leu Ala Gly Ser Pro Ala Ile Lys Lys Gly Ile
                725                 730                 735
Leu Gln Thr Val Lys Val Val Asp Glu Leu Val Lys Val Met Gly Arg
            740                 745                 750
His Lys Pro Glu Asn Ile Val Ile Glu Met Ala Arg Glu Asn Gln Thr
        755                 760                 765
Thr Gln Lys Gly Gln Lys Asn Ser Arg Glu Arg Met Lys Arg Ile Glu
    770                 775                 780
Glu Gly Ile Lys Glu Leu Gly Ser Gln Ile Leu Lys Glu His Pro Val
785                 790                 795                 800
Glu Asn Thr Gln Leu Gln Asn Glu Lys Leu Tyr Leu Tyr Tyr Leu Gln
                805                 810                 815
Asn Gly Arg Asp Met Tyr Val Asp Gln Glu Leu Asp Ile Asn Arg Leu
```

```
                820             825             830
Ser Asp Tyr Asp Val Asp His Ile Val Pro Gln Ser Phe Leu Lys Asp
            835             840             845

Asp Ser Ile Asp Asn Lys Val Leu Thr Arg Ser Asp Lys Asn Arg Gly
850             855             860

Lys Ser Asp Asn Val Pro Ser Glu Glu Val Lys Lys Met Lys Asn
865             870             875             880

Tyr Trp Arg Gln Leu Leu Asn Ala Lys Leu Ile Thr Gln Arg Lys Phe
                885             890             895

Asp Asn Leu Thr Lys Ala Glu Arg Gly Gly Leu Ser Glu Leu Asp Lys
            900             905             910

Ala Gly Phe Ile Lys Arg Gln Leu Val Glu Thr Arg Ala Ile Thr Lys
        915             920             925

His Val Ala Gln Ile Leu Asp Ser Arg Met Asn Thr Lys Tyr Asp Glu
        930             935             940

Asn Asp Lys Leu Ile Arg Glu Val Lys Val Ile Thr Leu Lys Ser Lys
945             950             955             960

Leu Val Ser Asp Phe Arg Lys Asp Phe Gln Phe Tyr Lys Val Arg Glu
                965             970             975

Ile Asn Asn Tyr His His Ala His Asp Ala Tyr Leu Asn Ala Val Val
            980             985             990

Gly Thr Ala Leu Ile Lys Lys Tyr Pro Lys Leu Glu Ser Glu Phe Val
            995             1000            1005

Tyr Gly Asp Tyr Lys Val Tyr Asp Val Arg Lys Met Ile Ala Lys
        1010            1015            1020

Ser Glu Gln Glu Ile Gly Lys Ala Thr Ala Lys Tyr Phe Phe Tyr
        1025            1030            1035

Ser Asn Ile Met Asn Phe Phe Lys Thr Glu Ile Thr Leu Ala Asn
        1040            1045            1050

Gly Glu Ile Arg Lys Arg Pro Leu Ile Glu Thr Asn Gly Glu Thr
        1055            1060            1065

Gly Glu Ile Val Trp Asp Lys Gly Arg Asp Phe Ala Thr Val Arg
        1070            1075            1080

Lys Val Leu Ser Met Pro Gln Val Asn Ile Val Lys Lys Thr Glu
        1085            1090            1095

Val Gln Thr Gly Gly Phe Ser Lys Glu Ser Ile Leu Pro Lys Arg
        1100            1105            1110

Asn Ser Asp Lys Leu Ile Ala Arg Lys Lys Asp Trp Asp Pro Lys
        1115            1120            1125

Lys Tyr Gly Gly Phe Asp Ser Pro Thr Val Ala Tyr Ser Val Leu
        1130            1135            1140

Val Val Ala Lys Val Glu Lys Gly Lys Ser Lys Lys Leu Lys Ser
        1145            1150            1155

Val Lys Glu Leu Leu Gly Ile Thr Ile Met Glu Arg Ser Ser Phe
        1160            1165            1170

Glu Lys Asn Pro Ile Asp Phe Leu Glu Ala Lys Gly Tyr Lys Glu
        1175            1180            1185

Val Lys Lys Asp Leu Ile Ile Lys Leu Pro Lys Tyr Ser Leu Phe
        1190            1195            1200

Glu Leu Glu Asn Gly Arg Lys Arg Met Leu Ala Ser Ala Gly Glu
        1205            1210            1215

Leu Gln Lys Gly Asn Glu Leu Ala Leu Pro Ser Lys Tyr Val Asn
        1220            1225            1230
```

```
Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 118
<211> LENGTH: 1053
<212> TYPE: PRT
<213> ORGANISM: Staphylococcus aureus

<400> SEQUENCE: 118

Met Lys Arg Asn Tyr Ile Leu Gly Leu Asp Ile Gly Ile Thr Ser
1               5                   10                  15

Gly Tyr Gly Ile Ile Asp Tyr Glu Thr Arg Asp Val Ile Asp Ala Gly
                20                  25                  30

Val Arg Leu Phe Lys Glu Ala Asn Val Glu Asn Asn Glu Gly Arg Arg
            35                  40                  45

Ser Lys Arg Gly Ala Arg Arg Leu Lys Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Phe Ser Ala Ala Leu Leu His Leu
                100                 105                 110

Ala Lys Arg Arg Gly Val His Asn Val Asn Glu Val Glu Glu Asp Thr
            115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
    195                 200                 205

Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
```

```
            225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
                260                 265                 270

Glu Lys Leu Glu Tyr Tyr Glu Lys Phe Gln Ile Ile Glu Asn Val Phe
                275                 280                 285

Lys Gln Lys Lys Lys Pro Thr Leu Lys Gln Ile Ala Lys Glu Ile Leu
                290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
                340                 345                 350

Lys Ile Leu Thr Ile Tyr Gln Ser Ser Glu Asp Ile Gln Glu Glu Leu
                355                 360                 365

Thr Asn Leu Asn Ser Glu Leu Thr Gln Glu Glu Ile Glu Gln Ile Ser
                370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
                420                 425                 430

Gln Lys Glu Ile Pro Thr Thr Leu Val Asp Asp Phe Ile Leu Ser Pro
                435                 440                 445

Val Val Lys Arg Ser Phe Ile Gln Ser Ile Lys Val Ile Asn Ala Ile
                450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Ile Ile Arg Thr Thr
                500                 505                 510

Gly Lys Glu Asn Ala Lys Tyr Leu Ile Glu Lys Ile Lys Leu His Asp
                515                 520                 525

Met Gln Glu Gly Lys Cys Leu Tyr Ser Leu Glu Ala Ile Pro Leu Glu
                530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
                580                 585                 590

Ser Ser Ser Asp Ser Lys Ile Ser Tyr Glu Thr Phe Lys Lys His Ile
                595                 600                 605

Leu Asn Leu Ala Lys Gly Lys Gly Arg Ile Ser Lys Thr Lys Lys Glu
                610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655
```

```
Met Asn Leu Leu Arg Ser Tyr Phe Arg Val Asn Asn Leu Asp Val Lys
                660                 665                 670

Val Lys Ser Ile Asn Gly Gly Phe Thr Ser Phe Leu Arg Arg Lys Trp
            675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Lys
                725                 730                 735

Gln Ala Glu Ser Met Pro Glu Ile Glu Thr Gln Glu Tyr Lys Glu
                740                 745                 750

Ile Phe Ile Thr Pro His Gln Ile Lys His Ile Lys Asp Phe Lys Asp
                755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
                820                 825                 830

Asp Pro Gln Thr Tyr Gln Lys Leu Lys Leu Ile Met Glu Gln Tyr Gly
                835                 840                 845

Asp Glu Lys Asn Pro Leu Tyr Lys Tyr Tyr Glu Glu Thr Gly Asn Tyr
                850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
                900                 905                 910

Arg Phe Asp Val Tyr Leu Asp Asn Gly Val Tyr Lys Phe Val Thr Val
                915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
                980                 985                 990

Glu Val Asn Met Ile Asp Ile Thr Tyr Arg Glu Tyr Leu Glu Asn Met
                995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
        1040                1045                1050

<210> SEQ ID NO 119
<211> LENGTH: 1300
```

<212> TYPE: PRT
<213> ORGANISM: Franciscella tularensis

<400> SEQUENCE: 119

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
            35                  40                  45

Lys Ala Lys Gln Ile Ile Asp Lys Tyr His Gln Phe Phe Ile Glu Glu
        50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
            165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
            245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
            325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400
```

```
Asp Leu Ser Gln Gln Val Phe Asp Asp Tyr Ser Val Ile Gly Thr Ala
            405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
            435                 440                 445

Lys Tyr Leu Ser Leu Glu Thr Ile Lys Leu Ala Leu Glu Glu Phe Asn
            450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
            485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
            515                 520                 525

Leu Leu Asp Gln Thr Asn Asn Leu Leu His Lys Leu Lys Ile Phe His
530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
            565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
            645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
            690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
            725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
            755                 760                 765

Ile Ser Glu Ser Tyr Ile Asp Ser Val Val Asn Gln Gly Lys Leu Tyr
            770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
            805                 810                 815
```

```
Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
            835                 840                 845

Ile Ala Asn Lys Asn Lys Asp Asn Pro Lys Lys Glu Ser Val Phe Glu
            850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
            885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
            930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
      1010                1015                1020

Tyr Gln Lys Leu Glu Lys Met Leu Ile Glu Lys Leu Asn Tyr Leu
      1025                1030                1035

Val Phe Lys Asp Asn Glu Phe Asp Lys Thr Gly Gly Val Leu Arg
      1040                1045                1050

Ala Tyr Gln Leu Thr Ala Pro Phe Glu Thr Phe Lys Lys Met Gly
      1055                1060                1065

Lys Gln Thr Gly Ile Ile Tyr Tyr Val Pro Ala Gly Phe Thr Ser
      1070                1075                1080

Lys Ile Cys Pro Val Thr Gly Phe Val Asn Gln Leu Tyr Pro Lys
      1085                1090                1095

Tyr Glu Ser Val Ser Lys Ser Gln Glu Phe Phe Ser Lys Phe Asp
      1100                1105                1110

Lys Ile Cys Tyr Asn Leu Asp Lys Gly Tyr Phe Glu Phe Ser Phe
      1115                1120                1125

Asp Tyr Lys Asn Phe Gly Asp Lys Ala Ala Lys Gly Lys Trp Thr
      1130                1135                1140

Ile Ala Ser Phe Gly Ser Arg Leu Ile Asn Phe Arg Asn Ser Asp
      1145                1150                1155

Lys Asn His Asn Trp Asp Thr Arg Glu Val Tyr Pro Thr Lys Glu
      1160                1165                1170

Leu Glu Lys Leu Leu Lys Asp Tyr Ser Ile Glu Tyr Gly His Gly
      1175                1180                1185

Glu Cys Ile Lys Ala Ala Ile Cys Gly Glu Ser Asp Lys Lys Phe
      1190                1195                1200

Phe Ala Lys Leu Thr Ser Val Leu Asn Thr Ile Leu Gln Met Arg
      1205                1210                1215

Asn Ser Lys Thr Gly Thr Glu Leu Asp Tyr Leu Ile Ser Pro Val
```

```
                        1220                1225                1230

Ala  Asp  Val  Asn  Gly  Asn  Phe  Phe  Asp  Ser  Arg  Gln  Ala  Pro  Lys
         1235                1240                1245

Asn  Met  Pro  Gln  Asp  Ala  Asp  Ala  Asn  Gly  Ala  Tyr  His  Ile  Gly
         1250                1255                1260

Leu  Lys  Gly  Leu  Met  Leu  Leu  Gly  Arg  Ile  Lys  Asn  Asn  Gln  Glu
         1265                1270                1275

Gly  Lys  Lys  Leu  Asn  Leu  Val  Ile  Lys  Asn  Glu  Glu  Tyr  Phe  Glu
         1280                1285                1290

Phe  Val  Gln  Asn  Arg  Asn  Asn
         1295                1300

<210> SEQ ID NO 120
<211> LENGTH: 1306
<212> TYPE: PRT
<213> ORGANISM: Acidaminococcus sp.

<400> SEQUENCE: 120

Thr  Gln  Phe  Glu  Gly  Phe  Thr  Asn  Leu  Tyr  Gln  Val  Ser  Lys  Thr  Leu
 1                    5                   10                  15

Arg  Phe  Glu  Leu  Ile  Pro  Gln  Gly  Lys  Thr  Leu  Lys  His  Ile  Gln  Glu
              20                  25                  30

Gln  Gly  Phe  Ile  Glu  Glu  Asp  Lys  Ala  Arg  Asn  Asp  His  Tyr  Lys  Glu
         35                  40                  45

Leu  Lys  Pro  Ile  Ile  Asp  Arg  Ile  Tyr  Lys  Thr  Tyr  Ala  Asp  Gln  Cys
 50                  55                  60

Leu  Gln  Leu  Val  Gln  Leu  Asp  Trp  Glu  Asn  Leu  Ser  Ala  Ala  Ile  Asp
 65                  70                  75                  80

Ser  Tyr  Arg  Lys  Glu  Lys  Thr  Glu  Glu  Thr  Arg  Asn  Ala  Leu  Ile  Glu
              85                  90                  95

Glu  Gln  Ala  Thr  Tyr  Arg  Asn  Ala  Ile  His  Asp  Tyr  Phe  Ile  Gly  Arg
         100                 105                 110

Thr  Asp  Asn  Leu  Thr  Asp  Ala  Ile  Asn  Lys  Arg  His  Ala  Glu  Ile  Tyr
         115                 120                 125

Lys  Gly  Leu  Phe  Lys  Ala  Glu  Leu  Phe  Asn  Gly  Lys  Val  Leu  Lys  Gln
 130                 135                 140

Leu  Gly  Thr  Val  Thr  Thr  Thr  Glu  His  Glu  Asn  Ala  Leu  Leu  Arg  Ser
 145                 150                 155                 160

Phe  Asp  Lys  Phe  Thr  Thr  Tyr  Phe  Ser  Gly  Phe  Tyr  Glu  Asn  Arg  Lys
              165                 170                 175

Asn  Val  Phe  Ser  Ala  Glu  Asp  Ile  Ser  Thr  Ala  Ile  Pro  His  Arg  Ile
              180                 185                 190

Val  Gln  Asp  Asn  Phe  Pro  Lys  Phe  Lys  Glu  Asn  Cys  His  Ile  Phe  Thr
         195                 200                 205

Arg  Leu  Ile  Thr  Ala  Val  Pro  Ser  Leu  Arg  Glu  His  Phe  Glu  Asn  Val
 210                 215                 220

Lys  Lys  Ala  Ile  Gly  Ile  Phe  Val  Ser  Thr  Ser  Ile  Glu  Glu  Val  Phe
 225                 230                 235                 240

Ser  Phe  Pro  Phe  Tyr  Asn  Gln  Leu  Leu  Thr  Gln  Thr  Gln  Ile  Asp  Leu
              245                 250                 255

Tyr  Asn  Gln  Leu  Leu  Gly  Gly  Ile  Ser  Arg  Glu  Ala  Gly  Thr  Glu  Lys
              260                 265                 270

Ile  Lys  Gly  Leu  Asn  Glu  Val  Leu  Asn  Leu  Ala  Ile  Gln  Lys  Asn  Asp
         275                 280                 285
```

```
Glu Thr Ala His Ile Ile Ala Ser Leu Pro His Arg Phe Ile Pro Leu
    290                 295                 300
Phe Lys Gln Ile Leu Ser Asp Arg Asn Thr Leu Ser Phe Ile Leu Glu
305                 310                 315                 320
Glu Phe Lys Ser Asp Glu Glu Val Ile Gln Ser Phe Cys Lys Tyr Lys
                325                 330                 335
Thr Leu Leu Arg Asn Glu Asn Val Leu Glu Thr Ala Glu Ala Leu Phe
            340                 345                 350
Asn Glu Leu Asn Ser Ile Asp Leu Thr His Ile Phe Ile Ser His Lys
        355                 360                 365
Lys Leu Glu Thr Ile Ser Ser Ala Leu Cys Asp His Trp Asp Thr Leu
370                 375                 380
Arg Asn Ala Leu Tyr Glu Arg Arg Ile Ser Glu Leu Thr Gly Lys Ile
385                 390                 395                 400
Thr Lys Ser Ala Lys Glu Lys Val Gln Arg Ser Leu Lys His Glu Asp
                405                 410                 415
Ile Asn Leu Gln Glu Ile Ser Ala Ala Gly Lys Glu Leu Ser Glu
            420                 425                 430
Ala Phe Lys Gln Lys Thr Ser Glu Ile Leu Ser His Ala His Ala Ala
        435                 440                 445
Leu Asp Gln Pro Leu Pro Thr Thr Leu Lys Lys Gln Glu Glu Lys Glu
450                 455                 460
Ile Leu Lys Ser Gln Leu Asp Ser Leu Leu Gly Leu Tyr His Leu Leu
465                 470                 475                 480
Asp Trp Phe Ala Val Asp Glu Ser Asn Glu Val Asp Pro Glu Phe Ser
                485                 490                 495
Ala Arg Leu Thr Gly Ile Lys Leu Glu Met Glu Pro Ser Leu Ser Phe
            500                 505                 510
Tyr Asn Lys Ala Arg Asn Tyr Ala Thr Lys Lys Pro Tyr Ser Val Glu
        515                 520                 525
Lys Phe Lys Leu Asn Phe Gln Met Pro Thr Leu Ala Ser Gly Trp Asp
530                 535                 540
Val Asn Lys Glu Lys Asn Asn Gly Ala Ile Leu Phe Val Lys Asn Gly
545                 550                 555                 560
Leu Tyr Tyr Leu Gly Ile Met Pro Lys Gln Lys Gly Arg Tyr Lys Ala
                565                 570                 575
Leu Ser Phe Glu Pro Thr Glu Lys Thr Ser Glu Gly Phe Asp Lys Met
            580                 585                 590
Tyr Tyr Asp Tyr Phe Pro Asp Ala Ala Lys Met Ile Pro Lys Cys Ser
        595                 600                 605
Thr Gln Leu Lys Ala Val Thr Ala His Phe Gln Thr His Thr Thr Pro
610                 615                 620
Ile Leu Leu Ser Asn Asn Phe Ile Glu Pro Leu Glu Ile Thr Lys Glu
625                 630                 635                 640
Ile Tyr Asp Leu Asn Asn Pro Glu Lys Glu Pro Lys Lys Phe Gln Thr
                645                 650                 655
Ala Tyr Ala Lys Lys Thr Gly Asp Gln Lys Gly Tyr Arg Glu Ala Leu
            660                 665                 670
Cys Lys Trp Ile Asp Phe Thr Arg Asp Phe Leu Ser Lys Tyr Thr Lys
        675                 680                 685
Thr Thr Ser Ile Asp Leu Ser Ser Leu Arg Pro Ser Ser Gln Tyr Lys
690                 695                 700
Asp Leu Gly Glu Tyr Tyr Ala Glu Leu Asn Pro Leu Leu Tyr His Ile
```

```
                705                 710                 715                 720
        Ser Phe Gln Arg Ile Ala Glu Lys Glu Ile Met Asp Ala Val Glu Thr
                        725                 730                 735
        Gly Lys Leu Tyr Leu Phe Gln Ile Tyr Asn Lys Asp Phe Ala Lys Gly
                        740                 745                 750
        His His Gly Lys Pro Asn Leu His Thr Leu Tyr Trp Thr Gly Leu Phe
                        755                 760                 765
        Ser Pro Glu Asn Leu Ala Lys Thr Ser Ile Lys Leu Asn Gly Gln Ala
                        770                 775                 780
        Glu Leu Phe Tyr Arg Pro Lys Ser Arg Met Lys Arg Met Ala His Arg
        785                 790                 795                 800
        Leu Gly Glu Lys Met Leu Asn Lys Lys Leu Lys Asp Gln Lys Thr Pro
                        805                 810                 815
        Ile Pro Asp Thr Leu Tyr Gln Glu Leu Tyr Asp Tyr Val Asn His Arg
                        820                 825                 830
        Leu Ser His Asp Leu Ser Asp Glu Ala Arg Ala Leu Leu Pro Asn Val
                        835                 840                 845
        Ile Thr Lys Glu Val Ser His Glu Ile Ile Lys Asp Arg Arg Phe Thr
                        850                 855                 860
        Ser Asp Lys Phe Phe Phe His Val Pro Ile Thr Leu Asn Tyr Gln Ala
        865                 870                 875                 880
        Ala Asn Ser Pro Ser Lys Phe Asn Gln Arg Val Asn Ala Tyr Leu Lys
                        885                 890                 895
        Glu His Pro Glu Thr Pro Ile Ile Gly Ile Asp Arg Gly Glu Arg Asn
                        900                 905                 910
        Leu Ile Tyr Ile Thr Val Ile Asp Ser Thr Gly Lys Ile Leu Glu Gln
                        915                 920                 925
        Arg Ser Leu Asn Thr Ile Gln Gln Phe Asp Tyr Gln Lys Lys Leu Asp
                        930                 935                 940
        Asn Arg Glu Lys Glu Arg Val Ala Ala Arg Gln Ala Trp Ser Val Val
        945                 950                 955                 960
        Gly Thr Ile Lys Asp Leu Lys Gln Gly Tyr Leu Ser Gln Val Ile His
                        965                 970                 975
        Glu Ile Val Asp Leu Met Ile His Tyr Gln Ala Val Val Val Leu Glu
                        980                 985                 990
        Asn Leu Asn Phe Gly Phe Lys Ser Lys Arg Thr Gly Ile Ala Glu Lys
                        995                 1000                1005
        Ala Val Tyr Gln Gln Phe Glu Lys Met Leu Ile Asp Lys Leu Asn
                1010                1015                1020
        Cys Leu Val Leu Lys Asp Tyr Pro Ala Glu Lys Val Gly Gly Val
                1025                1030                1035
        Leu Asn Pro Tyr Gln Leu Thr Asp Gln Phe Thr Ser Phe Ala Lys
                1040                1045                1050
        Met Gly Thr Gln Ser Gly Phe Leu Phe Tyr Val Pro Ala Pro Tyr
                1055                1060                1065
        Thr Ser Lys Ile Asp Pro Leu Thr Gly Phe Val Asp Pro Phe Val
                1070                1075                1080
        Trp Lys Thr Ile Lys Asn His Glu Ser Arg Lys His Phe Leu Glu
                1085                1090                1095
        Gly Phe Asp Phe Leu His Tyr Asp Val Lys Thr Gly Asp Phe Ile
                1100                1105                1110
        Leu His Phe Lys Met Asn Arg Asn Leu Ser Phe Gln Arg Gly Leu
                1115                1120                1125
```

```
Pro Gly Phe Met Pro Ala Trp Asp Ile Val Phe Glu Lys Asn Glu
    1130                1135                1140

Thr Gln Phe Asp Ala Lys Gly Thr Pro Phe Ile Ala Gly Lys Arg
    1145                1150                1155

Ile Val Pro Val Ile Glu Asn His Arg Phe Thr Gly Arg Tyr Arg
    1160                1165                1170

Asp Leu Tyr Pro Ala Asn Glu Leu Ile Ala Leu Leu Glu Glu Lys
    1175                1180                1185

Gly Ile Val Phe Arg Asp Gly Ser Asn Ile Leu Pro Lys Leu Leu
    1190                1195                1200

Glu Asn Asp Asp Ser His Ala Ile Asp Thr Met Val Ala Leu Ile
    1205                1210                1215

Arg Ser Val Leu Gln Met Arg Asn Ser Asn Ala Ala Thr Gly Glu
    1220                1225                1230

Asp Tyr Ile Asn Ser Pro Val Arg Asp Leu Asn Gly Val Cys Phe
    1235                1240                1245

Asp Ser Arg Phe Gln Asn Pro Glu Trp Pro Met Asp Ala Asp Ala
    1250                1255                1260

Asn Gly Ala Tyr His Ile Ala Leu Lys Gly Gln Leu Leu Leu Asn
    1265                1270                1275

His Leu Lys Glu Ser Lys Asp Leu Lys Leu Gln Asn Gly Ile Ser
    1280                1285                1290

Asn Gln Asp Trp Leu Ala Tyr Ile Gln Glu Leu Arg Asn
    1295                1300                1305

<210> SEQ ID NO 121
<211> LENGTH: 1306
<212> TYPE: PRT
<213> ORGANISM: Artificial sequence
<220> FEATURE:
<223> OTHER INFORMATION: synthetic sequence

<400> SEQUENCE: 121

Thr Gln Phe Glu Gly Phe Thr Asn Leu Tyr Gln Val Ser Lys Thr Leu
1               5                   10                  15

Arg Phe Glu Leu Ile Pro Gln Gly Lys Thr Leu Lys His Ile Gln Glu
            20                  25                  30

Gln Gly Phe Ile Glu Glu Asp Lys Ala Arg Asn Asp His Tyr Lys Glu
        35                  40                  45

Leu Lys Pro Ile Ile Asp Arg Ile Tyr Lys Thr Tyr Ala Asp Gln Cys
    50                  55                  60

Leu Gln Leu Val Gln Leu Asp Trp Glu Asn Leu Ser Ala Ala Ile Asp
65                  70                  75                  80

Ser Tyr Arg Lys Glu Lys Thr Glu Glu Thr Arg Asn Ala Leu Ile Glu
                85                  90                  95

Glu Gln Ala Thr Tyr Arg Asn Ala Ile His Asp Tyr Phe Ile Gly Arg
            100                 105                 110

Thr Asp Asn Leu Thr Asp Ala Ile Asn Lys Arg His Ala Glu Ile Tyr
        115                 120                 125

Lys Gly Leu Phe Lys Ala Glu Leu Phe Asn Gly Lys Val Leu Lys Gln
    130                 135                 140

Leu Gly Thr Val Thr Thr Thr Glu His Glu Asn Ala Leu Leu Arg Ser
145                 150                 155                 160

Phe Asp Lys Phe Thr Thr Tyr Phe Ser Gly Phe Tyr Glu Asn Arg Lys
                165                 170                 175
```

```
Asn Val Phe Ser Ala Glu Asp Ile Ser Thr Ala Ile Pro His Arg Ile
            180                 185                 190

Val Gln Asp Asn Phe Pro Lys Phe Lys Glu Asn Cys His Ile Phe Thr
        195                 200                 205

Arg Leu Ile Thr Ala Val Pro Ser Leu Arg Glu His Phe Glu Asn Val
    210                 215                 220

Lys Lys Ala Ile Gly Ile Phe Val Ser Thr Ser Ile Glu Glu Val Phe
225                 230                 235                 240

Ser Phe Pro Phe Tyr Asn Gln Leu Leu Thr Gln Thr Gln Ile Asp Leu
                245                 250                 255

Tyr Asn Gln Leu Leu Gly Gly Ile Ser Arg Glu Ala Gly Thr Glu Lys
            260                 265                 270

Ile Lys Gly Leu Asn Glu Val Leu Asn Leu Ala Ile Gln Lys Asn Asp
        275                 280                 285

Glu Thr Ala His Ile Ile Ala Ser Leu Pro His Arg Phe Ile Pro Leu
    290                 295                 300

Phe Lys Gln Ile Leu Ser Asp Arg Asn Thr Leu Ser Phe Ile Leu Glu
305                 310                 315                 320

Glu Phe Lys Ser Asp Glu Glu Val Ile Gln Ser Phe Cys Lys Tyr Lys
                325                 330                 335

Thr Leu Leu Arg Asn Glu Asn Val Leu Glu Thr Ala Glu Ala Leu Phe
            340                 345                 350

Asn Glu Leu Asn Ser Ile Asp Leu Thr His Ile Phe Ile Ser His Lys
        355                 360                 365

Lys Leu Glu Thr Ile Ser Ser Ala Leu Cys Asp His Trp Asp Thr Leu
    370                 375                 380

Arg Asn Ala Leu Tyr Glu Arg Arg Ile Ser Glu Leu Thr Gly Lys Ile
385                 390                 395                 400

Thr Lys Ser Ala Lys Glu Lys Val Gln Arg Ser Leu Lys His Glu Asp
                405                 410                 415

Ile Asn Leu Gln Glu Ile Ile Ser Ala Ala Gly Lys Glu Leu Ser Glu
            420                 425                 430

Ala Phe Lys Gln Lys Thr Ser Glu Ile Leu Ser His Ala His Ala Ala
        435                 440                 445

Leu Asp Gln Pro Leu Pro Thr Thr Leu Lys Lys Gln Glu Glu Lys Glu
    450                 455                 460

Ile Leu Lys Ser Gln Leu Asp Ser Leu Leu Gly Leu Tyr His Leu Leu
465                 470                 475                 480

Asp Trp Phe Ala Val Asp Glu Ser Asn Glu Val Asp Pro Glu Phe Ser
                485                 490                 495

Ala Arg Leu Thr Gly Ile Lys Leu Glu Met Glu Pro Ser Leu Ser Phe
            500                 505                 510

Tyr Asn Lys Ala Arg Asn Tyr Ala Thr Lys Lys Pro Tyr Ser Val Glu
        515                 520                 525

Lys Phe Lys Leu Asn Phe Gln Met Pro Thr Leu Ala Ser Gly Trp Asp
    530                 535                 540

Val Asn Lys Glu Lys Asn Asn Gly Ala Ile Leu Phe Val Lys Asn Gly
545                 550                 555                 560

Leu Tyr Tyr Leu Gly Ile Met Pro Lys Gln Lys Gly Arg Tyr Lys Ala
                565                 570                 575

Leu Ser Phe Glu Pro Thr Glu Lys Thr Ser Glu Gly Phe Asp Lys Met
            580                 585                 590
```

```
Tyr Tyr Asp Tyr Phe Pro Asp Ala Ala Lys Met Ile Pro Lys Cys Ser
            595                 600                 605
Thr Gln Leu Lys Ala Val Thr Ala His Phe Gln Thr His Thr Thr Pro
    610                 615                 620
Ile Leu Leu Ser Asn Asn Phe Ile Glu Pro Leu Glu Ile Thr Lys Glu
625                 630                 635                 640
Ile Tyr Asp Leu Asn Asn Pro Glu Lys Glu Pro Lys Lys Phe Gln Thr
                645                 650                 655
Ala Tyr Ala Lys Lys Thr Gly Asp Gln Lys Gly Tyr Arg Glu Ala Leu
            660                 665                 670
Cys Lys Trp Ile Asp Phe Thr Arg Asp Phe Leu Ser Lys Tyr Thr Lys
        675                 680                 685
Thr Thr Ser Ile Asp Leu Ser Ser Leu Arg Pro Ser Ser Gln Tyr Lys
    690                 695                 700
Asp Leu Gly Glu Tyr Tyr Ala Glu Leu Asn Pro Leu Leu Tyr His Ile
705                 710                 715                 720
Ser Phe Gln Arg Ile Ala Glu Lys Glu Ile Met Asp Ala Val Glu Thr
                725                 730                 735
Gly Lys Leu Tyr Leu Phe Gln Ile Tyr Asn Lys Asp Phe Ala Lys Gly
            740                 745                 750
His His Gly Lys Pro Asn Leu His Thr Leu Tyr Trp Thr Gly Leu Phe
        755                 760                 765
Ser Pro Glu Asn Leu Ala Lys Thr Ser Ile Lys Leu Asn Gly Gln Ala
    770                 775                 780
Glu Leu Phe Tyr Arg Pro Lys Ser Arg Met Lys Arg Met Ala His Arg
785                 790                 795                 800
Leu Gly Glu Lys Met Leu Asn Lys Lys Leu Lys Asp Gln Lys Thr Pro
                805                 810                 815
Ile Pro Asp Thr Leu Tyr Gln Glu Leu Tyr Asp Tyr Val Asn His Arg
            820                 825                 830
Leu Ser His Asp Leu Ser Asp Glu Ala Arg Ala Leu Leu Pro Asn Val
        835                 840                 845
Ile Thr Lys Glu Val Ser His Glu Ile Ile Lys Asp Arg Arg Phe Thr
    850                 855                 860
Ser Asp Lys Phe Phe Phe His Val Pro Ile Thr Leu Asn Tyr Gln Ala
865                 870                 875                 880
Ala Asn Ser Pro Ser Lys Phe Asn Gln Arg Val Asn Ala Tyr Leu Lys
                885                 890                 895
Glu His Pro Glu Thr Pro Ile Ile Gly Ile Asp Arg Gly Glu Arg Asn
            900                 905                 910
Leu Ile Tyr Ile Thr Val Ile Asp Ser Thr Gly Lys Ile Leu Glu Gln
        915                 920                 925
Arg Ser Leu Asn Thr Ile Gln Gln Phe Asp Tyr Gln Lys Lys Leu Asp
    930                 935                 940
Asn Arg Glu Lys Glu Arg Val Ala Ala Arg Gln Ala Trp Ser Val Val
945                 950                 955                 960
Gly Thr Ile Lys Asp Leu Lys Gln Gly Tyr Leu Ser Gln Val Ile His
                965                 970                 975
Glu Ile Val Asp Leu Met Ile His Tyr Gln Ala Val Val Val Leu Glu
            980                 985                 990
Asn Leu Asn Phe Gly Phe Lys Ser  Lys Arg Thr Gly Ile  Ala Glu Lys
        995                 1000                1005
Ala Val  Tyr Gln Gln Phe Glu  Lys Met Leu Ile Asp  Lys Leu Asn
```

```
            1010                1015                1020
Cys Leu Val Leu Lys Asp Tyr Pro Ala Glu Lys Val Gly Gly Val
    1025                1030                1035

Leu Asn Pro Tyr Gln Leu Thr Asp Gln Phe Thr Ser Phe Ala Lys
    1040                1045                1050

Met Gly Thr Gln Ser Gly Phe Leu Phe Tyr Val Pro Ala Pro Tyr
    1055                1060                1065

Thr Ser Lys Ile Asp Pro Leu Thr Gly Phe Val Asp Pro Phe Val
    1070                1075                1080

Trp Lys Thr Ile Lys Asn His Glu Ser Arg Lys His Phe Leu Glu
    1085                1090                1095

Gly Phe Asp Phe Leu His Tyr Asp Val Lys Thr Gly Asp Phe Ile
    1100                1105                1110

Leu His Phe Lys Met Asn Arg Asn Leu Ser Phe Gln Arg Gly Leu
    1115                1120                1125

Pro Gly Phe Met Pro Ala Trp Asp Ile Val Phe Glu Lys Asn Glu
    1130                1135                1140

Thr Gln Phe Asp Ala Lys Gly Thr Pro Phe Ile Ala Gly Lys Arg
    1145                1150                1155

Ile Val Pro Val Ile Glu Asn His Arg Phe Thr Gly Arg Tyr Arg
    1160                1165                1170

Asp Leu Tyr Pro Ala Asn Glu Leu Ile Ala Leu Leu Glu Glu Lys
    1175                1180                1185

Gly Ile Val Phe Arg Asp Gly Ser Asn Ile Leu Pro Lys Leu Leu
    1190                1195                1200

Glu Asn Asp Asp Ser His Ala Ile Asp Thr Met Val Ala Leu Ile
    1205                1210                1215

Arg Ser Val Leu Gln Met Ala Asn Ser Asn Ala Ala Thr Gly Glu
    1220                1225                1230

Asp Tyr Ile Asn Ser Pro Val Arg Asp Leu Asn Gly Val Cys Phe
    1235                1240                1245

Asp Ser Arg Phe Gln Asn Pro Glu Trp Pro Met Asp Ala Asp Ala
    1250                1255                1260

Asn Gly Ala Tyr His Ile Ala Leu Lys Gly Gln Leu Leu Leu Asn
    1265                1270                1275

His Leu Lys Glu Ser Lys Asp Leu Lys Leu Gln Asn Gly Ile Ser
    1280                1285                1290

Asn Gln Asp Trp Leu Ala Tyr Ile Gln Glu Leu Arg Asn
    1295                1300                1305

<210> SEQ ID NO 122
<211> LENGTH: 872
<212> TYPE: PRT
<213> ORGANISM: Homo sapiens

<400> SEQUENCE: 122

Met Gly Ser Leu Leu Ala Leu Leu Ala Leu Leu Leu Leu Trp Gly Ala
1               5                   10                  15

Val Ala Glu Gly Pro Ala Lys Lys Val Leu Thr Leu Glu Gly Asp Leu
            20                  25                  30

Val Leu Gly Gly Leu Phe Pro Val His Gln Lys Gly Gly Pro Ala Glu
        35                  40                  45

Asp Cys Gly Pro Val Asn Glu His Arg Gly Ile Gln Arg Leu Glu Ala
    50                  55                  60
```

Met Leu Phe Ala Leu Asp Arg Ile Asn Arg Asp Pro His Leu Leu Pro
65                  70                  75                  80

Gly Val Arg Leu Gly Ala His Ile Leu Asp Ser Cys Ser Lys Asp Thr
            85                  90                  95

His Ala Leu Glu Gln Ala Leu Asp Phe Val Arg Ala Ser Leu Ser Arg
        100                 105                 110

Gly Ala Asp Gly Ser Arg His Ile Cys Pro Asp Gly Ser Tyr Ala Thr
    115                 120                 125

His Gly Asp Ala Pro Thr Ala Ile Thr Gly Val Ile Gly Gly Ser Tyr
130                 135                 140

Ser Asp Val Ser Ile Gln Val Ala Asn Leu Leu Arg Leu Phe Gln Ile
145                 150                 155                 160

Pro Gln Ile Ser Tyr Ala Ser Thr Ser Ala Lys Leu Ser Asp Lys Ser
                165                 170                 175

Arg Tyr Asp Tyr Phe Ala Arg Thr Val Pro Pro Asp Phe Phe Gln Ala
            180                 185                 190

Lys Ala Met Ala Glu Ile Leu Arg Phe Phe Asn Trp Thr Tyr Val Ser
        195                 200                 205

Thr Val Ala Ser Glu Gly Asp Tyr Gly Glu Thr Gly Ile Glu Ala Phe
210                 215                 220

Glu Leu Glu Ala Arg Ala Arg Asn Ile Cys Val Ala Thr Ser Glu Lys
225                 230                 235                 240

Val Gly Arg Ala Met Ser Arg Ala Ala Phe Glu Gly Val Val Arg Ala
                245                 250                 255

Leu Leu Gln Lys Pro Ser Ala Arg Val Ala Val Leu Phe Thr Arg Ser
            260                 265                 270

Glu Asp Ala Arg Glu Leu Leu Ala Ala Ser Gln Arg Leu Asn Ala Ser
        275                 280                 285

Phe Thr Trp Val Ala Ser Asp Gly Trp Gly Ala Leu Glu Ser Val Val
    290                 295                 300

Ala Gly Ser Glu Gly Ala Ala Glu Gly Ala Ile Thr Ile Glu Leu Ala
305                 310                 315                 320

Ser Tyr Pro Ile Ser Asp Phe Ala Ser Tyr Phe Gln Ser Leu Asp Pro
                325                 330                 335

Trp Asn Asn Ser Arg Asn Pro Trp Phe Arg Glu Phe Trp Glu Gln Arg
            340                 345                 350

Phe Arg Cys Ser Phe Arg Gln Arg Asp Cys Ala Ala His Ser Leu Arg
        355                 360                 365

Ala Val Pro Phe Glu Gln Glu Ser Lys Ile Met Phe Val Val Asn Ala
    370                 375                 380

Val Tyr Ala Met Ala His Ala Leu His Asn Met His Arg Ala Leu Cys
385                 390                 395                 400

Pro Asn Thr Thr Arg Leu Cys Asp Ala Met Arg Pro Val Asn Gly Arg
                405                 410                 415

Arg Leu Tyr Lys Asp Phe Val Leu Asn Val Lys Phe Asp Ala Pro Phe
            420                 425                 430

Arg Pro Ala Asp Thr His Asn Glu Val Arg Phe Asp Arg Phe Gly Asp
        435                 440                 445

Gly Ile Gly Arg Tyr Asn Ile Phe Thr Tyr Leu Arg Ala Gly Ser Gly
    450                 455                 460

Arg Tyr Arg Tyr Gln Lys Val Gly Tyr Trp Ala Glu Gly Leu Thr Leu
465                 470                 475                 480

Asp Thr Ser Leu Ile Pro Trp Ala Ser Pro Ser Ala Gly Pro Leu Pro

```
                485             490             495
Ala Ser Arg Cys Ser Glu Pro Cys Leu Gln Asn Glu Val Lys Ser Val
            500             505             510

Gln Pro Gly Glu Val Cys Cys Trp Leu Cys Ile Pro Cys Gln Pro Tyr
            515             520             525

Glu Tyr Arg Leu Asp Glu Phe Thr Cys Ala Asp Cys Gly Leu Gly Tyr
            530             535             540

Trp Pro Asn Ala Ser Leu Thr Gly Cys Phe Glu Leu Pro Gln Glu Tyr
545             550             555             560

Ile Arg Trp Gly Asp Ala Trp Ala Val Gly Pro Val Thr Ile Ala Cys
            565             570             575

Leu Gly Ala Leu Ala Thr Leu Phe Val Leu Gly Val Phe Val Arg His
            580             585             590

Asn Ala Thr Pro Val Val Lys Ala Ser Gly Arg Glu Leu Cys Tyr Ile
            595             600             605

Leu Leu Gly Gly Val Phe Leu Cys Tyr Cys Met Thr Phe Ile Phe Ile
            610             615             620

Ala Lys Pro Ser Thr Ala Val Cys Thr Leu Arg Arg Leu Gly Leu Gly
625             630             635             640

Thr Ala Phe Ser Val Cys Tyr Ser Ala Leu Leu Thr Lys Thr Asn Arg
            645             650             655

Ile Ala Arg Ile Phe Gly Gly Ala Arg Glu Gly Ala Gln Arg Pro Arg
            660             665             670

Phe Ile Ser Pro Ala Ser Gln Val Ala Ile Cys Leu Ala Leu Ile Ser
            675             680             685

Gly Gln Leu Leu Ile Val Val Ala Trp Leu Val Val Glu Ala Pro Gly
            690             695             700

Thr Gly Lys Glu Thr Ala Pro Glu Arg Arg Glu Val Val Thr Leu Arg
705             710             715             720

Cys Asn His Arg Asp Ala Ser Met Leu Gly Ser Leu Ala Tyr Asn Val
            725             730             735

Leu Leu Ile Ala Leu Cys Thr Leu Tyr Ala Phe Lys Thr Arg Lys Cys
            740             745             750

Pro Glu Asn Phe Asn Glu Ala Lys Phe Ile Gly Phe Thr Met Tyr Thr
            755             760             765

Thr Cys Ile Ile Trp Leu Ala Phe Leu Pro Ile Phe Tyr Val Thr Ser
            770             775             780

Ser Asp Tyr Arg Val Gln Thr Thr Thr Met Cys Val Ser Val Ser Leu
785             790             795             800

Ser Gly Ser Val Val Leu Gly Cys Leu Phe Ala Pro Lys Leu His Ile
            805             810             815

Ile Leu Phe Gln Pro Gln Lys Asn Val Val Ser His Arg Ala Pro Thr
            820             825             830

Ser Arg Phe Gly Ser Ala Ala Arg Ala Ser Ser Leu Gly Gln
            835             840             845

Gly Ser Gly Ser Gln Phe Val Pro Thr Val Cys Asn Gly Arg Glu Val
            850             855             860

Val Asp Ser Thr Thr Ser Ser Leu
865             870

<210> SEQ ID NO 123
<211> LENGTH: 182
<212> TYPE: PRT
<213> ORGANISM: Artificial sequence
```

```
<220> FEATURE:
<223> OTHER INFORMATION: synthetic sequence

<400> SEQUENCE: 123

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Arg Ile Ile
                20                  25                  30

Phe Leu Gly Lys Gly Thr Ser Ala Ala Asp Ala Val Glu Val Pro Ala
            35                  40                  45

Pro Ala Ala Val Leu Gly Gly Pro Glu Pro Leu Met Gln Ala Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
                100                 105                 110

Ser Tyr Ser His Leu Ala Ala Leu Ala Gly Asn Pro Ala Ala Thr Ala
            115                 120                 125

Ala Val Lys Thr Ala Leu Ser Gly Asn Pro Val Pro Ile Leu Ile Pro
    130                 135                 140

Cys His Arg Val Val Gln Gly Asp Leu Asp Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 124
<211> LENGTH: 181
<212> TYPE: PRT
<213> ORGANISM: Artificial sequence
<220> FEATURE:
<223> OTHER INFORMATION: synthetic sequence

<400> SEQUENCE: 124

Asp Lys Asp Cys Glu Met Lys Arg Thr Thr Leu Asp Ser Pro Leu Gly
1               5                   10                  15

Lys Leu Glu Leu Ser Gly Cys Glu Gln Gly Leu His Glu Ile Lys Leu
                20                  25                  30

Leu Gly Lys Gly Thr Ser Ala Ala Asp Ala Val Glu Val Pro Ala Pro
            35                  40                  45

Ala Ala Val Leu Gly Gly Pro Glu Pro Leu Met Gln Ala Thr Ala Trp
    50                  55                  60

Leu Asn Ala Tyr Phe His Gln Pro Glu Ala Ile Glu Glu Phe Pro Val
65                  70                  75                  80

Pro Ala Leu His His Pro Val Phe Gln Gln Glu Ser Phe Thr Arg Gln
                85                  90                  95

Val Leu Trp Lys Leu Leu Lys Val Val Lys Phe Gly Glu Val Ile Ser
                100                 105                 110

Tyr Gln Gln Leu Ala Ala Leu Ala Gly Asn Pro Ala Ala Thr Ala Ala
            115                 120                 125

Val Lys Thr Ala Leu Ser Gly Asn Pro Val Pro Ile Leu Ile Pro Cys
    130                 135                 140

His Arg Val Val Ser Ser Ser Gly Ala Val Gly Gly Tyr Glu Gly Gly
```

```
               145                 150                 155                 160
Leu Ala Val Lys Glu Trp Leu Leu Ala His Glu Gly His Arg Leu Gly
                        165                 170                 175

Lys Pro Gly Leu Gly
            180
```